US012767625B2

(12) United States Patent
Stephens et al.

(10) Patent No.: US 12,767,625 B2
(45) Date of Patent: Oct. 20, 2026

(54) COMPOUNDS, COMPOSITIONS, AND METHODS TO TREAT METABOLIC DISEASE

(71) Applicant: Board of Supervisors of Louisiana State University and Agricultural and Mechanical College, Baton Rouge, LA (US)

(72) Inventors: Jacqueline Stephens, Baton Rouge, LA (US); Allison J. Richard, Baton Rouge, LA (US); Anik Boudreau, Arnaudville, LA (US)

(73) Assignee: BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 1031 days.

(21) Appl. No.: 17/760,093

(22) PCT Filed: Feb. 8, 2021

(86) PCT No.: PCT/US2021/017055
§ 371 (c)(1),
(2) Date: Aug. 3, 2022

(87) PCT Pub. No.: WO2021/159062
PCT Pub. Date: Aug. 12, 2021

(65) Prior Publication Data

US 2023/0129745 A1 Apr. 27, 2023

Related U.S. Application Data

(60) Provisional application No. 62/971,054, filed on Feb. 6, 2020.

(51) Int. Cl.

| | |
|---|---|
| ***C07C 39/04*** | (2006.01) |
| ***A61K 31/192*** | (2006.01) |
| ***A61K 36/282*** | (2006.01) |
| ***A61K 45/06*** | (2006.01) |
| ***A61P 3/04*** | (2006.01) |
| ***C07C 39/19*** | (2006.01) |

(52) U.S. Cl.
CPC ............ *C07C 39/04* (2013.01); *A61K 31/192* (2013.01); *A61K 36/282* (2013.01); *A61K 45/06* (2013.01); *A61P 3/04* (2018.01); *C07C 39/19* (2013.01)

(58) Field of Classification Search
CPC ....... A61K 31/192; A61K 31/222; A61P 3/00; A61P 3/04
See application file for complete search history.

(56) References Cited

U.S. PATENT DOCUMENTS

2009/0142425 A1 6/2009 Jager et al.

FOREIGN PATENT DOCUMENTS

| | | | |
|---|---|---|---|
| BR | 102014032012 | A2 | 1/2019 |
| JP | 2006-000081 | A | 1/2006 |
| JP | 2016-199481 | A | 12/2016 |
| KR | 102069712 | B1 | 1/2020 |

OTHER PUBLICATIONS

Boudreau et al., "SCOPA, a Botanical Extract of Artemisia Scoparia, Inhibits Lipolysis and is Associated with Metabolic Improvements In Vivo", Diabetes, vol. 66, No. Supplement 1, p. A670, abstract No. 2575-PUB (2017).*

Abdel Motaal, A. et al. In vivo anti-inflammatory activity of caffeoylquinic acid derivatives from Solidago virgaurea in rats. Pharm Biol. 54(12):2864-2870 (2016).

Able, A.A. et al. Loss of DBC1 (CCAR2) affects TNFα-induced lipolysis and Glut4 gene expression in murine adipocytes. J Mol Endocrinol, 61:195-205 (2018).

Aggarwal, S. et al. An extract of *Artemisia dracunculus* L. stimulates insulin secretion from β cells, activates AMPK and suppresses inflammation. J Ethnopharmacol. 170:98-105 (2015).

Ahmad, K.S. et al. Ethnopharmacological studies of indigenous plants in Kel village, Neelum Valley, Azad Kashmir, Pakistan. J Ethnobiol Ethnomed. 13(1):68 (2017).

Ahmed, A. et al. Transcriptional Activation of Inflammatory Genes: Mechanistic Insight into Selectivity and Diversity. Biomolecules, 5:3087-3111 (2015).

Antebi, A. Nuclear receptor signal transduction in C. elegans. WormBook, downloaded from NCBI Bookshelf, a service of the National Library of Medicine, National Institutes of Health. 56 pages (2015).

Arkan, M.C. et al. IKK-β links inflammation to obesity-induced insulin resistance. Nat Med., 11(2):191-198 (2005).

Ashrafi, K. et al. Genome-wide RNAi analysis of Caenorhabditis elegans fat regulatory genes. Nature, 421, pp. 268-272 (2003).

Baker, R.G. et al. NF-κB, inflammation, and metabolic disease. Cell Metab. 13(1):11-22 (2011).

Baugh, J.E. et al. The modulation of STAT5A/GR complexes during fat cell differentiation and in mature adipocytes. Obesity (Silver Spring), 15(3):583-590 (2007).

(Continued)

*Primary Examiner* — Kevin E Weddington

(74) *Attorney, Agent, or Firm* — Baker, Donelson, Bearman, Caldwell & Berkowitz, PC

(57) ABSTRACT

This invention is directed to compounds, compositions, and methods to treat metabolic diseases. For example, the invention is drawn to compounds identified in extracts from *Artemisia scoparia* for the treatment of metabolic disease.

7 Claims, 51 Drawing Sheets

Specification includes a Sequence Listing.

(56) References Cited

OTHER PUBLICATIONS

Bénard-Laribière, A. et al. Prevalence and prescription patterns of oral glucocorticoids in adults: A retrospective cross-sectional and cohort analysis in France. BMJ Open, 7(7):1-7 (2017).
Bhupathiraju, S. N. and Hu, F. B. Epidemiology of obesity and Diabetes and Their Cardiovascular Complications. Circulation Research 118(11):1723-35 (2016).
Bolton, J. L. et al. The Multiple Biological Targets of Hops and Bioactive Compounds. Chem. Res. Toxicol. 32, 222-233 (2019).
Bora, K.S., Sharma A. The Genus Artemisia: A Comprehensive Review. Pharm Biol. 49(1):101-109 (2011).
Boudreau, A. et al. An ethanolic extract of Artemisia scoparia (SCO) inhibits lipolysis in vivo and has anti-lipolytic effects on murine adipocytes in vitro. Am J Physiol Metab. 315(5): E1053-E1061 (2018).
Boudreau, A. et al. Distinct fractions of an Artemisia scoparia extract contain compounds with new adipogenic bioactivity. Frontiers in nutrition 6 (18), 13 pages (2019).
Boyd, W.A. et al. A high-throughput method for assessing chemical toxicity using a Caenorhabditis elegans reproduction assay. Toxicol Appl Pharmacol. 245: 153-159 (2010).
Bugianesi, E. et al. Insulin resistance in non-diabetic patients with non-alcoholic fatty liver disease: Sites and mechanisms. Diabetologia, 48(4):634-642 (2005).
Burden, N. et al. Testing Chemical Safety: What is Needed to Ensure the Widespread Application of Non-animal Approaches? PLoS Biol 13(5): e1002156, 8 pages (2015).
Burhans, M. S. Contribution of Adipose Tissue Inflammation to the Development of Type 2 Diabetes Mellitus. Compr Physiol.; 9(1): 1-58 (2018).
Burke S.J. et al. IL-1β reciprocally regulates chemokine and insulin secretion in pancreatic β-cells via NF-κB. Am J Physiol Metab, 309:E715-E726 (2015).
Burke, S.J. and Collier, J.J. Transcriptional Regulation of Chemokine Genes: A Link to Pancreatic Islet Inflammation? Biomolecules, 5:1020-1034 (2015).
Burke, S.J. et al. NF-κB and STAT1 control CXCL1 and CXCL2 gene transcription. Am J Physiol Metab, 306:E131-E149, 19 pages (2014).
Burke, S.J. et al. One week of continuous corticosterone exposure impairs hepatic metabolic flexibility, promotes islet β-cell proliferation, and reduces physical activity in male C57BL/6 J mice. J Steroid Biochem Mol Biol. 195:105468, 12 pages (2019).
Burke, S.J. et al. Pancreatic β-Cell production of CXCR3 ligands precedes diabetes onset. BioFactors, 42:703-715 (2016).
Burke, S.J. et al. Regulation of iNOS gene transcription by IL-1β and IFN-γ requires a coactivator exchange mechanism. Mol Endocrinol, 27:1724-1742 (2013).
Caccamese, S. et al. Separation ofcis andtrans isomers of naturally occurring hydroxycinnamic acids by high-pressure liquid chromatography. Chromatographia, 12, 545-547 (1979).
Campbell, J.E. et al. Adipogenic and lipolytic effects of chronic glucocorticoid exposure. Am J Physiol—Cell Physiol. 300(1):198-209 (2011).
Cao, H. et al. Adipocyte lipid chaperone aP2 is a secreted adipokine regulating hepatic glucose production. Cell Metab, 17:768-778 (2013).
Castañar, L. Pure shift NMR: Past, present, and future. Magn. Reson. Chem. 56, 874-875 (2018).
Catalán, V. et al. Increased adipose tissue expression of lipocalin-2 in obesity is related to inflammation and matrix metalloproteinase-2 and metalloproteinase-9 activities in humans. J Mol Med (Berl). 87(8):803-813 (2009).
Cawthorn, W.P. and Sethi, J.K. TNF-α and adipocyte biology. FEBS Lett. 582(1):117-131 (2008).
Cha, J.-D. et al. Chemical Composition and Antimicrobial Activity of the Essential Oils of Artemisia scoparia and A. capillaris. Planta Med. 71(2):186-190 (2005).
Chandrasekharan I, Khan HA, Ghanim A. Flavonoids from Artemisia scoparia. Planta Med. 1981.
Chigurupati, S. et al. A step ahead of PPARγ full agonists to PPARγ partial agonists: Therapeutic perspectives in the management of diabetic insulin resistance. Eur J Pharmacol., 755:50-57 (2015).
Chini, E.D. et al. Deleted in breast cancer-1 (DBC-1) in the interface between metabolism, aging and cancer. Biosci Rep, 33:637-643 (2013).
Cho, J.-Y. et al. Antihypertensive Effects of Artemisia scoparia Waldst in Spontaneously Hypertensive Rats and Identification of Angiotensin I Converting Enzyme Inhibitors. Molecules, 20(11):19789-19804 (2015).
Cho, J.-Y. et al. Sesquiterpene lactones and scopoletins from Artemisia scopari Waldst. & Kit. and their angiotensin I-converting enzyme inhibitory activities. Food Sci Biotechnol. 25(6):1701-1708 (2016).
Choi, E. and Kim, G. Effect of artemisia species on cellular proliferation and apoptosis in human breast cancer cells via estrogen receptor-related pathway. J Tradit Chinese Med, 33(5):658-663 (2013).
Choi, E. et al. Anticancer, antiobesity, and anti-inflammatory activity of Artemisia species in vitro. J Tradit Chinese Med, 33(1):92-97 (2013).
Choi, J.H. et al. Antidiabetic actions of a non-agonist PPARγ ligand blocking Cdk5-mediated phosphorylation. Nature. 477(7365):477-481 (2011).
Choi, J.H. et al. Anti-diabetic drugs inhibit obesity-linked phosphorylation of PPARgamma by Cdk5. Nature, 466(7305):451-456 (2010).
Choi, S.-S. et al. A novel non-agonist peroxisome proliferator-activated receptor γ (PPARγ) ligand UHC1 blocks PPARγ phosphorylation by cyclin-dependent kinase 5 (CDK5) and improves insulin sensitivity. J Biol Chem. 289(38):26618-26629 (2014).
Choi, S.-S. et al. Artepillin C, as a PPARγ Ligand, Enhances Adipocyte Differentiation and Glucose Uptake in 3T3-L1 Cells. Biochemical Pharmacology 81(7):925-33 (2011).
Christian, F. et al. The Regulation of NF-κB Subunits by Phosphorylation. Cells 5(1):12 (2016).
Cignarelli, A. et al. Pharmacologic agents for type 2 diabetes therapy and regulation of adipogenesis. Arch. Physiol. Biochem. 119(4), 139-150 (2013).
Cole, R.D. et al. The nematode Caenorhabditis elegans as a model of organophosphate-induced mammalian neurotoxicity. Toxicol Appl Pharmacol. 194:248-256 (2004).
Corsi, a.K. et al. Transparent window into biology: A primer on Caenorhabditis elegans. WormBook, downloaded from NCBI Bookshelf, a service of the National Library of Medicine, National Institutes of Health, 37 pages (2015).
Covert, M.W. et al. Achieving stability of lipopolysaccharide-induced NF-κB activation. Science, 309:1854-1857 (2005).
Dalby, M.J. et al. Diet induced obesity is independent of metabolic endotoxemia and TLR4 signalling, but markedly increases hypothalamic expression of the acute phase protein, SerpinA3N. Sci Rep. 8:15648, 15 pages (2018).
Kaikaew, K. et al. Sex Difference in Corticosterone-Induced Insulin Resistance in Mice. Endocrinology, 160(10):2367-2387 (2019).
Kamath, R.S. et al. Systematic functional analysis of the Caenorhabditis elegans genome using RNAi. Nature, 421, pp. 231-237 (2003).
Kang, S. et al. Identification of nuclear hormone receptor pathways causing insulin resistance by transcriptional and epigenomic analysis. Nat Cell Biol. 17(1):44-56 (2015).
Kawakami, M. et al. Human Recombinant TNF Suppresses Lipoprotein Lipase Activity and Stimulates Lipolysis in 3T3-L1 Cells. Journal of Biochemistry 101(2):331-38 (1987).
Kenyon CJ. The genetics of ageing. Nature, 464(7288):504-512 (2010).
Khan, M.A. et al. In Vitro Attenuation of Thermal-Induced Protein Denaturation by Aerial Parts of Artemisia scoparia. J Evid Based Complementary Altern Med. 2015;20(1):9-12 (2015).
Kheterpal, I. et al. Bioactives from *Artemisia dracunculus* L. enhance insulin sensitivity via modulation of skeletal muscle protein phosphorylation. Nutrition, 30(7-8 Suppl.), S43-S51 (2014).

(56) References Cited

OTHER PUBLICATIONS

Kheterpal, I. et al. Regulation of insulin action by an extract of *Artemisia dracunculus* L. in primary human skeletal muscle culture: A proteomics approach. Phyther Res. 24(9):1278-1284 (2010).
Kilroy, G. et al. The Ubiquitin Ligase Siah2 Regulates PPARγ Activity in Adipocytes. Endocrinology, 153:1206-1218 (2012).
Kim, J.-Y. et al. Obesity-Associated Improvements in Metabolic Profile through Expansion of Adipose Tissue. The Journal of Clinical Investigation, 117(9):2621-37 (2007).
Kim, Y. et al. 4,5-Di-O-Caffeoylquinic Acid from Ligularia fischeri Suppresses Inflammatory Responses Through TRPV1 Activation. Phytother Res., 31(10):1564-1570 (2017).
Kirk-Ballard, H. et al. An extract of *Artemisia dracunculus* L. inhibits ubiquitinproteasome activity and preserves skeletal muscle mass in a murine model of diabetes. PLoS One, 8(2):1-12 (2013).
Kitagawa, I. et al. Capillartemisin A and B, Two New Choleretic Principles from Artemisiae Capillaris Herba Chem Pharm Bull (Tokyo), 31(1):352-55 (1983).
Kong, S. et al. Deleted in Breast Cancer 1 Suppresses B Cell Activation through ReIB and is Regulated by IKKα Phosphorylation. J Immunol 2015;195:3685-3693 (2015).
Kort, R. et al. Evidence for trans-cis isomerization of the p-coumaric acid chromophore as the photochemical basis of the photocycle of photoactive yellow protein. FEBS Lett., 382,73-78 (1996).
Kuk, JL, Ardern, CI. Age and sex differences in the clustering of metabolic syndrome factors: Association with mortality risk. Diabetes Care, 33(11):2457-2461 (2010).
Kusminski, C. M. et al. Targeting Adipose Tissue in the Treatment of Obesity-Associated Diabetes. Nature Reviews Drug Discovery 15(9):639-60 (2016).
Lacasa, D. et al. Permissive action of glucocorticoids on catecholamine-induced lipolysis: Direct "in vitro" effects on the fat cell β-adrenoreceptor-coupled-adenylate cyclase system. Biochem Biophys Res Commun. 153(2):489-497 (1988).
Lai, C.H. et al. Identification of novel human genes evolutionarily conserved in Caenorhabditis elegans by comparative proteomics. Genome Res. 10:703-713 (2000).
Langin, D. and Arner, P. Importance of TNFα and neutral lipases in human adipose tissue lipolysis. Trends Endocrinol Metab. 17(8):314-320 (2006).
Lehmann, J.M. et al. An antidiabetic thiazolidinedione is a high affinity ligand for peroxisome proliferator-activated receptor γ (PPARγ). J Biol Chem. 270(22):12953-12956 (1995).
Li, D. et al. Lipocalin-2—The myth of its expression and function. Basic Clin Pharmacol Toxicol, bcpt. 13332 (2019).
Li, P. et al. SGK1 inhibitor reverses hyperglycemia partly through decreasing glucose absorption. J Mol Endocrinol. 56(4):301-309 (2016).
Li, P. et al. SGK1 is regulated by metabolic-related factors in 3T3-L1 adipocytes and overexpressed in the adipose tissue of subjects with obesity and diabetes. Diabetes Res Clin Pract. 2013;102(1):35-42 (2013).
Lipscombe, L.L. et al. Thiazolidinediones and Cardiovascular Outcomes in Older Patients With Diabetes. JAMA, 298(22):2634-2643 (2007).
Liu, X. et al. Biological Activities of Artemisinin Derivatives Beyond Malaria. Curr Top Med Chem. 19(3):205-222 (2019).
Livingston, JN, Lockwood, DH. Effect of glucocorticoids on the glucose transport system of isolated fat cells. J Biol Chem. 250(21):8353-8360 (1975).
Lu, B.-W. et al. More than anti-malarial agents: therapeutic potential of artemisinins in neurodegeneration. Neural Regen Res. 14(9):1494 (2019).
Lundgren, M. et al. Glucocorticoids Down-Regulate Glucose Uptake Capacity and Insulin-Signaling Proteins in Omental But Not Subcutaneous Human Adipocytes. J Clin Endocrinol Metab. 89(6):2989-2997 (2004).
Macotela, Y. et al. Sex and depot differences in adipocyte insulin sensitivity and glucose metabolism. Diabetes, 58(4):803-812 (2009).
Marchesini, G. et al. Nonalcoholic Fatty Liver Disease: A Feature of the Metabolic Syndrome. Diabetes, 50:1844-1850 (2001).
Massaro, M. et al. Therapeutic potential of the dual peroxisome proliferator activated receptor (PPAR)α/γ agonist aleglitazar in attenuating TNF-α-mediated inflammation and insulin resistance in human adipocytes. Pharmacol Res. 107:125-136 (2016).
Matsui, Y. et al. Metformin Reduces Body Weight Gain and Improves Glucose Intolerance in High-Fat Diet-Fed C57BL/6J Mice. Biol Pharm Bull., 33(6):963-970 (2010).
Mauvais-Jarvis, F. et al. A model to explore the interaction between muscle insulin resistance and beta-cell dysfunction in the development of type 2 diabetes. Diabetes, 49(12):2126-2134 (2000).
McCormack, S. et al. Pharmacologic targeting of sirtuin and PPAR signaling improves longevity and mitochondrial physiology in respiratory chain complex I mutant Caenorhabditis elegans. Mitochondrion, 22:45-59 (2015).
Miles, PDG et al. TNF-alpha-induced insulin resistance in vivo and its prevention by troglitazone. Diabetes, 46(11):1678-1683 (1997).
Mirza, A.Z. et al. Role of PPAR receptor in different diseases and their ligands: Physiological importance and clinical implications. Eur J Med Chem., 502-513 (2019).
Mita, T. et al. FABP4 is secreted from adipocytes by adenyl cyclase-PKA- and guanylyl cyclase-PKG-dependent lipolytic mechanisms. Obesity, 23:359-367 (2015).
Mitchell, D. H. et al. Synchronous growth and aging of Caenorhabditis elegans in the presence of fluorodeoxyuridine. Journals Gerontol. vol. 34, Issue 1, pp. 28-36 (1979).
Moreno-Navarrete, J.M. et al. DBC1 is involved in adipocyte inflammation and is a possible marker of human adipose tissue senescence. Obesity, 23:519-522 (2015).
Moreno-Navarrete, J.M. et al. Deleted in breast cancer 1 plays a functional role in adipocyte differentiation. Am J Physiol Metab, 308:E554-E561 (2015).
Morgan, S.A. et al. 11β-HSD1 is the major regulator of the tissue-specific effects of circulating glucocorticoid excess. Proc Natl Acad Sci USA 111 (24) E2482-E2491 (2014).
Morigny, P. et al. Adipocyte Lipolysis and Insulin Resistance. Biochimie 125:259-66 (2016).
Morselli, C. et al. Chronic high fat diet consumption impairs metabolic health of male mice. Inflamm cell Signal, 1(6):1-11 (2014).
Muschiol, D. et al. Life cycle and population growth rate of Caenorhabditis elegans studied by a new method. BMC Ecol., 9:14, 13 pages (2009).
Nakashima, K. et al. Identification of a naturally occurring retinoid X receptor agonist from Brazilian green propolis. Biochim Biophys Acta—Gen Subj. 1840(10):3034-3041 (2014).
Nam, S.-Y. et al. Anti-inflammatory effects of Artemisia scoparia and its active constituent, 3,5-dicaffeoyl-epi-quinic acid against activated mast cells. Immunopharmacol Immunotoxicol. 40(1):52-58 (2018).
Nass, R. and Hamza, I. The Nematode C. elegans as an Animal Model to Explore Toxicology In Vivo: Solid and Axenic Growth Culture Conditions and Compound Exposure Parameters . In: Current Protocols in Toxicology, 1.9.1-1.9.18, 18 pages (2007).
Ng, L.-K. et al. Effects of moisture content in cigar tobacco on nicotine extraction: Similarity between Soxhlet and focused open-vessel microwave-assisted techniques. J. Chromatogr A. 1011: 213-9 (2003).
Noble, T. et al. An integrated serotonin and octopamine neuronal circuit directs the release of an endocrine signal to control C. Elegans body fat. Cell Metab. 18, 672-684 (2013).
Yang, J.S. et al. OASIS: Online application for the survival analysis of lifespan assays performed in aging research. PLoS One, vol. 6, issue 8, e23525, 11 pages (2011).
Zangger, K. Pure shift NMR. Prog. Nucl. Magn. Reson. Spectrosc., 86-87:1-20 (2015).
Zhao, P. and Stephens, J.M. STAT1, NF-κB and ERKs play a role in the induction of lipocalin-2 expression in adipocytes. Mol Metab. 2(3):161-170 (2013).
Zhao, P. et al. The induction of lipocalin-2 protein expression in vivo and in vitro. J Biol Chem. 289(9):5960-5969 (2014).

(56) References Cited

OTHER PUBLICATIONS

Zhao, Y. et al. [Advances in caffeoylquinic acid research]. Zhongguo Zhong Yao Za Zhi, 31(11):869-874 (2006).
Dalle, H. et al. Adipocyte Glucocorticoid Receptor Deficiency Promotes Adipose Tissue Expandability and Improves the Metabolic Profile Under Corticosterone Exposure. Diabetes, 68(2):305 LP—317 (2019).
Danforth, E. Failure of adipocyte differentiation causes type II diabetes mellitus? Nat Genet. 26(1):13, 1 page (2000).
Dey, M. et al. Plant extracts from central Asia showing antiinflammatory activities in gene expression assays. Phytother. Res. 22, 929-934 (2008).
Dietz, B. M. et al. DESIGNER Extracts as Tools to Balance Estrogenic and Chemopreventive Activities of Botanicals for Women's Health. J. Nat. Prod. 80, 2284-2294 (2017).
Divertie, G.D. et al. Stimulation of Lipolysis in Humans by Physiological Hypercortisolemia. Diabetes, 40(10):1228 LP—1232 (1991).
Diwanay, S. et al. Immunoprotection by botanical drugs in cancer chemotherapy. Journal of Ethnopharmacology, vol. 90(1), 49-55 (2004).
Doyle, S.L. and O'Neill, LAJ. Toll-like receptors: From the discovery of NFκB to new insights into transcriptional regulations in innate immunity. Biochem Pharmacol, 72:1102-1113 (2006).
Dugave, C. and Demange, L. Cis-Trans Isomerization of Organic Molecules and Biomolecules: Implications and Applications. Chem. Rev., 103, 2475-2532 (2003).
Dunn, F. L. et al. Selective Modulation of PPARγ Activity Can Lower Plasma Glucose without Typical Thiazolidinedione Side-Effects in Patients with Type 2 Diabetes. Journal of Diabetes and Its Complications, 25(3), 151-158 (2011).
Engin, A. The Pathogenesis of Obesity-Associated Adipose Tissue Inflammation. in Advances in experimental medicine and biology. vol. 960, pp. 221-245 (2017).
EPA. ToxCast database, Exploring ToxCasr Data, webpage https://www.epa.gov/comptox-tools/exploring-toxcast-data, last accessed Apr. 16, 2024, 7 pages.
Ertunc, M.E. et al. Secretion of fatty acid binding protein aP2 from adipocytes through a nonclassical pathway in response to adipocyte lipase activity. J Lipid Res, 56:423-434 (2015).
Escande, C. et al. Deleted in breast cancer 1 limits adipose tissue fat accumulation and plays a key role in the development of metabolic syndrome phenotype. Diabetes, 64:12-22 (2015).
Falvo, J.V. et al. Transcriptional control of the TNF Gene. Curr Dir Autoimmun, 11:27-60 (2010).
Fardet, L. et al. Prevalence of long-term oral glucocorticoid prescriptions in the UK over the past 20 years. Rheumatology (Oxford), 50(11):1982-1990 (2011).
Feldman, P. M. et al. PPAR Modulators and PPAR Pan Agonists for Metabolic Diseases: The Next Generation of Drugs Targeting Peroxisome Proliferator-Activated Receptors? Current Topics in Medicinal Chemistry, 8(9), 728-749 (2008).
Ferguson, M. et al. A method for ranking compounds based on their relative toxicity using neural networking, C. elegans, axenic liquid culture, and the COPAS parameters TOF and EXT. Open Access Bioinformatics, 2: 139-144 (2010).
Floyd, ZE, Stephens, JM. Controlling a master switch of adipocyte development and insulin sensitivity: Covalent modifications of PPARγ. Biochim Biophys Acta—Mol Basis Dis. 1822(7):1090-1095 (2012).
Frühbeck, G et al. Regulation of Adipocyte Lipolysis. Nutrition Research Reviews 27(01):63-93 (2014).
Gaggini, M. et al. Non-alcoholic fatty liver disease (NAFLD) and its connection with insulin resistance, dyslipidemia, atherosclerosis and coronary heart disease. Nutrients, 5(5):1544-1560 (2013).
Gathercole, L.L. et al. Glucocorticoid Modulation of Insulin Signaling in Human Subcutaneous Adipose Tissue. J Clin Endocrinol Metab. 92(11):4332-4339 (2007).
Geng, C.-A. et al. Three new anti-HBV active constituents from the traditional Chinese herb of Yin-Chen (*Artemisia scoparia*). J Ethnopharmacol. 2015;176:109-117 (2015).
Gilani, A.H. and Janbaz, K.Z. Hepatoprotective effects of artemisia scoparia against carbon tetrachloride: an environmental contaminant. J Pak Med Assoc. 44(3):65-68 (1994).
Goudeau, J. et al. Fatty acid desaturation links germ cell loss to longevity through NHR-80/HNF4 in C. elegans. PLoS Biol 9(3): e1000599, 16 pages (2011).
Gravato-Nobre, m. J. et al. Multiple genes affect sensitivity of Caenorhabditis elegans to the bacterial pathogen Microbacterium nematophilum. Genetics, 171(3): 1033-1045 (2005).
Gueugneau, M. et al. Increased Serpina3n release into circulation during glucocorticoid-mediated muscle atrophy. J Cachexia Sarcopenia Muscle, 9(5):929-946 (2018).
Gustafson, B. et al. Insulin Resistance and Impaired Adipogenesis. Trends in Endocrinology & Metabolism 26(4):193-200 (2015).
Habib, M. and Waheed, I. Evaluation of anti-nociceptive, anti-inflammatory and antipyretic activities of Artemisia scoparia hydromethanolic extract. J Ethnopharmacol, 145(1):18-24 (2013).
Hammarstedt, A. et al. The Effect of PPARγ Ligands on the Adipose Tissue in Insulin Resistance. Prostaglandins, Leukotrienes and Essential Fatty Acids 73(1):65-75 (2005).
Harvey, I. et al. Glucocorticoid-Induced Metabolic Disturbances are Exacerbated in Obese Male Mice. Endocrinology, 159(6):2275-2287 (2018).
Hauser, S. et al. Degradation of the peroxisome proliferator-activated receptor γ is linked to ligand-dependent activation. J Biol Chem. 275(24):18527-18533 (2000).
Heestand, B.N. et al. Dietary Restriction Induced Longevity is Mediated by Nuclear Receptor NHR-62 in Caenorhabditis elegans. PLoS Genet 9(7): e1003651, 15 pages (2015).
Heydemann, A. An overview of murine high fat diet as a model for type 2 diabetes mellitus. J Diabetes Res., 2016:1-14 (2016).
Higgins, L. S. et al. Selective Peroxisome Proliferator-Activated Receptor γ (PPARγ) Modulation as a Strategy for Safer Therapeutic PPARγ Activation. in American Journal of Clinical Nutrition, 91(1), 267S-270S (2010).
Hilmer, S. N. ADME-tox issues for the elderly. Expert Opin Drug Metab Toxicol. (2008).
Hochberg, I. et al. Gene expression changes in subcutaneous adipose tissue due to Cushing's disease. J Mol Endocrinol., 55(2):81-94 (2015).
Hohmeier, H.E. et al. Isolation of INS-1-derived cell lines with robust ATP-sensitive K+ channel-dependent and -independent glucose-stimulated insulin secretion. Diabetes, 49:424-430 (2000).
Holzenberger, M. et al. IGF-1 receptor regulates lifespan and resistance to oxidative stress in mice. Nature 421, 182-187 (2003).
Hong, J.-H. et al. Artemisia capillaris Inhibits Lipid Accumulation in 3T3-L1 Adipocytes and Obesity in C57BL/6J Mice Fed a High Fat Diet. J Med Food. 12(4):736-745 (2009).
Houtkooper, R.H. et al. Metabolic Networks of Longevity. Cell, 142, 6 pages (2010).
Huan, Y. et al. A novel specific peroxisome proliferator-activated receptor γ (PPARγ) modulator YR4-42 ameliorates hyperglycemia and dyslipidemia and hepatic steatosis in diet-induced obese mice. Diabetes, Obes Metab. 21(11):2553-2563 (2019).
Huneck, S. et al. Seco-guaianolides and other constituents from Artemisia species. Phytochemistry, 25, 883-889 (1986).
Hunt, P.R. et al. Toxicity ranking of heavy metals with screening method using adult Caenorhabditis elegans and propidium iodide replicates toxicity ranking in rat. Food Chem Toxicol. 50: 3280-3290 (2012).
Hunt, P.R. The C. elegans model in toxicity testing. J. Appl. Toxicol., 37:50-59 (2017).
Hussain, W. et al. Quantitative ethnobotanical appraisal of medicinal plants used by inhabitants of lower Kurram, Kurram agency, Pakistan. Avicenna J phytomedicine, 8(4):313-329 (2018).
Hussain, W. et al. Quantitative study of medicinal plants used by the communities residing in Koh-e-Safaid Range, northern Pakistani-Afghan borders. J Ethnobiol Ethnomed. 2018;14(1):30 (2018).
Iio, A. et al. Ethanolic extracts of Brazilian red propolis promote adipocyte differentiation through PPARγ activation. Phytomedicine, 17(12):974-979 (2010).
International Search Report for PCT/US2021/017055 mailed Jul. 27, 2021, 6 pages.

(56) References Cited

OTHER PUBLICATIONS

Itani, O.A. et al. Glucocorticoids stimulate human sgk1 gene expression by activation of a GRE in its 5'-flanking region. Am J Physiol Endocrinol Metab. 283(5):E971-9 (2002).
Jakupovic, J. et al. Sesquiterpene lactones from Artemisia ludoviciana. Phytochemistry, 30(5), 1573-1577 (1991).
Nolan, J.J. et al. Improvement in glucose tolerance and insulin resistance in obese subjects treated with troglitazone. N Engl J Med. 331(18):1188-1193 (1994).
Obanda, D.N. et al. Bioactives of *Artemisia dracunculus* L. enhance insulin sensitivity by modulation of ceramide metabolism in rat skeletal muscle cells. Nutrition, 30(7-8 Suppl.), S59-S66 (2014).
Obanda, D.N. et al. Bioactives of *Artemisia dracunculus* L. mitigate the role of ceramides in attenuating insulin signaling in rat skeletal muscle cells. Diabetes. 2012;61(3):597-605 (2012).
Oeckinghaus A, Ghosh S. The NF-kappaB family of transcription factors and its regulation. Cold Spring Harb Perspect Biol, 1:a000034, 14 pages (2009).
Ohmura, E. et al. Association of Free Fatty Acids (FFA) and Tumor Necrosis Factor-α (TNF-α) and Insulin-Resistant Metabolic Disorder. Hormone and Metabolic Research 39(3):212-17 (2007).
Okuno, I. et al. Studies on Choleretic Consituents in Artemisia capillaris THUNB. Chem. Pharm. Bull., 36, 769-775 (1988).
Olefsky, J. M. and Glass, Ch. K. Macrophages, Inflammation, and Insulin Resistance. Annual Review of Physiology 72(1):219-46 (2010).
Olefsky, J.M. Treatment of insulin resistance with peroxisome proliferator-activated receptor γ agonists. J Clin Invest. 106(4):467-472 (2000).
Overman, R.A. et al. Prevalence of oral glucocorticoid usage in the United States: A general population perspective. Arthritis Care Res., 65(2):294-298 (2013). Free access Prevalence of oral glucocorticoid usage in the United States: A general population perspective (wiley.com).
Page, A, Johnstone, IL. The cuticle. WormBook, downloaded from NCBI Bookshelf, a service of the National Library of Medicine, National Institutes of Health, 19 pages (2007).
Park, S. et al. Scoparone interferes with STAT3-induced proliferation of vascular smooth muscle cells. Exp Mol Med. 47, e145, 8 pages (2015).
Patel, R. et al. Minireview: New molecular mediators of glucocorticoid receptor activity in metabolic tissues. Mol Endocrinol. 28(7):999-1011 (2014).
Pathare, P. P. et al. Coordinate regulation of lipid metabolism by novel nuclear receptor partnerships. PLoS Genet. 8(4): e1002645, 18 pages (2012).
Penfornis, P. and Marette, A. Inducible nitric oxide synthase modulates lipolysis in adipocytes. J Lipid Res, 46:135-42 (2005).
Peraldi, P. et al. Thiazolidinediones block tumor necrosis factor-α-induced inhibition of insulin signaling. J Clin Invest. 100(7):1863-1869 (1997).
Perl, A-KT et al. Early restriction of peripheral and proximal cell lineages during formation of the lung. Proc Natl Acad Sci USA. 99(16):10482-10487 (2002).
Perry, R. J. et al. Mechanism for leptin 's acute insulin-independent effect to reverse diabetic ketoacidosis. J Clin Invest. 127(2):657-669 (2017).
Pesticide database, http://pesticideinfo.org/—para 00204.
Phansalkar, R.S. et al. Evolution of Quantitative Measures in NMR: Quantum Mechanical qHNMR Advances Chemical Standardization of a Red Clover (Trifolium pratense) Extract. J. Nat. Prod., 80, 3, 634-647 (2017).
Promyo, K. et al. Artemisia scoparia attenuates amyloid β accumulation and tau hyperphosphorylation in spontaneously hypertensive rats. Food Sci Biotechnol., 26(3):775-782 (2017).
Przybytec, J. T. High Purity Solvent Guide. Burdick and Jackson Laboratories, Inc. (1980).
Puangpraphant, S. et al. Dicaffeoylquinic acids in Yerba mate (Ilex paraguariensis St. Hilaire) inhibit NF-κB nucleus translocation in macrophages and induce apoptosis by activating caspases-8 and -3 in human colon cancer cells. Mol Nutr Food Res. 55(10):1509-1522 (2011).
Qi, W. et al. The ω-3 fatty acid α-linolenic acid extends Caenorhabditis elegans lifespan via NHR-49/PPARα and oxidation to oxylipins. Aging Cell, 16: 1125-1135 (2017).
Ranasinghe, P. et al. Prevalence and Trends of Metabolic Syndrome among Adults in the Asia-Pacific Region: A Systematic Review. BMC Public Health 17(1):1-9 (2017).
Remington's Pharmaceutical Sciences. 21st edition, Lippincott Williams and Wilkins (2005).
Ribnicky, D.M. et al. Antihyperglycemic activity of TarralinTM, an ethanolic extract of *Artemisia dracunculus* L. Phytomedicine. 13(8):550-557 (2006).
Ribnicky, D.M. et al. *Artemisia dracunculus* L. polyphenols complexed to soy protein show enhanced bioavailability and hypoglycemic activity in C57BL/6 mice. Nutrition, 30(7-8 Suppl.), S4-S10 (2014).
Richard A.J. et al. Pyruvate dehydrogenase complex (PDC) subunits moonlight as interaction partners of phosphorylated STAT5 in adipocytes and adipose tissue. J Biol Chem., 292(48):19733-19742 (2017).
Richard, A. J. Artemisia Scoparia Enhances Adipocyte Development and Endocrine Function in Vitro and Enhances Insulin Action in Vivo. PloS One, 9(6):1-8 (2014).
Richard, A. J. et al. Artemisia Extracts Activate PPARγ, Promote Adipogenesis, and Enhance Insulin Sensitivity in Adipose Tissue of Obese Mice. Nutrition 30(7-8 SUPPL.):S31-6 (2014).
Robinson-Rechavi, M. et al. Explosive lineage-specific expansion of the orphan nuclear receptor HNF4 in nematodes. J Mol Evol, 60:577-586 (2005).
Rosen, E.D., Spiegelman, B.M. What we talk about when we talk about fat. Cell, 156(1-2):20-44 (2014).
Roy, S. et al. Combination of dipeptidylpeptidase IV inhibitor and low dose thiazolidinedione: Preclinical efficacy and safety in db/db mice. Life Sci. 81(1):72-79 (2007).
Ruan, H. et al. Troglitazone antagonizes tumor necrosis factor-α-induced reprogramming of adipocyte gene expression by inhibiting the transcriptional regulatory functions of NF-κB. J Biol Chem. 278(30):28181-28192 (2003).
Ryu, K.J. et al. Therapeutic effects of Artemisia scoparia Waldst. et Kitaib in a murine model of atopic dermatitis. Clin Exp Dermatol. 2018;43(7):798-805 (2018).
Sajid, M. et al. Evaluation of Artemisia scoparia for hemostasis promotion activity. Pak J Pharm Sci. 30(5):1709-1713 (2017).
Sajid, M. et al. Proficiencies of Artemisia scoparia against CCI4 induced DNA damages and renal toxicity in rat. BMC Complement Altern Med. 16(1):149 (2016).
Saklayen, M. G. The Global Epidemic of the Metabolic Syndrome. Current Hypertension Reports 20(2):12 (2018).
Sakoda, H. et al. Dexamethasone-induced insulin resistance in 3T3-L1 adipocytes is due to inhibition of glucose transport rather than insulin signal transduction. Diabetes, 49(10):1700-1708 (2000).
Sanchez, A. M. et al. On the Mechanism of the Acid/Base-Catalyzed Thermal Cis-Trans Isomerization of Methyl Orange. J. Org. Chem., 64, 1604-1609 (1999).
Schernthaner-Reiter, M. et al. Strong association of serum- and glucocorticoid-regulated kinase 1 with peripheral and adipose tissue inflammation in obesity. Int J Obes. 39:1143-1150 (2015).
Scherp, P. et al. Proteomic analysis reveals cellular pathways regulating carbohydrate metabolism that are modulated in primary human skeletal muscle culture due to treatment with bioactives from *Artemisia dracunculus* L. J Proteomics, 75(11):3199-3210 (2012).
Sergi, D. et al. SerpinA3N is a novel hypothalamic gene upregulated by a highfat diet and leptin in mice. Genes Nutr. 2018;13:28 (2018).
Serr, J. et al. Acute Up-Regulation of Adipose Triglyceride Lipase and Release of Non-Esterified Fatty Acids by Dexamethasone in Chicken Adipose Tissue. Lipids. 46(9):813-820 (2011).
Sharma, V. M. and Puri, V. Mechanism of TNF-α-Induced Lipolysis in Human Adipocytes Uncovered. Obesity 24(5):990, 1 page (2016).
Shen, Y. et al. Adipocyte glucocorticoid receptor is important in lipolysis and insulin resistance due to exogenous steroids, but not insulin resistance caused by high fat feeding. Mol Metab., 6(10):1150-1160 (2017).

(56) References Cited

OTHER PUBLICATIONS

Sierra-Ramos, C. et al. SGK1 activation exacerbates diet-induced obesity, metabolic syndrome and hypertension. J Endocrinol. 244(1):149-162 (2019).
Simmler, C. et al. Isolation and structural characterization of dihydrobenzofuran congeners of licochalcone A. Fitoterapia, 121, 6-15 (2017).
Singh A, Sarin R. Artemisia scoparia—A new source of artemisinin. Bangladesh J Pharmacol. 5(1):17-20 (2010).
Singh, H.P. et al. In vitro screening of essential oil from young and mature leaves of Artemisia scoparia compared to its major constituents for free radical scavenging activity. Food Chem Toxicol. 48(4):1040-1044 (2010).
Sluder, A.E. et al. The nuclear receptor superfamily has undergone extensive proliferation and diversification in nematodes. Genome Res., 9:103-120 (1999).
Smith, U. et al. Adipose tissue regulates insulin sensitivity: role of adipogenesis, de novo lipogenesis and novel lipids. J Intern Med., 280(5):465-475 (2016).
Soccio, R. E. et al. Thiazolidinediones and the Promise of Insulin Sensitization in Type 2 Diabetes. Cell Metabolism 20(4):573-91 (2014).
Soriano, P. Generalized IacZ expression with the ROSA26 Cre reporter strain. Nat Genet. 21(1):70-71 (1999).
Stephens, J. M. and Pekala, P H. Transcriptional Repression of the C/EBP-Alpha and GLUT4 Genes in 3T3-L1 Adipocytes by Tumor Necrosis Factor-Alpha. Regulations is Coordinate and Independent of Protein Synthesis. The Journal of Biological Chemistry 267(19):13580-84 (1992).
Stephens, J. M. et al. Tumor Necrosis Factor-Alpha-Induced Insulin Resistance in 3T3-L1 Adipocytes is Accompanied by a Loss of Insulin Receptor Substrate-1 and GLUT4 Expression without a Loss of Insulin Receptor-Mediated Signal Transduction. The Journal of Biological Chemistry 272(2):971-76 (1997).
Stiernagle, T. Maintenance of C. elegans. WormBook, downloaded from NCBI Bookshelf. A service of the National Library of Medicine, National Institutes of Health, 12 pages (2006).
Strawford, A. et al. Adipose tissue triglyceride turnover, de novo lipogenesis, and cell proliferation in humans measured with 2H2O. Am J Physiol Metab. 286(4):E577-E588 (2004).
Strohmayer, E. A. et al. Glucocorticoids and cardiovascular risk factors. Endocrinol Metab Clin North Am, 40(2):409-17 (2011).
Sun, K. et al. Dichotomous effects of VEGF-A on adipose tissue dysfunction. Proc Natl Acad Sci. 109(15):5874-5879 (2012).
Swanson, R.L. et al. Induction of Settlement of Larvae of the Sea Urchin Holopneustes purpurascens by Histamine From a Host Alga. Biol. Bull. 206: 161-72 (2004).
Takahashi, E. et al. Proteomic analysis of serum biomarkers for prediabetes using the Long-Evans Agouti rat, a spontaneous animal model of type 2 diabetes mellitus. J Diabetes Investig. 8(5):661-671 (2017).
Tani, H. et al. Isolation, Identification, and Synthesis of a New Prenylated Cinnamic Acid Derivative from Brazilian Green Propolis and Simultaneous Quantification of Bioactive Components by LC-MS/MS. J Agric Food Chem., 67(44):12303-12312 (2019).
Tchoukalova, Y. D. et al. In vivo adipogenesis in rats measured by cell kinetics in adipocytes and plastic-adherent stroma-vascular cells in response to high-fat diet and thiazolidinedione. Diabetes, 61(1):137-144 (2012).
Thomas, I. et al. Metformin; a Review of Its History and Future: From Lilac to Longevity. Pediatric Diabetes 18(1):10-16 (2017).
Tibetan Medicinal Plants. Edited by C. Kletter & M. Kriechbaum. Stuttgart: Medpharm Scientific Publishers (2001).
Tontonoz, P. et al. mPPAR gamma 2: tissue-specific regulator of an adipocyte enhancer. Genes Dev. 8(10):1224-1234 (1994).
Tralau, T. et al. Wind of change challenges toxicological regulators. Environ Health Perspect, 120:1489-1494 (2012).
Tu, Y. Artemisinin—A Gift from Traditional Chinese Medicine to the World (Nobel Lecture). Angew Chemie—Int Ed. 55(35):10210-10226 (2016).
Van Gilst, M.R. et al. Nuclear hormone receptor NHR-49 controls fat consumption and fatty acid composition in C. elegans. PLoS Biol. I 3(2): e53, 12 pages (2005).
Vandanmagsar, B. et al. *Artemisia dracunculus* L. extract ameliorates insulin sensitivity by attenuating inflammatory signalling in human skeletal muscle culture. Diabetes, Obes Metab., 16(8):728-738 (2014).
Vaure, C. and Liu, Y. A comparative review of toll-like receptor 4 expression and functionality in different animal species. Front Immunol, 5:316 (2014).
Vegiopoulos, A. et al. Glucocorticoids, metabolism and metabolic diseases. Mol Cell Endocrinol. 275(1-2):43-61 (2007).
Viatour, P. et al. Phosphorylation of NF-κB and IκB proteins: Implications in cancer and inflammation. Trends Biochem Sci. 30(1):43-52 (2005).
Vidal-Puig, A. Adipose Tissue Expandability, Lipotoxicity and the Metabolic Syndrome. Endocrinol Nutr 60(Supl. 1):39-43 (2013).
Wan, P. et al. Anti-inflammatory effects of dicaffeoylquinic acids from Ilex kudingcha on lipopolysaccharide-treated RAW264.7 macrophages and potential mechanisms. Food Chem Toxicol., 126:332-342 (2019).
Wang, K.S. et al. Artemisinin inhibits inflammatory response via regulating NF-κB and MAPK signaling pathways. Immunopharmacol Immunotoxicol. 39(1):28-36 (2017).
Wang, L. et al. Natural product agonists of peroxisome proliferator-activated receptor gamma (PPARγ): a review. Biochem Pharmacol., 92(1):73-89 (2014).
Wang, M.C. et al. RNAi screening for fat regulatory genes with SRS microscopy. Nat Methods 8, 135-138 (2011).
Wang, Q.A. et al. Peroxisome Proliferator-Activated Receptor γ and Its Role in Adipocyte Homeostasis and Thiazolidinedione-Mediated Insulin Sensitization. Mol Cell Biol. 38(10): e00677-17, 15 pages (2018).
Wang, Q.A. et al. The AdipoChaser mouse. Adipocyte, 3(2):146-150 (2014).
Wang, Q.A. et al. Tracking adipogenesis during white adipose tissue development, expansion and regeneration. Nat Med, 19(10): 1338-44 (2013).
Wang, X. et al. Anti-inflammatory effects and mechanism of the total flavonoids from Artemisia scoparia Waldst. et kit. in vitro and in vivo. Biomed Pharmacother., 104:390-403 (2018).
Wang, Y. et al. Lipocalin-2 is an inflammatory marker closely associated with obesity, insulin resistance, and hyperglycemia in humans. Clin Chem. 53(1):34-41 (2007).
Wang, Z.O. et al. Artemisia scoparia extract attenuates non-alcoholic fatty liver disease in diet-induced obesity mice by enhancing hepatic insulin and AMPK signaling independently of FGF21 pathway. Metabolism, 62:1239-1249 (2013).
Wang, Zh.O. et al. Bioactives of *Artemisia dracunculus* L enhance cellular insulin signaling in primary human skeletal muscle culture. Metabolism, 57(SUPPL. 1), S58-S64 (2008).
Weinoehrl, S. et al. Comparative Evaluation of Two Different *Artemisia dracunculus* L. Cultivars for Blood Sugar Lowering Effects in Rats. Phyther Res. 26(4):625-629 (2012).
Weisberg, S.P. et al. Obesity is associated with macrophage accumulation in adipose tissue. J Clin Invest, 112:1796-808 (2003).
White, U.A. et al. Differences in In Vivo Cellular Kinetics in Abdominal and Femoral Subcutaneous Adipose Tissue in Women. Diabetes. 2016;65(6):1642-1647 (2016).
Wicks, Sh. et al. Artemisia Supplementation Differentially Affects the Mucosal and Luminal Ileal Microbiota of Diet-Induced Obese Mice. Nutrition 30(7-8):S26-30 (2014).
Wijayatunga, N. N. et al. An integrative transcriptomic approach to identify depot differences in genes and microRNAs in adipose tissues from high fat fed mice. Oncotarget. 9(10):9246-9261 (2018).
Williams, P. L. and Dusenbery, D.B. Using the nematode caenorhabditis elegans to predict mammalian acute lethality to metallic salts. Toxicol Ind Health, vol. 4, issue 4 (1998).
Witters, L. A. The Blooming of the French Lilac. The Journal of Clinical Investigation 108(8):1105-7 (2001).
Written Opinion for PCT/US2021/017055 mailed Jul. 27, 2021, 9 pages.

(56) References Cited

OTHER PUBLICATIONS

Xiong H, Pears C, Woollard A. An enhanced C. elegans based platform for toxicity assessment. Sci Rep., 7: 9839, 11 pages (2017).
Xu, A. et al. Adipocyte fatty acid-binding protein is a plasma biomarker closely associated with obesity and metabolic syndrome. Clin Chem, 52:405-413 (2006).
Xu, C. et al. Direct effect of glucocorticoids on lipolysis in adipocytes. Mol Endocrinol. 23(8), 21 pages (2009).
Yahagi, T. et al. Inhibitory effect of chemical constituents from Artemisia scoparia Waldst. et Kit. on triglyceride accumulation in 3T3-L1 cells and nitric oxide production in RAW 264.7 cells. J Nat Med. 68(2):414-420 (2014).
Yamamoto, K. et al. Development of Dihydrodibenzooxepine Peroxisome Proliferator-Activated Receptor (PPAR) Gamma Ligands of a Novel Binding Mode as Anticancer Agents: Effective Mimicry of Chiral Structures by Olefinic E / Z-Isomers. J Med Chem., 61(22):10067-10083 (2018).
Yan, Q.-W. et al. The adipokine lipocalin 2 is regulated by obesity and promotes insulin resistance. Diabetes, 56(10):2533-2540 (2007).

* cited by examiner

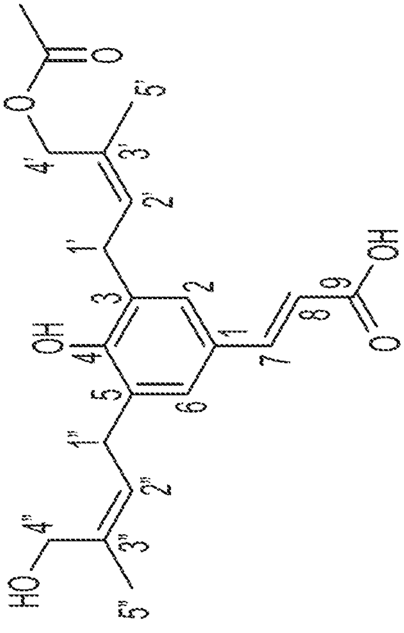
Chemical Formula: $C_{21}H_{26}O_6$
Exact Mass: 374.1729
Molecular Weight: 374.4330
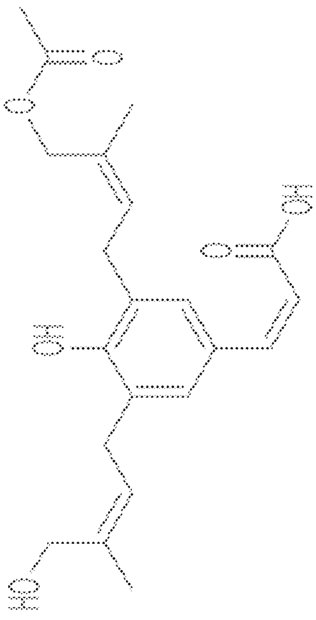
Chemical Formula: $C_{21}H_{26}O_6$
Exact Mass: 374.1729
Molecular Weight: 374.4330
FIG. 1

| | 7, 8-*trans-p*-coumaric acid | | | | 7, 8-*cis-p*-coumaric acid | | | |
|---|---|---|---|---|---|---|---|---|
| | 1 | 2 | 3 | 4 | 5 | 6 | 7 | 8 |
| $R_1$ | OAc | OAc | H | H | OAc | OAc | H | H |
| $R_2$ | H | H | OAc | OAc | H | H | OAc | OAc |
| $R_3$ | H | OH | H | OH | H | OH | H | OH |
| $R_4$ | OH | H | OH | H | OH | H | OH | H |
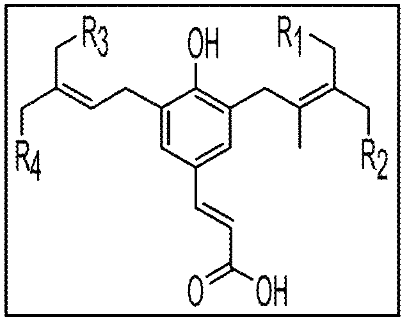
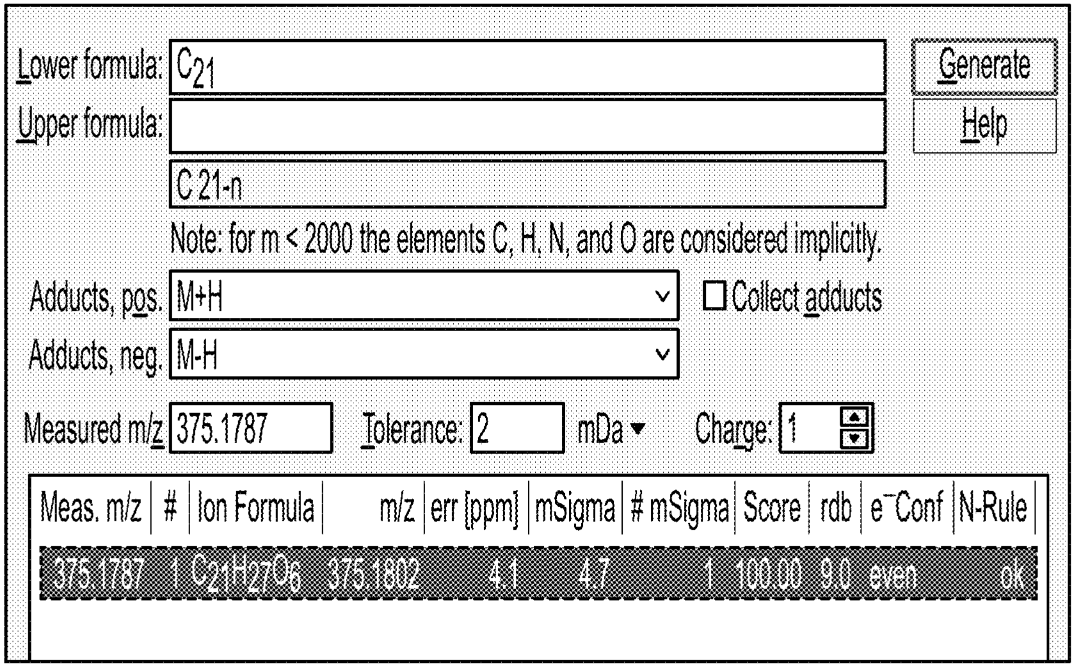
FIG. 1 CON'T Chemical Formula: $C_{19}H_{24}O_4$ Exact Mass: 316.1675

Molecular Weight: 316.3970

**3-[4'-Hydroxyphenyl]-5-prenyl-*p*-coumaric acid**

Capillartemisin A

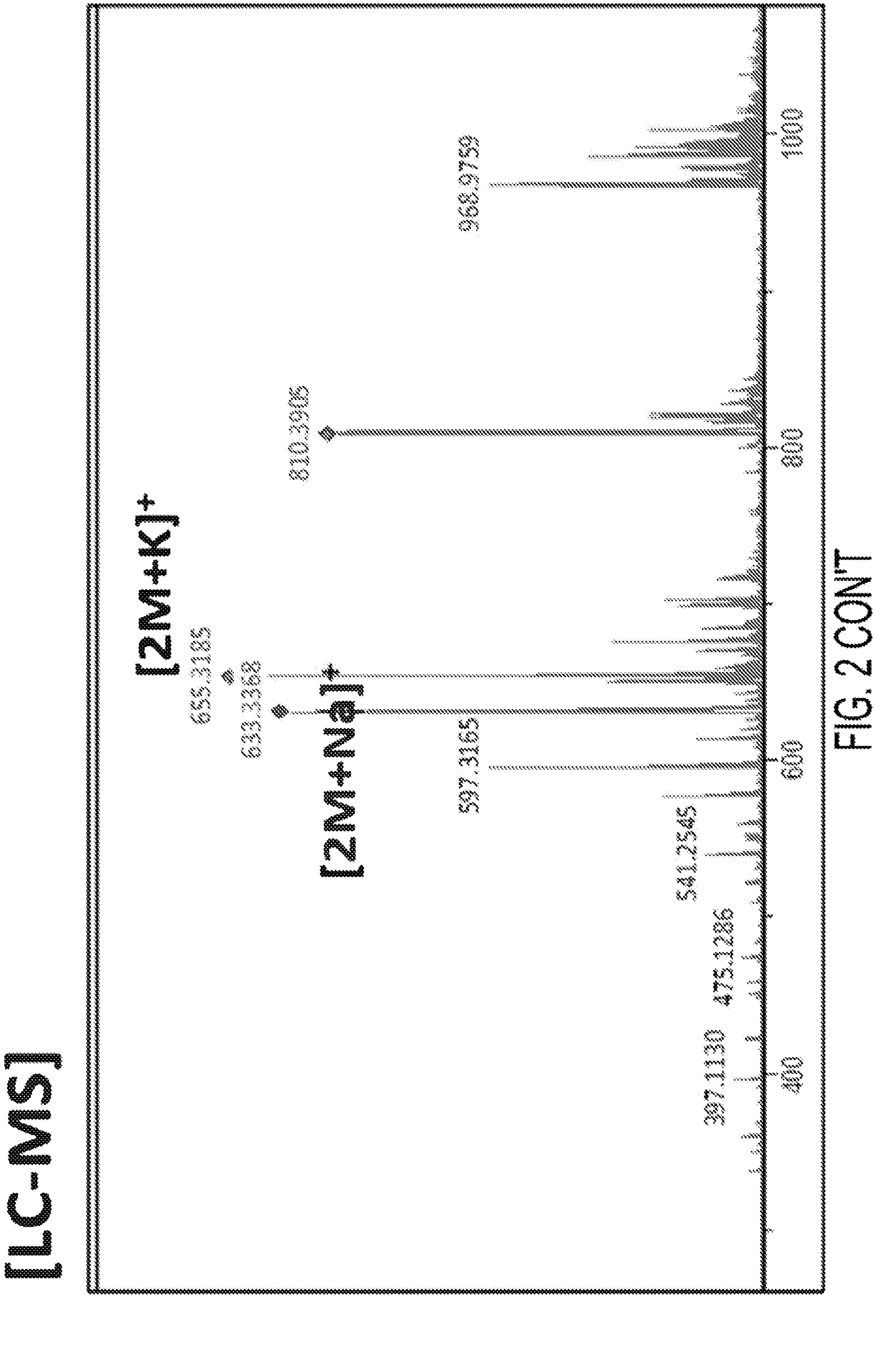
FIG. 2 CON'T

Chemical Formula: $C_{19}H_{24}O_4$

Exact Mass: 316.1675

Molecular Weight: 316.3970

3-[5'-Hydroxyphenyl]-5-prenyl-p-coumaric acid

Capillartemisin B

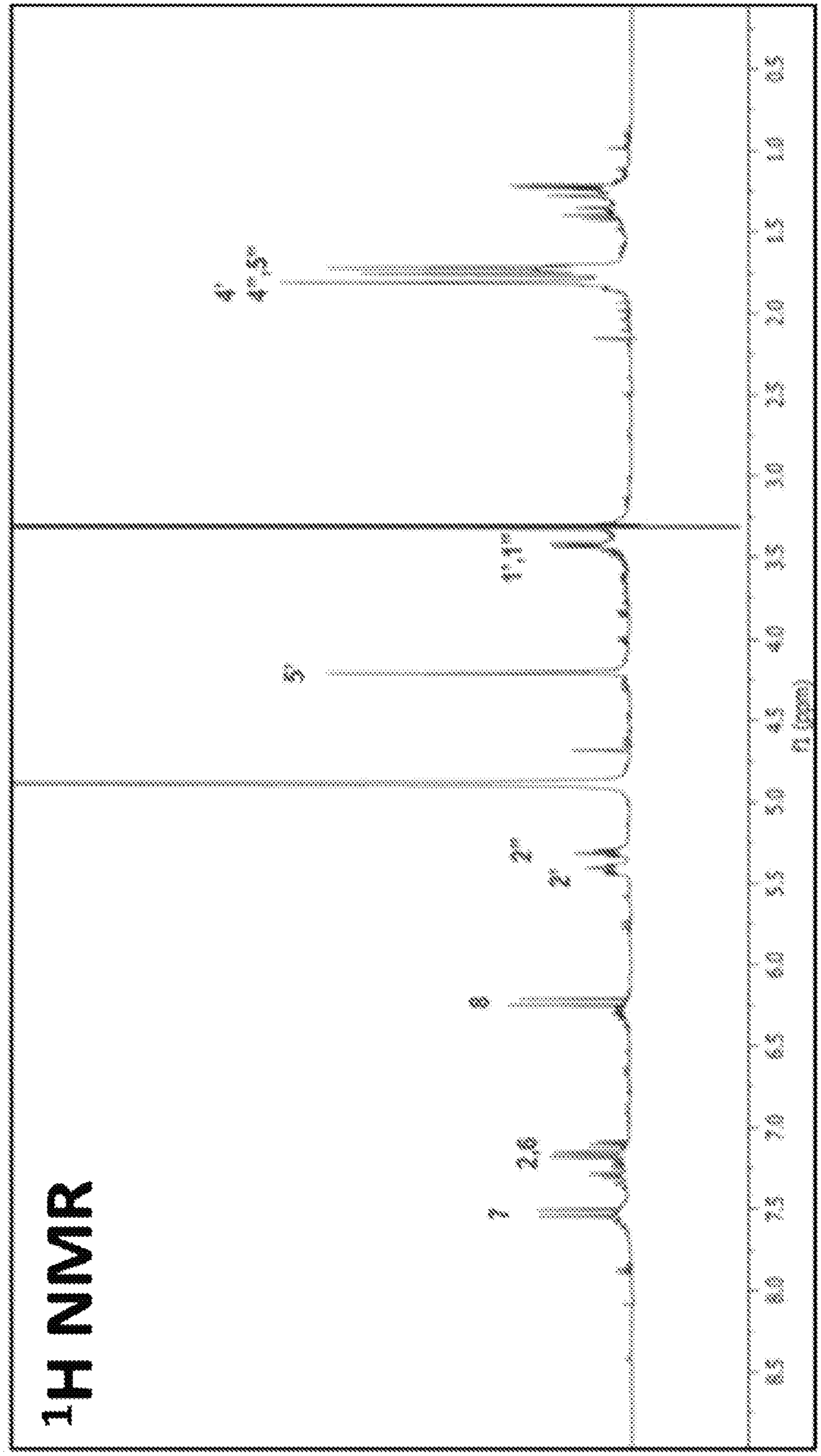
FIG. 3 CON'T

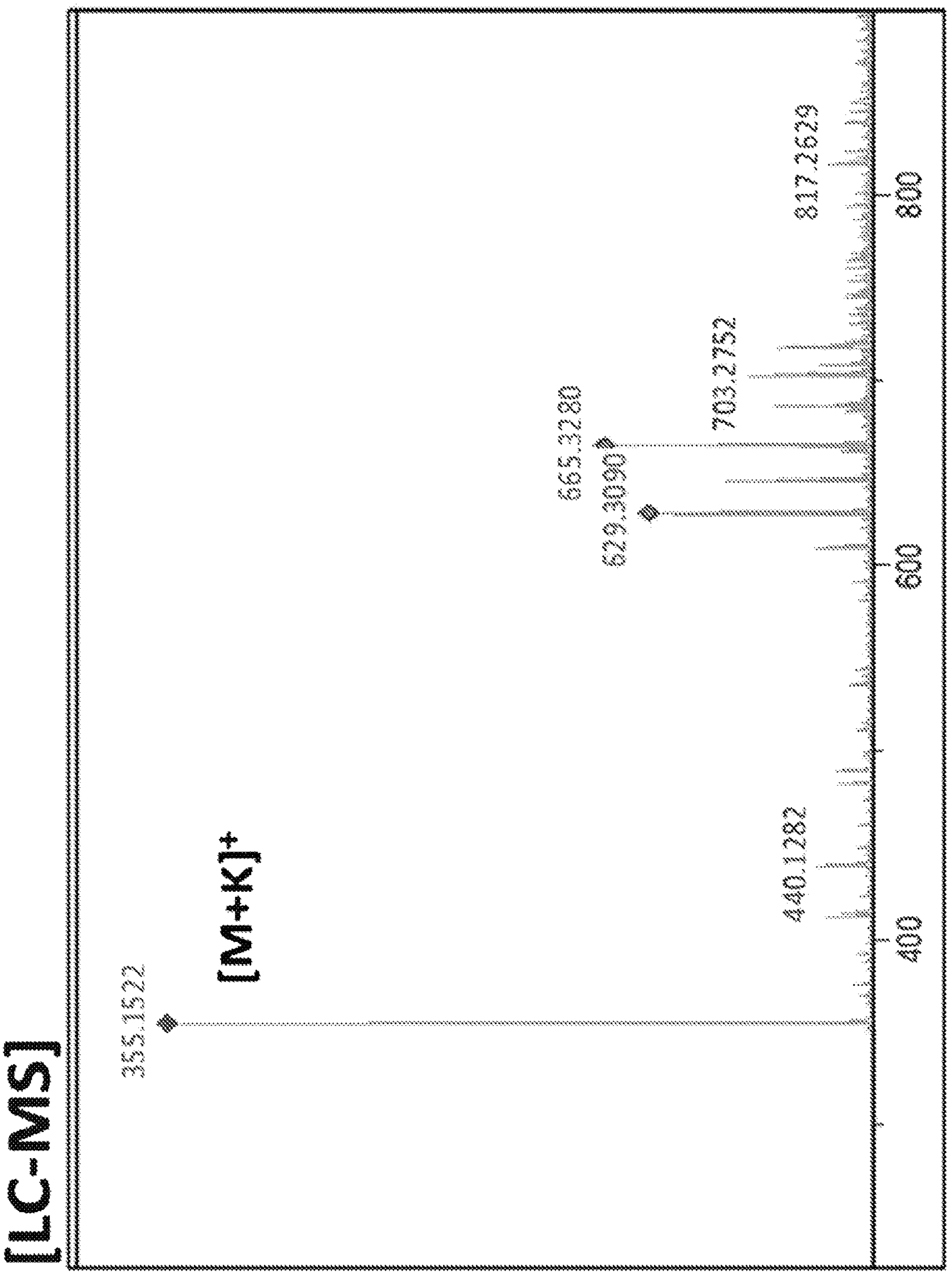
FIG. 3 CONT'

Scoprenyl
3-(*trans*-ωOAcetyl-prenyl), 4-OH, 5-(*trans*-ωOH-prenyl) *trans*-cinnamic acid
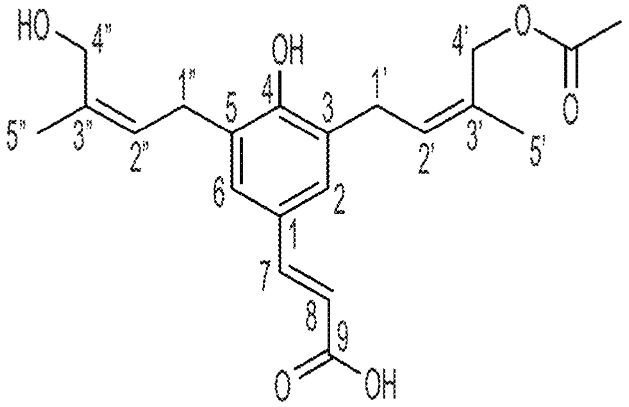
Chemical Formula: $C_{21}H_{26}O_6$
Exact Mass: 374.1729
Molecular Weight: 374.4330
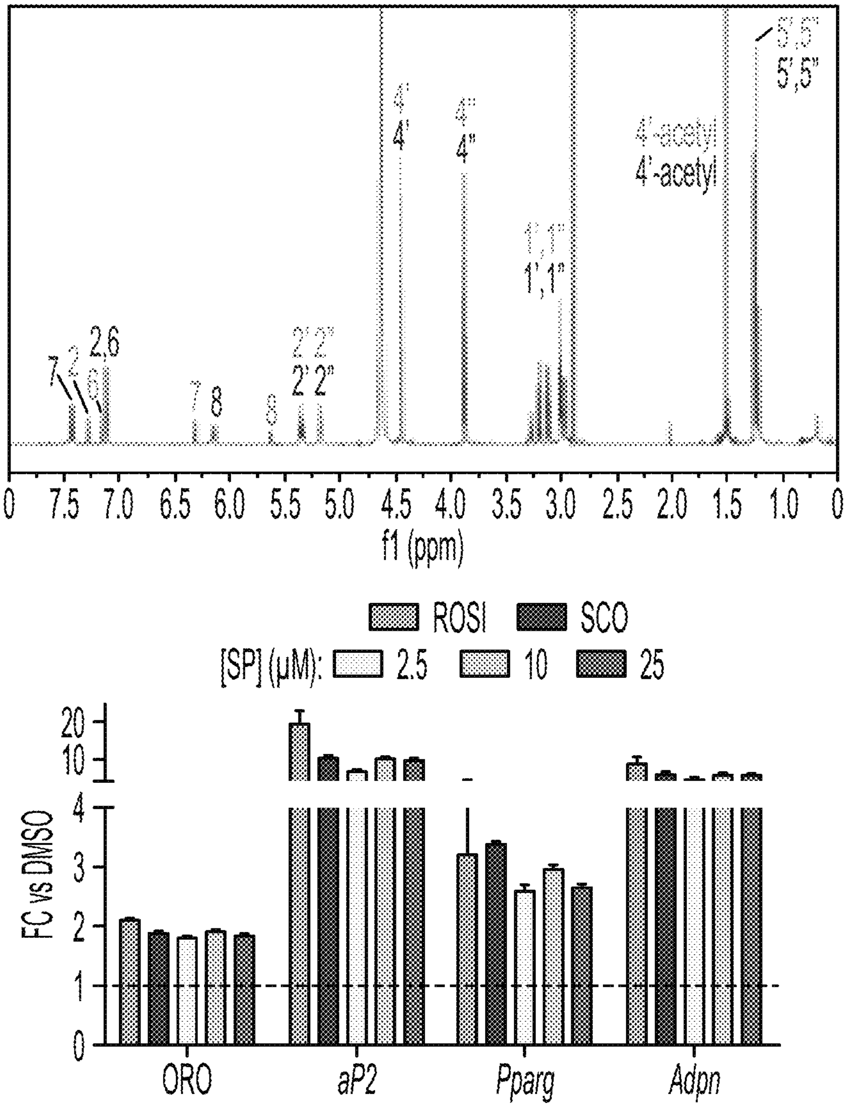
FIG. 5

Capillartemisin A
**3-[4'-Hydroxyphenyl]-5-prenyl-*p*-coumaric acid**
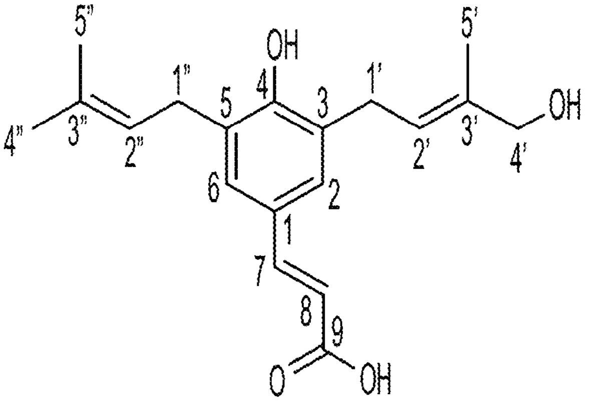
Chemical Formula: $C_{19}H_{24}O_4$
Exact Mass: 316.1675
Molecular Weight: 316.3970
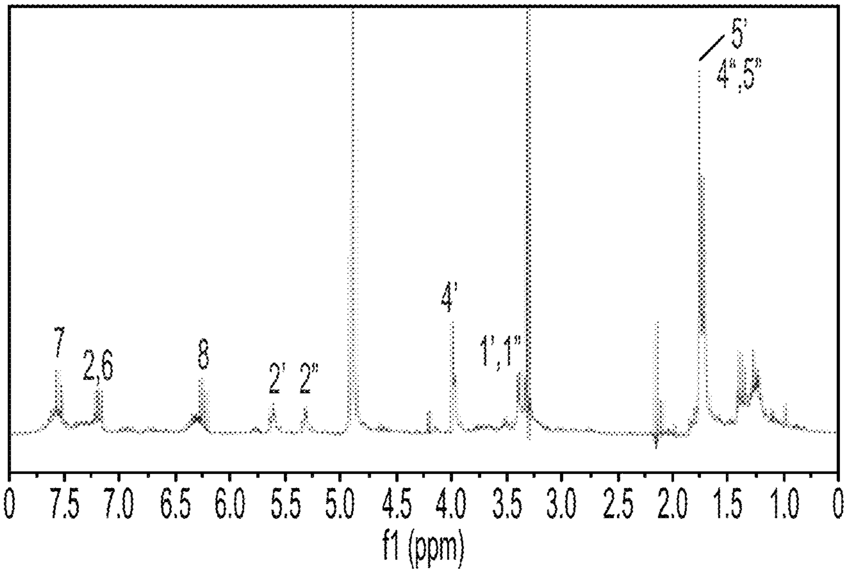
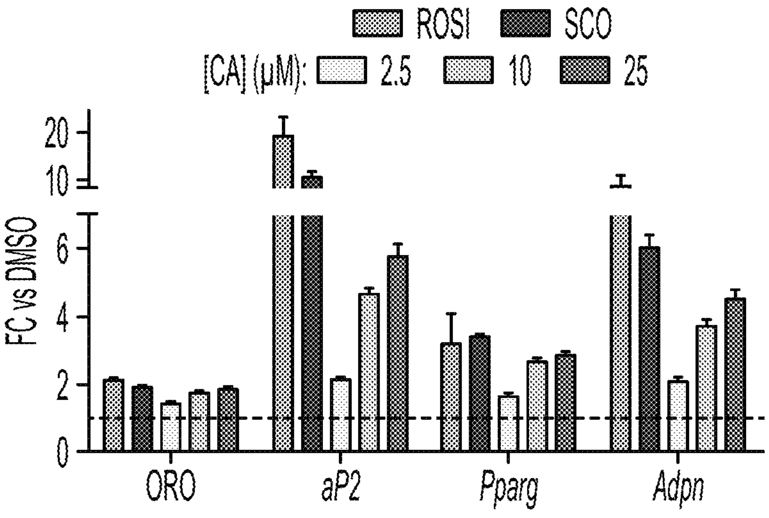
FIG. 5 CONT.

Capillartemisin B
3-[5'-Hydroxyphenyl]-5-prenyl-p-coumaric acid
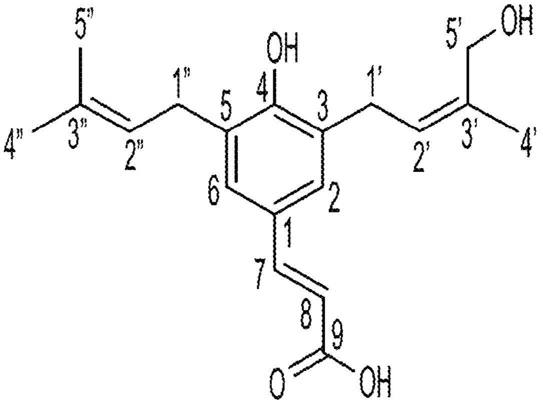
Chemical Formula: $C_{19}H_{24}O_4$
Exact Mass: 316.1675
Molecular Weight: 316.3970
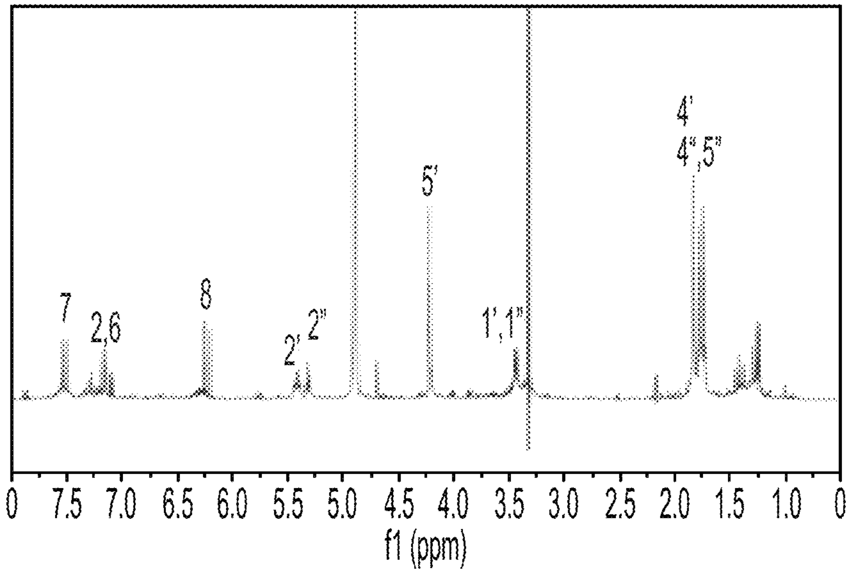
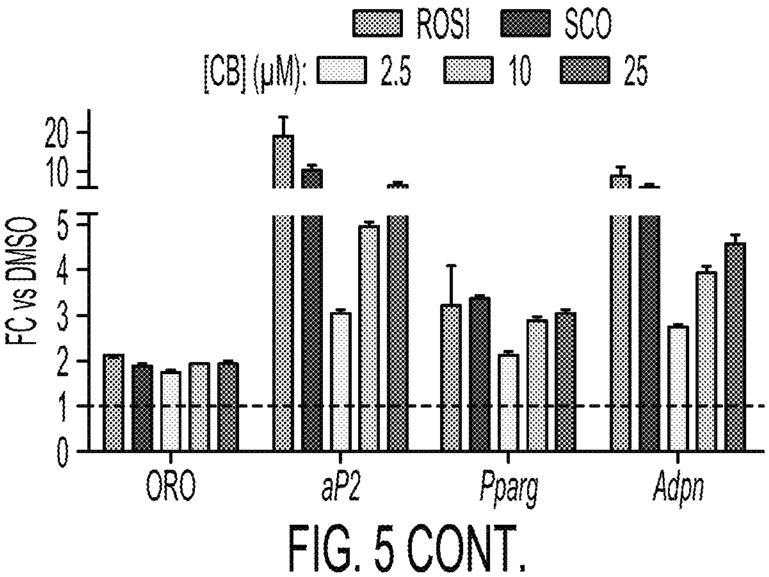
FIG. 5 CONT.

1a

1b

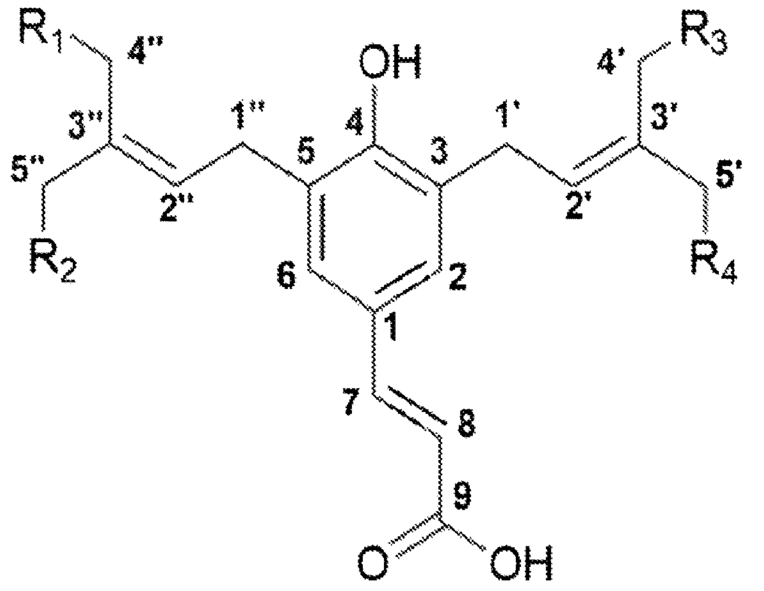
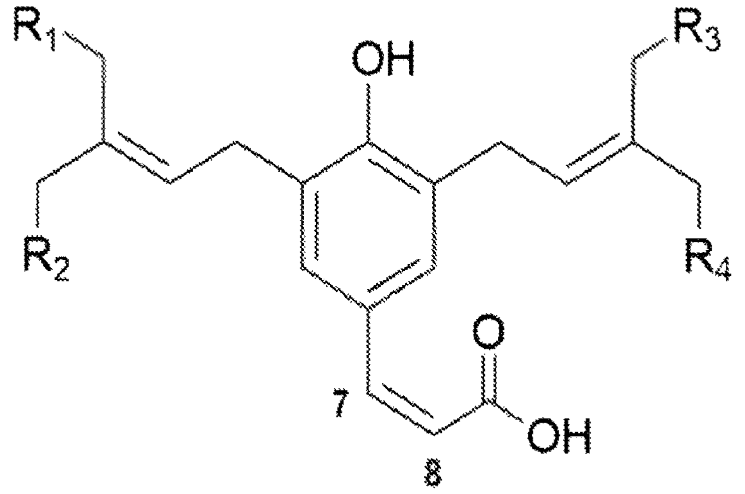
| | $\Delta_{7,8}$ | $R_1$ | $R_2$ | $R_3$ | $R_4$ |
|---|---|---|---|---|---|
| **1a/b** | *trans/cis* | OH | H | OAc | H |
| **1c/d** | *trans/cis* | OH | H | H | OAc |
| **1e/f** | *trans/cis* | H | OH | OAc | H |
| **1g/h** | *trans/cis* | H | OH | H | OAc |
| **2** | *trans/cis* | H | H | OH | H |
| **3** | *trans/cis* | H | H | H | OH |
FIG. 22

$^1H$ and $^{13}C$ NMR spectroscopic data of compound 1a and 1b in $CD_3OD$[a]

| | 1a[b] | | 1b[b] | |
|---|---|---|---|---|
| Position | $\delta_H$, ($J$ in Hz) | $\delta_C$, type | $\delta_H$, ($J$ in Hz) | $\delta_C$, type |
| 1 | | 128.1, C | | 129.2, C |
| 2 | 7.164, d (2.3) | 128.6, CH | 7.213, d (1.8) | 130.5, CH |
| 3 | | 129.4, C | | 128.3, C |
| 4 | | 155.9, C | | 154.1, C |
| 5 | | 129.2, C | | 128.5, C |
| 6 | 7.174, d (2.3) | 129.1, CH | 7.319, d (1.8) | 130.5, CH |
| 7 | 7.453, d (15.8) | 144.9, CH | 6.437, d (12.6) | 136.2, CH |
| 8 | 6.280, d (15.8) | 118.5, CH | 5.814, d (12.6) | 122.6, CH |
| 9 | | 173.0, C | | 173.0, C |
| 1' | 3.412, d (8.3) | 29.5, $CH_2$ | 3.379, d (7.2) | 29.6, $CH_2$ |
| 2' | 5.560, t (7.7) | 129.5, CH | 5.544, t (7.2) | 129.9, CH |
| 3' | | 132.2, C | | 131.7, C |
| 4' | 4.733, s | 64.2, $CH_2$ | 4.729, s | 64.4, $CH_2$ |
| 5' | 1.796, s | 21.7, $CH_3$ | 1.771, s | 21.7, $CH_3$ |
| 1" | 3.421, d (8.3) | 29.9, $CH_2$ | 3.379, d (7.2) | 29.6, $CH_2$ |
| 2" | 5.400, t (7.6) | 126.8, CH | 5.392, t (7.2) | 127.1, CH |
| 3" | | 136.5, C | | 136.2, C |
| 4" | 4.206, s | 61.9, $CH_2$ | 4.198, s | 61.9, $CH_2$ |
| 5" | 1.809, s | 22.1, $CH_3$ | 1.796, s | 22.0, $CH_3$ |
| CO-4' | | 173.1, C | | 173.1, C |
| OAc-4' | 2.045, s | 20.8, $CH_3$ | 2.045, s | 20.8, $CH_3$ |

[a]Assignments supported by HSQC and HMBC experiments. [b]900 and 225 MHz, in $CD_3OD$.

FIG. 24

The relative ratios of 1a and 1b, calculated using the 100% quantitative NMR method with normalized integration values.

| hydrogen | **1a** | **1b** |
|---|---|---|
| 7 | 100.00 | 38.56 |
| 6 | 98.95 | 38.13 |
| 2 | 106.38 | 40.35 |
| 8 | 94.54 | 38.74 |
| 4' | 85.57 | 42.18 |
| 4'' | 88.62 | 35.38 |
| OAc-4' | 104.00 | 35.16 |
| normalized integral value | 96.87 | 38.36 |
| calculated purity (%) | 71.63 | 28.37 |
| ±SD | 5.70 | 1.86 |

FIG. 25

Primer sequences for gene expression analysis.

| gene name and symbol | forward primer, 3'-5' | reverse primer, 3'-5' |
|---|---|---|
| adiponectin (Adipoq) | TGTCTGTACGATTGTCAGTGG | GCAGGATTAAGAGGAACAGGAG |
| adipocyte protein 2 (aP2)/Fatty acid binding protein 3 (Fabp4) | CCCTCCTGTGCTGCAGCCTTTC | GTGGCAAAGCCCACTCCCACTT |
| peroxisome proliferator-activated receptor gamma (Ppparg) | TCACAAGAAATTACCATGGTTGACA | CGAGTGGTCTTCCATCACGG |
| non-POU-domain-containing, octamer binding protein (Nono) | CATCATCAGCATCACCACCA | TCTTCAGGTCAATAGTCAAGCC |

FIG. 26

COMPOUNDS, COMPOSITIONS, AND METHODS TO TREAT METABOLIC DISEASE

GOVERNMENT SUPPORT

This invention was made with government support under P50 AT002776 awarded by the National Institutes of Health. The government has certain rights in the invention.

REFERENCE TO A SEQUENCE LISTING

This application contains a Sequence Listing in computer readable form. The computer readable form is incorporated herein by reference. Said ASCII copy, created on Jan. 4, 2023, is named 2932719-000112-US2_SL.txt and is 4,640 bytes in size.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

This invention is directed to compounds, compositions, and methods to treat metabolic diseases. For example, the invention is drawn to compounds identified in extracts from *Artemisia scoparia* for the treatment of metabolic disease.

BACKGROUND OF THE INVENTION

Adipose tissue (AT) is a critical player in metabolic regulation (Kusminski, Bickel, and Scherer 2016). Obesity, the main disorder involving AT, is arguably the greatest health issue currently affecting the Western world, as it is the major driver of the high rates of cardiovascular disease and insulin resistance in developed nations (Bhupathiraju and Hu 2016; Ranasinghe et al. 2017; Saklayen 2018). In obese states, the normal functions of adipose tissue are disrupted, contributing to whole-body metabolic dysfunction (Vidal-Puig 2013). Although the inhibition of fat cell development may intuitively sound like a beneficial strategy to reduce obesity and associated disorders, obesity is associated with impaired adipocyte differentiation, along with ectopic lipid deposition and metabolic dysfunction in muscle and liver (Danforth 2000; Gustafson et al. 2015; Kim et al. 2007; Smith and Kahn 2016).

SUMMARY OF THE INVENTION

The present invention provides a botanical composition comprising an extract isolated from *Artemisa scoparia*. In embodiments, the extract comprises a compound of Formula (V)

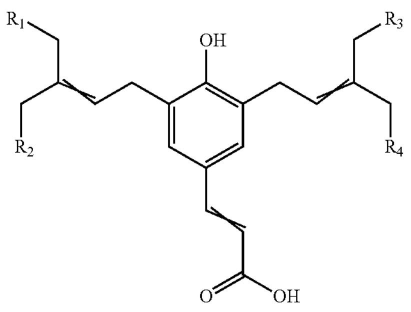

wherein  bonds can be cis or trans; $R_1$ comprises H, OH, and OAc, $R_2$ comprises H, OH, and OAc; $R_3$ comprises H, OH, and OAc; $R_4$ comprises H, OH, and OAc, or any combination thereof.

In embodiments, the botanical extract comprises a polar solvent or a nonpolar solvent. For example, the polar solvent comprises ethyl alcohol (ethanol), ethyl acetate, butyl alcohol (butanol), methyl alcohol (methanol), n-propanol, and water. For example, the non-polar solvent comprises isooctane, hexane, diethyl ether, or chloroform.

In embodiments, the botanical composition comprises an isomer of Formula (V).

In embodiments, the botanical composition comprises a compound of

Formula (I)

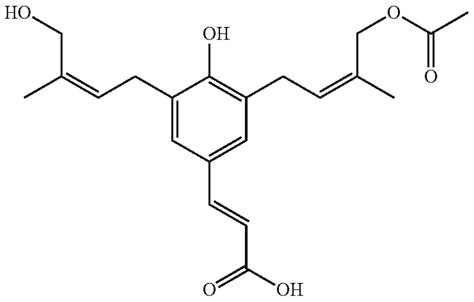

,

Formula (II)

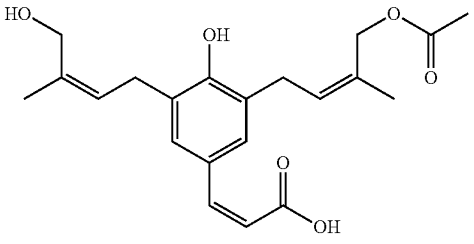

,

Formula (III)

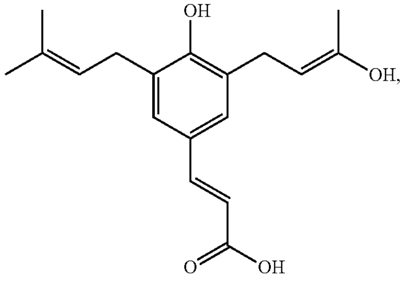

-continued

Formula (IV)

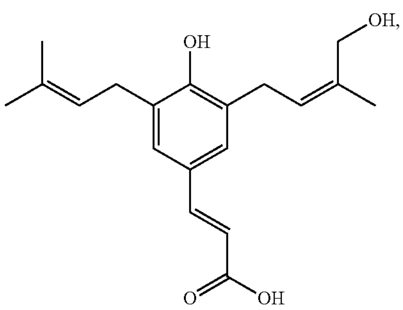

or any combination thereof.

In embodiments, the botanical composition comprises a compound that is an isomer of Formula (I), Formula (II), Formula (III), or Formula (IV).

Aspects of the invention are also directed towards a pharmaceutical composition. For example, such pharmaceutical composition can comprise a therapeutically effective amount of a botanical extract of *Artemisa scoparia.*

In embodiments, the pharmaceutical composition comprises a compound of

Formula (V)

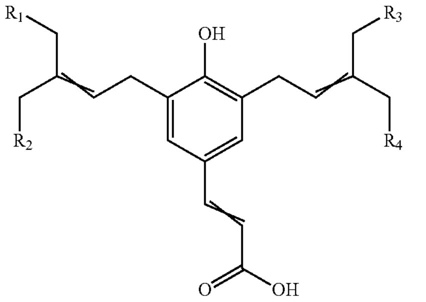

wherein  bonds can be cis or trans; $R_1$ comprises H, OH, and OAc, $R_2$ comprises H, OH, and OAc; $R_3$ comprises H, OH, and OAc; $R_4$ comprises H, OH, and OAc, or any combination thereof, and a pharmaceutically acceptable carrier, excipient, or diluent.

In embodiments, the pharmaceutical extract can comprise a botanical extract described herein, wherein the botanical extract comprises a polar solvent or a non-polar solvent. For example, the polar solvent comprises ethyl alcohol (ethanol), ethyl acetate, butyl alcohol (butanol), methyl alcohol (methanol), n-propanol, and water. For example, the non-polar solvent comprises isooctane, hexane, diethyl ether, or chloroform.

In embodiments, the pharmaceutical composition comprises an isomer of Formula (V).

In embodiments, the pharmaceutical composition comprises a compound of:

Formula (I)

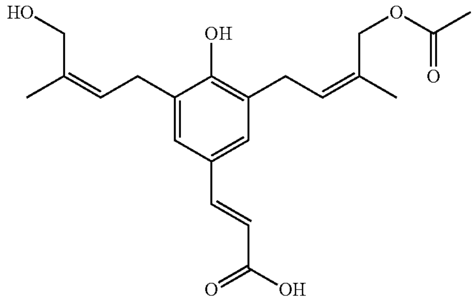

,

Formula (II)

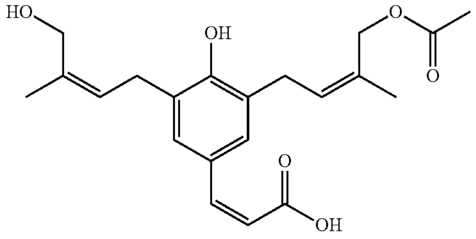

,

Formula (III)

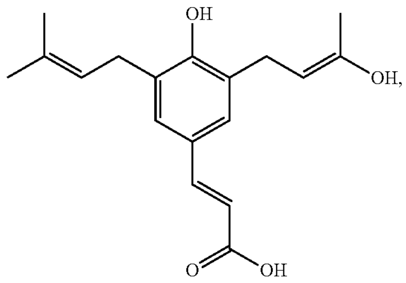

Formula (IV)

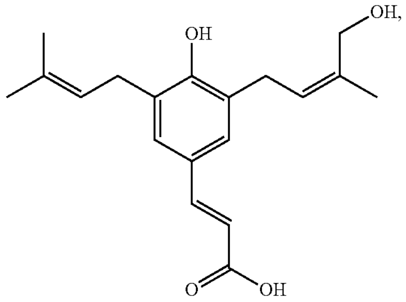

or any combination thereof.

In embodiments, the pharmaceutical composition comprises a compound that is an isomer of Formula (I), Formula (II), Formula (III), or Formula (IV).

In embodiments, the pharmaceutical composition can further comprise one or more additional active agents. For example, such one or more additional active agents can synergize with a compound of Formula (V).

Aspects of the invention are further drawn to a method of treating or preventing a metabolic disease, for example obesity, diabetes, or metabolic syndrome. For example, the method can comprise administering to a subject in need thereof a therapeutically effective amount of the botanical extract as described herein or a pharmaceutical composition as described herein. For example, the therapeutically effective amount can comprise about 0.1 μg/kg to about 1000 mg/kg.

Aspects of the invention are also drawn to a method of treating or preventing a drug-induced metabolic disturbance.

For example, the method can comprise administering to a subject in need thereof a therapeutically effective amount of the botanical extract as described herein or a pharmaceutical composition as described herein. For example, the therapeutically effective amount can comprise about 0.1 μg/kg to about 1000 mg/kg.

Aspects of the invention are still further drawn to a method of extending the lifespan of a subject. For example, the method can comprise administering to a subject in need thereof a therapeutically effective amount of the botanical extract as described herein or a pharmaceutical composition as described herein. For example, the therapeutically effective amount can comprise about 0.1 μg/kg to about 1000 mg/kg.

Also, aspects of the invention are drawn to a method of preparing a botanical extract, such as a botanical extract isolated from *Artemisa scoparia*. In embodiments, the method comprises: obtaining fresh plant material; grinding the plant material to a powder; combining the powder with a liquid comprising at least one of water and ethanol to concentrate the solution to obtain an alcohol extract of the plant materials; extracting plant material by liquid to form a liquid extract; and separating the liquid extract from the plant material.

In embodiments, the liquid extract comprises a compound of

Formula (V)

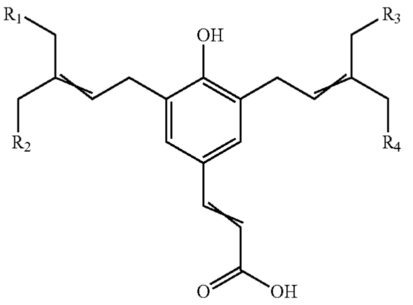

wherein  bonds can be cis or trans; $R_1$ comprises H, OH, and OAc, $R_2$ comprises H, OH, and OAc; $R_3$ comprises H, OH, and OAc; $R_4$ comprises H, OH, and OAc, or any combination thereof.

For example, the liquid extract comprises a compound of:

Formula (I)

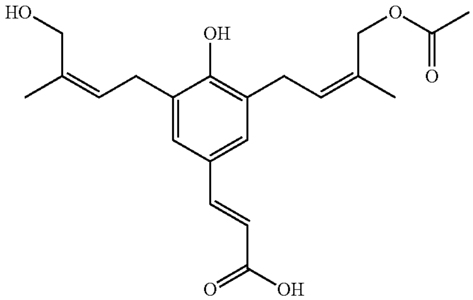

,

-continued

Formula (II)

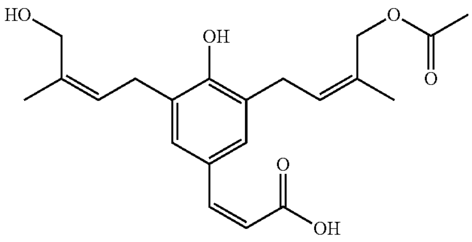

,

Formula (III)

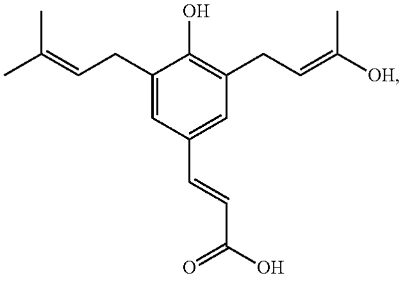

Formula (IV)

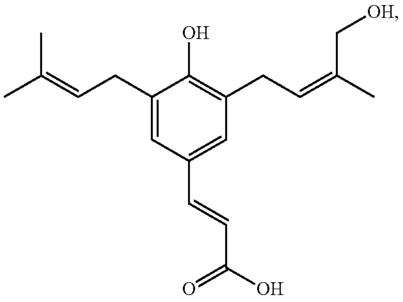

or any combination thereof.

Aspects of the invention are further drawn to a therapeutic composition prepared by the methods as described herein.

Other objects and advantages of this invention will become readily apparent from the ensuing description.

Figure 1:
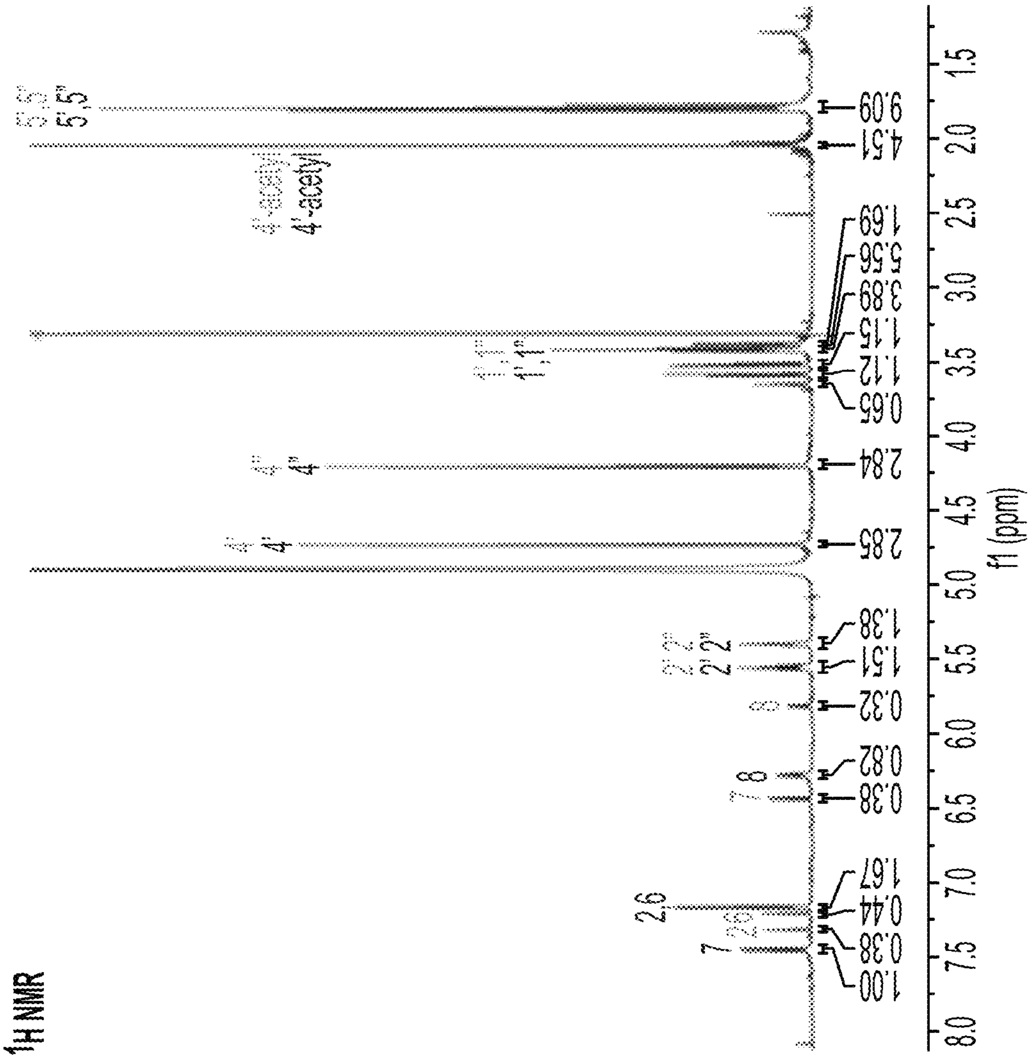
FIG. 1 shows the elucidated structures in EA-3-2 isolate. The structures of the major and the most abundant minor compound in the isolate EA-3-2 were elucidated by ID ($^1$H and $^{13}$C) and 2D (COSY, NUS-HSQC, NUS-HMBC) NMR as well as LC-MS analysis as 3-(trans-oOAcetyl-prenyl); 4-OH, 5-(trans-ωOH-prenyl) trans-cinnamic acid; and 3-(trans-oOAcetyl-prenyl), 4-OH, 5-(trans-ωOH-prenyl) cis-cinnamic acid. The structure involves three E Z isomerism, which lead to the formation of up to eight isomers, i.e., the two currently assigned plus six further isomers. The multiple E/Z isomerism explains the difficulties observed during purification.
Figure 2:
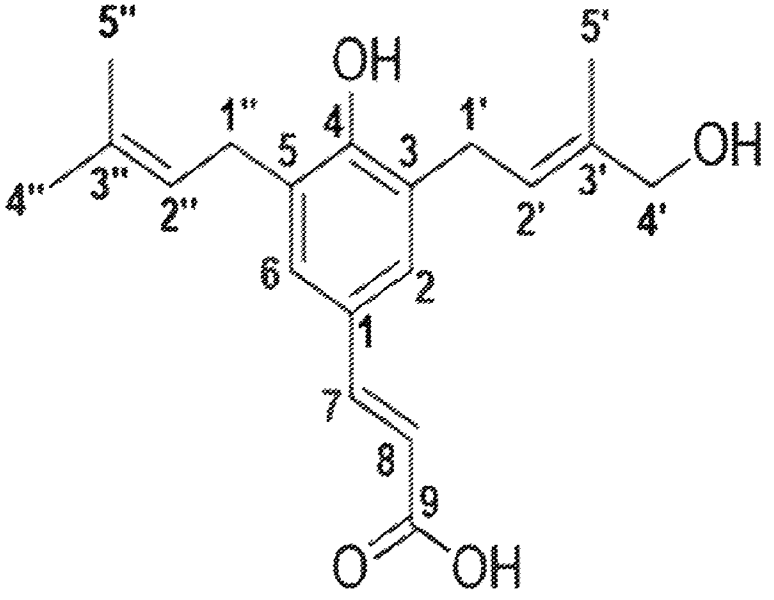
FIG. 2 shows the elucidated structures in EA-3-1 isolate. The structures of the major compound in the isolate EA-3-1 were elucidated by 1D ($^1$H and $^{13}$C) and 2D (COSY, NUS-HSQC, NUS-HMBC) NMR as well as LC-MS analysis as capillartemisin A. The 4'-hydroxylation was evident from the $^{13}$C resonance at 68.8 ppm. This sample contains many other components; a deeper understanding of the cis trans and other Residual Complexity of this cpd/sample will be completed.
Figure 2:
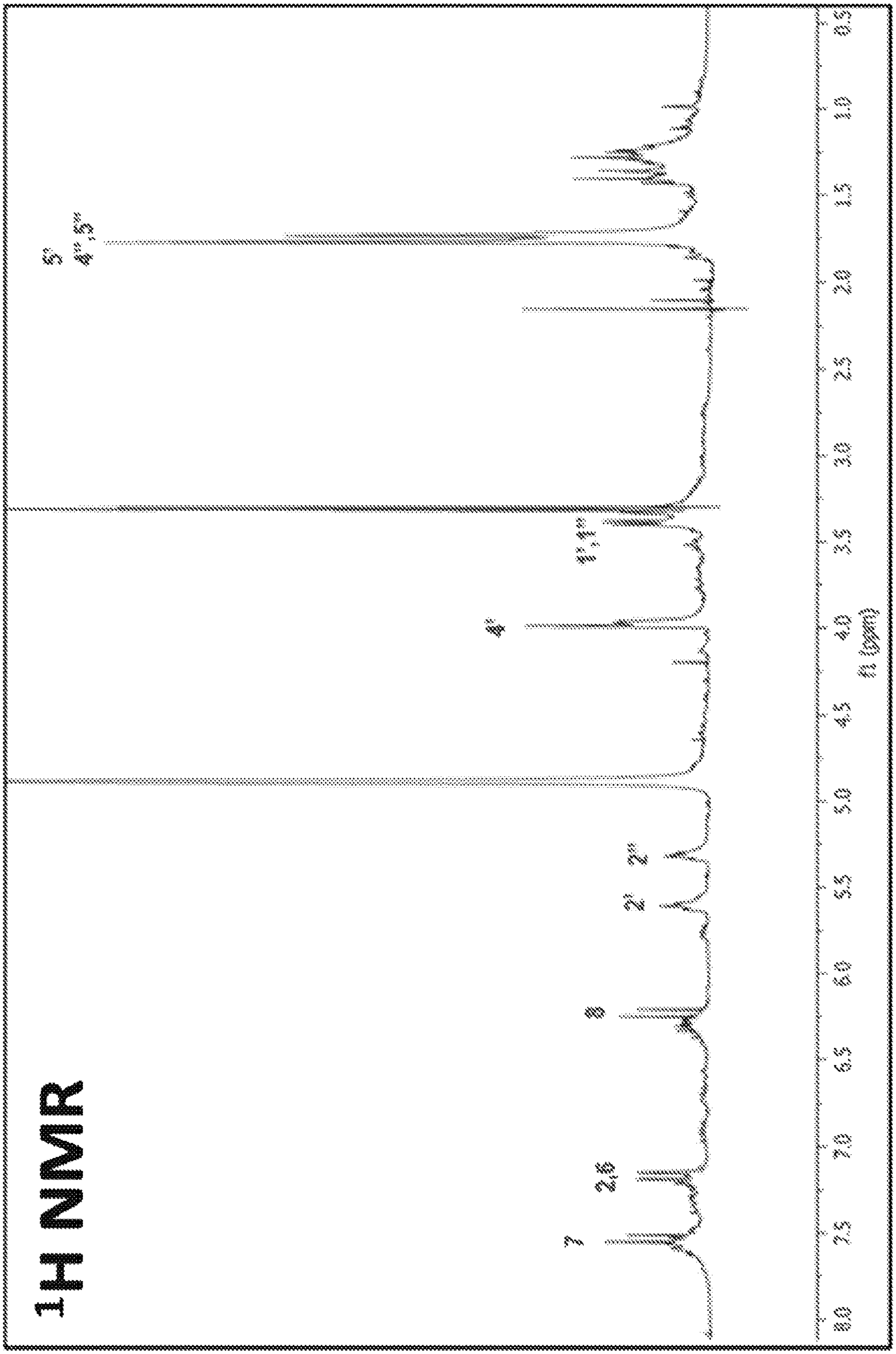
Figure 3:
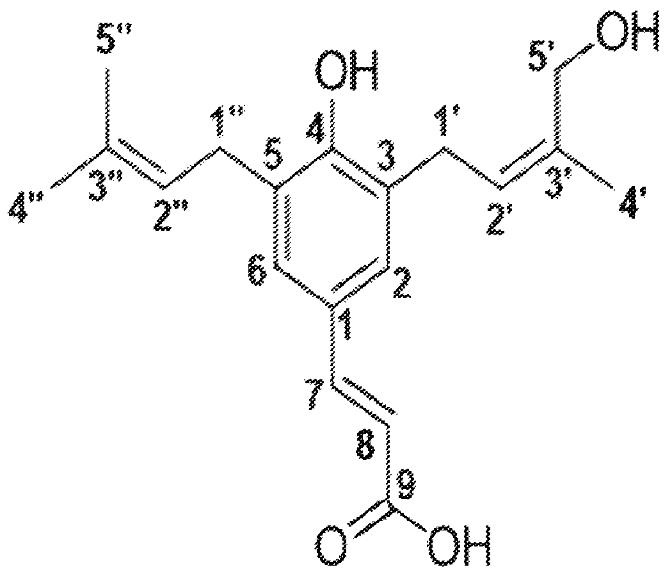
FIG. 3 shows the elucidated structures in EA-5-1 isolate. The structures of the major compound in the isolate EA-5-1 were elucidated by 1D ($^1H$ and $^{13}C$) and 2D (COSY, NUS-HSQC, NUS-HMBC) NMR as well as LC-MS analysis as capillartemisin A. The 4'-hydroxylation was evident from the $^{13}C$ resonance at 61.9 ppm. This sample also contains many other components; a deeper understanding of the cis trans and other Residual Complexity of this cpd/sample will be completed.
Figure 4:
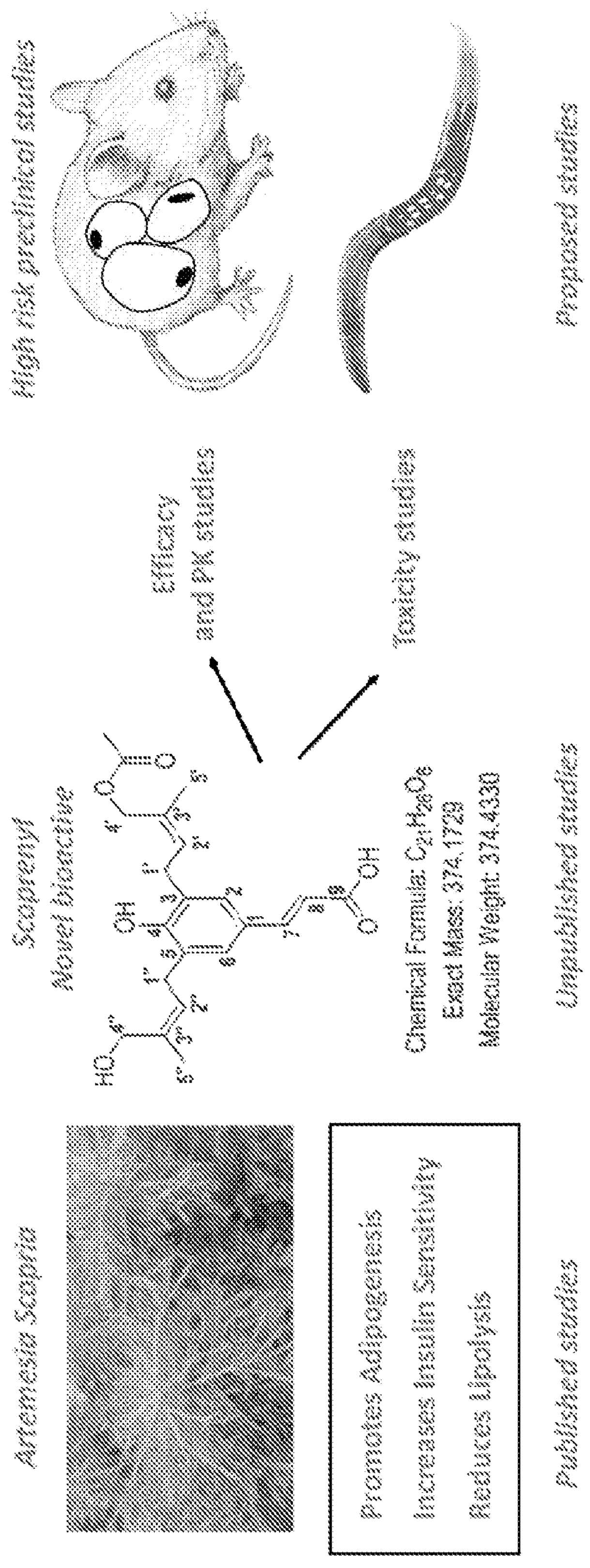

FIG. 4 shows experimental studies described herein.

FIG. 5 shows purified compounds from *A. scoparia* promote adipogenesis in 3T3-L1 cells. Left and middle: Chemical structures, molecular details, and NMR spectra of a new compound, which we have named scoprenyl, and two capillartemisins purified from SCO extract. Right: Neutral lipid staining by Oil Red O (ORO), and expression of adipogenic marker genes: fatty acid binding protein 4 (Fabp4/aP2), peroxisome proliferator activated receptor gamma (Pparg), and adiponectin (Adpn). For each graph, the purified compound was examined at the 3 indicated doses. Rosiglitazone (ROSI) and SCO were used at 2 μM and 50 μg/ml respectively as positive controls. Data are shown as fold change (FC) versus a DMSO vehicle control. The dashed lines mark the level of the DMSO control set to 1.

Figure 6:
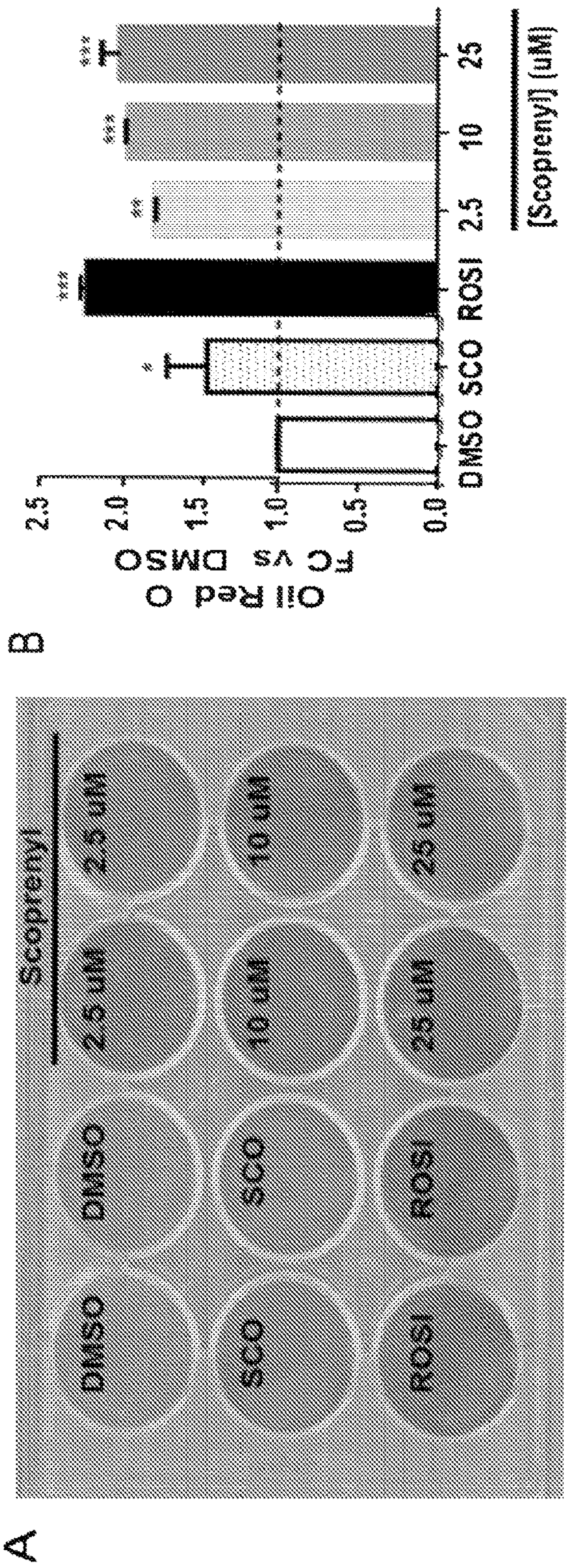

FIG. 6 shows SCO and scoprenyl promote adipogenesis of human primary preadipocytes. Human preadipocytes isolated from the subcutaneous AT of a lean donor were induced to differentiate in the presence of DMSO (vehicle control), 50 μg/ml SCO, 2 μM ROSI, or scoprenyl (2.5, 10, or 25 μM). Seven days after induction, cells were fixed and stained with Oil Red O. A) Plate was scanned to produce image shown. B) Stain was then eluted in isopropyl alcohol, and absorbance was measured in the eluates at 540 nm. Data are expressed as absorbance fold-change vs. DMSO controls. Significance was assessed using one-way ANOVA and Dunnett's multiple comparisons test. *P<0.05; P<0.01, *P<0.001, ****P<0.0001 vs respective DMSO controls.

Figure 7:
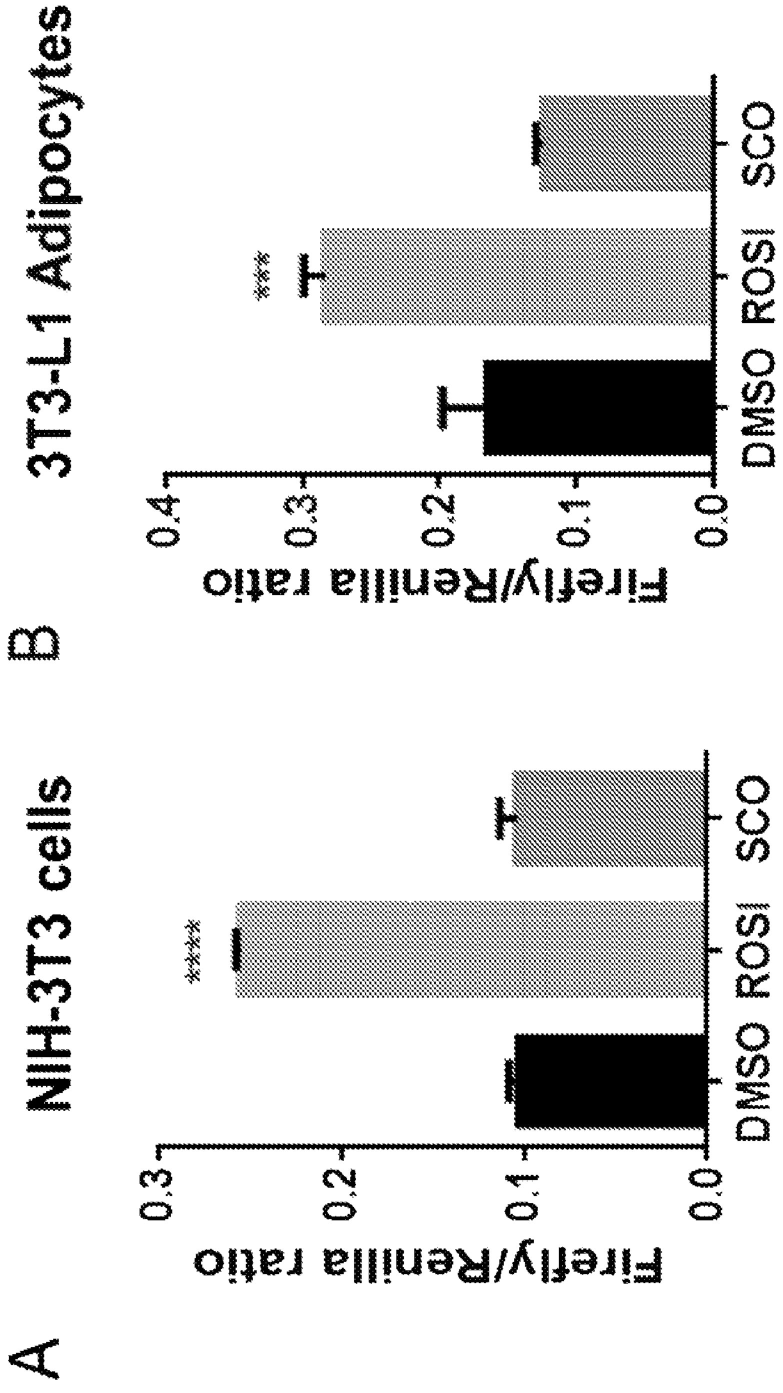

FIG. 7 shows SCO does not activate PPRE-driven transcriptional activity in NIH-3T3 cells ectopically expressing PPARγ, or in 3T3-L1 adipocytes. NIH-3T3 cells stably transfected with full-length PPARγ (A), or mature 3T3-L1 adipocytes (B) were transiently transfected with a vector containing a DR-1 type PPRE and a firefly luciferase reporter, using the Lipofectamine 3000 transfection reagent. Cells were treated with 2 μM ROSI, 50 μg/ml of SCO, or DMSO vehicle control overnight, and a CMV/renilla vector was co-transfected to normalize for transfection efficiency. Relative light units (RLU) were calculated by dividing firefly luciferase activity by renilla luciferase activity. Each condition was performed in triplicate.

Figure 8:
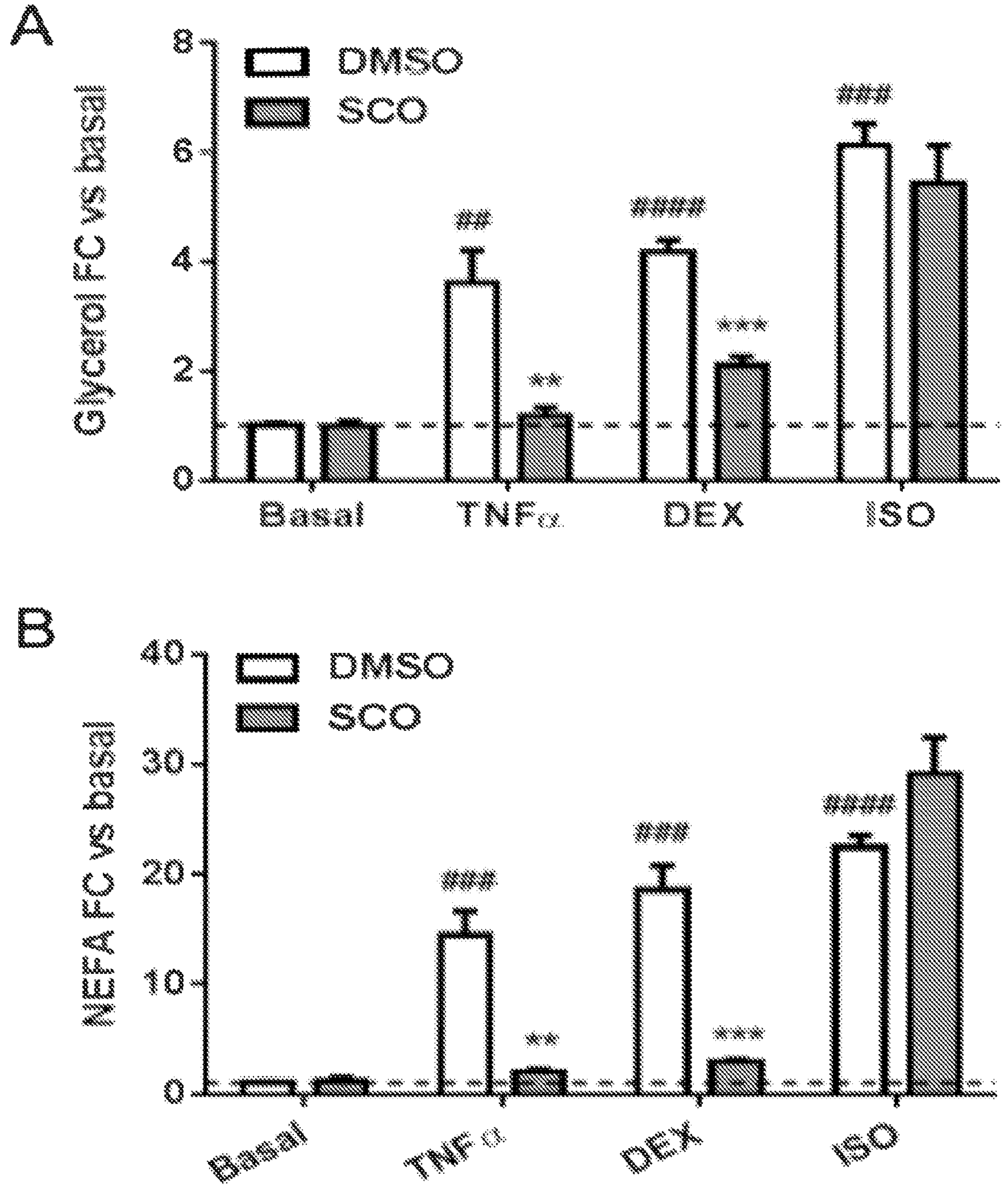

FIG. 8 shows SCO reduces TNFα- and dexamethasone-induced, but not adrenergic-stimulated or basal lipolysis in 3T3-L1 adipocytes. Differentiated 3T3-L1 adipocytes were pretreated for 3 days with 50 μg/ml SCO, then overnight with 0.75 nM TNFa, 500 nM dexamethasone (DEX), or equal volumes of their vehicles (DMSO, 0.1% BSA in PBS, or ethanol, respectively). Culture medium was replaced with lipolysis incubation medium containing 0 (Basal, TNFa, and DEX) or 2 nM isoproterenol (ISO). Medium was assayed for glycerol (A) and NEFA (B) concentrations after 2.5-4 hours, and fold-change was calculated versus the mean of DMSO controls in the basal condition. Data are displayed as mean+/−SEM. N=2-3 replicate cell culture wells per condition. Significance was assessed using one-way ANOVA and Dunnett's multiple comparisons test. *p<0.05, p<0.01, *p<0.001 and for SCO treatment vs respective control. ##p<0.01, ###p<0.001, and ####p<0.0001 for TNFa, DEX, or ISO treatment vs basal. Data shown are representative of an experiment that was repeated 3 times on independent batches of adipocytes.

Figure 9:
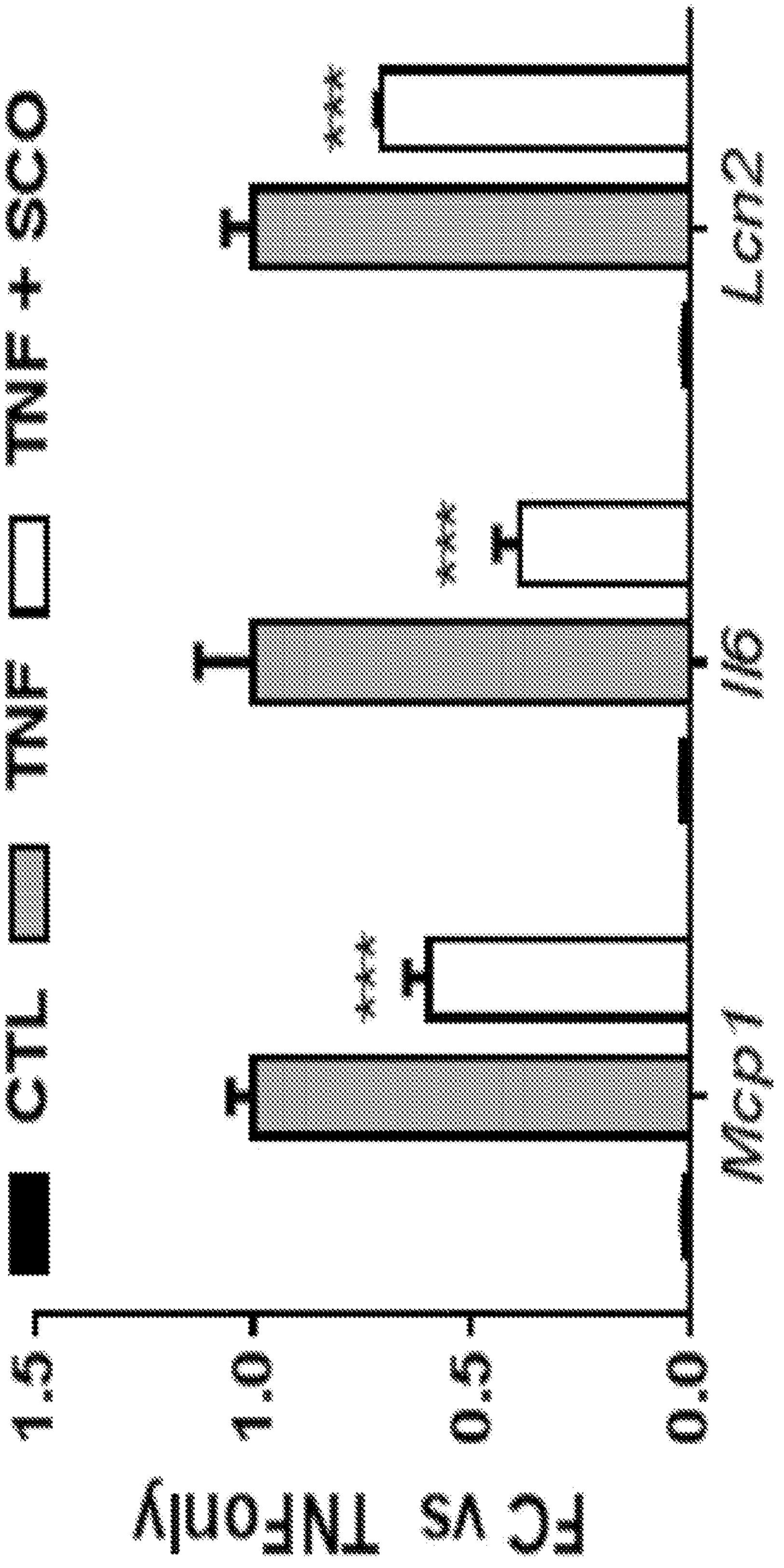

FIG. 9 shows SCO inhibits TNFα-induced expression of inflammatory genes in murine adipocytes. Mature 3T3-L1 adipocytes were pretreated with 50 μg/ml SCO for 3 days, then with 0.75 nM TNFα overnight. Cells were harvested for RNA isolation, and gene expression was assayed by qPCR. Target gene data were normalized to the reference gene Nono. Foldchange was calculated versus the mean of TNFα-only controls for each gene. Significance was assessed using one-way ANOVA and Dunnett's multiple comparisons test. ***P<0.001 for effect of SCO vs. TNFa-only controls. Results were replicated in two additional experiments on independent batches of adipocytes.

Figure 10:
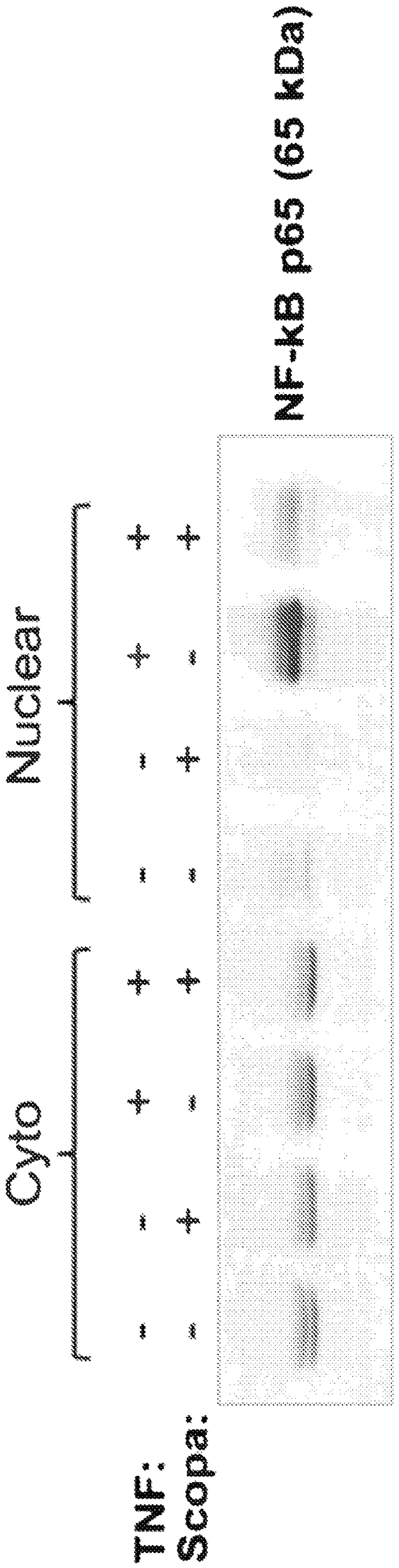

FIG. 10 shows SCO inhibits nuclear translocation of NF-kB p65 in TNFα-treated adipocytes. 3T3-L1 adipocytes pretreated for 3 days with 50 μg/ml SCO or DMSO vehicle were then treated with 0.5 nM TNFa for 20 minutes. Cytosolic and nuclear compartments were isolated and analyzed by immunoblotting for the presence of NF-kB p65.

Figure 11:
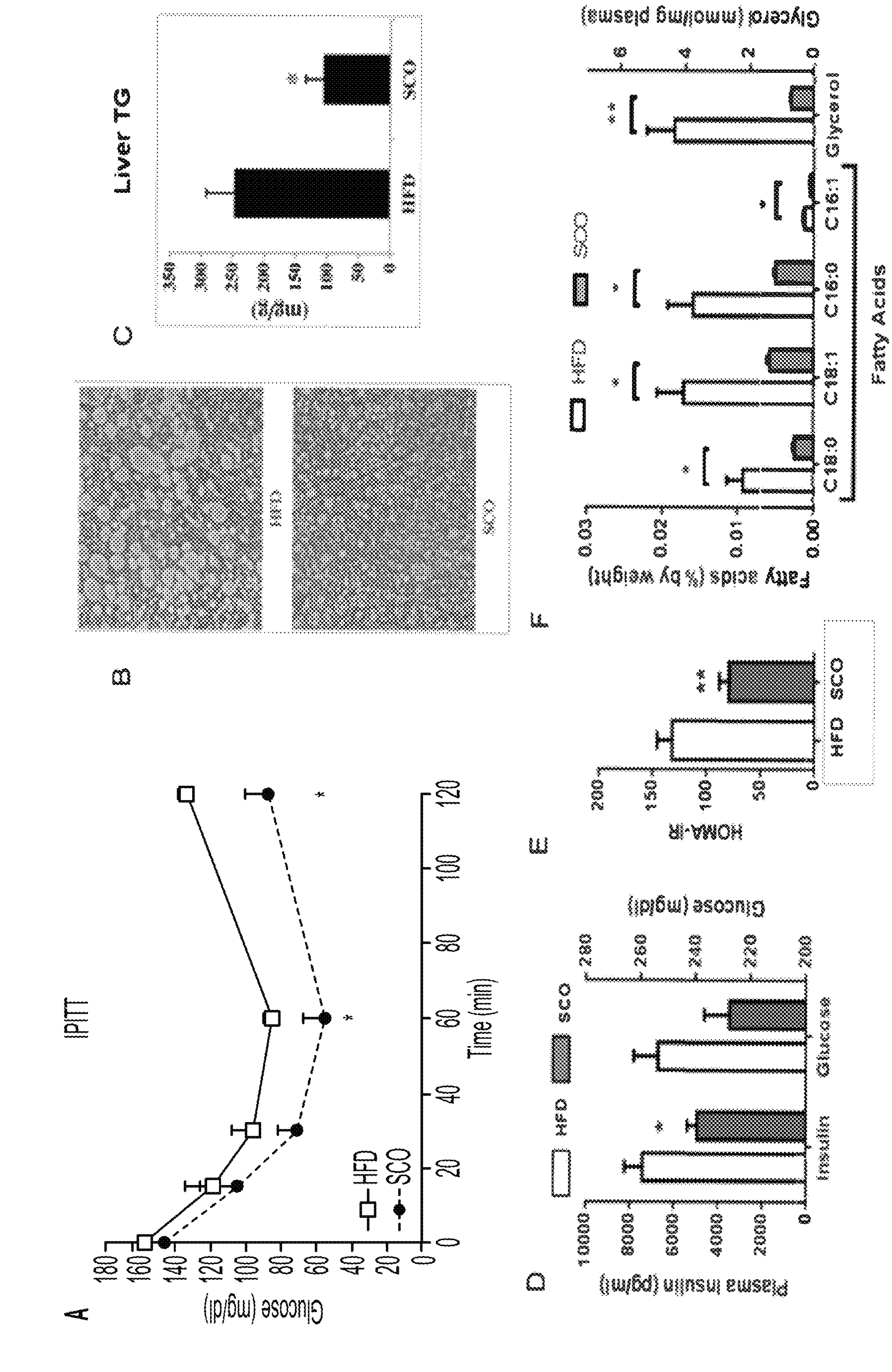

FIG. 11 shows SCO improves parameters of metabolic dysfunction in diet-induced obese (DIO) mice. C57BL/6 male mice were fed HFD for 10-13 weeks to induce DIO prior to feeding the mice HFD+/−SCO (1% w/w in the diet) for an additional 4 weeks. A) Insulin tolerance tests (ITTs) were performed by monitoring blood glucose levels at the indicated time points following a single intraperitoneal (IP) injection of insulin. Data are presented as mean+/−SEM (n=5). *p<0.05 and **p<0.01 for SCO versus HFD at the indicated time points. B) Liver hematoxylin and eosin staining. C) Liver triglyceride (TG) levels. D) Following a 4-hour fast, serum insulin and glucose levels were measured. * denotes significant difference relative to HFD control (p<0.02). E) HOMA-IR was calculated from fasting insulin and glucose levels. ** denotes p<0.01. Data are presented as mean±SEM (n=9-10). F) Mice were fasted for 4 hours, food was returned to the cages, and mice were sacrificed 4 hours later. Serum lipids and glycerol were extracted and analyzed by GC-MS. Data are presented as mean+/−standard error of the mean (SEM) (n=5 mice per group); * denotes p<0.05, ** denotes p<0.01. ITT assays were performed at 3 weeks on HFD+/−SCO diet, whereas all other assessments were performed at the end of the study (4 weeks on diet). Panels A-C: 51, panels D and E: 7, panel F: 5

Figure 12:
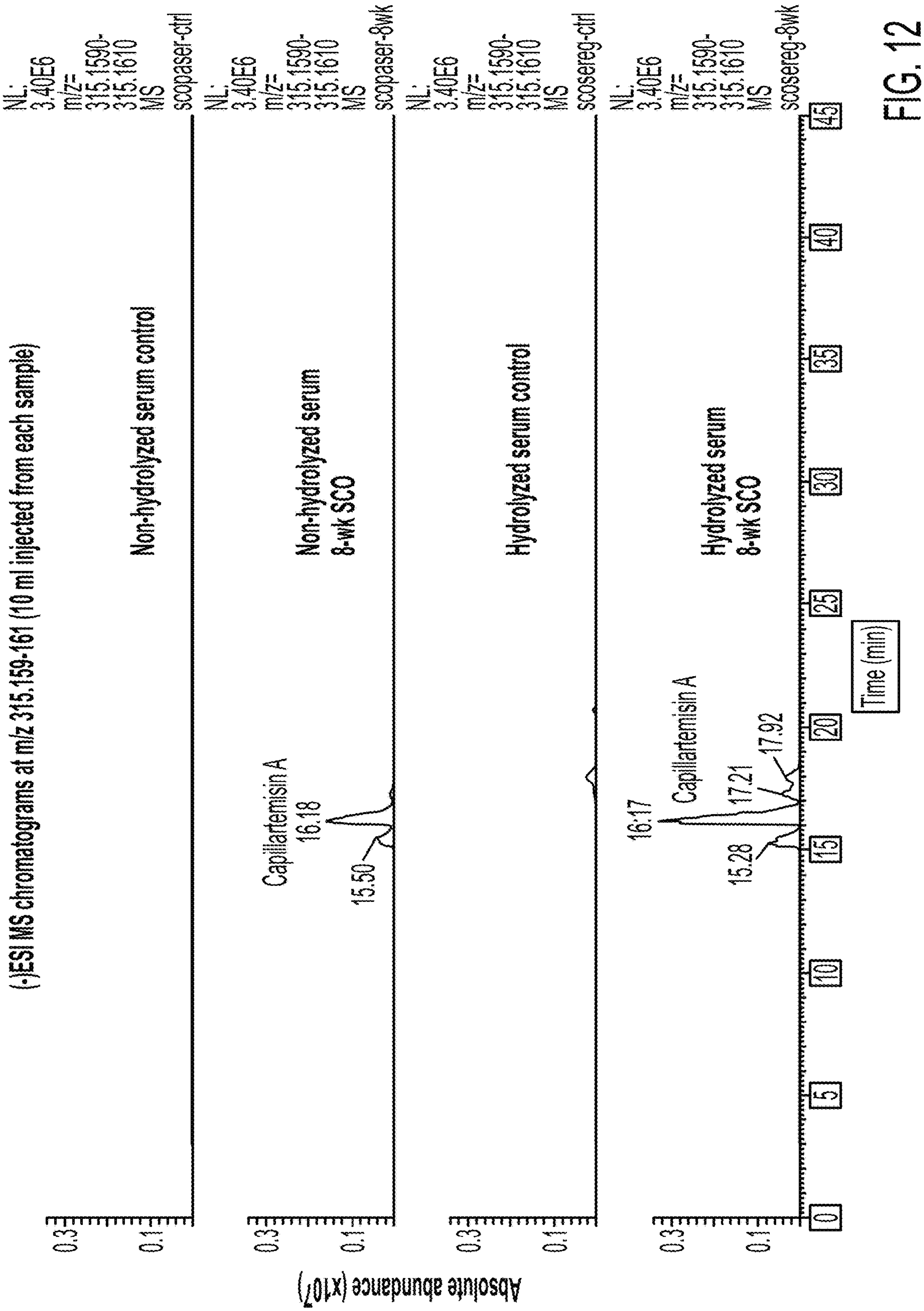

FIG. 12 shows LC-MS chromatograms of serum samples from mice maintained on a HFD diet or HFD containing 1% *Artemisia scoparia* extract for 8 weeks. Serum samples of control or SCO-treated mice were analyzed directly without enzyme hydrolysis after protein precipitation (top 2 panels) or after glucuronidase enzyme digestion followed by solvent partitioning (lower 2 panels). Chromatograms were created using selected ion monitoring of m/z 315.159-315.161 specific to capillartemisins. In addition to specific mass, the identity of capillartemisin A was confirmed using our in-house library of spectral data that was confirmed using NMR spectroscopy.

Figure 13:
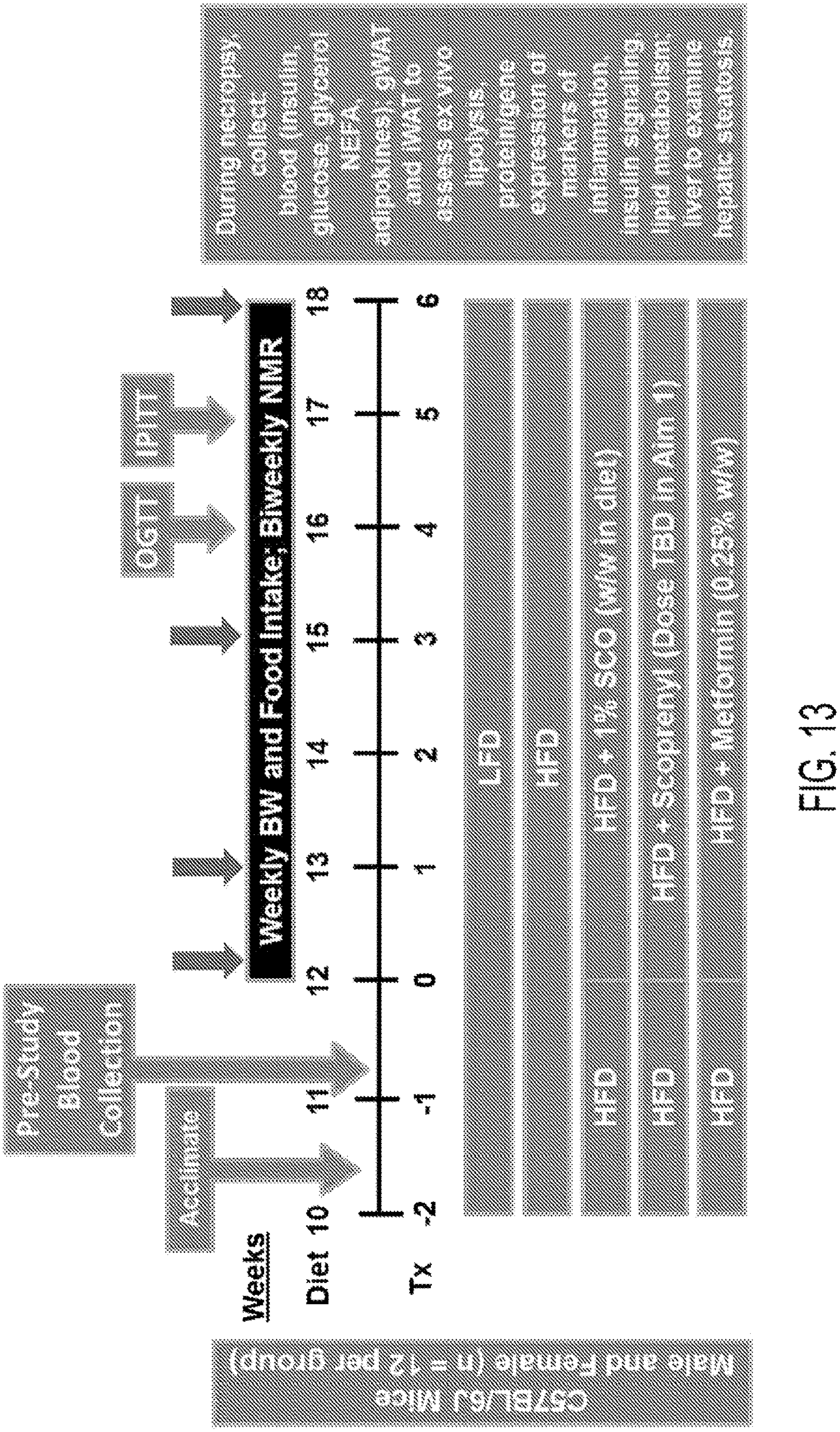

FIG. 13 shows timeline and procedures for assessment of SP efficacy in HFD-fed mice. Beginning at 6 weeks of age (WOA), mice will be fed 10% kcal fat low fat diet (LFD) or 45% kcal fat high fat diet (HFD). Weeks on diet is shown above the time line, while weeks on treatment (Tx) is below. Treatments, beginning for HFD-fed mice at 12 weeks on diet (18 WOA) by switching the mice to diet supplemented with SCO, scoprenyl, or metformin, will last for 6 weeks. Body weight (BW), food intake, and body composition via NMR will be measured at regular intervals. Glucose tolerance and insulin sensitivity will be assessed after 4 weeks of treatment by oral glucose tolerance (OGTT) and intraperitoneal-insulin tolerance test (IPITT), respectively. Red arrows indicate blood collections via submandibular vein to assess amount of SP in circulation.

Figure 14:
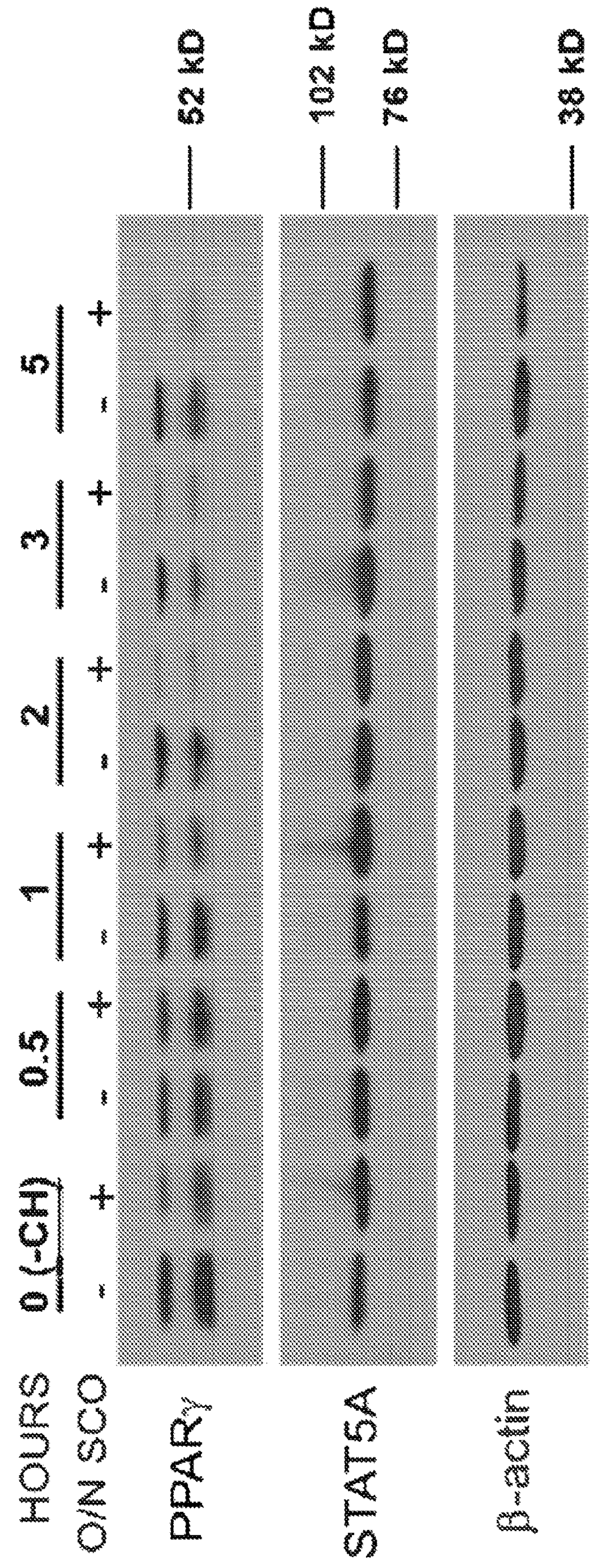

FIG. 14 shows SCO induces the degradation of PPARγ in mature adipocytes. Mature 3T3-L1 adipocytes were treated overnight with DMSO or SCO (50 μg/ml). TO samples were harvested after overnight SCO treatment and before addition of cycloheximide. Cycloheximide was added, and cells were harvested after 0.5, 1, 2, 3, or 5 hours. Whole-cell lysates were prepared, and 100 μg of protein were analyzed by Western blot.

Figure 15:
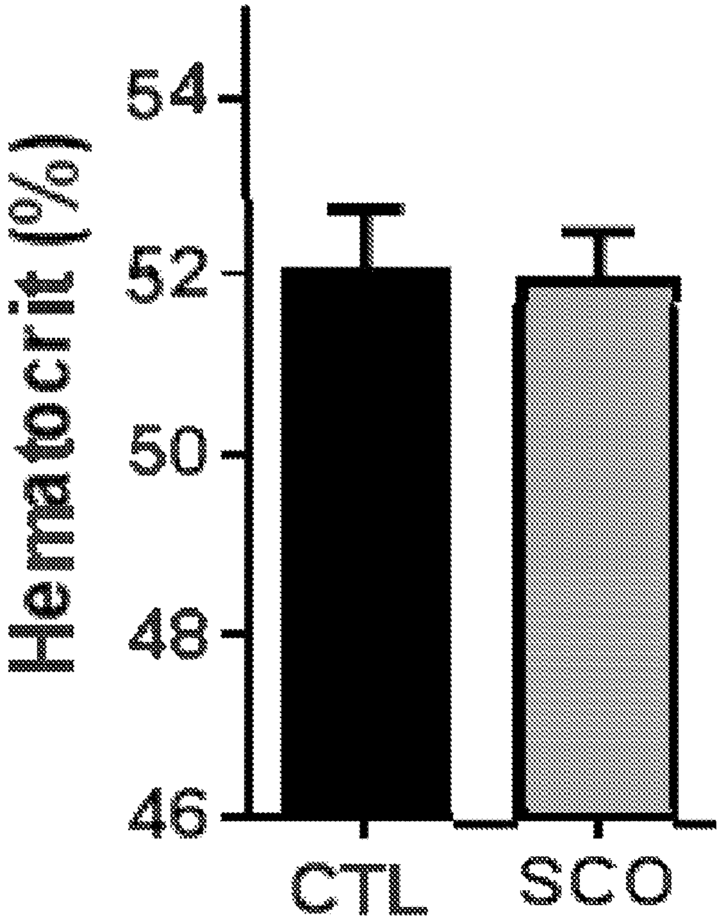

FIG. 15 shows SCO does not alter hematocrit levels in HFD-fed mice. C57BL/6J male mice (13 weeks of age) were fed HFD (CTL) or HFD+1% w/w SCO for 12 weeks. Submandibular blood was collected in heparinized capillary tubes and centrifuged to determine hematocrit percentage. Data are plotted as mean±SEM; CTL (n=7) and SCO (n=11).

Figure 16:
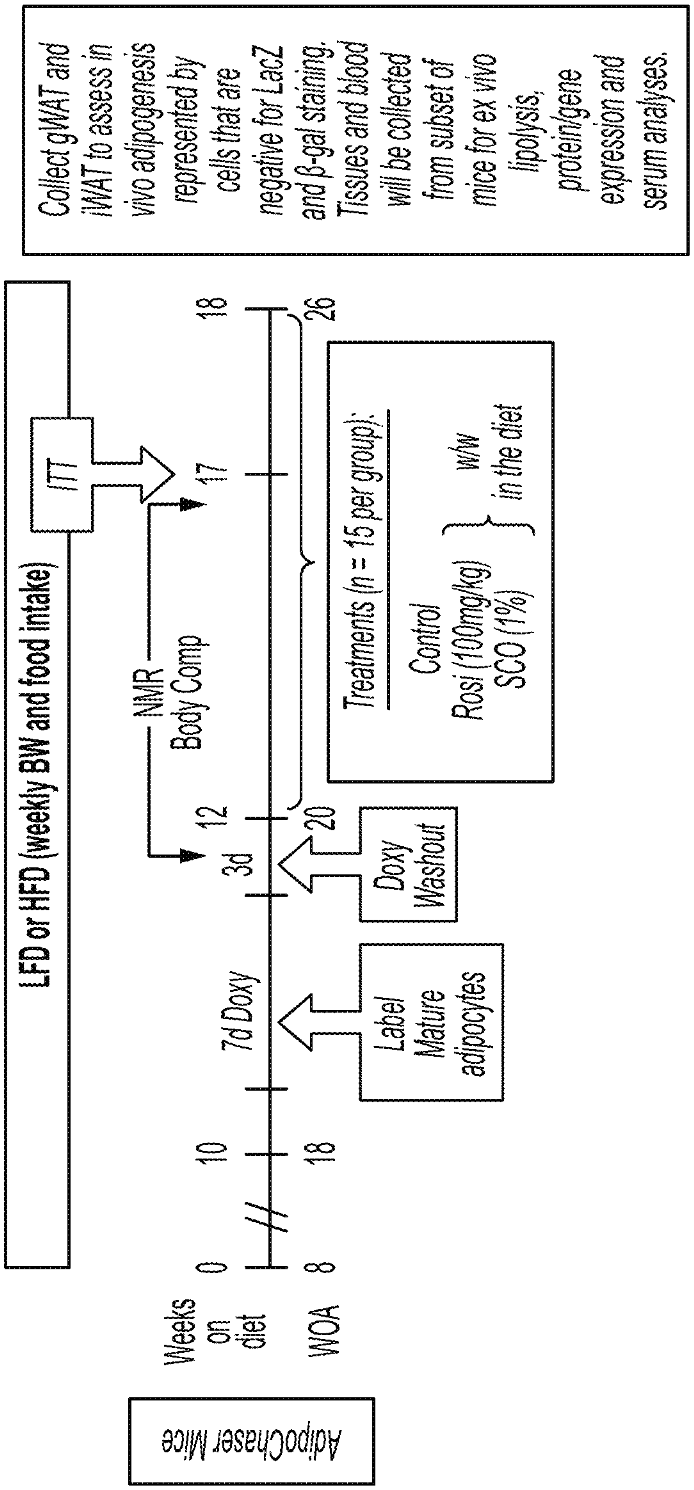

FIG. 16 shows timeline & procedures for study using AdipoChaser mice.

Figure 17:
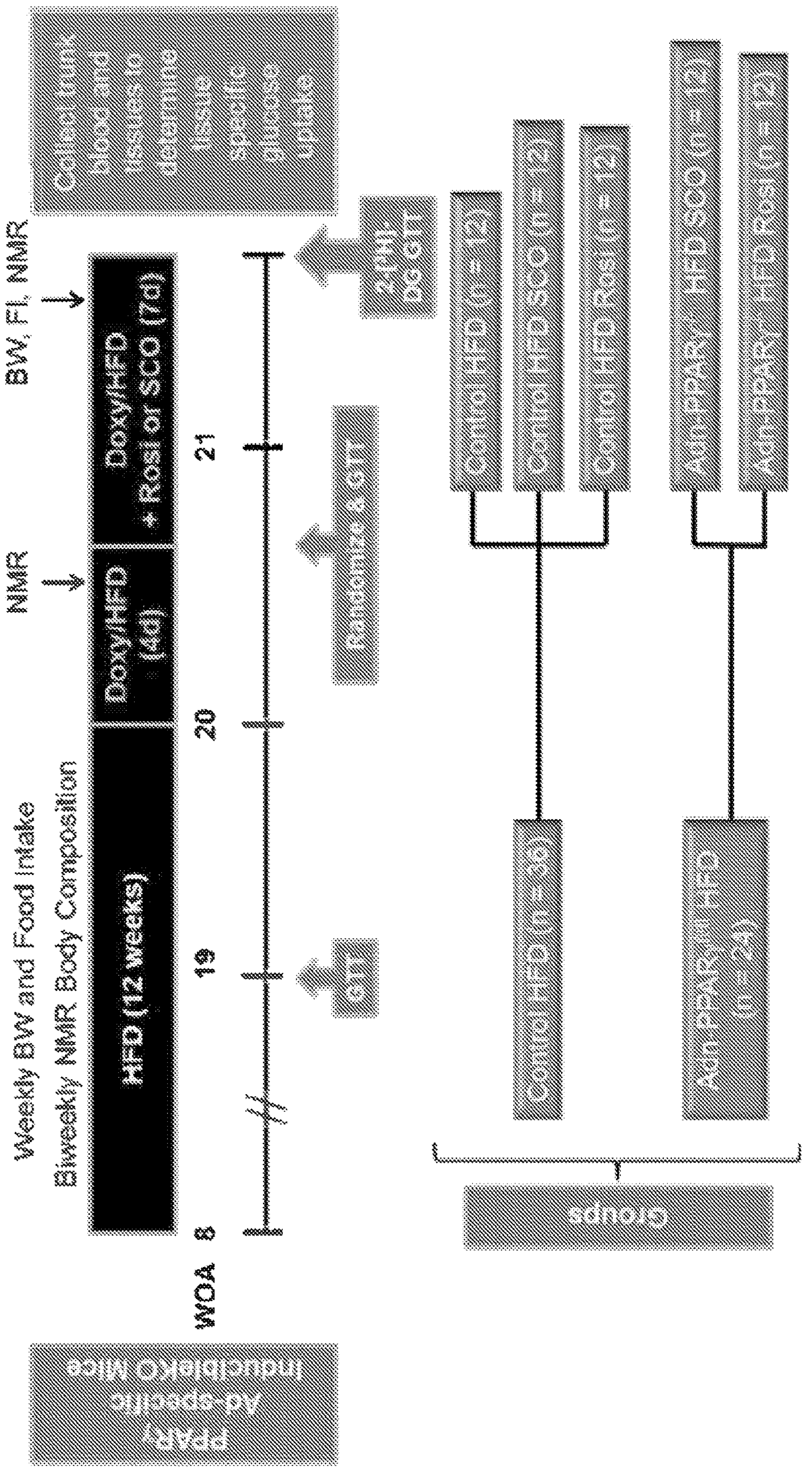

FIG. 17 shows timeline and procedures for study using inducible adipocyte-specific PPARγ KO mice to determine if SCO is dependent on PPARγ in mature adipocytes to improve metabolic function in HFD-fed mice.

Figure 18:
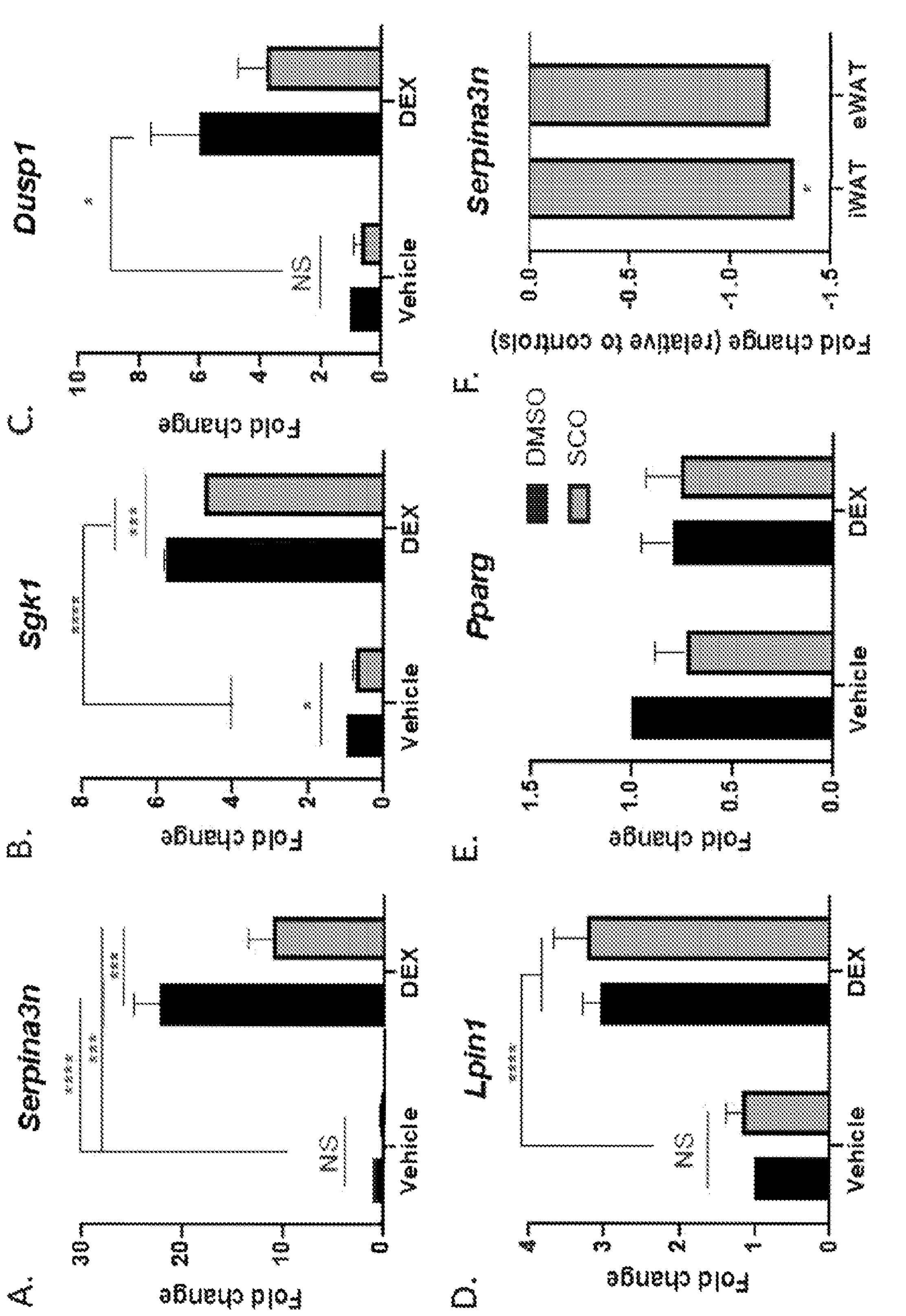

FIG. 18 shows SCO attenuates the DEX-induced expression of Serpina3n and Sgk1 in fat cells. Mature 3T3-L1 adipocytes were pretreated for three days with 50 μg/ml SCO or DMSO vehicle, then with 500 nM dexamethasone (DEX) for six hours (A-E). RNA was isolated and reverse transcribed. Gene expression was assayed by qPCR using Nono as the reference gene, and data are normalized to 'DMSO Vehicle' and expressed as means+/−SD. Mouse AT array (F). RNA from inguinal (iWAT) and epididymal (eWAT) white AT depots from male C57BL/6J mice fed a HFD with or without SCO supplementation for 4 weeks was isolated and reverse transcribed. Gene expression analysis was performed using Illumina mouse expression arrays. Significance was assessed by two-way ANOVA for the cell data and by Bayesian-moderated t-test for array data, and is expressed as *p<0.05, p<0.01, *p<0.001 and ****p<0.0001 when compared to control.

Figure 19:
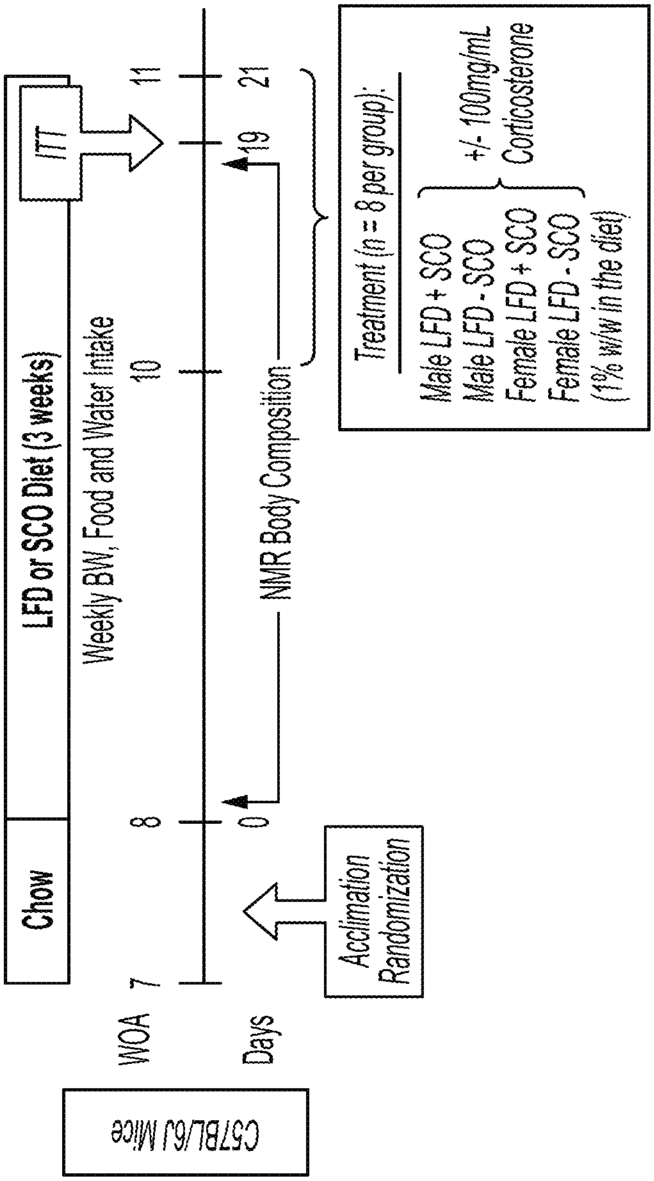

FIG. 19 shows timeline & procedures for animal study examining ability of SCO to attenuate GC-induced insulin resistance.

Figure 20:
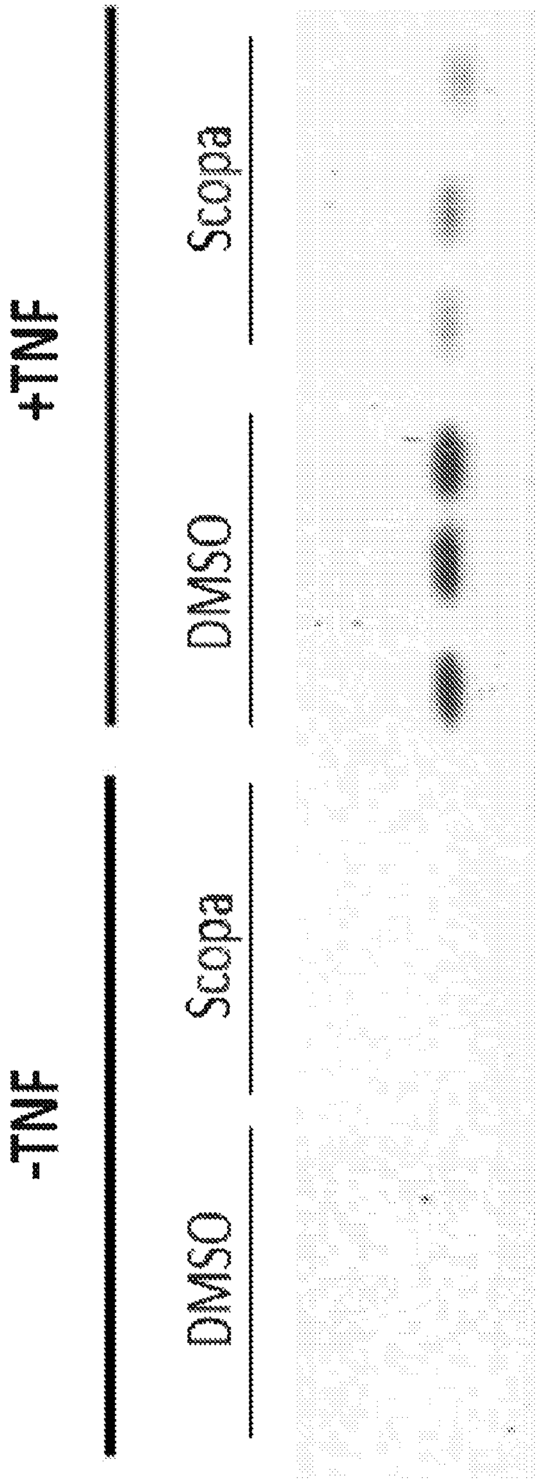

FIG. 20 shows SCO inhibits TNFα-induced LCN2 secretion in adipocytes. Mature 3T3-L1 adipocytes were pretreated with 50 μg/ml SCO or DMSO vehicle for 3 days prior to harvest. On the last day of SCO treatment, adipocytes were treated with 0.75 nM TNF or 0.1% BSA vehicle overnight. The following day, medium on all cells was replaced with low-glucose phenol-red-free DMEM containing either vehicle or 0.75 nM TNFα. Conditioned medium was collected after 4 hours for immunoblotting, and 125 μg was used for Western Blot analysis. n=3 per treatment condition.

Figure 21:
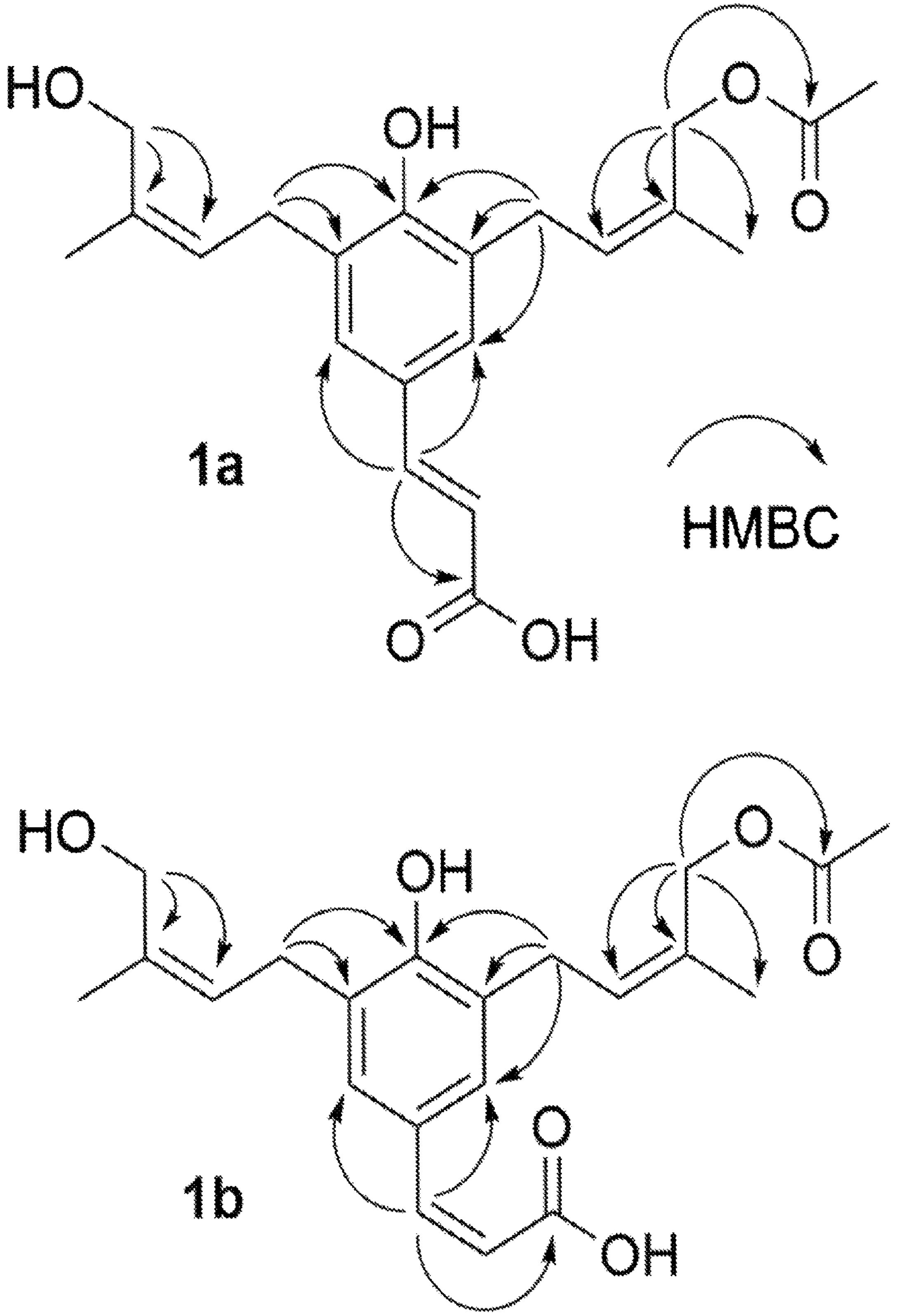

FIG. 21 shows key HMBC correlations of compounds 1a and 1b, shown as H to C arrows.

FIG. 22 shows the cis-trans isomerism of di-prenylated acetoxy coumaric acids allows for eight stereoisomers of 1. The presence of such a complex diasteromeric mixture is supported by pure shift $^{1}$H NMR and LCHRMS measurements. Compounds 2 and 3 are capillartemisin A and capillartemisin B, respectively.

Figure 23:
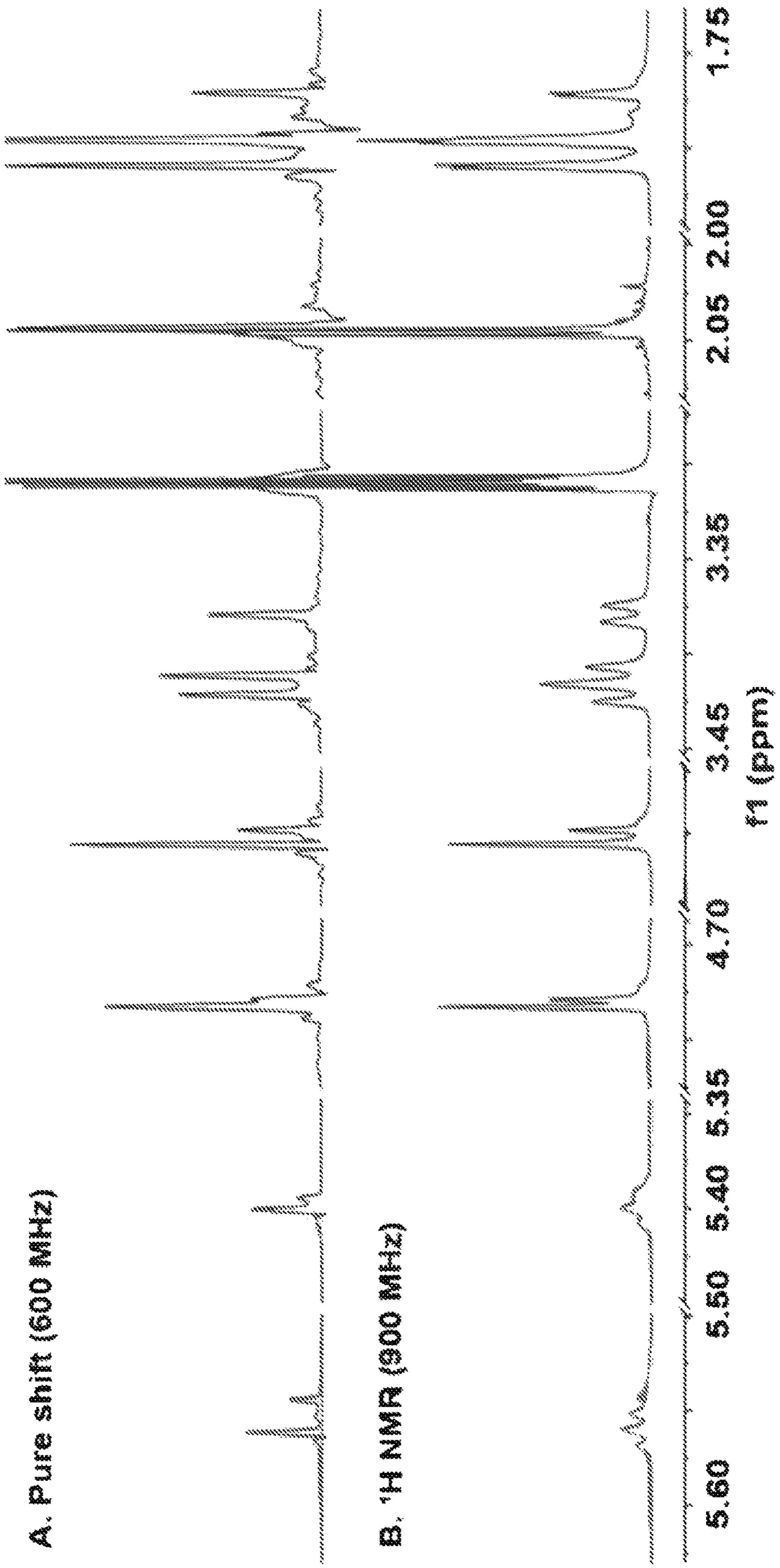

FIG. 23 shows the pure shift spectroscopic data, which showed the presence of the diastereomeric components within the purified mixture of 1a and 1b.

FIG. 24 shows $^{1}$H and $^{13}$C NMR spectroscopic data of compound 1a and 1b in $CD_3OD^{a}$.

FIG. 25 shows the relative ratios of 1a and 1b, calculated using the 100% quantitative NMR method with normalized integration values.

FIG. 26 shows primer sequences for gene expression analysis. FIG. 26 discloses the "forward primer" sequences as SEQ ID NOS 13-15 and 1 and the "reverse primer" sequences as SEQ ID NOS 16-18 and 2, all respectively, in order of appearance.

Figure 27:
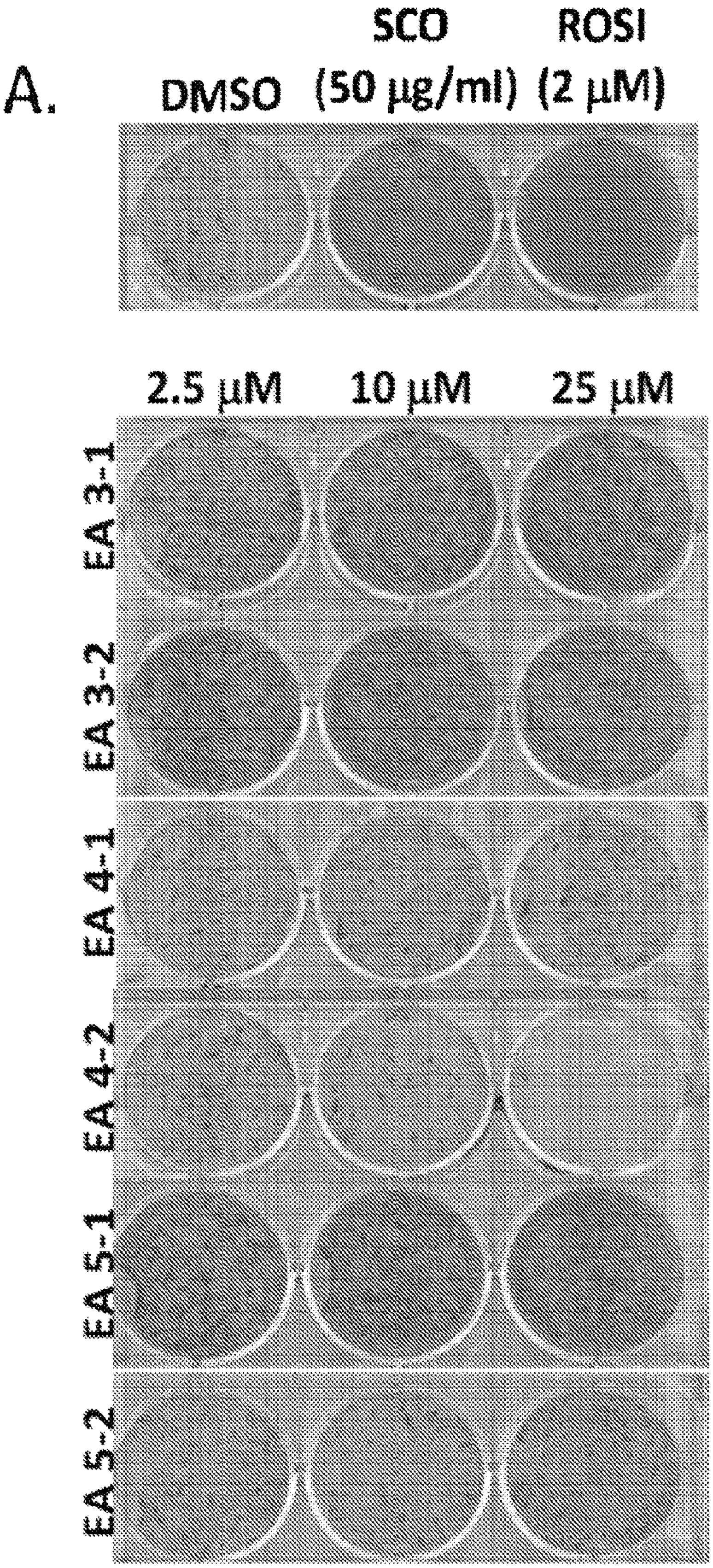
Figure 27:
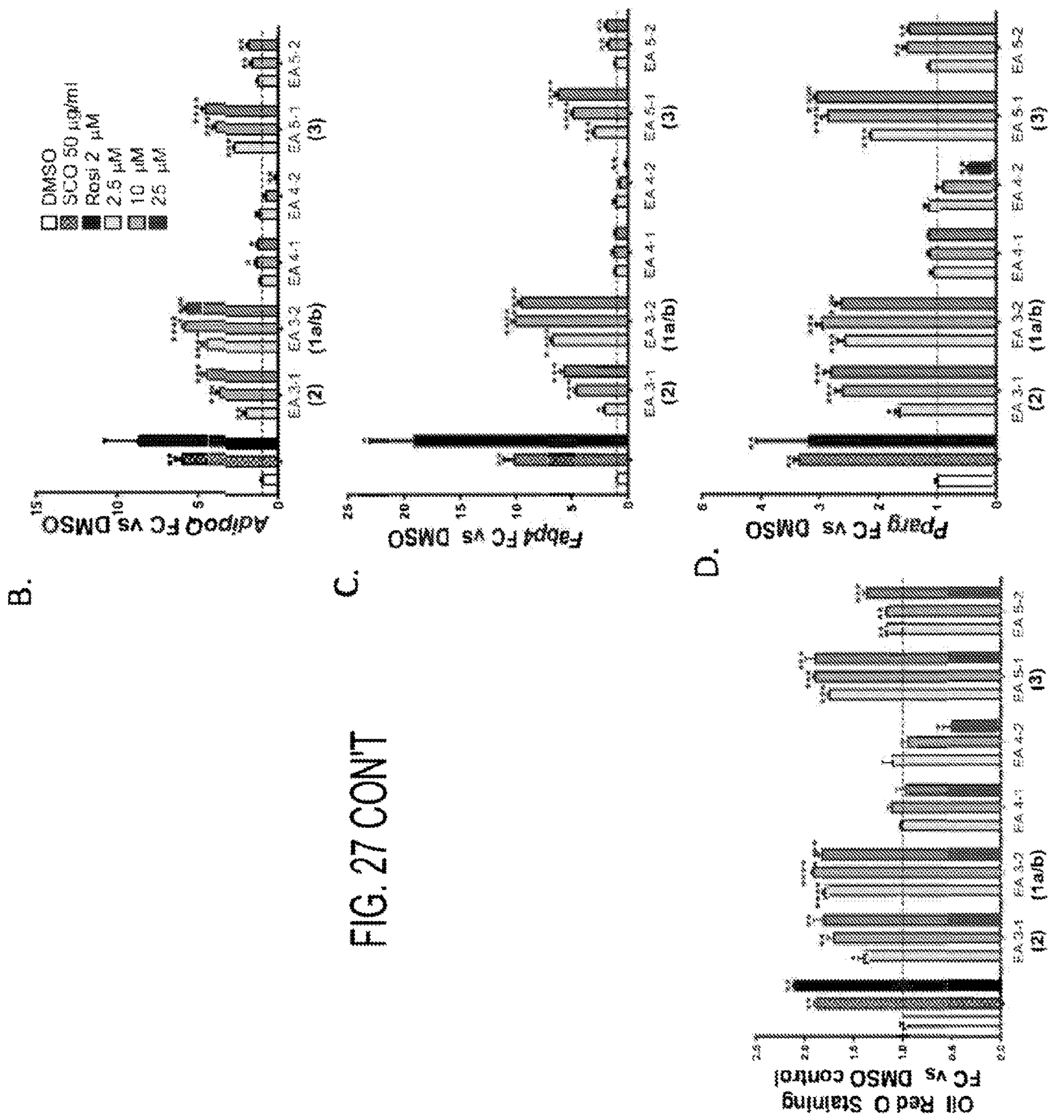

FIG. 27 shows compounds 1a/b, 2 and 3 from *A. scoparia* promote adipogenesis: 3T3-L1 cells were induced to differentiate using half-strength MDI cocktail containing DMSO vehicle, 50 μg/ml SCO, 2 μM ROSI, or one of three doses of test compounds (2.5, 10, or 25 μM). Cells were then either fixed and stained with Oil Red O (4 days post-differentiation) (panel A), or harvested (3 days post differentiation) for RNA isolation and gene expression analysis of adiponectin (AdipoQ), fatty acid binding protein 4 (Fabp4), or Ppary (panels B-D). All treatments compared to their respective DMSO controls. The Effects of SCO and ROSI were analyzed by t-test, while the effects of individual test compounds were analyzed by one-way ANOVA. *P>0.05, P<0.01, *P<0.001, ****P<0.0001 vs DMSO controls.

Figure 28:
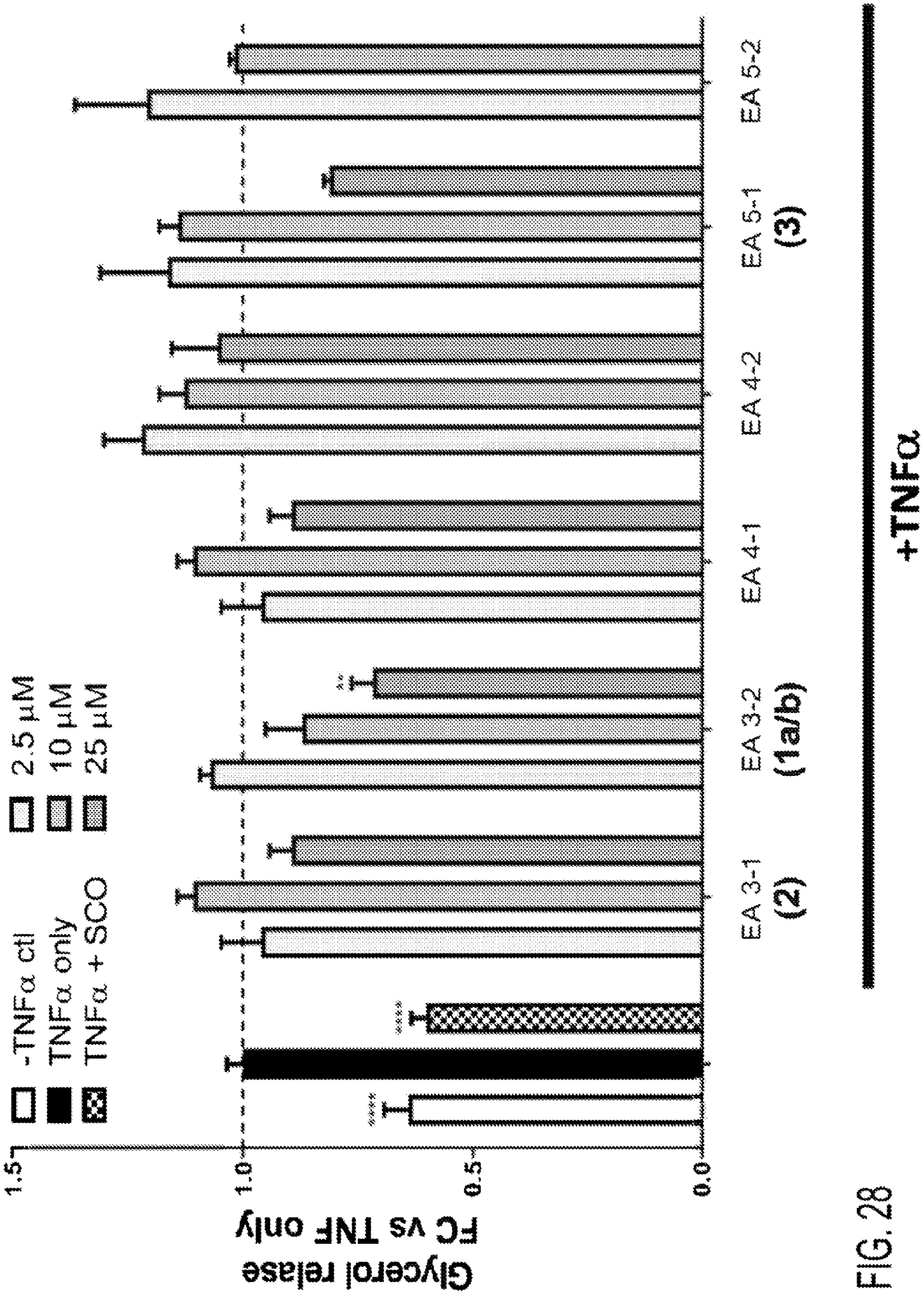

FIG. 28 shows Compounds from *A. scoparia* inhibit TNFα-induced lipolysis. Fully differentiated 3T3-L1 adipocytes pretreated for three days with 50 μg/ml SCO or varying doses of test compounds (2.5, 10, or 25 μM), then overnight with 0.75 nM TFNα (or vehicle). After 4 hours, the conditioned medium was collected and assayed for glycerol. Data was expressed as fold-change vs TNFα-only treatment. Data from no-TNFα controls and each test compound were analyzed by one-way ANOVA. P<0.01, **P<0.0001 vs TNFα-only condition.

Figure 29:
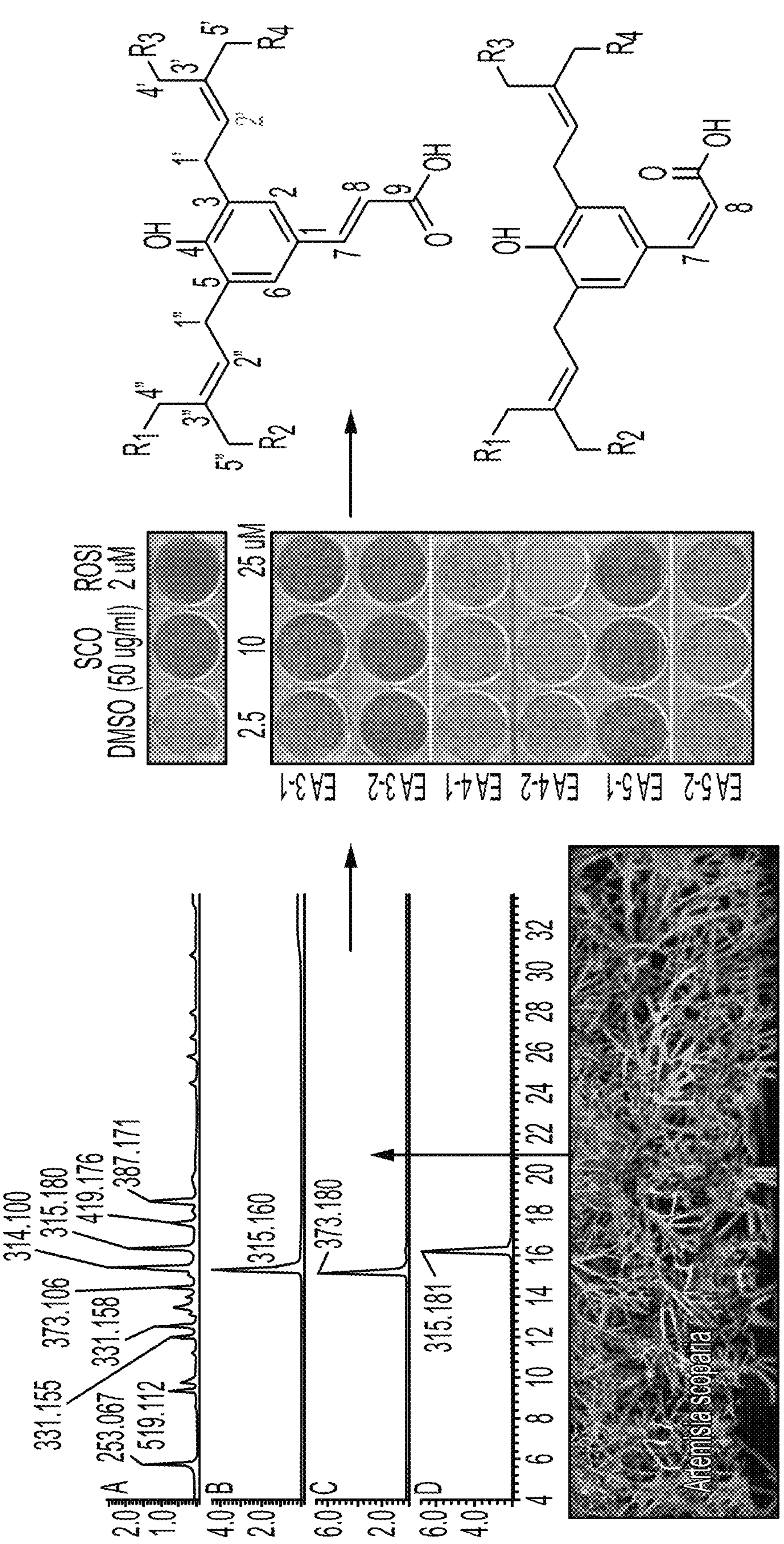

FIG. 29 shows a schematic.

Figure 30:
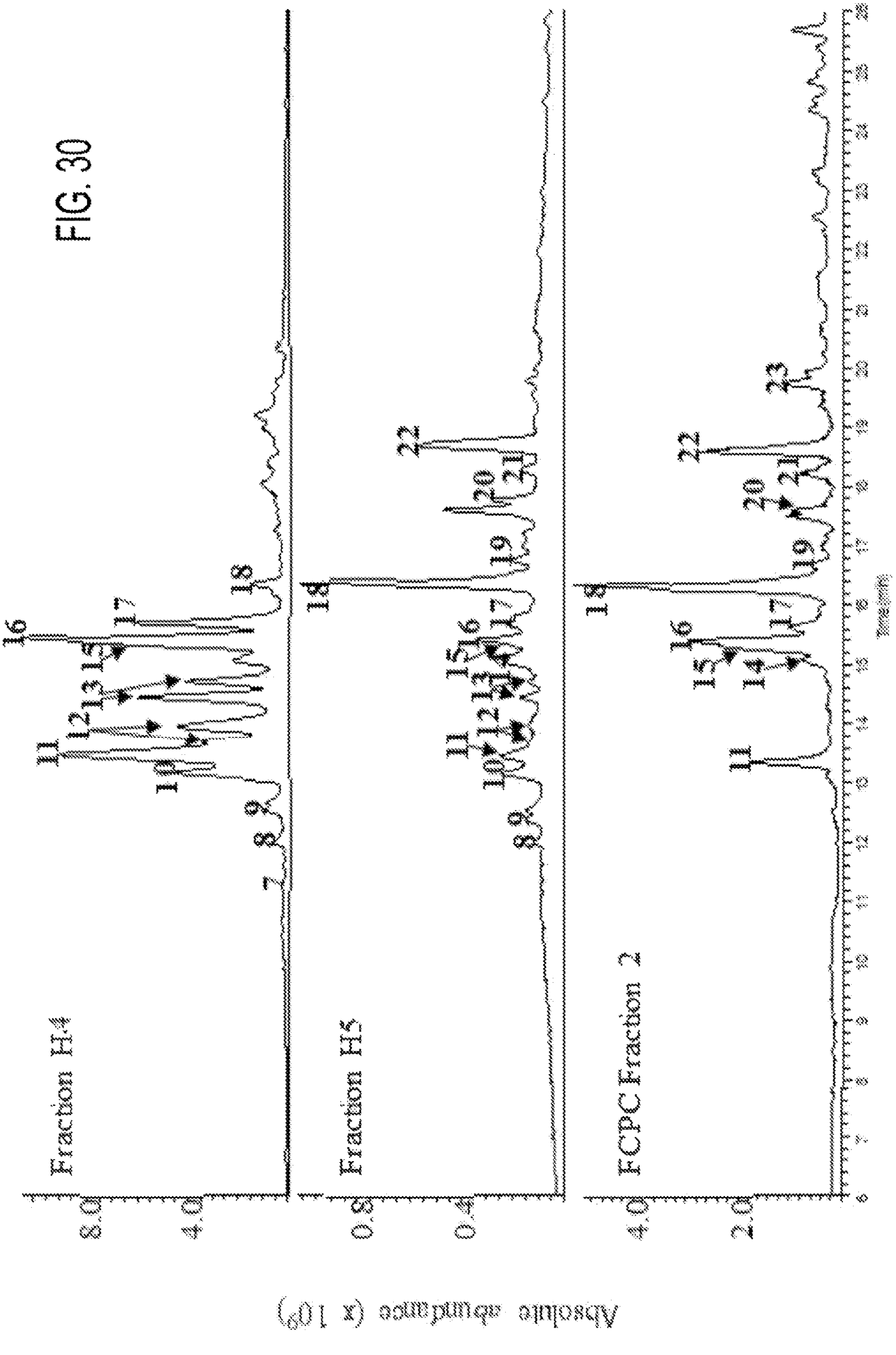

FIG. 30 (−) ESI MS total ion current chromatograms of three fractions of EA with pro-adipogenic activity.

Figure 31:
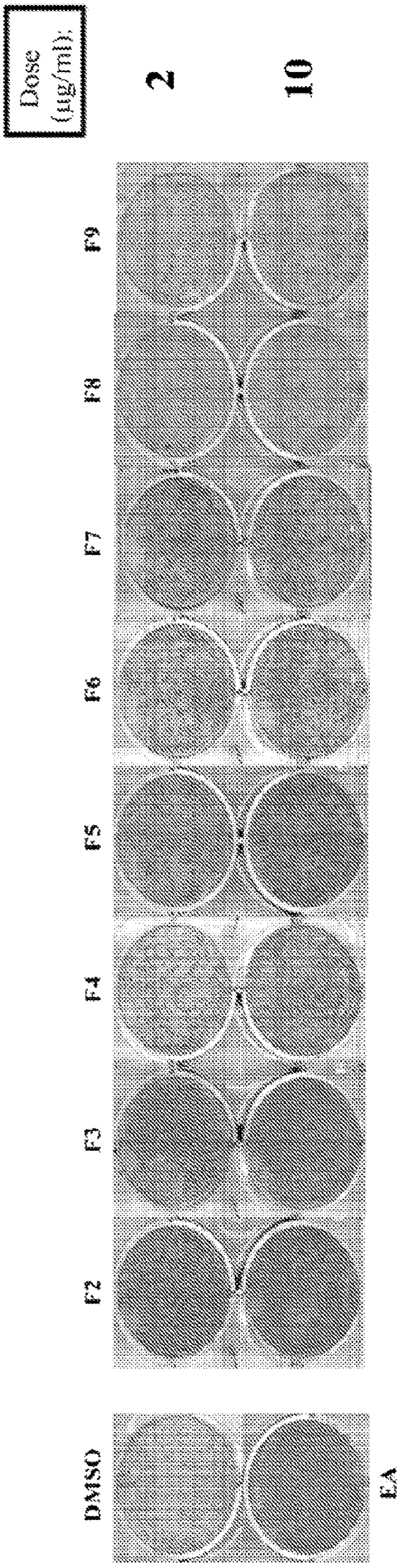

FIG. 31 shows adipogenesis in 3T3-L1 cells is enhanced by FCPC subfractions of EA. Cells were induced to differentiate using half-strength MDI cocktail containing DMSO vehicle, 20 μg/ml of EA, or 2 or 10 μg/ml of each FCPC subfraction of EA. 4 days after induction, cells were fixed, stained with Oil Red O, and scanned. Wells were treated and stained in triplicate; images shown are from one representative well for each condition.

Figure 32:
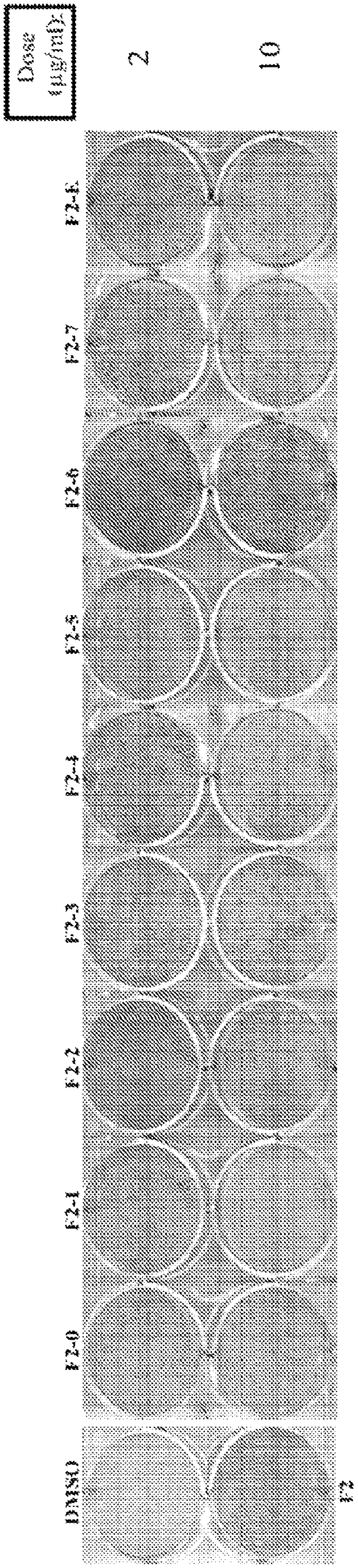

FIG. 32 shows adipogenesis in 3T3-L1 cells is enhanced by subfractions of EA-F2. Cells were induced to differentiate using half-strength MDI cocktail containing DMSO vehicle, 10 μg/ml of F2, or 2 or 10 μg/ml of each EA-F2 subfraction. 4 days after induction, cells were fixed, stained with Oil Red O, and scanned. Wells were treated and stained in triplicate; images shown are from one representative well for each condition.

Figure 33:
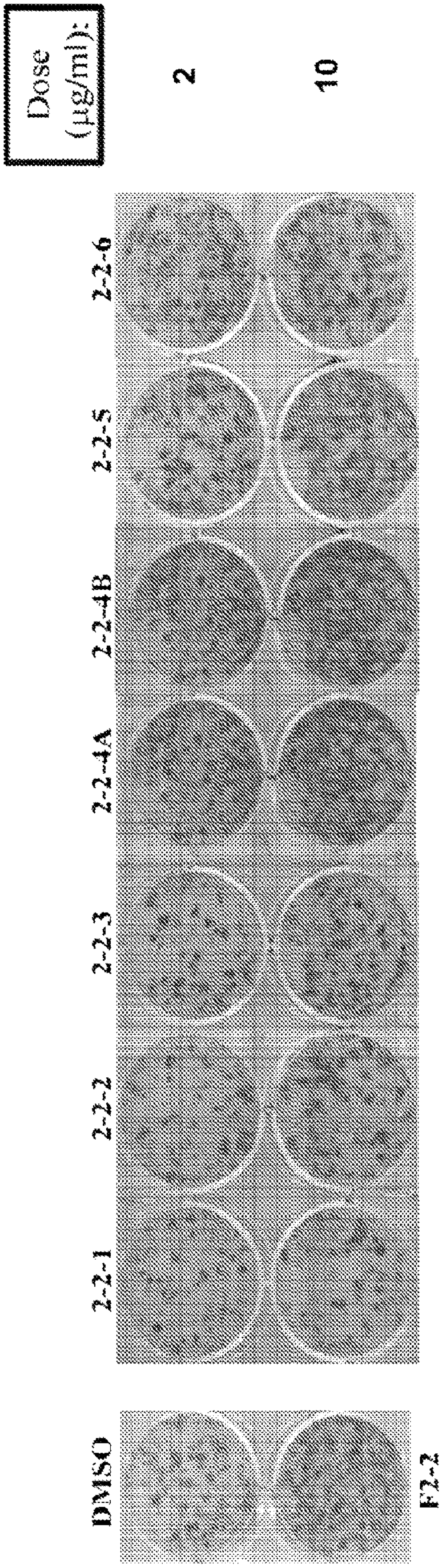

FIG. 33 shows adipogenesis in 3T3-L1 cells is enhanced by subfractions of EA-F2-2. Cells were induced to differentiate using half-strength MDI cocktail containing DMSO vehicle, 10 μg/ml of F2-2, or 5 or 20 μg/ml of each EA-F2 subfraction. 4 days after induction, cells were fixed, stained with Oil Red O, and scanned. Wells were treated and stained in triplicate; images shown are from one representative well for each condition.

Figure 34:
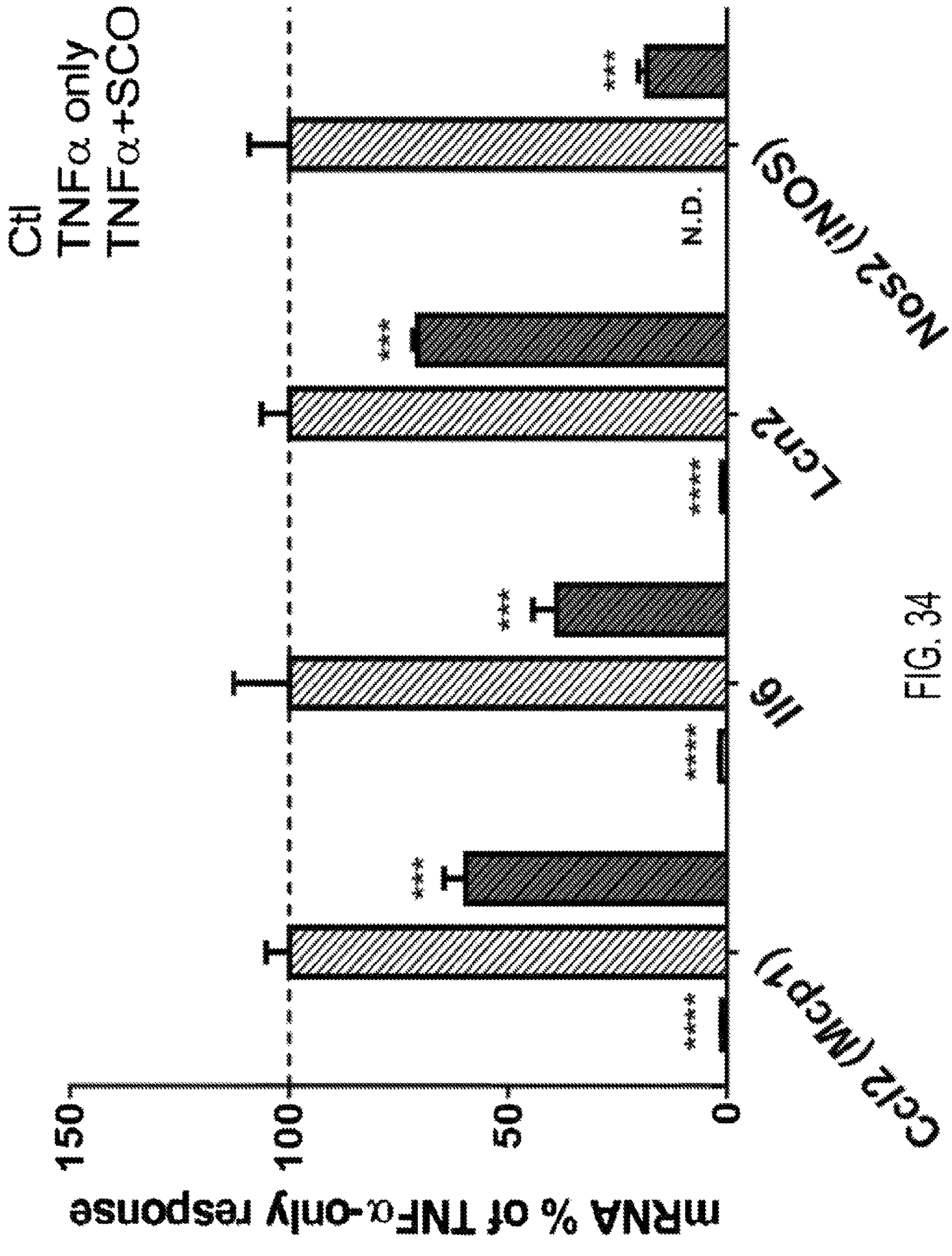

FIG. 34 shows SCO inhibits TNFα-induced expression of inflammatory genes in 3T3-L1 adipocytes. Mature 3T3-L1 adipocytes were pretreated with 50 μg/ml SCO for 3-days, then with 0.75 nM TNFα for 18 hours. Cells were harvested for RNA isolation, and gene expression was assayed by qPCR. Target gene data were normalized to the reference gene Nono. Fold-change was calculated versus the mean of TNFα-only controls for each gene. Data are shown as means+/−SE; n=4 biological replicates per condition. N.D.: Nos2 was below detection level for the qPCR assay. Data for each gene were analyzed by one-way ANOVA (for Ccl2, Il6, and Lcn2) or t-test (for Nos2). Significance expressed as *P<0.001, **P<0.0001 vs. TNFα-only controls. Results were replicated in two additional experiments on independent batches of cells.

Figure 35:
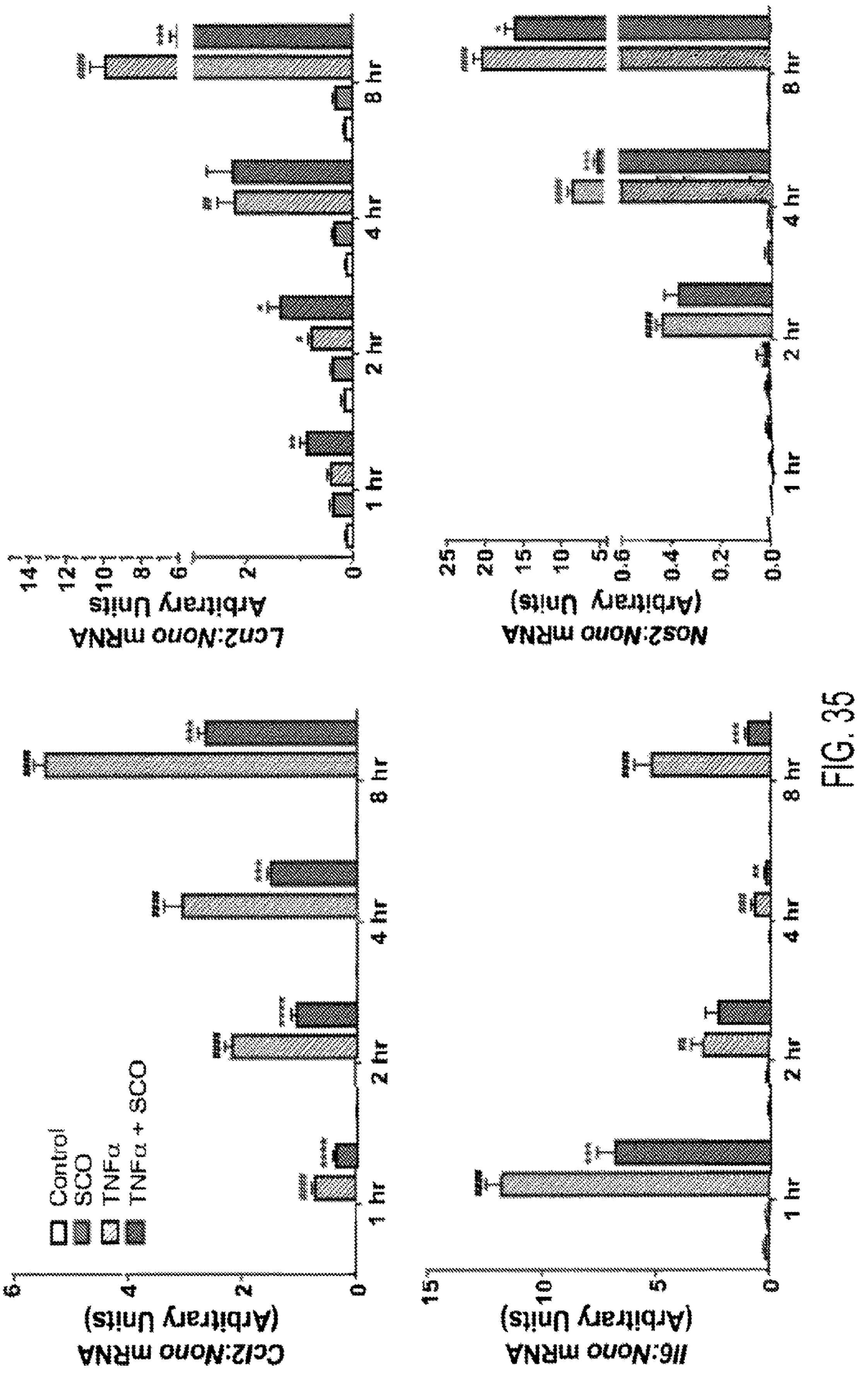

FIG. 35 shows Time course of TNFα- and SCO-induced changes in inflammatory gene expression. Mature 3T3-L1 adipocytes were pretreated with 50 μg/ml SCO or DMSO vehicle for 3 days prior to harvest. Media was replaced with low-glucose DMEM supplemented with 2% BSA, and cells were treated with 0.75 nM TNFα or 0.1% BSA vehicle for the times indicated and harvested for RNA isolation. Expression of the inflammatory genes was assessed by qPCR and normalized to the reference gene Nono. One-way ANOVA was performed for each time point. ##P<0.01, ###P<0.001, and ####P<0.0001 for effect of TNFα vs CON; *P<0.05, P<0.01, *P<0.001, and ****P<0.0001 for effect of SCO vs. respective controls (CON or TNFα only). Results were replicated on an independent batch of cells.

Figure 36:
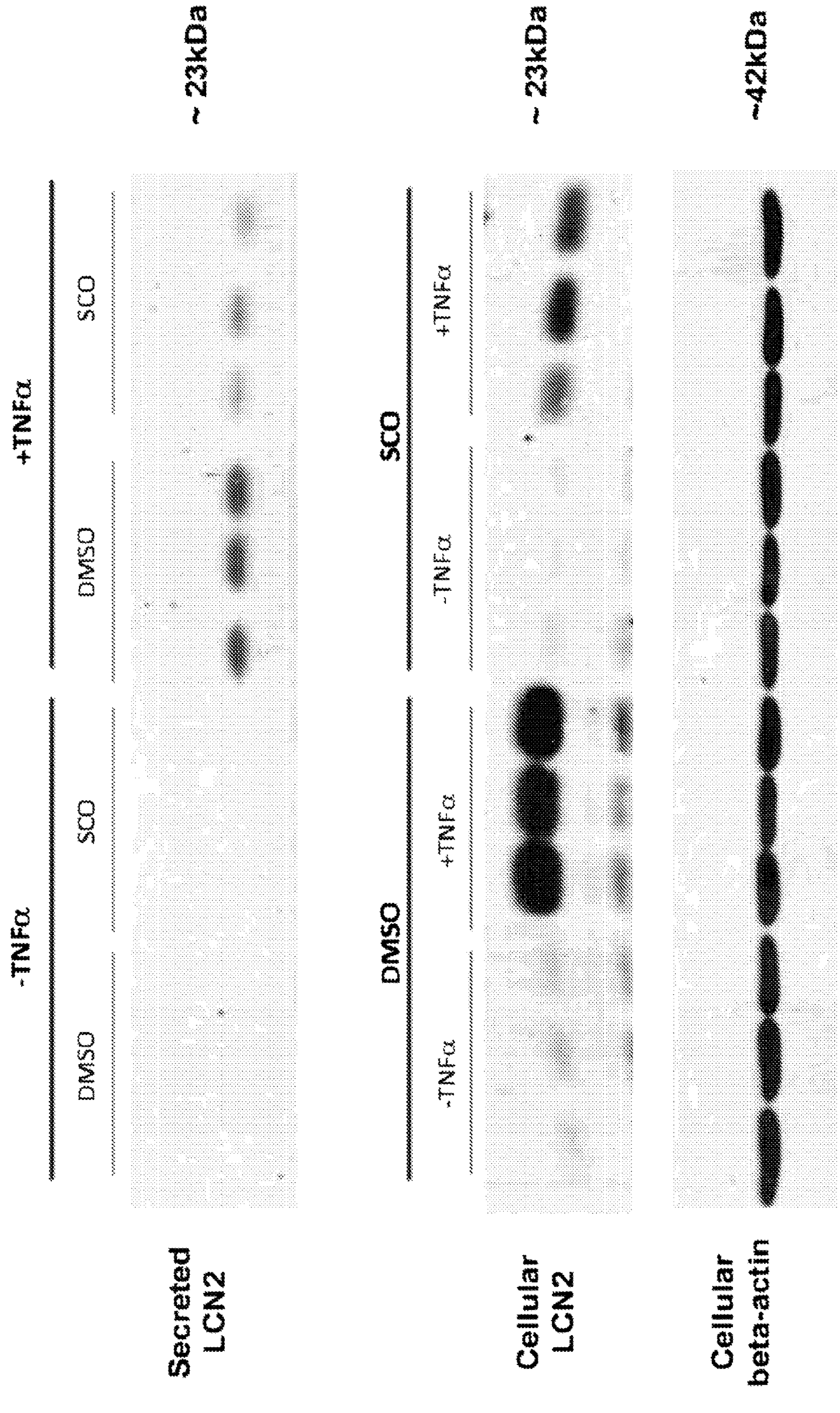

FIG. 36 shows SCO inhibits TNFα-induced cellular levels and secretion of LCN2 in adipocytes. Mature 3T3-L1 adipocytes were pretreated with 50 μg/ml SCO or DMSO vehicle for 3 days prior to harvest. On the last day of SCO treatment, cells were treated with 0.75 nM or 0.1% BSA vehicle for 18 hours. Medium on all cells was then replaced with low-glucose phenol-red-free DMEM containing either vehicle or 0.75 nM TNFα. After 4 hours, samples of conditioned media were collected and cells were harvested in RIPA buffer for immunoblotting. 125 μg (media) or 75 μg (whole-cell extracts) of total protein were loaded in each well.

Figure 37:
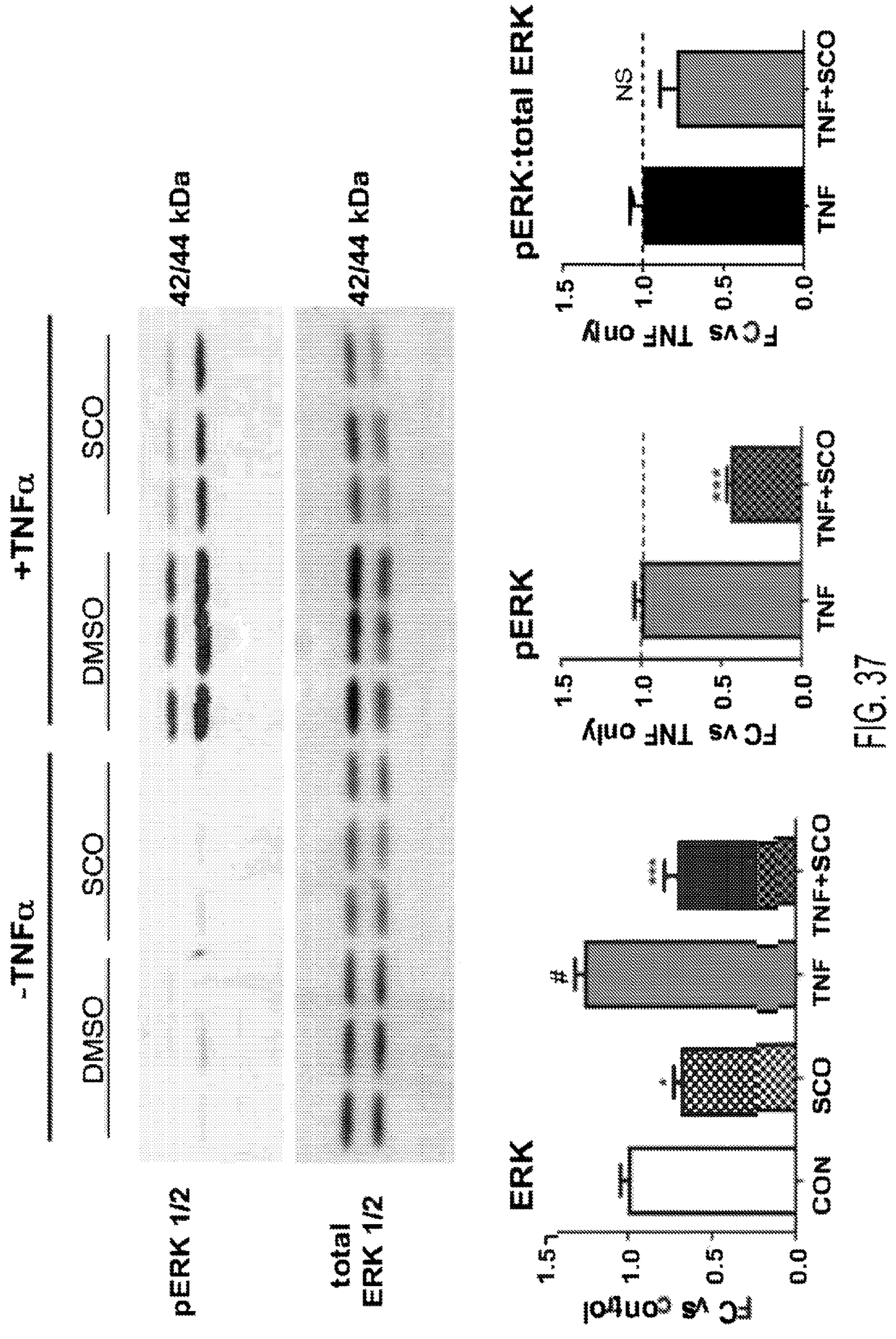

FIG. 37 shows SCO reduces total and phosphorylated ERK levels in 3T3-L1 adipocytes. Mature 3T3-L1 adipocytes were pretreated with 50 μg/ml SCO or DMSO vehicle for 3 days, with 18-hour (overnight) serum deprivation (0.3% BSA) and 0.5 nM TNFα treatment on the last day. Cells were harvested in RIPA buffer and analyzed by Western blot. Blot images and quantitation data are shown. *P<0.05 and ***P<0.001 for effect of SCO vs. respective controls (CON or TNFα only); #P<0.05 for effect of TNFα vs CON; NS: not significant. Results were replicated in two additional experiments on independent batches of cells.

Figure 38:
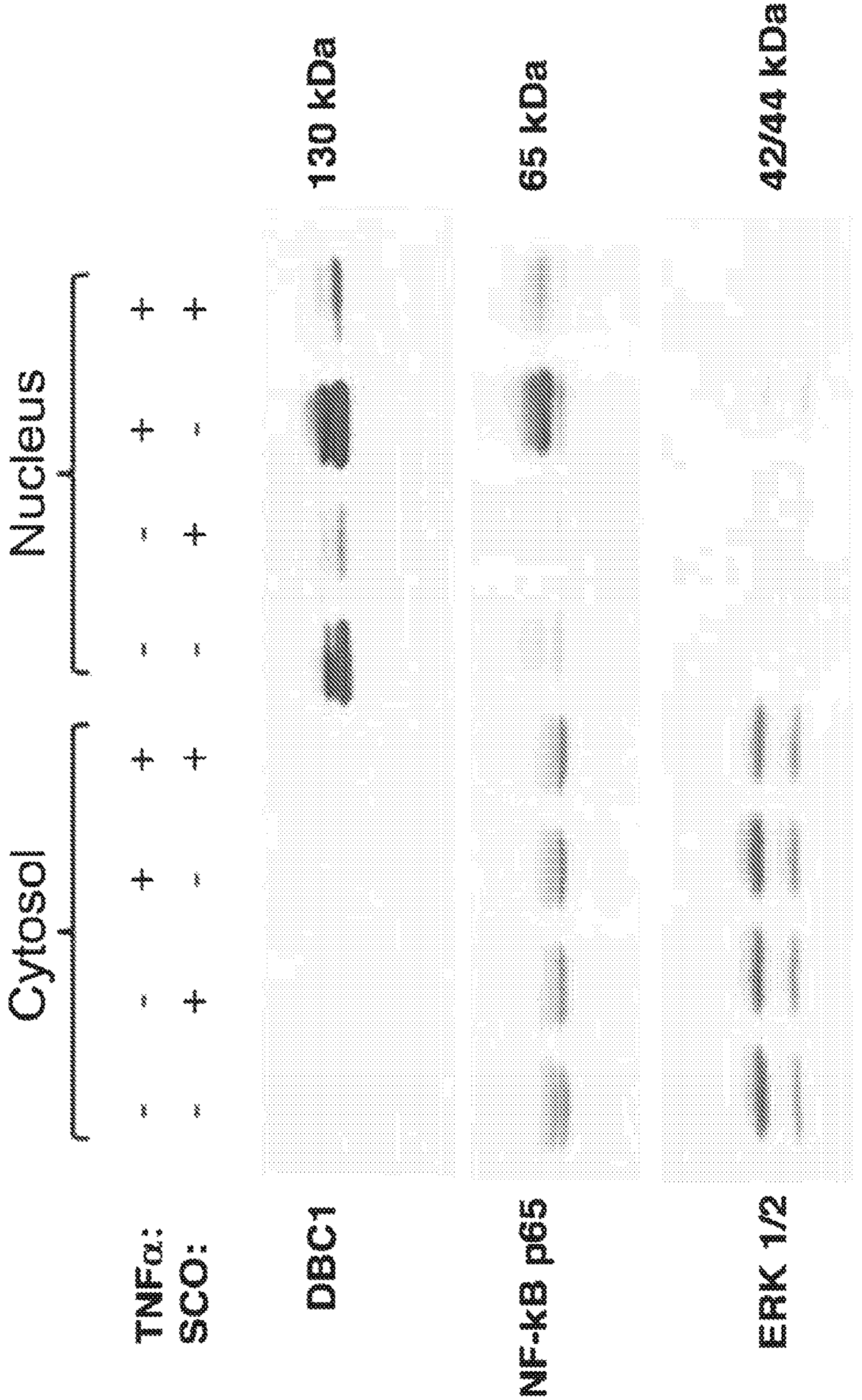

FIG. 38 shows SCO reduces nuclear DBC1 and TNFα-induced p65 nuclear translocation in 3T3-L1 adipocytes. Mature 3T3-L1 adipocytes were pretreated for 3 days with 50 μg/ml SCO or DMSO vehicle, then with 0.5 nM TNFα for 20 minutes. Cells were harvested, and the cytosolic and nuclear compartments were isolated. Immunoblotting was performed to detect DBC1, p65 phosphorylated at Ser536. ERK 1/2 was included as a loading control for the cytoplasmic fractions.

Figure 39:
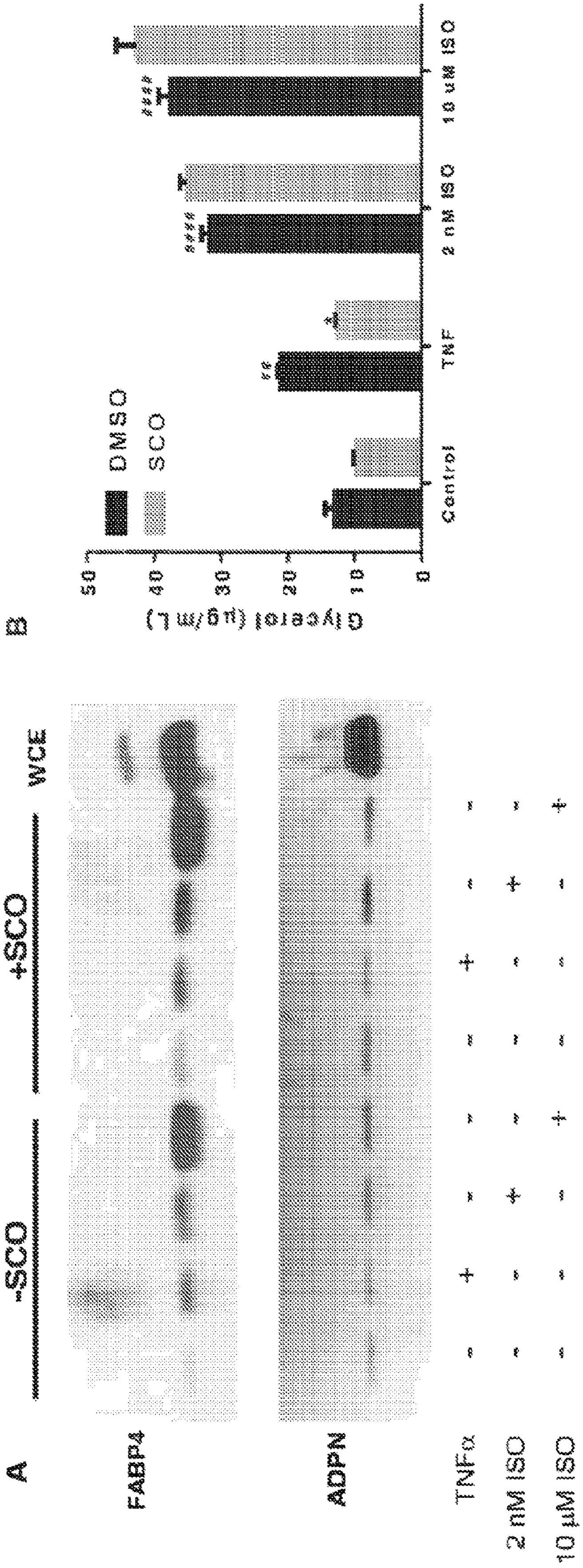

FIG. 39 shows SCO does not reduce TNFα- or isoproterenol-induced FABP4 secretion. Mature 3T3-L1 adipocytes were pretreated with 50 μg/ml SCO or DMSO vehicle for 3 days prior to harvest. On the last day of SCO treatment, cells were treated with 0.75 nM or 0.1% BSA vehicle overnight (18 hours). The following day, medium on all cells was replaced with low-glucose phenol-red-free DMEM containing either vehicle, 0.75 nM TNFα, 2 nM or 10 μM isoproterenol (ISO). Samples of conditioned media were collected after 4 hours. (Panel A) 75 μg of total protein were loaded in each well and analyzed with standard immunoblotting techniques. Membranes were probed for FABP4. Blot images are shown. WCE: whole-cell extract control lysate. (Panel B) 50 μl of conditioned media were also assayed for glycerol content. Effects of TNFα and isoproterenol versus control in the DMSO condition were analyzed by one-way ANOVA: ##P<0.01; ####P<0.0001 vs DMSO control. The effect of SCO was assessed in each condition versus the respective DMSO condition by t-tests. *P<0.05. All other interactions were non-significant.

Figure 40:
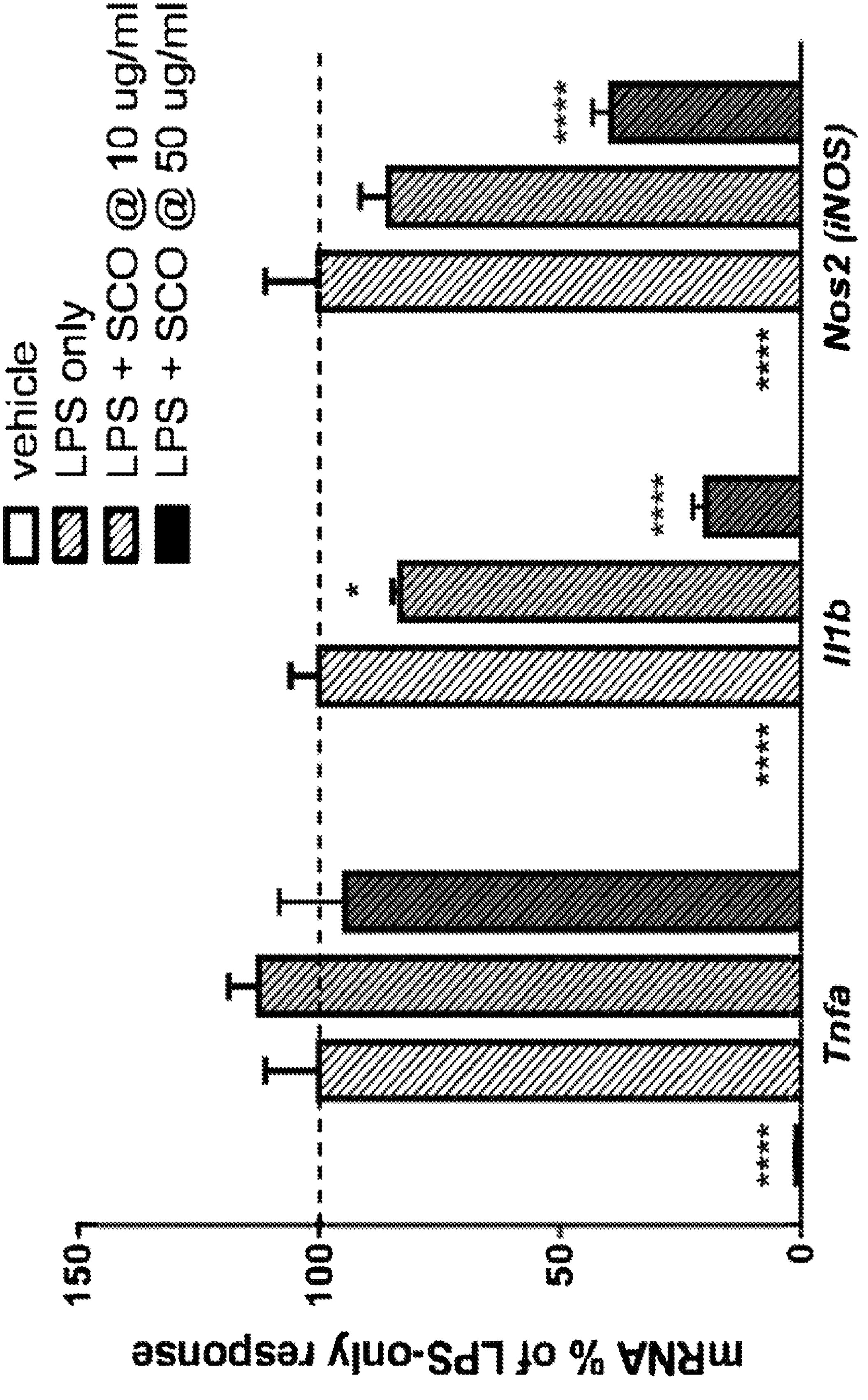

FIG. 40 shows SCO reduces LPS-induced expression of Il1b and Nos2 (iNOS), but not Tnfa in RAW 264.7 macrophages. RAW macrophages were pretreated with 10 or 50 μg/ml SCO for 2 hours, then with 1 μg/ml LPS for 5.5 hours. RNA was isolated and reverse transcribed. Gene expression was assayed by qPCR, using Nono as the reference gene, and fold-change was calculated versus the average of the LPS-only condition for each gene. Data are shown as means+/−SE; n=4 biological replicates per condition. Data for each gene were analyzed by one-way ANOVA. Significance expressed as *P<0.05, ****P<0.0001 vs. LPS-only controls. Results were replicated in three independent experiments.

Figure 41:
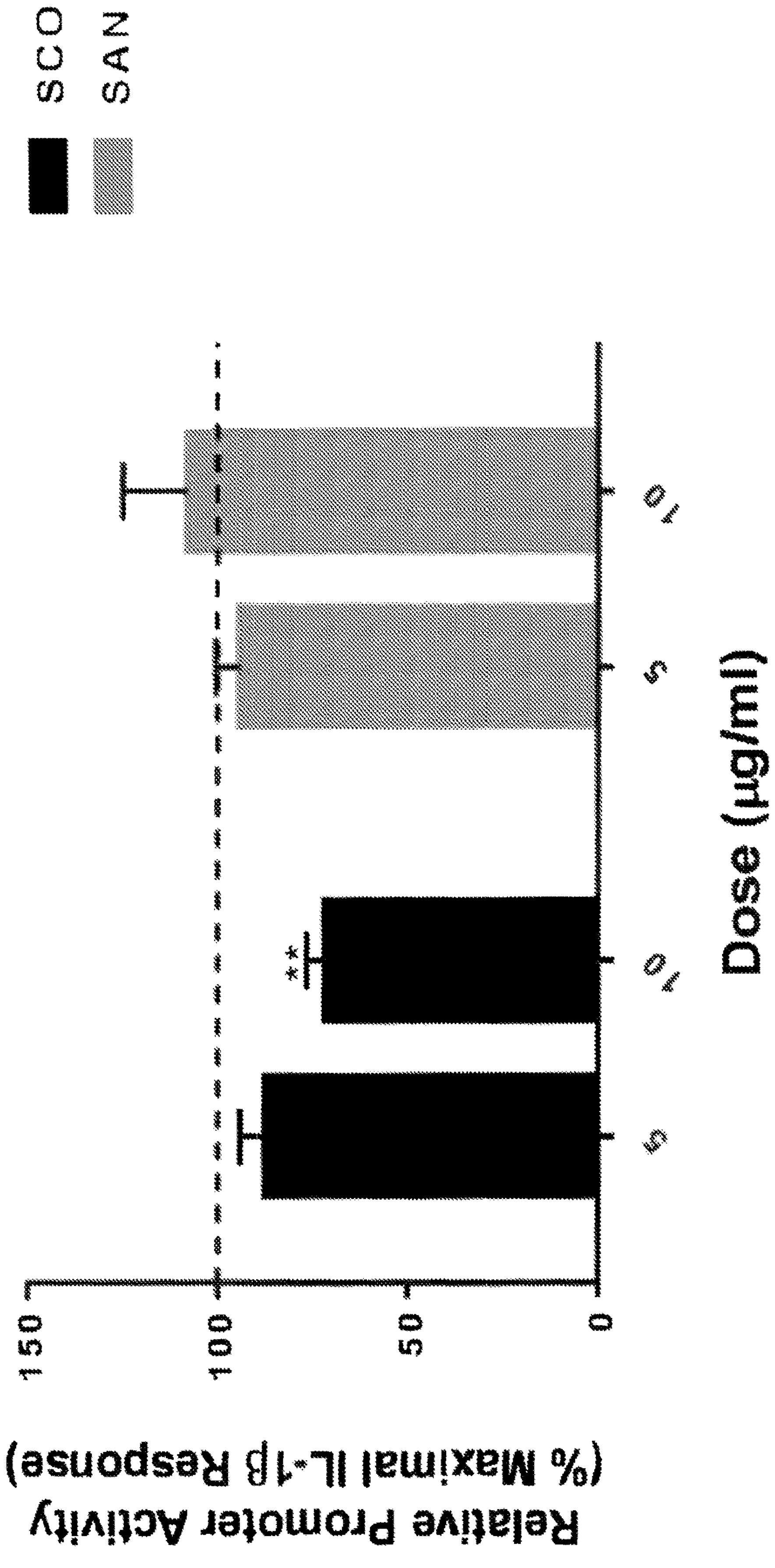

FIG. 41 shows SCO inhibits IL-10-stimulated NF-κB promoter activity in rat insulinoma cells. 832/13 cells were transduced with an adenovirus overexpressing a luciferase reporter construct driven by a promoter containing 5 copies of a consensus KB element (5×NF-κB-Luc). 12 h post-transduction, cells were untreated, or treated overnight with 5 and 10 μg/mL of SCO or an extract of *Artemisia santolinaefolia* (SAN). Cells were then stimulated for 4 h with 1 ng/mL IL-10. NF-kB promoter activity was induced 28.6-fold (for the SCO experiment) or 31.1-fold (for the SAN experiment) by IL-1b treatment. Promoter activity in cells pretreated with the extracts is expressed as % of this maximal induction. Data are means±SEM of 4 individual experiments, each performed in triplicate. **, P<0.01 versus control.

Figure 42:
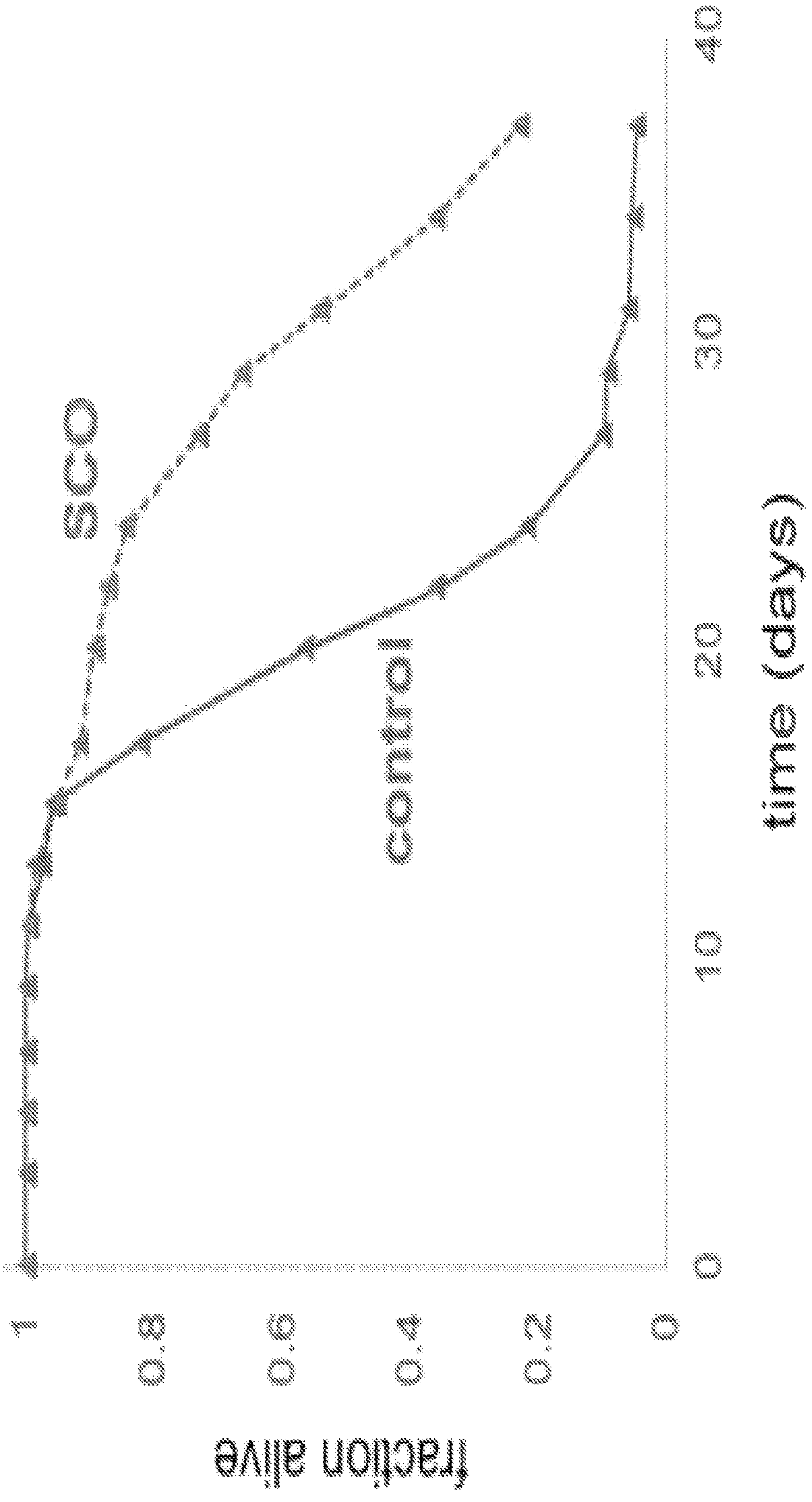

FIG. 42 shows SCO increases lifespan in *C. elegans*. Worms were cultured on NGM agar plates seeded with *E. coli* OP50 as a food source. The NGM medium was supplemented with either DMSO (control) or 500 μg/ml SCO. 200 worms were scored per condition. The fraction of worms alive at different time points is plotted.

DETAILED DESCRIPTION OF THE INVENTION

Throughout human history, botanicals have been used as therapeutics, and many pharmaceuticals in use today have been derived, directly or indirectly, from plant compounds. A primary challenge in botanical research is that plant extracts are comprised of hundreds of compounds, and it is difficult to identify which of these compounds confer biological activity. Also, the isolation of specific compounds from plant extracts can be challenging.

*Artemisa scoparia* is a Eurasian species in the genus *Artemisia*, in the sunflower family. Dozens of extract fractions were screened for their ability to promote adipocyte development, as has been shown for parent SCO extracts isolated from *Artemisia scoparia* (SCO). As described herein, the inventors have identified the structures of at least three botanically-derived compounds that are active ingredients within SCO extracts, all of which are prenylated coumaric acid derivatives (PCAs). Two of these compounds, capillartemisin A and capillartemisin B, have been previously reported in *A. scoparia* (Kitagawa et al. 1983), but until now their use to treat metabolic disease remained unknown. The third compound, for example, the compound of Formula I or Formula II, was previously unknown. As described herein, pharmaceutical compositions comprising these botanically-derived compounds can promote adipocyte differentiation and, without wishing to be bound by theory, improve overall metabolic health based on studies of parent SCO extract in diabetic mice.

Detailed descriptions of one or more embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context dictates otherwise. The use of the word "a" or "an" when used in conjunction with the term "comprising" in the claims and/or the specification can refer to "one," but it is also consistent with "one or more," "at least one," and "one or more than one."

Wherever any of the phrases "for example," "such as," "including" and the like are used herein, the phrase "and without limitation" is understood to follow unless explicitly stated otherwise. Similarly, "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" refers to the process including at least steps a, b and c. Wherever the terms "a" or "an" are used, "one or more" is understood, unless such interpretation is nonsensical in context.

As used herein the term "about" is used herein to refer to approximately, roughly, around, or in the region of. When the term "about" is used in conjunction with a numerical range, it modifies that range by extending the boundaries above and below the numerical values set forth. For example, the term "about" is used herein to modify a numerical value above and below the stated value by a variance of 20 percent up or down (higher or lower).

As described herein, aspects of the invention refer to compositions and methods comprising botanically-derived extracts and compounds.

As used herein, "botanical" can refer to a material that is or may be tree-, plant-, weed- or herb-derived. As used herein, "botanically derived" can refer to a material capable of having been derived from a botanical, as by isolation or extraction; however, "botanically derived" is not limited in this application to materials which actually are isolated or extracted from a botanical, but also includes materials obtained commercially or synthetically. As used herein, Aspects of the invention are drawn to botanically-derived compounds isolated from *Artemisa scoparia*. For example, the botanically-derived compounds can include, but are not limited to:

Formula (I)

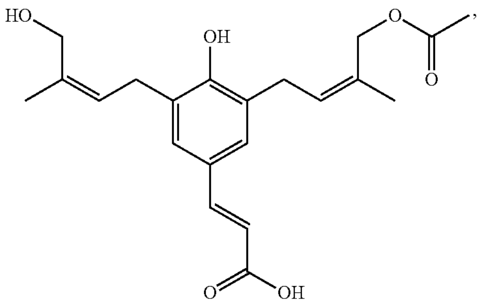

Formula (II)

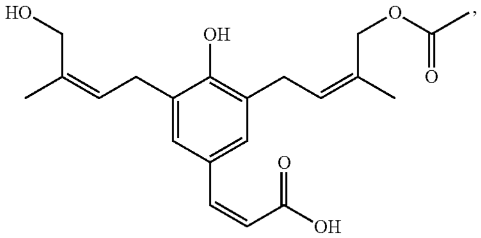

Formula (III)

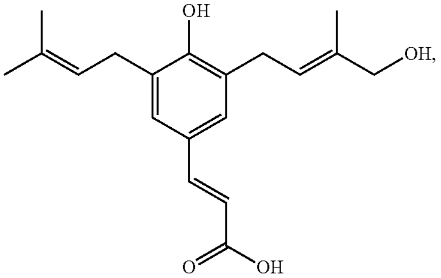

or

Formula (IV)

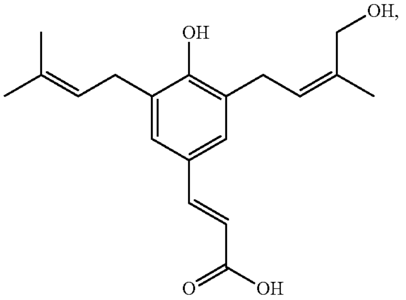

Embodiments can further comprise "isomers" of the botanically-derived compounds. The term "isomer" can refer to compounds that have the same composition and molecular weight, but differ in physical and/or chemical properties. Such substances have the same number and kind of atoms but differ in structure. The structural difference may be in constitution (geometric isomers) or in an ability to rotate the plane of polarized light (stereoisomers). See, for example, Formula (I) and Formula (II), which each have the chemical formula of $C_{21}H_{26}O_6$, exact mass of 374.1729, and molecular weight of 374.4330.

The term "botanically-derived extract", "plant extract", or "botanical extract" can refer to any extract obtainable from a plant or any portion thereof. For example, the plant extract can comprise the active ingredient/s thereof. Thus, the plant extract can be obtained from the fruit, the skin or rind of the fruit, the seeds, the bark, the leaves, the roots, the rhizome, the root bark or the stem of a plant, or a combination of same. In embodiments, "extracted" or an "extraction" can refer to the process and product, respectively, of separating a substance from a matrix wherein the matrix can be solid or liquid. In embodiments, the matrix is a plant, a plant product, or extract thereof. As used herein the term "botanical composition" can refer to a composition that is comprises material derived from a plant, a part of a plant, or a combination thereof.

The botanically-derived extract can be obtained from *Artemisa scoparia*. According to an embodiment of the invention, the plant extract is an aqueous extract, a hydrophilic extract, a non-polar extract or a polar extract. For example, the plant extract is an ethanolic extract. A representative extraction procedure includes the one disclosed in Boudreau, Anik, et al. "Distinct fractions of an *Artemisia scoparia* extract contain compounds with new adipogenic bioactivity." *Frontiers in nutrition* 6 (2019): 18, which is incorporated by reference herein in ites entirety. Plant extracts can be divided into polar and non-polar extracts, and hydrophilic and hydrophobic extracts.

Thus, the plant extracts can be purified by the use of a polar solvent (i.e. polar extract) such as, without being limited to, ethyl alcohol (ethanol), butyl alcohol (butanol), methanol, water, acetic acid, tetrahydrofuran, N,N-dimethylformamide, dichloromethane, ethyl acetate, acetonitrile, dimethylformamide, dimethyl sulfoxide, acetone, or n-propanol. As used herein, the term "solvent" can refer to a substance capable of dissolving or dispersing one or more substances. As used herein, the term "polar solvent" can refer to a solvent that comprises dipole moments. For example, a polar solvent can be miscible with water and polar solvents. For example, a polar solvent can comprise chemical species in which the distribution of electrons between covalently bonded atoms is not even. For example, the polarity of solvents can be assessed by measuring any parameter known to those of skill in the art, including dielectric constant, polarity index, and dipole moment (see, e.g., Przybytec (1980) "High Purity Solvent Guide," Burdick and Jackson Laboratories, Inc.). The polar extracts of the invention can comprise any percentage of polar solvent including, but not limited to, for example 1-10% polar solvent, 10-20% polar solvent, 20-30% polar solvent, 30-40% polar solvent, 40-50% polar solvent, 50-60% polar solvent, 70-80% polar solvent, 80-90% polar solvent and 90-100% polar solvent.

In other embodiments, the plant extracts can be purified by the use of a non-polar solvent (i.e. non-polar extract) such as, without being limited to, isooctane, hexane, pentane, benzene, chrloroform, diethyl ether, hydrocarbons, cyclohexane, toluene, or 1,4-dioxane. As used herein, "nonpolar" and "non-polar" can be used interchangabely. As used herein, the term "nonpolar solvent" can refer to a solvent comprising molecules that do not have an overall dipole. For example, the solvent comprises molecules comprising bonds between atoms with similar electrogenativities (e.g. a carbon-hydrogen bond). For example, the nonpolar molecule comprises equal sharing of electrons between atoms or the arrangement of polar bonds leads to overall no net molecular dipole moment. The non-polar extracts of the invention can comprise any percentage of non-polar solvent, including but not limited to, for example, 1-10% non-polar solvent, 10-20% non-polar solvent, 20-30% non-polar solvent, 30-40% non-polar solvent, 40-50% non-polar solvent, 50-60% non-polar solvent, 70-80% non-polar solvent, 80-90% non-polar solvent, and 90-100% non-polar solvent.

Hydrophobic molecules can be non-polar and thus can interact with (e.g. associate, aggregate, etc.) other neutral molecules and non-polar solvents. For example, nonpolar or hydrophobic molecules can interact through non-covalent interactions. For example, the non-covalent interaction is a van der Waals interaction. For example, the van der Waals interaction are London forces. Hydrophilic molecules can be polar and dissolve by water and other polar substances.

Thus, the plant extracts of the invention can be produced by any method known in the art including a polar extract such as a water (aqueous) extract or an alcohol extract (e.g., butanol, ethanol, methanol, hydroalcoholic, see for example Swanson R L et al., 2004, Biol. Bull. 206: 161-72) or a non-polar extract (e.g., hexane or isooctane, see for example, Ng L K and Hupe M. 2003, J. Chromatogr A. 1011: 213-9; Diwanay S, et al., 2004, J. Ethnopharmacol. 90: 49-55.

Regardless of the exact solvent employed, plant extracts can be made by placing a plant sample (e.g., leaves, seeds) in a mortar along with a small quantity of liquid (e.g., 10 ml of water, alcohol or an organic solvent for every 2 grams of plant sample) and grinding the sample thoroughly using a pestle. When the plant sample is completely ground, the plant extract is separated from the ground plant material, such as by centrifugation, filtering, cation-exchange chromatography, and the like, and the collected liquid can be further processed if need be (such as by a concentrating column and the like), active ingredients can be separated from this extract via affinity chromatography, mass chromatography and the like.

Extraction methods are known to the skilled artisan. See, for example, Boudreau, Anik, et al. "Distinct fractions of an *Artemisia scoparia* extract contain compounds with new adipogenic bioactivity." Frontiers in nutrition 6 (2019): 18, which is incorporated herein by reference in its entirety.

For example, ethanolic extracts can be prepared from greenhouse-grown plants as described in the literature. The ethanolic extract of *Artemisia scoparia* (SCO, 10 g) can be dissolved in water (200 ml) and partitioned 3 times with hexane (3×200 ml). Hexane partitions can be combined and dried by rotary evaporation to produce the H crude fraction. The water portion can be further partitioned 3 times with ethyl acetate (3×200 ml). The ethyl acetate (EA) partitions can be combined and dried by rotary evaporation to produce the EA crude fraction. Remaining water can be dried of residual solvents by rotary evaporation and by freeze drying to produce the W crude fraction.

The SCO EA crude fraction can be fractionated using a semipreparatory high-performance liquid chromatography (HPLC) system consisting of Waters™ Alliance e2695 Separations Module and 2998 Photodiode Array Detector with a Phenonmenex Synergi 4 μm 80 Å Hydro-RP column 250×21.2 mm. The mobile phases consisted of two components: Solvent A (0.5% ACS grade acetic acid in double distilled de-ionized $H_2O$), and Solvent B (acetonitrile). Separation can be completed using a gradient run of 25% B in A to 95% B over 35 min at a flow rate of 8 mL/min. Five fractions, H1-H5, can be obtained.

The SCO EA crude fraction can also be subjected to fast centrifugal partition chromatography (FCPC) fractionation using countercurrent chromatography separation (CCS) with a biphasic solvent system (HEMWat+3) composed of Hexanes/Ethyl-Acetate/Methanol/Water (6:4:6:4 v/v) on a Kromaton (Annonay, France) bench-scale fast centrifugal partition chromatography system FCPC1000, v 1.0, equipped with a 1,000 ml volume rotor. For fractionation, the column can be first filled with the lower phase 40 ml/min using a Chrom Tech® PR-Pump while rotating at 300 rpm.

The system can be then equilibrated with upper phase at a flow rate of 10 ml/min and 750 rpm. A 2 g sample of SCO can be suspended in 10 ml of each phase of the solvent system used for separation, sonicated and filtered (Millipore filter type NY11). The sample can be injected with the upper phase flow at 10 ml/min and rotor rotation of 750 rpm. UV detection can be performed at 254 nm using a Visacon VUV-24 detector, and fractions can be collected manually. Ten fractions, F1-F10, can be obtained.

F2 of the above FCPC fractions can be further fractionated using a semipreparatory HPLC system consisting of Waters™ 600 Controller and 486 Tunable Absorbance Detector with a Phenonmenex Synergi 10 μm 80 Å MAX-RP column 250x21.2 mm. The mobile phases consisted of two components: Solvent A (0.10% ACS grade acetic acid in double distilled deionized $H_2O$), and Solvent B (100% acetonitrile). For the initial separation, a gradient run of 40% B in A to 70% B over 35 min was used at a flow rate of 15 ml/min. SCO fraction 2-2 can be further fractionated using the same semipreparatory HPLC system with a Phenomenex Kinetex 5 μm C18 100 Å LC column 250×10.0 mm. The mobile phases consisted of two components: Solvent A (0.1% ACS grade formic acid in double distilled de-ionized $H_2O$), and Solvent B (100% acetonitrile). For the secondary separation, a gradient run of 40% B in A to 80% B over 80 min was used at a flow rate of 5 ml/min. Fractions can be collected manually as defined by UV (254 nm) peak designations for both separations.

The plant extracts can be further treated to purify those active ingredients such as those having biological activities described herein. Active ingredients can be purified from plant extracts or used synthetically. In embodiments, active ingredients can refer to an ingredient that is biologically active. In embodiments, biological activity can refer to the in vivo activities of a compound, such as physiological responses that result upon in vivo administration of a compound, composition comprising the compound, or other mixtures.

For example, the active ingredients present in the plant extracts of the invention can include, but are not limited to:

Formula (V)

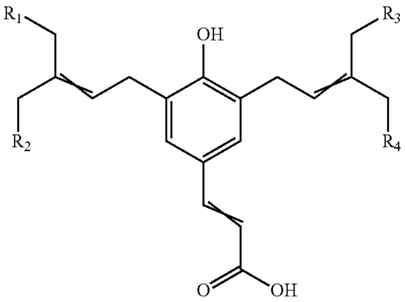

wherein  bonds can be cis or trans; $R_1$ comprises H, OH, and OAc, $R_2$ comprises H, OH, and OAc; $R_3$ comprises H, OH, and OAc; $R_4$ comprises H, OH, and OAc, or any combination thereof.

For example, the active ingredients present in the plant extracts of the invention can include, but are not limited to:

Formula (I)

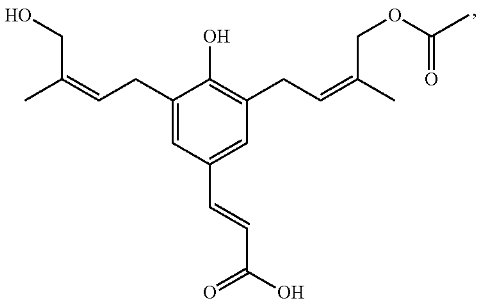

Formula (II)

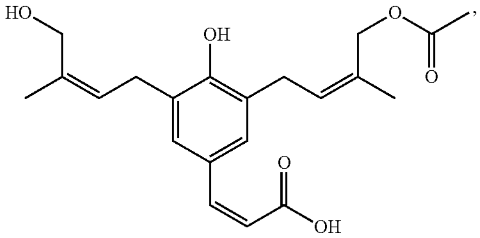

Formula (III)

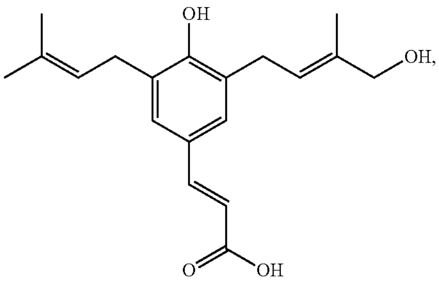

or

Formula (IV)

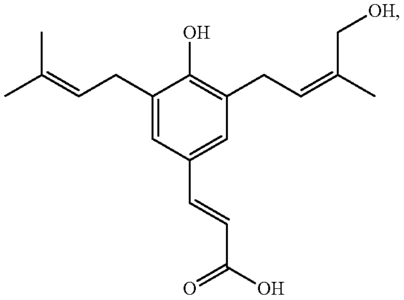

Aspects of the invention are drawn to pharmaceutical compositions, such as those useful for preventing or treating a metabolic disorder. In embodiments, the compositions of the disclosure can comprise a single botanically-derived extract or can comprise several botanically derived extracts. In other embodiments, the compositions of the disclosure can comprise a single botanically-derived compound or can comprise several botanically-derived compounds. Thus, according to one embodiment of the disclosure, the composition comprises an *Artemisia scoparia* plant extract or compounds isolated therefrom (i.e., Formula (I), Formula (II), Formula (III), Formula (IV), or Formula (V)).

The concentration of the plant extract or compounds therefrom within the composition can vary, such as dependent on the therapeutic effect desired and/or the extraction method utilized. For example, a concentration of each of the plant extract or compounds therefrom within the composition can be in a range of about 0.01 to 10%, 10% to 20%, 20% to 30%, 30% to 40%, 40% to 50%, 50% to 60%, 60% to 70%, 70% to 80%, 80% to 90%, or 90% to 100%.

The compositions of the disclosure can be administered to the subject per se, or in a pharmaceutical composition. As used herein a "pharmaceutical composition" can refer to a preparation of one or more active ingredient(s) described herein, such as Formula I, Formula II, Formula III, Formula IV, or Formula V, with other chemical components such as physiologically suitable carriers and excipients. The purpose of the composition is to facilitate administration of the active ingredients (e.g., botanically-derived extract) to the subject.

As used herein the term "active ingredient" can refer to the botanically-derived extract, compositions isolated therefrom, or a synthetic composition derived therefrom that is biologically active. For example, one or more active ingredients can be accountable for the intended biological effect (i.e., for treatment or prevention of a metabolic disease).

Embodiments herein can further comprise one or more one or more additional active agents. The phrase "additional active agent" can refer to an agent, other than a compound(s) of the inventive composition, that exerts a pharmacological, or any other beneficial activity. Such additional active agents include, but are not limited to, an antidiabetic agent, a corticosteroid, or an anti-obesity agent. In embodiments, the additional active agent can synergize with one or more of the botanically-derived composition. For the example, the additional active agent can comprise one or more botanically-derived compound(s) or composition(s), such as from a fraction of a SCO extract. For example, the additional active agent can comprise a synthetic compound, for example a synthetic compound based on or derived from a compound of a botanical extract. In embodiments, the additional active agent can comprise a pharmaceutical or a drug, such as but not limiting to a glucocorticoid.

The phrases "physiologically acceptable carrier" and "pharmaceutically acceptable carrier" which can be interchangeably used can refer to a carrier, excipient, or diluent that does not cause significant irritation to the subject and does not abrogate the biological activity and properties of the administered active ingredients. An adjuvant is included under these phrases.

The term "excipient" can refer to an inert substance added to the composition (pharmaceutical composition) to further facilitate administration of an active ingredient of the present invention.

Techniques for formulation and administration of drugs can be found in "Remington's Pharmaceutical Sciences," Mack Publishing Co., Easton, Pa., latest edition, which is incorporated herein by reference.

The pharmaceutical compositions can be formulated for numerous types of administrations. For example, suitable routes of administration can, for example, include oral, rectal, transmucosal, transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

One can administer the pharmaceutical composition in a local rather than systemic manner, for example, by injecting the composition including the active ingredient (e.g., plant extract or compounds isolated therefrom) and a physiologically acceptable carrier directly into a tissue region of a patient.

In one embodiment, the pharmaceutical composition is formulated for oral administration. As used herein the phrase "oral administration" can refer to administration of the composition of the disclosure by mouth e.g. in the form of a liquid, a solution, a tablet, a capsule, a tincture, a gummy, or an elixir.

In another embodiment, the pharmaceutical composition is formulated for administration by injection.

Compositions of the disclosure can be manufactured by processes well known in the art, e.g., by means of conventional mixing, dissolving, granulating, dragee-making, levigating, emulsifying, encapsulating, entrapping or lyophilizing processes.

Compositions for use in accordance with embodiments of the invention thus can be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the composition can be formulated in aqueous solutions, such as in physiologically compatible buffers such as Hank's solution, Ringer's solution, or physiological salt buffer. For transmucosal administration, penetrants appropriate to the barrier to be permeated are used in the formulation. Such penetrants are known in the art.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). The composition can be sterile and can be fluid to the extent that easy syringability exists. It can be stable under the conditions of manufacture and storage and can be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In embodiments, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the compound in the required amount in an appropriate solvent with one or a combination of ingredients enumerated herein, as required, followed by filtered sterilization. Dispersions can be prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

For oral administration, the composition can be formulated readily by combining the active compounds with carriers (e.g. pharmaceutically acceptable carriers) known in the art. Such carriers enable the composition to be formulated as tablets, pills, dragees, capsules, liquids, tinctures, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients can be fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). For example, disintegrating agents can be added, such as cross-linked polyvinyl pyrrolidone, agar, or alginic acid or a salt thereof such as sodium alginate.

Dragee cores are provided with suitable coatings. For this purpose, concentrated sugar solutions can be used which can contain gum arabic, talc, polyvinyl pyrrolidone, carbopol gel, polyethylene glycol, titanium dioxide, lacquer solutions and suitable organic solvents or solvent mixtures. Dyestuffs or pigments can be added to the tablets or dragee coatings for identification or to characterize different combinations of active compound doses.

Compositions which can be used orally, include push-fit capsules made of gelatin as well as soft, sealed capsules made of gelatin and a plasticizer, such as glycerol or sorbitol. The push-fit capsules can contain the active ingredients in admixture with filler such as lactose, binders such as starches, lubricants such as talc or magnesium stearate and, optionally, stabilizers. In soft capsules, the active ingredients can be dissolved or suspended in suitable liquids, such as fatty oils, liquid paraffin, or liquid polyethylene glycols. In addition, stabilizers can be added. All formulations for oral administration should be in dosages suitable for the chosen route of administration.

For buccal administration, the compositions can take the form of tablets or lozenges formulated in conventional manner.

The composition described herein can be formulated for parenteral administration, e.g., by bolus injection or continuous infusion. Formulations for injection can be presented in unit dosage form, e.g., in ampoules or in multidose containers with optionally, an added preservative. The compositions can be suspensions, solutions or emulsions in oily or aqueous vehicles, and can contain formulatory agents such as suspending, stabilizing and/or dispersing agents.

Compositions for parenteral administration include aqueous solutions of the active preparation in water-soluble form. Additionally, suspensions of the active ingredients can be prepared as appropriate oily or water-based injection suspensions. Suitable lipophilic solvents or vehicles include fatty oils such as sesame oil, or synthetic fatty acids esters such as ethyl oleate, triglycerides or liposomes. Aqueous injection suspensions can contain substances, which increase the viscosity of the suspension, such as sodium carboxymethyl cellulose, sorbitol or dextran. Optionally, the suspension can also contain suitable stabilizers or agents which increase the solubility of the active ingredients to allow for the preparation of highly concentrated solutions.

In embodiments, the active ingredient can be in powder form for constitution with a suitable vehicle, e.g., sterile, pyrogen-free water-based solution, before use.

The composition of embodiments can also be formulated in rectal compositions such as suppositories or retention enemas, using, e.g., conventional suppository bases such as cocoa butter or other glycerides.

The composition of embodiments can also be formulated in inhalable compositions. For example, the inhalable composition is formulated to for use in a nebulizer.

Compositions suitable for use in context of embodiments of the invention include compositions wherein the active ingredients are contained in an amount effective to achieve the intended purpose, such as to prevent or treat a metabolic disease.

As used herein the phrase "therapeutically effective amount" can refer to an amount of an active ingredient (i.e. botanically-derived extract or an active ingredient or compound thereof, as described above) effective in preventing or treating a metabolic disease. Determination of a therapeutically effective amount is well within the capability of those skilled in the art, especially in light of the detailed disclosure provided herein.

In embodiments, the therapeutically effective amount is at least about 0.1 mg/kg body weight, at least about 0.25 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 3500 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight.

The dosage can vary depending upon a number of factors known to those of ordinary skill in the art, such as the pharmacodynamic characteristics of the active ingredient and its mode and route of administration; time of administration of active ingredient; age, sex, health and weight of the subject; nature and extent of symptoms; kind of concurrent treatment, frequency of treatment and the effect desired; and rate of excretion.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage can vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Depending on the severity of the condition and the responsiveness of the subject to treatment, dosing can be of a single or a plurality of administrations, with course of treatment lasting from several days to several weeks, several months or several years, or until cure is effected or diminution of the disease state is achieved. Alternatively, the compositions are administered in order to prevent occurrence of a metabolic disorder in a subject at risk of developing a metabolic disorder. The compositions can be administered for prolonged periods of time (e.g. several days, several weeks, several months or several years) as to prevent occurrence of a metabolic disorder.

According to an embodiment of the disclosure, the compositions can be administered at least once a day. For example, the compositions can be administered daily. According to another embodiment, the compositions can be administered twice a day, three times a day or more. In embodiments, the compositions can be administered weekly, such as about once a week or about twice a week. In embodiments, the compositions can be administered monthly, such as about once a month or about twice a month.

According to an embodiment of the disclosure, the composition can be administered to a subject chronically. Such is the case, for example, when treating a subject afflicted with a chronic disease or condition. In other embodiments, the composition can be administered to a subject as long as the subject is at risk of a disease or condition, or as long as symptoms of a disease or condition persists. For example, embodiments of the invention can be administered to a subject for at least 7 days, at least 10 days, at least 12 days, at least 14 days, at least 16 days, at least 18 days, at least 21 days, at least 24 days, at least 27 days, at least 30 days, at least 60 days, at least 90 days, or longer than 90 days.

The amount of a composition to be administered will be dependent on the subject being treated, the severity of the affliction, the manner of administration, the judgment of the prescribing physician, and the like. The exact amount of a composition to be administered can be chosen by the individual physician in view of the patient's condition. (See, e.g., Fingl, E. et al. (1975), "The Pharmacological Basis of Therapeutics," Ch. 1, p. 1.)

The compositions of the disclosure can be formulated as a unit dosage form. In such form, the preparation is subdivided into unit doses containing appropriate quantities of the active ingredients such as for a single administration. The unit dosage form can be a packaged preparation, the package containing discrete quantities of preparation, for example, an ampule, a dispenser, an adhesive bandage, a non-adhesive bandage, a wipe, a baby wipe, a gauze, a pad and a sanitary pad.

The quantity of active compound in a unit dose of preparation can be varied or adjusted according to the particular application.

Compositions of the disclosure can be presented in a pack or dispenser device, such as a kit, which can contain one or more unit dosage forms containing the active ingredient. The pack can, for example, comprise metal or plastic foil, such as a blister pack. The pack or dispenser device can be accompanied by instructions for administration. The pack or dispenser device can also be accompanied by a notice in a form prescribed by a governmental agency regulating the manufacture, use, or sale of pharmaceuticals, which notice is reflective of approval by the agency of the form of the compositions for human or veterinary administration. Such notice, for example, can include labeling approved by the U.S. Food and Drug Administration for prescription drugs or of an approved product insert. Compositions comprising a preparation of the invention formulated in a pharmaceutically acceptable carrier can also be prepared, placed in an appropriate container, and labeled for treatment of an indicated condition, as detailed herein.

Since the compositions of the disclosure are utilized in vivo, the compositions can be of high purity and substantially free of harmful contaminants, e.g., at least National Food (NF) grade. Compositions as described herein can be at least analytical grade. Compositions as described herein can be at least pharmaceutical grade. To the extent that a given compound must be synthesized prior to use, such synthesis or subsequent purification can result in a product that is substantially free of any contaminating toxic agents that can have been used during the synthesis or purification procedures.

Aspects of the invention are further drawn to methods of treating or preventing a metabolic disease in a subject in need thereof, the method comprising administering to the subject a therapeutically effective amount of a composition described herein comprising a botanically-derived extract or compound, thereby treating and/or preventing the metabolic disease in the subject.

The term "treating" can refer to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

The term "preventing" can refer to keeping a disease, disorder or condition from occurring in a subject. In some cases, the subject can be at risk for developing the disease but has not yet been diagnosed as having the disease.

Subjects that can be treated according to this aspect of the invention include mammals such as human beings or domesticated animals including, but not limited to, horses (i.e. equine), cattle, goat, sheep, pig, dog, cat, camel, alpaca, llama and yak, male or female, at any age that is in need of treatment or prevention of a metabolic disease.

As used herein, the term "subject in need thereof" can refer to a subject that would benefit biologically, medically, or in a quality of life from the treatment, a subject exhibiting one or more symptoms or indications described herein, and/or a subject at risk of, or suffering from, a disease, disorder or condition that is amenable to treatment or amelioration with the compositions or methods described herein. For example, the disease or indication comprises metabolic disease.

The term "metabolism" can refer to, for example, the sum of the processes by which a particular substance is handled in the living body, and/or the sum of the metabolic activities taking place. For example, metabolism can refer to the chemical changes in living cells by which energy is provided for vital processes and activities and new material is assimilated.

The term "metabolic disease" can refer to a group of identified disorders in which errors of metabolism, imbalances in metabolism, or sub-optimal metabolism occur. The metabolic diseases as described herein also include diseases that can be treated through the modulation of metabolism, although the disease itself may or may not be caused by a specific metabolic defect. Non-limiting examples of metabolic diseases that can be treated or prevented by embodiments herein include Type 2 diabetes, obesity, obesity-related conditions, insulin resistance and metabolic syndrome.

The term "metabolic health" can refer to the presence or absence of metabolic disease. For example, metabolic health can refer to having less than ideal or ideal levels of blood sugar, triglycerides, high-density lipoprotein (HDL) cholesterol, blood pressure, and/or waist circumference. For example, a subject with poor metabolic health can be afflicted with or at risk of a metabolic disease. Such subject can have less than ideal levels of blood sugar, triglycerides, high-density lipoprotein (HDL) cholesterol, blood pressure, and/or waist circumference.

In embodiments, the compositions and methods described herein can be used to treat or prevent metabolic disturbances induced by therapeutics or drugs. As used herein, the phrase "drug-induced metabolic disturbances" can refer to a metabolic disturbance induced by any agent or ingredient whose administration to a subject can result in metabolic disturbances. As used herein the term "metabolic disturbance" can refer to any metabolic disease, perturbation, or disorder. For example, the metabolic disturbances can comprise elevated glucocorticoids, obesity, overproduction of cortisol, insulin resistance, and nonalcoholic fatter liver disease.

"Diabetes" can refer to a heterogeneous group of disorders that share impaired glucose tolerance in common. Its diagnosis and characterization, including pre-diabetes, type I and type II diabetes, and a variety of syndromes characterized by impaired glucose tolerance, impaired fasting glucose, and abnormal glycosylated hemoglobin, are well known in the art. It can be characterized by hyperglycemia, glycosuria, ketoacidosis, neuropathy or nephropathy, increased hepatic glucose production, insulin resistance in various tissues, insufficient insulin secretion and enhanced or poorly controlled glucagon secretion from the pancreas.

The term "obesity" as used herein is defined in the WHO classifications of weight. Underweight is less than 18.5 BMI (thin); healthy is 18.5-24.9 BMI (normal); grade 1 overweight is 25.0-29.9 BMI (overweight); grade 2 overweight is 30.0-39.0 BMI (obesity); grade 3 overweight is greater than or equal to 40.0 BMI. BMI is body mass index (morbid obesity) and is $kg/m^2$. Waist circumference can also be used to indicate a risk of metabolic complications. Waist circumference can be measured (in cm) at midpoint between the lower border of ribs and the upper border of the pelvis. Other measures of obesity include, but are not limited to, skinfold thickness and bioimpedance, which is based on the principle that lean mass conducts current better than fat mass because it is primarily an electrolyte solution.

The term "obesity-related condition" can refer to any disease or condition that is caused by or associated with (e.g., by biochemical or molecular association) obesity or that is caused by or associated with weight gain and/or related biological processes that precede clinical obesity. Examples of obesity-related conditions include, but are not limited to, diabetes (e.g., type 1 diabetes, type 2 diabetes, and gestational diabetes), metabolic syndrome, hyperglycemia, hyperinsulinemia, impaired glucose tolerance, impaired fasting glucose, dyslipidemia, hypertriglyceridemia, insulin resistance, hypercholesterolemia, atherosclerosis, coronary artery disease, peripheral vascular disease, and hypertension. For example, "metabolic syndrome" can refer to a syndrome marked by the presence of a combination of factors (e.g. high blood pressure, abdominal obesity, high triglyceride levels, low HDL levels, and high fasting levels of blood sugar) that are linked to an increased risk of cardiovascular disease and type 2 diabetes. For example, metabolic syndrome can be marked by the presence of three or more of such factors.

Regardless of the indication, a therapeutically effective amount of a composition comprising the botanically-derived extract or compound, or a unit dosage form which comprises the same, is administered to the subject. The term "administration" can refer to introducing a substance, such as the botanically-derived compound or extract, into a subject. Any route of administration can be utilized including, such as those described herein.

The term "subject" or "patient" can refer to any organism to which aspects of the invention can be administered, e.g., for experimental, diagnostic, prophylactic, and/or therapeutic purposes. Subjects to which compounds of the disclosure can be administered include mammals, such as primates, for example humans. For veterinary applications, a wide variety of subjects are be suitable, for example, livestock such as cattle, sheep, goats, cows, swine, and the like; poultry, such as chickens, ducks, geese, turkeys, and the like; and domesticated animals, such as pets, for example dogs and cats. For diagnostic or research applications, a wide variety of mammals are suitable subjects, including rodents (for example, mice, rats, hamsters), rabbits, primates, and swine such as inbred pigs and the like. The term "living subject" can refer to a subject noted above or another organism that is alive. The term "living subject" can also refer to the entire subject or organism and not just a part excised (e.g., a liver or other organ) from the living subject.

Kits

Aspects of the invention are directed towards kits.

The term "kit" can refer to a set of articles that facilitates the process, method, assay, analysis, or manipulation of a sample. The kit can include instructions for using the kit (eg, instructions for the method of the invention), materials, solutions, components, reagents, chemicals, or enzymes required for the method, and other optional components.

For example, the compositions as described herein can be provided in a kit. In one embodiment, the kit includes (a) a container that contains the compositions described herein or components thereof (e.g., solvents, buffers, extracts, botanical compounds), and optionally (b) informational material. The informational material can be descriptive, instructional, marketing or other material that encompasses the methods described herein and/or the use of the agents for therapeutic benefit. In an embodiment, the kit also includes a second agent, such as at least one additional active agent.

The informational material of the kits is not limited in its form. In one embodiment, the informational material can include information about production of the compound, molecular weight of the compound, concentration, date of expiration, batch or production site information, and so forth. In one embodiment, the informational material encompasses methods of manufacturing one or more botanical compositions, and/or methods of administering botanical compositions to a subject, e.g., in a suitable dose, dosage form, or mode of administration (e.g., a dose, dosage form, or mode of administration described herein), to treat a subject). The information can be provided in a variety of formats, include printed text, computer readable material, video recording, or audio recording, or information that provides a link or address to substantive material.

The composition in the kit can include other ingredients, such as a solvent or buffer, culture media, a stabilizer, or a preservative. The compositions of the kit thereof can be provided in any form, e.g., liquid, dried or lyophilized form, and can be substantially pure and/or sterile. When the compositions are provided in a liquid solution, the liquid solution can be an aqueous solution or an alcohol solution. When the compositions or components thereof are provided as a dried form, reconstitution, for example, is by the addition of a suitable solvent. The solvent, e.g., sterile water or buffer, can optionally be provided in the kit. The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes the botanical composition and the second agent, e.g., in a desired ratio. For example, the kit includes a plurality of syringes, ampules, foil packets, blister packs, or medical devices, e.g., each containing a single combination unit dose. The containers of the kits can be air-tight, waterproof (e.g., impermeable to changes in moisture or evaporation), and/or light-tight. The kit optionally includes a device suitable for administration of the composition, e.g., a syringe or other suitable delivery device. The device can be provided pre-loaded with one or both of the agents or can be empty, but suitable for loading.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1—Scoprenyl—a New Compound to Treat Metabolic Diseases

Botanicals have been used as therapeutics, and some pharmaceuticals in use today have been derived, directly or indirectly, from plant compounds. One such drug is metformin, originally derived from French lilac (*Galega officinalis*) and is now used as a first line therapeutic for the treatment of type 2 diabetes mellitus. Our screening of over 400 compounds for the ability to enhance lipid accumulation and promote adipocyte differentiation of 3T3-L1 adipocytes led to the identification of an ethanolic extract of *Artemisia scoparia* (SCO) as promoting adipocyte differentiation in vivo. Studies in diet-induced obese mice showed the SCO supplementation in the high-fat diet had beneficial effects on the adipose tissue, increasing adiponectin expression and insulin signaling and decreasing markers of inflammation. Additionally, SCO improved whole-body insulin sensitivity and reduced circulating triglycerides, glycerol, and free fatty acids.

Example 2

Adipose tissue (AT) is a critical player in metabolic regulation (Kusminski, Bickel, and Scherer 2016). Obesity, the main disorder involving AT, is arguably the greatest health issue currently affecting the Western world, as it is the major driver of the high rates of cardiovascular disease and insulin resistance in developed nations (Bhupathiraju and Hu 2016; Ranasinghe et al. 2017; Saklayen 2018). In obese states, the normal functions of adipose tissue are disrupted, contributing to whole-body metabolic dysfunction (Vidal-Puig 2013). Although the inhibition of fat cell development can sound like a beneficial strategy to reduce obesity and associated disorders, obesity is associated with impaired adipocyte differentiation, along with ectopic lipid deposition and metabolic dysfunction in muscle and liver (Danforth 2000; Gustafson et al. 2015; Kim et al. 2007; Smith and Kahn 2016). The insulin-sensitizing thiazolidinediones (TZDs) improve metabolic health through activation of peroxisome proliferator-activated receptor-γ (PPARγ) and promotion of adipogenesis (Hammarstedt et al. 2005; Soccio, Chen, and Lazar 2014). Concerns over side effects and safety have led to a decline in clinical use of TZDs in recent years, however selective PPARγ modulators (SPPARMs) that can enhance adipocyte differentiation are a subject of study as therapeutics for obesity-related metabolic disease (Chigurupati, Dhanaraj, and Balakumar 2015; Dunn et al. 2011; Feldman, Lambert, and Henke 2008; Higgins and Depaoli 2010).

Botanicals have been used as therapeutics, and some pharmaceuticals in use today have been derived, directly or indirectly, from plant compounds. One such drug is metformin, originally derived from French lilac (*Galega officinalis*) and is now used as a first line therapeutic for the treatment of type 2 diabetes mellitus (T2DM)(Thomas and Gregg 2017; Witters 2001). To identify proadipogenic/anti-diabetic compounds, we performed a blinded screen of over 400 botanical extracts for their ability to enhance lipid accumulation and promote adipocyte differentiation of 3T3-L1 adipocytes. These efforts led to the identification of an ethanolic extract of *Artemisia scoparia* (SCO) as promoting adipocyte differentiation in vitro (Allison J Richard, Fuller, et al. 2014; Richard, Burris, et al. 2014).

Following our discovery that SCO could improve adipocyte differentiation in vitro, we performed studies in diet-induced obese (DIO) mice to determine if SCO could have metabolically favorable effects in vivo. SCO supplementation in the high-fat diet (HFD) had beneficial effects on the adipose tissue, increasing adiponectin expression and insulin signaling, and decreasing markers of inflammation. In addition, SCO improved whole-body insulin sensitivity and reduced circulating triglycerides, glycerol, and free fatty acids (Richard, Burris, et al. 2014; Allison J. Richard, Fuller, et al. 2014). For these animal studies, the botanical was either administered by gavage or incorporated into the mouse food. Other studies examined the effects of SCO and these studies have observed a variety of effects for SCO. In one study, SCO was shown to increase in the ratio of Bacteroidetes to Firmicutes bacterial populations in the mucosal layer of the ileum in a mouse model of diet-induced obesity (Wicks et al. 2014).

A role of adipocytes/adipose tissue is to store and release lipid stores as needed. In fasted conditions, adrenergic input to the adipose tissue promotes the release of fatty acids to the circulation to be used as an energy source by other tissues, a process known as lipolysis. In contrast, in fed conditions, low adrenergic input and high insulin levels favor lipogenesis and energy storage in adipocytes. Insulin resistant states are associated with elevated rates of basal lipolysis in the fed state, which in turn lead to further metabolic dysfunction (Morigny et al. 2016). The pro-inflammatory conditions present in obesity and insulin resistance are known to contribute to this increased basal lipolysis. A major mediator of AT inflammation, tumor necrosis factor-alpha (TNFα) can induce lipolysis in adipocytes in the absence of adrenergic stimulation (Frahbeck et al. 2014; Kawakami et al. 1987; Sharma and Puri 2016). Gene expression studies from the Stephens labs indicate that SCO could reduce inflammatory markers in AT. We also observed that SCO reduced circulating FFAs and glycerol in mice (Boudreau, Richard, Jasmine A. Burrell, et al. 2018). Hence, we examined anti-lipolytic effects of SCO in vitro in cultured adipocytes. We observed that SCO could inhibit TNFα-induced lipolysis in cultured 3T3-L1 adipocytes and this was accompanied by changes in the levels and phosphorylation of two proteins involved in lipolysis, perilipin and hormone-sensitive lipase (Boudreau, Richard, Jasmine A. Burrell, et al. 2018). SCO reduced glycerol and free fatty acid release induced by TNFα, but not by isoproterenol (a β-adrenergic agonist), supporting a role for SCO in limiting inflammation-driven lipolysis in AT.

Like obesity, chronically elevated glucocorticoid levels promote metabolic disruptions such as insulin resistance, hypertension, and hepatic lipid accumulation reviewed here (Strohmayer 2011). Although high cortisol levels caused by naturally occurring Cushing's Syndrome are rare, synthetic glucocorticoids can be prescribed for chronic conditions such as asthma, autoimmune disorders, cancer and other inflammatory conditions (Benard-Laribiere et al. 2017; Fardet, Petersen, and Nazareth 2011; Overman, Yeh, and Deal 2013). The Cushingoid phenotype has been successfully recapitulated and studied in a variety of rodent models incorporating synthetic glucocorticoid administration and genetic manipulations. In both humans and rodents, high glucocorticoid levels have been found to increase adipose tissue lipolysis and to induce insulin resistance (Divertie, Jensen, and Miles 1991; Harvey et al. 2018; Hochberg et al. 2015; Shen et al. 2017). Given the clinical need for synthetic glucocorticoids and their widespread use, adjuvant therapies to combat the metabolic disturbances induced by these drugs would be beneficial. Since we have observed reductions in TNFα-induced lipolysis and improvements in insulin sensitivity with SCO treatment (Boudreau, Richard, Jasmine A Burrell, et al. 2018), we tested SCO's ability to regulate glucocorticoid-induced lipolysis in cultured adipocytes, in the presence or absence of the glucocorticoid receptor (GR) antagonist RU486. We found that SCO attenuated lipolysis to the same extent as RU486, and that the effects of RU486 and SCO on lipolysis were additive. These results indicate that SCO does not act directly on GR signaling and, therefore, without wishing to be bound by theory, can attenuate the lipolytic effects of glucocorticoids without inhibiting their therapeutic anti-inflammatory activity.

Inflammation in adipose tissue contributes to whole-body metabolic dysfunction (Engin 2017; Kawakami et al. 1987; Ohmura et al. 2007; Stephens, Lee, and Pilch 1997; Stephens and Pekala 1992). This process involves interactions between adipocytes and AT immune cells, for example, macrophages (Burhans et al. 2018; Olefsky and Glass 2010). To further characterize the effects of SCO in the context of AT inflammation, we induced activation of macrophages with lipopolysaccharide (LPS). We observed that SCO mitigated LPS-induced gene expression of interleukin 1 beta (Il-1b) and inducible nitric oxide synthase (iNOS), but not that of TNFa(Tnf). In TNFα-treated adipocytes, we have observed that SCO pretreatment mitigates induction of the inflammatory genes interleukin 6 (I16), C-C motif chemokine ligand 2 (Ccl2), and lipocalin 2 (Lcn2). Overall, these results show that, without wishing to be bound by theory, that SCO can potently reduce inflammatory gene expression in macrophages and adipocytes.

A challenge in botanical research is that plant extracts are comprised of hundreds of compounds, and it is difficult to identify which of these compounds confer biological activity. Activity-guided fractionation studies of SCO extracts have been performed for over a decade. There were a lot of complications (technical, mechanical, and personnel) along the way. We have screened dozens of extract fractions for their ability to promote adipocyte development as has been shown for the parent SCO extracts. This process revealed that SCO contains non-overlapping active fractions, indicating the presence of several compounds that can promote adipogenesis. See, for example, Boudreau et al. 2019, which is incorporated by reference herein in its entirety. We have recently elucidated the structures of three of these compounds, all of which are prenylated coumaric acid derivatives (PCAs). These compounds were purified by and the used for NMR structural and chemical compositions analysis. Two of these compounds, capillartemisin A and capillartemisin B, have been previously reported in *A. scoparia* (Kitagawa et al. 1983). The third compound, however, is new. For example, another prenylated coumaric acid, Artepillin C, has been shown to activate PPARγ and enhance adipogenesis (Choi et al. 2011).

Described herein is, for example, the discovery that three compounds isolated from SCO can promote adipocyte differentiation and, without wishing to be bound by theory, improve overall metabolic health based on studies of parent SCO extract in diabetic mice.

REFERENCES FROM THIS EXAMPLE

Bhupathiraju, Shilpa N. and Frank B. Hu. 2016. "Epidemiology Of obesity and Diabetes and Their Cardiovascular Complications." Circulation Research 118(11): 1723-35.

Boudreau, Anik, Alexander Poulev, David M. Ribnicky, Ilya Raskin, Thirumurugan Rathinasabapathy, Allison J. Richard, and Jacqueline M. Stephens. 2019. "Distinct Fractions of an *Artemisia Scoparia* Extract Contain Compounds with Novel Adipogenic Bioactivity." Frontiers in Nutrition 6:18.

Boudreau, Anik, Allison J. Richard, Jasmine A Burrell, William T. King, Ruth Dunn, Jean-Marc Schwarz, David M. Ribnicky, Jennifer Rood, J. Michael Salbaum, and Jacqueline M. Stephens. 2018. "An Ethanolic Extract of *Artemisia Scoparia* (SCO) Inhibits Lipolysis in Vivo and Has Anti-Lipolytic Effects on Murine Adipocytes in Vitro." American Journal of Physiology-Endocrinology and Metabolism ajpendo.00177.2018.

Boudreau, Anik, Allison J. Richard, Jasmine A. Burrell, William T. King, Ruth Dunn, Jean-Marc Schwarz, David M. Ribnicky, Jennifer Rood, J. Michael Salbaum, and Jacqueline M. Stephens. 2018. "An Ethanolic Extract of *Artemisia Scoparia* Inhibits Lipolysis in Vivo and Has Antilipolytic Effects on Murine Adipocytes in Vitro." American Journal of Physiology-Endocrinology and Metabolism 315(5):E1053-61.

Burhans, Maggie S., Derek K. Hagman, Jessica N. Kuzma, Kelsey A. Schmidt, and Mario Kratz. 2018. "Contribution of Adipose Tissue Inflammation to the Development of Type 2 Diabetes Mellitus." Pp. 1-58 in Comprehensive Physiology. Vol. 9. Wiley.

Chigurupati, Sridevi, Sokkalingam A. Dhanaraj, and Pitchai Balakumar. 2015. "A Step Ahead of PPARγ Full Agonists to PPARγ Partial Agonists: Therapeutic Perspectives in the Management of Diabetic Insulin Resistance." European Journal of Pharmacology 755:50-57.

Choi, Sun-Sil, Byung-Yoon Cha, Kagami Iida, Young-Sil Lee, Takayuki Yonezawa, Toshiaki Teruya, Kazuo Nagai, and Je-Tae Woo. 2011. "Artepillin C, as a PPARγ Ligand, Enhances Adipocyte Differentiation and Glucose Uptake in 3T3-L1 Cells." Biochemical Pharmacology 81(7):925-33.

Danforth, Elliot. 2000. "Failure of Adipocyte Differentiation Causes Type II Diabetes Mellitus?" Nature Genetics 26(1):13-13.

Dunn, Fredrick L., Linda S. Higgins, Jill Fredrickson, and Alex M. Depaoli. 2011. "Selective Modulation of PPARγ Activity Can Lower Plasma Glucose without Typical Thiazolidinedione Side-Effects in Patients with Type 2 Diabetes." Journal of Diabetes and Its Complications.

Engin, Atilla. 2017. "The Pathogenesis of Obesity-Associated Adipose Tissue Inflammation." Pp. 221-45 in Advances in experimental medicine and biology. Vol. 960.

Feldman, P., M. Lambert, and B. Henke. 2008. "PPAR Modulators and PPAR Pan Agonists for Metabolic Diseases: The Next Generation of Drugs Targeting Peroxisome Proliferator-Activated Receptors?" Current Topics in Medicinal Chemistry.

Frahbeck, Gema, Leire Mendez-Gimenez, Jose-Antonio Femindez-Formoso, Secundino Fernindez, and Amaia Rodriguez. 2014. "Regulation of Adipocyte Lipolysis." Nutrition Research Reviews 27(01):63-93.

Gustafson, Birgit, Shahram Hedjazifar, Silvia Gogg, Ann Hammarstedt, and Ulf Smith. 2015. "Insulin Resistance and Impaired Adipogenesis." Trends in Endocrinology & Metabolism 26(4):193-200.

Hammarstedt, A., C. X. Andersson, V. Rotter Sopasakis, and U. Smith. 2005. "The Effect of PPARγ Ligands on the Adipose Tissue in Insulin Resistance." Prostaglandins, Leukotrienes and Essential Fatty Acids 73(1):65-75.

Higgins, Linda Slanec and Alex M. Depaoli. 2010. "Selective Peroxisome Proliferator-Activated Receptor γ (PPARγ) Modulation as a Strategy for Safer Therapeutic PPARγ Activation." in American Journal of Clinical Nutrition.

Kawakami, M., T. Murase, H. Ogawa, S. Ishibashi, N. Mon, F. Takaku, and S. Shibata. 1987. "Human Recombinant TNF Suppresses Lipoprotein Lipase Activity and Stimulates Lipolysis in 3T3-L1 Cells." Journal of Biochemistry 101(2):331-38.

Kim, Ja-Young, Esther van de Wall, Mathieu Laplante, Anthony Azzara, Maria E. Trujillo, Susanna M. Hofmann, Todd Schraw, Jorge L. Durand, Hua Li, Guangyu Li, Linda A. Jelicks, Mark F. Mehler, David Y. Hui, Yves Deshaies, Gerald I. Shulman, Gary J. Schwartz, and Philipp E. Scherer. 2007. "Obesity-Associated Improvements in Metabolic Profile through Expansion of Adipose Tissue." The Journal of Clinical Investigation 117(9):2621-37.

Kitagawa, Isao, Yoichi Fukuda, Minoru Yoshihara, Johji Yamahara, and Masayuki Yoshikawa. 1983. "Capillartemisin A and B, Two New Choleretic Principles from *Artemisiae capillaris* Herba." CHEMICAL & PHARMACEUTICAL BULLETIN 31(1):352-55.

Kusminski, Christine M., Perry E. Bickel, and Philipp E. Scherer. 2016. "Targeting Adipose Tissue in the Treatment of Obesity-Associated Diabetes." Nature Reviews Drug Discovery 15(9):639-60.

Morigny, Pauline, Marianne Houssier, Etienne Mouisel, and Dominique Langin. 2016. "Adipocyte Lipolysis and Insulin Resistance." Biochimie 125:259-66.

Ohmura, E., D. Hosaka, M. Yazawa, A. Tsuchida, M. Tokunaga, H. Ishida, S. Minagawa, A. Matsuda, Y. Imai, S. Kawazu, and T. Sato. 2007. "Association of Free Fatty Acids (FFA) and Tumor Necrosis Factor-α (TNF-α) and Insulin-Resistant Metabolic Disorder." Hormone and Metabolic Research 39(3):212-17.

Olefsky, Jerrold M. and Christopher K. Glass. 2010. "Macrophages, Inflammation, and Insulin Resistance." Annual Review of Physiology 72(1):219-46.

Ranasinghe, P., Y. Mathangasinghe, R. Jayawardena, A. P. Hills, and A. Misra. 2017. "Prevalence and Trends of Metabolic Syndrome among Adults in the Asia-Pacific Region: A Systematic Review." BMC Public Health 17(1):1-9.

Richard, Allison J., Thomas P. Burris, David Sanchez-Infantes, Yongjun Wang, David M. Ribnicky, and Jacqueline M. Stephens. 2014. "*Artemisia* Extracts Activate PPARγ, Promote Adipogenesis, and Enhance Insulin Sensitivity in Adipose Tissue of Obese Mice." Nutrition 30(7-8 SUPPL.):531-6.

Richard, Allison J, Scott Fuller, Veaceslav Fedorcenco, Robbie Beyl, Thomas P. Burris, Randall Mynatt, David M. Ribnicky, and Jacqueline M. Stephens. 2014. "*Artemisia Scoparia* Enhances Adipocyte Development and Endocrine Function in Vitro and Enhances Insulin Action in Vivo." PloS One 9(6):1-8.

Richard, Allison J., Scott Fuller, Veaceslav Fedorcenco, Robbie Beyl, Thomas P. Burris, Randall Mynatt, David M. Ribnicky, and Jacqueline M. Stephens. 2014. "*Artemisia Scoparia* Enhances Adipocyte Development and Endocrine Function in Vitro and Enhances Insulin Action in Vivo." PLoS ONE 9(6):e98897.

Saklayen, Mohammad G. 2018. "The Global Epidemic of the Metabolic Syndrome." Current Hypertension Reports 20(2):12.

Sharma, Vishva M. and Vishwajeet Puri. 2016. "Mechanism of TNF-α-Induced Lipolysis in Human Adipocytes Uncovered." Obesity 24(5):990-990.

Smith, U. and B. B. Kahn. 2016. "Adipose Tissue Regulates Insulin Sensitivity: Role of Adipogenesis, de Novo Lipogenesis and Novel Lipids." Journal of Internal Medicine 280(5):465-75.

Soccio, Raymond E., Eric R. Chen, and Mitchell A. Lazar. 2014. "Thiazolidinediones and the Promise of Insulin Sensitization in Type 2 Diabetes." Cell Metabolism 20(4):573-91.

Stephens, J. M., J. Lee, and P. F. Pilch. 1997. "Tumor Necrosis Factor-Alpha-Induced Insulin Resistance in 3T3-L1 Adipocytes Is Accompanied by a Loss of Insulin Receptor Substrate-1 and GLUT4 Expression without a Loss of Insulin Receptor-Mediated Signal Transduction." The Journal of Biological Chemistry 272(2):971-76.

Stephens, J. M. and P. H. Pekala. 1992. "Transcriptional Repression of the C/EBP-Alpha and GLUT4 Genes in 3T3-L1 Adipocytes by Tumor Necrosis Factor-Alpha. Regulations Is Coordinate and Independent of Protein Synthesis." The Journal of Biological Chemistry 267 (19):13580-84.

Thomas, Inas and Brigid Gregg. 2017. "Metformin; a Review of Its History and Future: From Lilac to Longevity." Pediatric Diabetes 18(1):10-16.

Vidal-Puig, Antonio. 2013. "Adipose Tissue Expandability, Lipotoxicity and the Metabolic Syndrome." Endocrinol Nutr 60(Supl. 1):39-43.

Wicks, Shawna, Christopher M. Taylor, Meng Luo, Eugene Blanchard, David M. Ribnicky, William T. Cefalu, Randall L. Mynatt, and David A. Welsh. 2014. "*Artemisia* Supplementation Differentially Affects the Mucosal and Luminal Ileal Microbiota of Diet-Induced Obese Mice." Nutrition 30(7-8):S26-30.

Witters, L. A. 2001. "The Blooming of the French Lilac." The Journal of Clinical Investigation 108(8):1105-7.

Example 3—Efficacy, Pharmacokinetics, and Toxicity Studies of Scoprenyl, a New Bioactive Isolated from *Artemisia scoparia*

Botanicals have been used as therapeutics, and many pharmaceuticals in use today have been derived, directly or indirectly, from plant compounds. One such drug is metformin, originally derived from French lilac (*Galega officinalis*) and now used as a first line therapeutic for Type 2 diabetes mellitus. To study the effects of botanicals on adipocyte development, we screened over 400 botanical extracts from plants across the globe for the ability to modulate adipocyte differentiation in vitro. Less than 5% of the extracts we screened regulated adipogenesis, and only one of them could promote adipocyte development—an ethanolic extract of the botanical *Artemisia scoparia* (SCO). In addition to promoting adipogenesis in vitro, we have demonstrated that SCO decreases lipolysis in mice as well as in cultured adipocytes in a cell-autonomous manner, and that SCO supplementation in vivo did not induce weight loss but did protect mice from some of the negative effects of high-fat feeding. SCO can also attenuate some of the negative effects of glucocorticoids (GC) and tumor necrosis factor alpha (TNFα) on adipocytes. In another screening study, we observed that SCO significantly enhanced longevity in the nematode *C. elegans*. Collectively, our data on SCO demonstrate its capabilities to improve multiple aspects of systemic metabolic health.

We purified and identified three compounds in SCO that can promote lipid accumulation and adipogenic marker gene expression in murine preadipocytes. One of these compounds, which can be referred to as "scoprenyl" (SP), is a prenylated coumaric acid that we have shown can also promote adipogenesis in human preadipocytes. Without wishing to be bound by theory, at least some of the in vivo effects of SCO can be mediated by scoprenyl. The aims are to investigate the pharmacokinetics, in vivo bioactivity, and toxicity of scoprenyl.

Project Narrative: Obesity and Type 2 diabetes are global epidemics that negatively impact the quality of life. To combat these epidemics, new approaches are required that are safe, widely available and inexpensive. Many therapeutics are developed from compounds obtained from plants. Extracts of *Artemisia scoparia* (SCO) have anti-diabetic effects in vivo. Our in vivo studies will assess efficacy, pharmokinetics, and toxicity of scoprenyl, a component we purified from SCO.

Aims:

Previously, our lab screened over 400 botanical extracts from plants across the globe to examine their ability to modulate adipocyte differentiation in vitro. Less than 5% of the extracts we screened regulated adipogenesis, and only one of them could promote adipocyte development—an ethanolic extract of the botanical *Artemisia scoparia* (SCO). In addition to its ability to promote adipogenesis in vitro, we have also observed that SCO decreases lipolysis in vitro and in vivo. Our studies in mice revealed that SCO supplementation did not induce weight loss, but did protect mice from some of the negative effects of high-fat feeding, including fatty liver and elevated insulin levels. We also observed improvements in insulin signaling in adipose tissue adipose tissue with SCO supplementation. Moreover, our recent studies demonstrate that SCO can extend life span in *C. elegans*. Although it has taken many years, we have recently identified three bioactive compounds in the SCO extract that promote adipocyte development in vitro. NMR data confirm that one of these compounds is a prenylated coumaric acid, which can be referred to as "scoprenyl" (SP). Based on the activity of the SCO parent extract, SP can also promote metabolic health by enhancing adipogenesis and reducing ectopic lipid accumulation. Our aims will consist of validation of SP. The studies described herein will validate that scoprenyl is a viable therapeutic for drug development and treatment of metabolic disease states.

Aim 1: To assess pharmacological properties of scoprenyl (SP). Our studies have established that SCO extract can enhance adipocyte differentiation in vitro, and mitigate metabolic disruptions associated with obesity in mice. Recently, we identified SP as a constituent compound of SCO that can recapitulate the effects of SCO on adipogenesis in vitro, and we now will study SP as a therapeutic for high-fat diet-induced metabolic dysfunction. This will require validation of SP's pharmacological properties. We will assess SP's solubility and stability in vitro, as well as pharmacokinetics, bioavailability, and tissue distribution in vivo. Since SP can behave differently when assayed as a pure compound versus within a whole SCO extract, all in vivo parameters will be assessed using both SP alone and the SCO extract at a dose which we know to be effective in improving insulin sensitivity in HFD-fed mice. Data obtained in this aim will not only validate SP as a therapeutic, but will also validate the optimal SP dose for use, as we will be able to compare circulating levels of SP in mice gavaged with SP only versus the SCO extract.

Aim 2: SP's enhance glucose tolerance in diet-induced obese mice and assess in vivo metabolism of SP in a chronic feeding study. Our studies have shown beneficial effects of parent SCO extract in the C57Bl/6J mice, a well characterized mouse model of obesity and insulin resistance. We will validate that SP can also reduce some of the negative consequences of high-fat feeding in male and female mice. We will incorporate SP in the diet of the mice for six weeks; SP dose will be determined based on data obtained in Aim 1. We will also perform insulin and glucose tolerance tests, as well as measures of adipose tissue function and lipid metabolism. These studies will allow us to validate that SP improves metabolic health in the context of diet-induced metabolic dysfunction. In addition, because diet incorporation can alter pharmacological parameters of SP, we will collect serum and tissue samples from this study for analysis of SP content. These data will be compared to those obtained from gavaged animals in Aim 1.

Aim 3: To examine the toxicity of scoprenyl using the *C. elegans* model. Our data demonstrate that SCO parent extract extends life span in *C. elegans* (FIG. 42). This model system, which has been used for whole-animal early-stage toxicity studies, reduces the use of vertebrate animals in drug development and has been shown to be reliably predictive of toxicity in mammalian systems. In addition, many instances of conserved modes of toxic action have been observed between worms and mammals.

BACKGROUND

It is known that genetic, dietary, pathological, or aging-related disruptions of adipose tissue function are among the underlying causes of the global epidemic of metabolic diseases. Adipocytes not only store and release lipid, but are insulin sensitive and are the sole source of some endocrine hormones; disruption of any one of these adipocyte functions can lead to systemic metabolic dysfunction[1-3]. In addition, inhibition of adipocyte differentiation impairs adipose tissue expansion and has negative metabolic consequences. Adipocyte dysfunction is associated with ectopic lipid accumulation, inflammation in adipose tissue, and altered adipokine expression. Hence, the identification of specific compounds that improve or maintain adipocyte function and systemic metabolic health has merit.

We have been studying an extract of *Artemisia scoparia* (SCO) that improves adipocyte function in vitro and in vivo[47]. Throughout human history, botanicals have been used as therapeutics, and many pharmaceuticals in use today have been derived, directly or indirectly, from plant compounds. One such drug is metformin, originally derived from French lilac (*Galega officinalis*) and now used as a first line therapeutic for Type 2 diabetes mellitus (T2DM)[8,9]. To study the effects of botanicals on adipocyte development, we screened over 400 botanical extracts from plants across the globe for the ability to modulate adipocyte differentiation in vitro. Less than 5% of the extracts we screened regulated adipogenesis, and only one of them promoted adipocyte development—an ethanolic extract of the botanical *Artemisia scoparia* (SCO). In addition to promoting adipogenesis in vitro, we have demonstrated that SCO decreases lipolysis in mice as well as in cultured adipocytes in a cell-autonomous manner, and that SCO supplementation in vivo did not induce weight loss, but did protect mice from some of the negative effects of high-fat feeding. Our studies indicate that SCO can also attenuate some of the negative effects of both glucocorticoids (GC) and tumor necrosis factor alpha (TNF$\alpha$) on adipocytes. In another screening study, SCO was also shown to significantly enhance longevity in the nematode *C. elegans*. Our efforts have identified bioactive compounds in SCO (FIG. 5) that promote adipocyte development in vitro. SCO and its bioactives can also modulate several pathways that impact metabolic disease states.

*Artemisia*: There are over 1600 genera in Asteraceae and at least 68 different *Artemisia* species in this genus, many of which have a history of medicinal use[10]. *Artemisia annua*, a plant widely used in traditional Chinese medicine, is the source of the anti-malarial compound artemisinin, whose discovery was awarded the Nobel Prize in Physiology or Medicine in 2015[11]. Artemisinin-based combination therapies are recommended treatments for malaria, and artemisinin is being studied for a range of therapeutic effects related to cancer and other diseases[12-14]. Interestingly, SCO also contains artemisinin, and without wishing to be bound by theory, can be an alternative source for the therapeutic compound[15]. Although certain beneficial effects of *Artemisia* extracts are known[16-20], they have not been supported by rigorous basic or clinical research. One exception is the well documented effectiveness of *Artemisia dracunculus* L., to regulate insulin action[20,21,30,31,22-29]. However, the involvement of adipose tissue in the whole-body effects of *Artemisia* species has not been evaluated.

*Artemisia scoparia* (SCO): SCO has been investigated in various diseases. In a spontaneously hypertensive rat model of Alzheimer's disease, rats fed diets containing 2% (w/w) of SCO for 6 weeks had various improvements, including lower levels of amyloid R and phosphorylated tau proteins, compared to controls[32]. SCO extracts have several beneficial effects on carbon tetrachloride induced oxidative stress in rat kidneys, including reduction of DNA damage in renal nuclei[33], indicating a therapeutic role of SCO in renal oxidative stress-related disorders. Hepatoprotective, antitumor, antiviral, antihypertensive, hemostatic, and free radical-scavenging effects of SCO have also been reported[34-41]. Anti-inflammatory properties of SCO have been observed in several models[42-44]. Flavonoids from SCO reduce intracellular oxidative stress and inflammatory cytokine production in macrophages, and suppress inflammatory responses in a model of acute lung injury. In these studies, and without wishing to be bound by their, repression of NF-κB and MAP kinase signaling pathways can be the mechanism for these effects[45]. In a mouse model of atopic dermatitis, SCO and some of its components can reduce clinical symptoms of skin lesions and levels of various inflammatory mediators in both the lesions and the serum. DEQA (3,5-dicaffeoyl-epi-quinic acid), a major component of a butanol-extracted SCO fraction in these studies, can reduce caspase 1 activity[46]. Another study in mast cells also showed anti-inflammatory effects of both SCO and DEQA, including reduced cytokine expression and caspase activity[47]. Although we have detected DEQA in our SCO extracts, these compounds do not promote adipogenesis[4]. Ethnobotanical studies in various regions of Pakistan document the medicinal and common use of SCO as well as a high-fidelity level for SCO and diabetes[48-50]. This ethnobotanical research underscores the importance of traditional herbal preparations in remote regions, where they are often the only available form of medication, and highlights the wealth of traditional knowledge in such areas.

Innovation:

SCO has positive effects on human and murine cultured cells, as well as mice and nematodes in vivo.

SCO is used in traditional medicine for its anti-diabetic activities.

Scoprenyl, a new bioactive purified from SCO, promotes adipogenesis of mouse and human preadipocytes.

Significance: SCO enhances the development of both murine and human adipocytes in vitro, reduces lipolysis in mice and in adipocytes in a cell-autonomous manner, and mitigates metabolic dysfunction in vivo in a mouse model of diet-induced obesity ([5-7,51] and FIG. 6). Our studies seek to validate the pharmacokinetics, in vivo bioactivity, and toxicity of scoprenyl (SP), a new bioactive compound that we have identified in SCO extract.

Data:

Published data from our laboratory have shown that SCO promotes differentiation of 3T3-L1 adipocytes[67]. Activity-guided fractionation efforts have determined that non-overlapping fractions of SCO could recapitulate the effects of the SCO parent extract on adipogenesis, indicating the presence of several bioactive compounds[4]. Recently, we purified and identified three distinct compounds in the SCO parent extract that could independently promote lipid accumulation and adipogenic marker gene expression in 3T3-L1 cells (FIG. 5). One of these compounds, which can be referred to as "scoprenyl" (SP), is a new prenylated coumaric acid, while the other two bioactives, capillartemisin A and capillartemisin B, have been previously described in *Artemisae capillaris*[52]. Capillartemisin A has also recently been isolated and identified in Brazilian green propolis[53]. As shown in the right panels of FIG. 5, each of these compounds can promote adipogenesis as judged by adipocyte marker gene expression and lipid accumulation (assessed by Oil Red O staining for neutral lipid). To our knowledge, none of these compounds have been studied in the context of adipocyte development and/or metabolic disease states.

Human subcutaneous preadipocytes from two lean donors were purchased from Zenbio, Inc. As shown in FIG. 6, both the SCO parent extract and purified SP (scoprenyl) can promote adipogenesis in human preadipocytes. This adipogenic capability was observed in both donors, but only one donor is shown. The thiazolidinedione (TZD), rosiglitazone (ROSI) is a potent inducer of adipogenesis and was used as positive control.

Collaborators screened a nuclear receptor ligand-binding domain (LBD) library for activation by SCO in HEK293 cells, using vectors containing the LBDs of all 48 human nuclear receptors fused to the Gal4 DNA-binding domain, and a reporter construct encoding the Gal4 upstream activator sequence to drive luciferase expression. Of the 48 nuclear receptors, only peroxisome proliferator activated receptor gamma (PPARγ) was significantly activated by SCO in this model system[6,7]. We have recently examined the ability of SCO to modulate transcriptional activity of PPARγ in NIH-3T3 fibroblasts using a consensus PPAR response element (PPRE) from the acyl CoA oxidase promoter element linked to a luciferase reporter. In these studies, we observed that ROSI activates PPARγ transcription activity in NIH-3T3 cells transfected with ectopic PPARγ. To our surprise, however, we did not observe an induction of PPARγ transcription activity with SCO (FIG. 7, panel A). Based on these results and without wishing to be bound by theory, SCO needs an "adipocyte background" to modulate PPARγ activity, so we transfected mature 3T3-L1 adipocytes with the PPRE luciferase reporter and once again observed that ROSI activated PPARγ transcription activity, but SCO did not (FIG. 7, panel B). Collectively, all of our data indicate that SCO can regulate PPARγ activity in a manner dependent on context, such as gene-specific promoter sequences, cell-type-specific coactivators or corepressors, or post-translational modifications of PPARγ. However, these data indicate that, unlike TZDs, SCO is not a direct activator of PPARγ transcriptional activity in cells. It should be noted that the structures of SP and other SCO bioactives (FIG. 5) are not similar to known PPARγ ligands[54].

A class of PPARγ agonist with a dibenzoazepine scaffold has been identified[55], but these compounds are also distinct from our identified bioactives (FIG. 5). Many agonists of PPARγ have been identified in natural products and shown to improve metabolic parameters in diabetic animal models, e.g. honokiol, amorfrutin 1, amorfrutin B, amorphastilbol (reviewed in 56). Although SP impacts PPARγ in some cellular aspects, the mechanism(s) of action are not known. Moreover, SP does not appear to be a direct modulator of PPARγ transcriptional activity (FIG. 7).

Lipolysis is the release of fatty acids and glycerol from adipocytes. Obesity and insulin resistance are associated with both AT inflammation and elevated basal lipolysis[57]. Also, enhancement of lipolysis by the inflammatory cytokine TNFα, contributes to metabolic dysfunction[58-60]. Like TNFα, glucocorticoids (GCs) can also cause insulin resistance in vivo and promote lipolysis in cultured adipocytes[61-64]. We have shown that SCO supplementation of a high-fat diet (HFD) reduces circulating levels of free fatty acids (C18:0, C18:1, C16:0, and C16:1) and glycerol[5]. SCO inhibits TNFα-induced lipolysis in 3T3-L1 adipocytes, but has no significant effect on isoproterenol-induced lipolysis, which is mediated by adrenergic signaling[5]. SCO can also attenuate GC (dexamethasone)-induced lipolysis in adipocytes (FIG. 8), providing further evidence of a beneficial metabolic effect of SCO in the context of insulin resistance. Both products of lipolysis, glycerol and non-esterified fatty acids (NEFA), were assayed.

Cellular communication between immune cells and adipocytes plays an important role in insulin resistance, and it is well established that macrophage-derived TNFα levels in AT are elevated in conditions of obesity and insulin resistance. TNFα acts in a paracrine manner on preadipocytes to inhibit adipogenesis, and on adipocytes to induce production of inflammatory mediators and promote insulin resistance. Hence, we examined the ability of SCO to modulate TNFα-induced inflammatory cytokine gene expression in fat cells. SCO pretreatment significantly inhibited TNFα-induced expression of lipocalin-2 (Lcn2), interleukin 6 (Il6), and C-C motif chemokine ligand 2 (Ccl2), also known as monocyte chemoattractant protein 1 (Mcp1) in adipocytes (FIG. 9). These results are consistent with data showing that SCO supplementation of HFD reduced MCP-1 protein levels in retroperitoneal adipose tissue[6]. We also observed that SCO parent extract reduces the LPS induction of some genes in RAW 264.7 macrophages. In addition, SCO treatment of cultured pancreatic beta cells inhibits NF-kB promoter activity induced by interleukin-1 beta. Taken together, these observations show that SCO can have cell-autonomous anti-inflammatory effects in at least two other cell types.

NF-kB signaling is induced by TNFα in adipocytes, and contributes to metabolic dysfunction[60,65-67]. In addition, inflammatory cytokines induced by TNFα are known to be transcriptional targets of NF-kB (www.nf-kb.org). We have observed that a chronic pretreatment with SCO significantly attenuates TNFα-induced p65 nuclear translocation in mature 3T3-L1 adipocytes, indicating a role for NF-kB signaling in SCO's anti-inflammatory effects.

Notably, the TZD pioglitazone does not attenuate the ability of TNFα to activate NF-kB in 3T3-L1 adipocytes, despite inhibiting insulin signaling at these same time points[68]. In another study, the TZD troglitazone suppressed the expression of some NF-kB target genes, but did not inhibit IkBa phosphorylation, or NF-kB activation or DNA-binding activity in response to TNFα in 3T3-L1 adipocytes[69]. These studies also provided evidence that the p65 subunit of NF-kB and PPARγ could antagonize each other's transcriptional activities[69]. Based on our observations with SCO, SCO can regulate a functional antagonism between p65 and PPARγ, and act on multiple integrated signals that impact adipocyte gene expression and function. We will continue our current work to validate the mechanisms involved in the ability of SCO and SP to affect adipocyte function. We note that SCO does not modulate NF-kB in a manner shared by two other PPARγ activators, indicating that SP and/or other SCO bioactives will be very distinct from drugs that target PPARγ.

We have validated the effects of the SCO parent extract in animal studies. For example, FIG. 11 represents studies in C57BL/6 male mice that had SCO incorporated into their high-fat diet for one month. As shown in FIG. 11, panel A, SCO improves glucose clearance in an insulin tolerance test, and results in a substantial decrease in liver lipid levels (FIG. 11, panels B and C). Although SCO supplementation did not significantly alter glucose levels after a 4-hour fast, SCO significantly reduced insulin levels (FIG. 11, panel D), and improved HOMA-IR. Serum samples were used to examine the products of lipolysis. As shown in FIG. 11, panel E, lower levels of circulating glycerol and fatty acids were observed with SCO treatment. These results are highly consistent with our in vitro observations that SCO reduces TNFa- and DEX-induced lipolysis in adipocytes in a cell-autonomous manner (FIG. 8). Collectively, these results indicate that adipose tissue and liver are targets of SCO bioactives, and the tissues from our efficacy studies will include an analysis of SP levels in both adipose tissue and liver.

Aim 1: To Assess Pharmacological Properties of SP.

Rationale: While we have established the ability of SCO diet supplementation to improve measures of metabolic health in a DIO mouse model (FIGS. 11 and 6,7,51), and have determined that SP recapitulates the effects of SCO on adipogenesis in murine and human preadipocytes (FIG. 5 and FIG. 6), further validation of SP as a therapeutic compound includes validation of its solubility and stability (in vitro), as well as its bioavailability, tissue distribution, and pharmacokinetic properties (in vivo). Because the presence of other compounds in SCO can alter the absorption and kinetics of SP, we will perform these analyses with both the isolated SP and the whole SCO extract. In addition, comparison of SP and SCO will validate the appropriate dose of SP needed to achieve comparable circulating levels to those obtained with administration of the parent SCO extract, and will therefore enhance our efficacy studies (Aim 2).

Preparation of SCO extracts and purified compounds: Ethanolic extracts will be prepared from greenhouse-grown plants as described previously[5,7]. We observed that hexane and ethyl acetate, but not water, partitions of SCO contain components that promote adipocyte development[4]. However, starting from the ethyl acetate fraction, we have performed two successive and distinct semi-preparatory HPLC protocols to obtain the three bioactives shown in FIG. 5. Without wishing to be bound by theory, the EtOH extract can contain a broader range of compounds compared to the EtOAc extract. Although SCO plant extracts are not a limiting factor, the purification of bioactives from SCO is arduous. Hence, we also plan to synthesize these compounds. There are currently no published methods for any of the three isolated SCO compounds we have identified, and the prenylation of the bioactives introduces challenges to their synthesis; however, we will refer to published synthetic routes for related compounds, such as artepillin C, baccharin, and drupanin, for method development. We will confirm that the synthetic SP has similar efficacy to the plant-purified SP using adipogenesis assays in murine 3T3-L1 cells as shown in FIG. 5.

In vitro solubility and stability assays of SP: Assessments of aqueous solubility and chemical and metabolic stability can provide estimations of in vivo compound availability and metabolic clearance, respectively. These are considered critical steps in early drug discovery stages. We will perform solubility studies in phosphate buffered saline (PBS) at pH 7.4 and pH 4.0 (to mimic acidic conditions in the stomach). We will also validate intrinsic clearance (CLint) of SP in murine liver S9 fractions that are enriched in microsomes and cytosol containing a wide variety of drug metabolizing enzymes. A half-life approach will be used to validate metabolic stability. Such parameters, for example, can be used to design the in vivo PK/bioavailability studies.

In vivo pharmacokinetic, bioavailability, and tissue distribution studies of SCO and SP: We will also conduct the in vivo portion of this aim. A single low dose of SP (1 mg/kg) or SCO (500 mg/kg, a dose shown to have efficacy on metabolic parameters in vivo) will be administered to mice either intravenously or by oral gavage. Blood will be collected after 0.25, 0.5, 1, 2, 4, 8, and 24 hours in both groups, with an additional collection after 5 minutes for the IV group only. Samples will be analyzed for SP levels. The initial 1 mg/kg SP dose was calculated based on the estimated percent of SP within the total SCO extract (less than 1%) and dose of SCO with demonstrated efficacy. If circulating SP is not readily detected at this low dose, we will test three to five higher doses. Various pharmacokinetic parameters will be calculated, and descriptive statistics will be generated using Phoenix WinNonlin software. At the 24-hour time point of the low-dose study, mice will be sacrificed, and liver, adipose tissue, lungs, kidneys, and brain will be collected to analyze tissue distribution of SP. For adipose tissue, we will focus analyses on gonadal and inguinal depots, but will collect other fat pads, such as mesenteric and retroperitoneal, and have them in storage should data indicate the need to analyze them. Of course, SP levels in fat tissue will be of interest to us, since, without being bound by theory, we consider adipose tissue to be the primary mediator of SCO's in vivo effects. We will validate whether SP accumulates in fat tissue, as we have demonstrated that SCO and SP have cell-autonomous effects on adipocytes and preadipocytes.

To conduct in vivo assessments of SP's bioavailability or pharmacokinetics, we sent six-year-old archived serum samples from our last SCO feeding study in high fat-fed mice for analysis. These samples were collected at the time of sacrifice after a 4-hour fast, in conditions that were not designed for detection of SCO compounds in the circulation. As indicated in FIG. 5, we have identified two other bioactives in SCO that enhance adipogenesis (capillartemisin A and capillartemisin B). We did not detect SP or capillartemisin B in these samples. However, capillartemisin A was detected (FIG. 12). Bioactive phytochemicals are present as glucuronide conjugates in serum; the presence of capillartemisin A in both hydrolyzed and non-hydrolyzed serum samples indicate that some portion of the bioavailable capillartemisin A is not modified, however this data cannot predict what portion of the capillartemisin A may be glucuronidated. The absence of capillartemisin B and SP from these samples does not indicate that they are non-bioavailable, but does indicate that, although similar in structure, all three compounds (FIG. 5) can behave differently in terms of their kinetics, bioavailability and/or stability.

Aim 2: SP Enhances Glucose Tolerance in Diet-Induced Obese Mice, and Validate In Vivo Metabolism of SP in a Chronic Feeding Study.

Rationale: SCO promotes adipogenesis in cultured 3T3-L1 adipocytes, and, without wishing to be bound by theory, these adipogenic effects are responsible for SCO's ability to enhance insulin sensitivity in mice fed a HFD. Our studies have revealed that SP can recapitulate the effects of SCO on adipogenesis in murine and human cells (FIG. 5 and FIG. 6). An efficacy study will be performed to validate SP as a therapeutic for high-fat diet induced metabolic dysfunction. Effects of SP will be compared to both SCO and metformin, the current first-line therapeutic for metabolic syndrome and insulin resistance. In addition, PK and bioavailability for SP incorporated into the diet will be assessed, as they can differ from what we observe in the gavage studies discussed in Aim 1. The tissue distribution of SP administered in the diet will also be crucial to our understanding of SP's pharmacological properties.

Without wishing to be bound by theory, Scoprenyl can improve metabolic dysfunction during diet-induced obesity in mice.

Validate SP's ability to improve metabolic function in DIO mice. The overall study design is shown in FIG. 13. C57BL/6J mice will be fed a HFD starting at 6 weeks of age (WOA). C57BL/6J mice fed a HFD starting at 6 weeks of age (WOA) will be ordered from Jackson Laboratories and will arrive at our facility at 16 weeks of age (WOA), after 10 weeks on 45% HFD (Research Diets D12451). A control group of mice fed low fat diet (LFD, Research Diets D12450H) from 6 weeks of age throughout the duration of the study will be included, and this group will be critical to assess the extent by which SP can resolve HFD-induced metabolic dysfunction. The LFD and HFD have identical sucrose contents. After a one-week acclimation period, blood will be collected for pre-study baseline measurements of circulating glucose, insulin, glycerol, NEFA, and the adipokines leptin and adiponectin. We will also measure body weight (BW) and body composition, and the mice will be randomized based on body weight and blood glucose levels. Two weeks after arrival of the animals (18 WOA, 12 weeks on HFD), treatments will be initiated with feeding of supplemented diets (1% w/w SCO, 0.25% w/w metformin, or SP at dose determined from Aim 1 studies). The doses of SCO[7,51] and metformin[71] have been selected based on previous studies demonstrating that they are sufficient to improve glucose tolerance and/or insulin sensitivity in a DIO mouse model. To assess glucose tolerance and insulin sensitivity, an oral glucose tolerance test (OGTT) and an intraperitoneal insulin tolerance test (IPITT) will be conducted after 4 and 5 weeks on experimental diets, respectively. For the OGTT, mice will be acclimated to the gavage needle by administering saline for at least 3 days prior to the assay. Following a 4-hour fast, blood will be collected via tail snip for baseline measures and then 2 g/kg glucose will be administered via oral gavage. In addition to the baseline time point (t=0), blood (~20 ul per time point) will be collected at 10, 20, 30, and 60 min post gavage to determine glucose and insulin levels. An additional 120 min blood collection (~5 µl) will be used for glucose assessment only. IPITTs will be performed in a similar manner with blood collections (~5 µl per time point) for glucose assessment only at t=0 and 10, 20, 40, and 60 min post IP injection of 1 U/kg body weight insulin. Effects of treatments on lipid metabolism will also be assessed by measuring circulating glycerol and NEFA levels, ex vivo lipolysis rates from adipose tissue explants, and lipid accumulation in liver (histology and triglyceride assays). Body weight and food intake will be measured weekly and body composition (by NMR) will be performed biweekly. Finally, circulating adiponectin and leptin levels will be assayed at the end of the study as readouts of adipocyte endocrine function. Glucose, insulin, glycerol, and NEFA levels will also be measured from blood collected at the end of the study.

Validate the metabolism of SP in vivo, in mice fed HFD supplemented with SCO or SP. PK and bioavailability studies will rely on oral gavage of SCO and SP, while our efficacy study will use diet supplementation. After 1 day, and 1, 3, and 5 weeks on supplemented diets, we will collect blood from 3 mice per group in rotating cohorts to assess levels of SP in circulation. This will allow us to validate whether there are substantial differences in PK and bioavailability between oral gavage and diet incorporation of SP and to compare the levels of circulating SP in diet-fed versus gavage conditions. It will also allow us to validate when steady state levels are reached and whether there is any accumulation in circulation with chronic administration. Tissues collected at the end of the study, adipose tissue (gonad and inguinal depots which can accumulate lipophilic compounds), liver, kidneys, and lung (highly perfused tissues), and brain (to determine CNS penetration) will be collected from 3 mice per SCO and SP treatment groups to be analyzed for SP content. This analysis will be important to validate tissue distribution and bioavailability of SP and if there is any bioaccumulation. Analysis of SP content in plasma and tissue samples will be performed at Inotiv. These analyses will also validate if there are any differences in PK and bioavailability of SP between males and females.

Aim 3: To Validate the Toxicity of Scoprenyl Using the *C. elegans* Model.

Assessing toxicity of candidate drug molecules in animals is an important step in validating therapeutic applicability. The nematode *C. elegans* provides an alternative animal model for assessing toxicity[75,78], which has consistently proven reliable and predictive of toxicity in mammalian species[79-83]. Greater than 80% of genes in *C. elegans* have known human homologs[84], and characterized drug molecules show similar modes of action in worms and mammalian systems[78].

Compared to other animals, *C. elegans* has a fast generation time; it grows from embryo to reproductive adult in roughly three days[85]. Upon reaching adulthood, *C. elegans* hermaphrodites begin to self-fertilize, each producing hundreds of offspring until sperm are depleted[86]. Thus, it is easy and relatively inexpensive to establish large, synchronous populations of worms, which can be used to analyze the toxicity of compounds at a wide range of concentrations. Importantly, toxicity screening in *C. elegans* allows one to assess responses at an organismal level, which cannot be done when toxicity is assessed in vitro using mammalian cell lines[78]. Further, wild-type *C. elegans* live only two to three weeks[86]. This provides a unique opportunity to validate safety and/or toxic effects on whole, intact animals at different life stages.

Worms can respond to SCO active compounds, and that this treatment is non-toxic at the tested concentration (500 µg/ml). However, the toxicity of the new SP compound (FIG. 5) has never been investigated. We will validate SP safety/toxicity using the *C. elegans* model system.

Without wishing to be bound by theory, Scoprenyl is non-toxic to both young and old animals.

Analyze acute toxicity and DART (developmental and reproductive toxicity): Toxicity in humans is best validated when multiple measures of toxicity are assessed in animal models. Recently, a platform for simultaneously scoring acute toxicity and DART in *C. elegans* was described[87]. We will apply this approach to validate SP's safety and/or toxicity. Analysis will be performed using 24-well plates. Each well will contain NGM solid medium seeded with *E. coli* OP50 as a food source[88]. DMSO (control) or varying concentrations of SP (nM to mM range) will be added to the NGM in the different wells. Five wild-type N2 hermaphrodites will be transferred to each well at the L1 larval stage, and plates will be maintained at 20° C.[87]. Pictures of the wells will be taken on each subsequent day. At non-toxic concentrations, wild-type Lis should develop into reproductive adults and begin producing progeny by the third day. The expanding populations should begin to starve by the fifth or sixth day as all the food is consumed. We will score acute toxicity by determining concentrations at which the PO animals die. We will score developmental and reproductive delay (i.e., DART) by quantifying differences in the time to starvation between experimental populations and controls[87]. For comparison, we will analyze SP alongside chemicals that are known to cause acute toxicity and/or DART at a wide range of concentrations in mammals and worms[87]. Examples include boric acid, warfarin, aldicarb, fenoxycarb, spirotetramat, and piperazine (ToxCast database, https://www.epa.gov/chemicalresearch/toxcast-chemicals; Pesticide database, http://pesticideinfo.org/). We will also validate SP safety and/or toxicity in bus (bacterially unswollen) mutants[89], which lack a protective cuticle[90] that, when intact, could interfere with an accurate assessment of toxic effects[87]. Without wishing to be bound by theory, SP will be less toxic than known toxic compounds.

Determine $LC_{50}$ at different time points during aging: Chemical toxicity can be exacerbated by aging; some chemicals can have more toxic effects in older animals than in younger ones[91]. This is an important consideration, because metabolic disease is most common among older populations[92], and viable therapeutic leads would need to be non-toxic to older individuals. We can easily validate chemical safety and/or toxicity during aging using *C. elegans* because of its short lifespan. We will administer varying concentrations of SP to *C. elegans* at different time points of adulthood (day 1, day 5, day 10, and day 15). Worms will initially be raised on standard NGM agar with OP50 and then moved to SP- or DMSO-supplemented plates on the relevant day of adulthood. We will score acute toxicity after treatment to determine the 24-hour, 48-hour, and 96-hour $LC_{50}$ for SP for the different age groups. To maintain adult populations that are separate from progeny, worms will be transferred to new plates every two days.

Statistical analysis: At least five replicates will be performed per concentration for the acute toxicity and DART analyses that start with L1 animals. Statistical analysis of delays in food consumption will be carried out using ANOVA tests. To validate 24-hour, 48-hour, and 96-hour $LC_{50}$ using worms of different ages, at least 100 worms will be scored for each concentration at each time point of adulthood. Each experiment will be repeated at least three times, and mean $LC_{505}$ at the different ages will be compared by ANOVA tests.

Summary: The first aim includes in vitro and in vivo assessments of SP's pharmacological properties. These will serve to demonstrate the presence of SP in animal sera and validate the appropriate SP dose and route of delivery for achieving doses comparable to those obtained with a SCO dose known to be effective in improving insulin sensitivity.

Once we have identified the best dose of SP to use, we will perform mouse studies in the second aim to validate that SP can reduce some of the negative consequences of diet-induced obesity. Further, we can also validate whether other bioactives that we have identified (FIG. 5) have similar activities, using the same mouse model. The third aim will validate safety and/or acute toxicity, as well as developmental and reproductive toxicity (DART) of SP in *C. elegans*, using a highly efficient, cost-effective, and predictive approach.

These studies will significantly improve upon or differentiate from existing clinical care. We know that SP can promote adipogenesis in vitro. There is evidence that promotion of adipogenesis in vivo is metabolically healthy, and the importance of adipogenesis and adipose tissue expansion has been recognized for nearly twenty years[93]. As described herein, we will characterize SP and validate its suitability as a therapeutic compound.

We can also synthesize derivatives of these compounds and explore their structure-activity relationships by validating their ability to promote adipogenesis in vitro and, ultimately, their efficacy in vivo.

Mouse PK Experiments: Male C57BL/6J mice (8-10 weeks of age) will be used. Animals arrive and acclimate at SLU vivarium space for 3-7 days. Following acclimation, the animals will be given a single dose of scoprenyl or the parent SCO extract, and euthanized 24 hours after dosing. Mice will be administered a single dose of each compound/extract intravenously (IV) or by oral (PO) gavage in nine mice per compound/extract per route of administration (ROA) (n=3 per bleeding time point). Volume for a single IV bolus or PO administration is limited to 20 mL/kg. A full PK curve (7-8 time points) will be obtained by sparse sampling with rotating cohorts of 3 mice per time point per compound/extract per ROA. Two or three timed blood samples will be obtained from each mouse. The first two samples will be obtained via peripheral blood collections using the submandibular procedure with retro-orbital route blood collections as a secondary option. The third and final sample will be obtained via cardiac puncture following euthanasia.

Mouse Efficacy Experiments: Male and female C57BL/6J mice fed low-fat diet (10% kcal fat) or high fat diet (45% kcal fat) for 12 weeks beginning at 6 weeks of age will be used. Following a 7-day quarantine and acclimation period within the PBRC CBC vivarium, mice (purchased from commercial vendor) will be fed diet supplemented with test compound/extract for 6 additional weeks. Blood for will be collected via submandibular vein of each mouse for baseline measures of adipokine, insulin, glucose, glycerol, and NEFA and for 3 mice (in rotating groups) at day 1 and weeks 1, 3, and 6 for pharmacokinetic measures. Mice will undergo the following procedures: measurement of body weight and body composition (via NMR), oral glucose tolerance tests (OGTT) and intraperitoneal insulin tolerance tests (IP-ITT). Mice will also be subjected to 4 hours of fasting prior to GTT or ITT and euthanasia. During GTTs and IP-ITTs, blood will be collected via tail snip at baseline and 5-6 designated time points between 0 and 120 min following glucose or insulin administration. For OGTTs, glucose will be delivered via oral gavage using a flexible, plastic gavage needle, and this procedure will be performed by a well-trained technician. Terminally, blood will be collected via cardiac puncture under deep anesthesia by isoflurane gas inhalation. Mice will be euthanized by isoflurane overdose or carbon dioxide inhalation followed by cervical dislocation, and tissues will be removed for RNA, protein analyses, and histology. Male and female mice will be used for all animal studies.

Survival blood collections for both PK and efficacy experiments are limited to a total volume of 10 mL/kg/animal over the course of 14 days.

REFERENCES CITED IN THIS EXAMPLE

1. Vidal-Puig A. Adipose tissue expandability, lipotoxicity and the metabolic syndrome. Endocrinol Nutr. 2013; 60(Supl. 1):39-43.
2. Kusminski C M, Bickel P E, Scherer P E. Targeting adipose tissue in the treatment of obesity-associated diabetes. Nat Rev Drug Discov. 2016; 15(9):639-660. doi:10.1038/nrd.2016.75
3. Rosen E D, Spiegelman B M. What we talk about when we talk about fat. Cell. 2014; 156(1-2):20-44.
4. Boudreau A, Poulev A, Ribnicky D M, et al. Distinct fractions of an Artemisia scoparia extract contain compounds with novel adipogenic bioactivity. Front Nutr. 2019; 6:18.
5. Boudreau A, Richard A J, Burrell J A, et al. An ethanolic extract of Artemisia scoparia (SCO) inhibits lipolysis in vivo and has anti-lipolytic effects on murine adipocytes in vitro. Am J Physiol Metab. August 2018: ajpendo.00177.2018.

6. Richard A J, Burns T P, Sanchez-Infantes D, Wang Y, Ribnicky D M, Stephens J M. Artemisia extracts activate PPARγ, promote adipogenesis, and enhance insulin sensitivity in adipose tissue of obese mice. Nutrition. 2014; 30(7-8 SUPPL.):531-536.
7. Richard A J, Fuller S, Fedorcenco V, et al. Artemisia scoparia enhances adipocyte development and endocrine function in vitro and enhances insulin action in vivo. PLoS One. 2014; 9(6):e98897.
8. Witters L A. The blooming of the French lilac. J Clin Invest. 2001; 108(8):1105-1107.
9. Thomas I, Gregg B. Metformin; a review of its history and future: from lilac to longevity. Pediatr Diabetes. 2017; 18(1):10-16. doi:10.1111/pedi.12473
10. Bora K S, Sharma A. The Genus Artemisia: A Comprehensive Review. Pharm Biol. 2011; 49(1):101-109.
11. Tu Y. Artemisinin—A Gift from Traditional Chinese Medicine to the World (Nobel Lecture). Angew Chemie— Int Ed. 2016; 55(35):10210-10226.
12. Wang K S, Li J, Wang Z, et al. Artemisinin inhibits inflammatory response via regulating NF-κB and MAPK signaling pathways. Immunopharmacol Immunotoxicol. 2017; 39(1):28-36.
13. Liu X, Cao J, Huang G, Zhao Q, Shen J. Biological Activities of Artemisinin Derivatives Beyond Malaria. Curr Top Med Chem. 2019; 19(3):205-222.
14. Lu B-W, Baum L, So K-F, Chiu K, Xie L-K. More than anti-malarial agents: therapeutic potential of artemisinins in neurodegeneration. Neural Regen Res. 2019; 14(9):1494.
15. Singh A, Sarin R. Artemisia scoparia—A new source of artemisinin. Bangladesh J Pharmacol. 2010; 5(1): 17-20. doi:10.3329/bjp.v5i1.4901
16. WRIGHT M, WATSON M F. Tibetan Medicinal Plants. Edited by C. Kletter & M. Kriechbaum. Stuttgart: Medpharm Scientific Publishers. 2001. 383pp., 77 full-colour plates. ISBN 3 88763 067 X. €138.00 (hardback). Edinburgh J Bot. 2002.
17. Cha J-D, Jeong M-R, Jeong S-I, et al. Chemical Composition and Antimicrobial Activity of the Essential Oils of Artemisia scoparia and A. capillaris. Planta Med. 2005; 71(2):186-190.
18. Chandrasekharan I, Khan H A, Ghanim A. Flavonoids from Artemisia scoparia. Planta Med. 1981.
19. Hong J-H, Hwang E-Y, Kim H-J, Jeong Y-J, Lee I S. Artemisia capillaris Inhibits Lipid Accumulation in 3T3-L1 Adipocytes and Obesity in C57BL/6J Mice Fed a High Fat Diet. J Med Food. 2009; 12(4):736-745.
20. Ribnicky D M, Poulev A, Watford M, Cefalu W T, Raskin I. Antihyperglycemic activity of Tarralin™, an ethanolic extract of Artemisia dracunculus L. Phytomedicine. 2006; 13(8):550-557.
21. Aggarwal S, Shailendra G, Ribnicky D M, Burk D, Karki N, Qingxia Wang M S. An extract of Artemisia dracunculus L. stimulates insulin secretion from 3 cells, activates AMPK and suppresses inflammation. J Ethnopharmacol. 2015; 170:98-105.
22. Obanda D N, Ribnicky D M, Raskin I, Cefalu W T. Bioactives of Artemisia dracunculus L. enhance insulin sensitivity by modulation of ceramide metabolism in rat skeletal muscle cells. Nutrition. 2014; 30(7-8 SUPPL.)
23. Kheterpal I, Scherp P, Kelley L, et al. Bioactives from Artemisia dracunculus L. enhance insulin sensitivity via modulation of skeletal muscle protein phosphorylation. Nutrition. 2014; 30(7-8 SUPPL.)
24. Ribnicky D M, Roopchand D E, Poulev A, et al. Artemisia dracunculus L. polyphenols complexed to soy protein show enhanced bioavailability and hypoglycemic activity in C57BL/6 mice. Nutrition. 2014; 30(7-8 SUPPL.):S4.
25. Vandanmagsar B, Haynie K R, Wicks S E, et al. Artemisia dracunculus L. extract ameliorates insulin sensitivity by attenuating inflammatory signalling in human skeletal muscle culture. Diabetes, Obes Metab. 2014; 16(8):728-738.
26. Kirk-Ballard H, Wang Z Q, Acharya P, et al. An extract of Artemisia dracunculus L. inhibits ubiquitin-proteasome activity and preserves skeletal muscle mass in a murine model of diabetes. PLoS One. 2013; 8(2):1-12.
27. Scherp P, Putluri N, LeBlanc G J, et al. Proteomic analysis reveals cellular pathways regulating carbohydrate metabolism that are modulated in primary human skeletal muscle culture due to treatment with bioactives from Artemisia dracunculus L. J Proteomics. 2012; 75(11):3199-3210.
28. Obanda D N, Hemandez A, Ribnicky D, et al. Bioactives of Artemisia dracunculus L. mitigate the role of ceramides in attenuating insulin signaling in rat skeletal muscle cells. Diabetes. 2012; 61(3):597-605.
29. Weinoehrl S, Feistel B, Pischel I, Kopp B, Butterweck V. Comparative Evaluation of Two Different Artemisia dracunculus L. Cultivars for Blood Sugar Lowering Effects in Rats. Phyther Res. 2012; 26(4):625-629.
30. Kheterpal I, Coleman L, Ku G, Wang Z Q, Ribnicky D, Cefalu W T. Regulation of insulin action by an extract of Artemisia dracunculus L. in primary human skeletal muscle culture: A proteomics approach. Phyther Res. 2010; 24(9):1278-1284.
31. Wang Z Q, Ribnicky D, Zhang X H, Raskin I, Yu Y, Cefalu W T. Bioactives of Artemisia dracunculus L enhance cellular insulin signaling in primary human skeletal muscle culture. Metabolism. 2008; 57(SUPPL. 1).
32. Promyo K, Cho J-Y, Park K-H, Jaiswal L, Park S-Y, Ham K-S. Artemisia scoparia attenuates amyloid R accumulation and tau hyperphosphorylation in spontaneously hypertensive rats. Food Sci Biotechnol. 2017; 26(3):775-782.
33. Sajid M, Khan M R, Shah N A, et al. Proficiencies of Artemisia scoparia against CCl4 induced DNA damages and renal toxicity in rat. BMC Complement Altem Med. 2016; 16(1):149.
34. Choi E, Park H, Lee J, Kim G. Anticancer, antiobesity, and anti-inflammatory activity of Artemisia species in vitro. J Tradit Chinese Med=Chung i tsa chih ying wen pan. 2013; 33(1):92-97.
35. Choi E, Kim G. Effect of Artemisia species on cellular proliferation and apoptosis in human breast cancer cells via estrogen receptor-related pathway. J Tradit Chinese Med=Chung i tsa chih ying wen pan. 2013; 33(5):658-663.
36. Geng C-A, Huang X-Y, Chen X-L, et al. Three new anti-HBV active constituents from the traditional Chinese herb of Yin-Chen (Artemisia scoparia). J Ethnopharmacol. 2015; 176:109-117.

37. Sajid M, Rashid Khan M R, Shah N A, et al. Evaluation of Artemisia scoparia for hemostasis promotion activity. Pak J Pharm Sci. 2017; 30(5):1709-1713.
38. Singh H P, Kaur S, Mittal S, Batish D R, Kohli R K. In vitro screening of essential oil from young and mature leaves of Artemisia scoparia compared to its major constituents for free radical scavenging activity. Food Chem Toxicol. 2010; 48(4):1040-1044.
39. Cho J-Y, Jeong S-J, Lee H La, et al. Sesquiterpene lactones and scopoletins from Artemisia scopari Waldst. & Kit. and their angiotensin I-converting enzyme inhibitory activities. Food Sci Biotechnol. 2016; 25(6):1701-1708.
40. Cho J-Y, Park K-H, Hwang D, et al. Antihypertensive Effects of Artemisia scoparia Waldst in Spontaneously Hypertensive Rats and Identification of Angiotensin I Converting Enzyme Inhibitors. Molecules. 2015; 20(11):19789-19804. doi:10.3390/molecules201119657 41. Gilani A H, Janbaz K H. Hepatoprotective effects of Artemisia scoparia against carbon tetrachloride: an environmental contaminant. J Pak Med Assoc. 1994; 44(3):65-68
42. Khan M A, Khan H, Tariq S A, Pervez S. In Vitro Attenuation of Thermal-Induced Protein Denaturation by Aerial Parts of Artemisia scoparia. J Evid Based Complementary Altem Med. 2015; 20(1):9-12
43. Yahagi T, Yakura N, Matsuzaki K, Kitanaka S. Inhibitory effect of chemical constituents from Artemisia scoparia Waldst. et Kit. on triglyceride accumulation in 3T3-L1 cells and nitric oxide production in RAW 264.7 cells. J Nat Med. 2014; 68(2):414-420.
44. Habib M, Waheed I. Evaluation of anti-nociceptive, anti-inflammatory and antipyretic activities of Artemisia scoparia hydromethanolic extract. J Ethnopharmacol. 2013; 145(1):18-24.
45. Wang X, Huang H, Ma X, et al. Anti-inflammatory effects and mechanism of the total flavonoids from Artemisia scoparia Waldst. et kit. in vitro and in vivo. Biomed Pharmacother. 2018; 104:390-403.
46. Ryu K J, Yoou M S, Seo Y, Yoon K W, Kim H M, Jeong H J. Therapeutic effects of Artemisia scoparia Waldst. et Kitaib in a murine model of atopic dermatitis. Clin Exp Dermatol. 2018; 43(7):798-805.
47. Nam S-Y, Han N-R, Rah S-Y, Seo Y, Kim H-M, Jeong H-J. Anti-inflammatory effects of Artemisia scoparia and its active constituent, 3,5-dicaffeoyl-epi-quinic acid against activated mast cells. Immunopharmacol Immunotoxicol. 2018; 40(1):52-58.
48. Hussain W, Badshah L, Ullah M, Ali M, Ali A, Hussain F. Quantitative study of medicinal plants used by the communities residing in Koh-e-Safaid Range, northern Pakistani-Afghan borders. J Ethnobiol Ethnomed. 2018; 14(1):30.
49. Hussain W, Ullah M, Dastagir G, Badshah L. Quantitative ethnobotanical appraisal of medicinal plants used by inhabitants of lower Kurram, Kurram agency, Pakistan. Avicenna J phytomedicine. 2018; 8(4):313-329.
50. Ahmad K S, Hamid A, Nawaz F, et al. Ethnopharmacological studies of indigenous plants in Kel village, Neelum Valley, Azad Kashmir, Pakistan. J Ethnobiol Ethnomed. 2017; 13(1):68.
51. Wang Z Q, Zhang X H, Yu Y, et al. Artemisia scoparia extract attenuates non-alcoholic fatty liver disease in diet-induced obesity mice by enhancing hepatic insulin and AMPK signaling independently of FGF21 pathway. Metabolism. 2013; 62:1239-1249.
52. Kitagawa I, Fukuda Y, Yoshihara M, Yamahara J, Yoshikawa M. Capillartemisin A and B, two new choleretic principles from Artemisiae capillaris Herba. Chem Pharm Bull. 1983; 31(1):352-355.
53. Tani H, Hikami S, Takahashi S, et al. Isolation, Identification, and Synthesis of a New Prenylated Cinnamic Acid Derivative from Brazilian Green Propolis and Simultaneous Quantification of Bioactive Components by LC-MS/MS. J Agric Food Chem. 2019; 67(44):12303-12312.
54. Mirza A Z, Althagafi I I, Shamshad H. Role of PPAR receptor in different diseases and their ligands: Physiological importance and clinical implications. Eur J Med Chem. March 2019:502-513.
55. Yamamoto K, Tamura T, Henmi K, et al. Development of Dihydrodibenzooxepine Peroxisome Proliferator-Activated Receptor (PPAR) Gamma Ligands of a Novel Binding Mode as Anticancer Agents: Effective Mimicry of Chiral Structures by Olefinic E/Z-Isomers. J Med Chem. 2018; 61(22):10067-10083.
56. Wang L, Waltenberger B, Pferschy-Wenzig E-M, et al. Natural product agonists of peroxisome proliferator-activated receptor gamma (PPARγ): a review. Biochem Pharmacol. 2014; 92(1):73-89.
57. Morigny P, Houssier M, Mouisel E, Langin D. Adipocyte lipolysis and insulin resistance. Biochimie. 2016; 125:259-266.
58. Langin D, Amer P. Importance of TNFα and neutral lipases in human adipose tissue lipolysis. Trends Endocrinol Metab. 2006; 17(8):314-320.
59. Frthbeck G, Mendez-Gimenez L, Femindez-Formoso J-A, Femindez S, Rodriguez A. Regulation of adipocyte lipolysis. Nutr Res Rev. 2014; 27(01):63-93.
60. Cawthorn W P, Sethi J K. TNF-α and adipocyte biology. FEBS Lett. 2008; 582(1):117-131.
61. Divertie G D, Jensen M D, Miles J M. Stimulation of Lipolysis in Humans by Physiological Hypercortisolemia. Diabetes. 1991; 40(10):1228 LP-1232.
62. Harvey I, Stephenson E J, Redd J R, et al. Glucocorticoid-Induced Metabolic Disturbances Are Exacerbated in Obese Male Mice. Endocrinology. 2018; 159 (6):2275-2287.
63. Hochberg I, Harvey I, Tran Q T, et al. Gene expression changes in subcutaneous adipose tissue due to Cushing's disease. J Mol Endocrinol. 2015; 55(2):81-94.
64. Shen Y, Roh H C, Kumari M, Rosen E D. Adipocyte glucocorticoid receptor is important in lipolysis and insulin resistance due to exogenous steroids, but not insulin resistance caused by high fat feeding. Mol Metab. 2017; 6(10):1150-1160.
65. Baker R G, Hayden M S, Ghosh S. NF-κB, inflammation, and metabolic disease. Cell Metab. 2011; 13(1):11-22.
66. Zhao P, Stephens J M. STAT1, NF-κB and ERKs play a role in the induction of lipocalin-2 expression in adipocytes. Mol Metab. 2013; 2(3):161-170.
67. Arkan M C, Hevener A L, Greten F R, et al. IKK-β links inflammation to obesity-induced insulin resistance. Nat Med. 2005; 11(2):191-198.
68. Peraldi P, Xu M, Spiegelman B M. Thiazolidinediones block tumor necrosis factor-α-induced inhibition of insulin signaling. J Clin Invest. 1997; 100(7):1863-1869.
69. Ruan H, Pownall H J, Lodish H F. Troglitazone antagonizes tumor necrosis factor-α-induced reprogramming of adipocyte gene expression by inhibiting the transcriptional regulatory functions of NF-κB. J Biol Chem. 2003; 278(30):28181-28192.
70. Kenyon C J. The genetics of ageing. Nature. 2010; 464(7288):504-512.
71. Matsui Y, Hirasawa Y, Sugiura T, Toyoshi T, Kyuki K, Ito M. Metformin Reduces Body Weight Gain and Improves Glucose Intolerance in High-Fat Diet-Fed C57BL/6J Mice. Biol Pharm Bull. 2010; 33(6):963-970.
72. Macotela Y, Boucher J, Tran T T, Kahn C R. Sex and depot differences in adipocyte insulin sensitivity and glucose metabolism. Diabetes. 2009; 58(4):803-812.
73. Heydemann A. An overview of murine high fat diet as a model for type 2 diabetes mellitus. J Diabetes Res. 2016; 2016:1-14.
74. Morselli E, Criollo A, Rodriguez-Navas C, Clegg D J. Chronic high fat diet consumption impairs metabolic health of male mice. Inflamm cell Signal. 2014; 1(6): 1-11.
75. Nass R, Hamza I. The Nematode C. elegans as an Animal Model to Explore Toxicology In Vivo: Solid and Axenic Growth Culture Conditions and Compound Exposure Parameters. In: Current Protocols in Toxicology; 2007.
76. Tralau T, Riebeling C, Pirow R, et al. Wind of change challenges toxicological regulators. Environ Health Perspect. 2012.
77. Burden N, Sewell F, Chapman K. Testing Chemical Safety: What Is Needed to Ensure the Widespread Application of Non-animal Approaches? PLoS Biol. 2015.
78. Hunt P R. The C. elegans model in toxicity testing. J Appl Toxicol. 2017.
79. Williams P L, Dusenbery D B. Using the nematode Caenorhabditis elegans to predict mammalian acute lethality to metallic salts. Toxicol Ind Health. 1988.
80. Cole R D, Anderson G L, Williams P L. The nematode Caenorhabditis elegans as a model of organophosphate-induced mammalian neurotoxicity. Toxicol Appl Pharmacol. 2004.
81. Ferguson, Boyer M S, Sprando R L. A method for ranking compounds based on their relative toxicity using neural networking, C. elegans, axenic liquid culture, and the COPAS parameters TOF and EXT. Open Access Bioinformatics. 2010
82. Boyd W A, McBride S J, Rice J R, Snyder D W, Freedman J H. A high-throughput method for assessing chemical toxicity using a Caenorhabditis elegans reproduction assay. Toxicol Appl Pharmacol. 2010.
83. Hunt P R, Olejnik N, Sprando R L. Toxicity ranking of heavy metals with screening method using adult Caenorhabditis elegans and propidium iodide replicates toxicity ranking in rat. Food Chem Toxicol. 2012.
84. Lai C H, Chou C Y, Ch'ang L Y, Liu C S, Lin W C. Identification of novel human genes evolutionarily conserved in Caenorhabditis elegans by comparative proteomics. Genome Res. 2000.
85. Corsi A K, Wightman B, Chalfie M. A Transparent window into biology: A primer on Caenorhabditis elegans. WormBook. 2015.
86. Muschiol D, Schroeder F, Traunspurger W. Life cycle and population growth rate of Caenorhabditis elegans studied by a new method. BMC Ecol. 2009.
87. Xiong H, Pears C, Woollard A. An enhanced C. elegans based platform for toxicity assessment. Sci Rep. 2017.
88. Stiernagle T. Maintenance of C. elegans. WormBook. 2006.
89. Gravato-Nobre M J, Nicholas H R, Nijland R, et al. Multiple genes affect sensitivity of Caenorhabditis elegans to the bacterial pathogen Microbacterium nematophilum. Genetics. 2005.
90. Page A, Johnstone I L. The cuticle. WormBook. 2007.
91. Hilmer S N. ADME-tox issues for the elderly. Expert Opin Drug Metab Toxicol. 2008.
92. Kuk J L, Ardem C I. Age and sex differences in the clustering of metabolic syndrome factors: Association with mortality risk. Diabetes Care. 2010.
93. Danforth E. Failure of adipocyte differentiation causes type II diabetes mellitus? Nat Genet. 2000; 26(1):13-13. doi:10.1038/79111

Example 4

Aims:

Nearly a decade ago, our lab screened over 400 botanical extracts from plants across the globe for the ability to modulate adipocyte differentiation in vitro. Less than 5% of the extracts we screened regulated adipogenesis, and only one of them could promote adipocyte development—an ethanolic extract of the botanical *Artemisia scoparia* (SCO). In addition to promoting adipogenesis in vitro, we have demonstrated that SCO decreases lipolysis in mice as well as in cultured adipocytes in a cell-autonomous manner, and that SCO supplementation in vivo did not induce weight loss but did protect mice from some of the negative effects of high-fat feeding.

Our more recent studies demonstrate that SCO can also attenuate some of the negative effects of glucocorticoids (GC) and tumor necrosis factor-alpha (TNFα) on adipocytes. SCO was also shown to significantly enhance longevity in *C. elegans*. In addition, we have recently identified three bioactive compounds in SCO that promote adipocyte development in vitro. Without wishing to be bound by theory, SCO promotes metabolic health and longevity by enhancing adipocyte development and reducing inflammation.

We will use a variety of in vitro and in vivo model systems to perform the validation studies. Overall, these aims will leverage our published and preliminary data to examine the metabolic mechanisms involved in SCO's action on adipocytes and metabolic health. Similar to metformin, SCO and its bioactives may work by affecting several pathways that impact metabolic diseases.

Aim 1: To validate the ability of SCO to promote adipogenesis in vivo and to validate that the effects of SCO are dependent on PPARγ expression. SCO promotes adipogenesis in both murine and human adipocytes. Our studies have shown that SCO enhances insulin sensitivity in high fat-fed mice. Without wishing to be bound by theory, the ability of SCO to increase adipogenesis during HFD feeding confers at least part of its insulin sensitizing effects. We will use the AdipoChaser mice, a state-of-the-art mouse model, to validate SCO's ability to promote adipocyte development in vivo. We will use another animal model (adipocyte-specific inducible PPARγ knockouts) to validate the ability of SCO to promote metabolic health is dependent on adipocyte PPARγ expression in adult male and female mice.

Aim 2: Underlying mechanisms involved in SCO to attenuate the metabolic dysfunction induced by glucocorticoids. Our data demonstrate that SCO can reduce GC-induced lipolysis. This observation is relevant because elevated lipolysis is associated with metabolic dysfunction.

Our studies in cultured adipocytes also revealed that SCO attenuates the ability of GCs to induce the expression of a subset of GC-regulated genes. We will validate the effects of SCO on GC action in adipocytes and to determine if SCO can attenuate GC-induced insulin resistance in vivo.

Aim 3: To validate the mechanisms involved in the ability of SCO and its bioactives to inhibit TNFα action in adipocytes. SCO promotes adipogenesis, but we have also observed other effects of this botanical extract, including anti-inflammatory properties. SCO can reduce some actions of the proinflammatory cytokine TNFα. This aim will include in vitro experiments in primary mouse adipocytes to assess the anti-inflammatory abilities of the SCO bioactives, as well as mechanistic experiments to validate how SCO modulates NF-κB activity in adipocytes.

Significance: These studies will assess metabolic mechanisms and pathways involved in the ability of SCO to modulate adipocyte function and systemic metabolic health. We will employ innovative mouse models to study adipogenesis in vivo and to validate the role of PPARγ in mediating SCO's effects. Additional experiments will also validate that SCO can mitigate GC-induced metabolic dysfunction. We will use mechanistic studies to validate the pathways responsible for SCO's anti-inflammatory effects in adipocytes and to evaluate the ability of individual bioactive compounds from SCO to mediate these effects. Overall, these aims will provide mechanistic information on SCO's significant effects on adipocyte function.

Background

Adipocytes: Genetic, dietary, pathological, or aging-related disruptions of adipose tissue (AT) function are among the underlying causes of the global epidemic of metabolic diseases. Adipocytes not only store and release lipids, but are insulin sensitive and are the sole source of some endocrine hormones; disruption of any one of these adipocyte functions can lead to systemic metabolic dysfunction[1-3]. In addition, inhibition of adipocyte differentiation impairs AT expansion and has negative metabolic consequences. Adipocyte dysfunction is associated with ectopic lipid accumulation, inflammation in AT, and altered adipokine expression. Hence, the identification of plant extracts and specific compounds that improve or maintain adipocyte function and systemic metabolic health has merit.

For the past decade, we have been studying an extract of *Artemisia scoparia* (SCO) that improves adipocyte function in vitro and in vivo[4-7].

*Artemisia*: There are >1600 genera in Asteraceae and at least 68 different *Artemisia* species in this genus, many of which have a history of medicinal use[8]. *Artemisia annua*, a plant widely used in traditional Chinese medicine, is the source of the anti-malarial compound artemisinin, whose discovery was awarded the Nobel prize in 2015[8]. Artemisinin-based combination therapies are a recommended treatment for malaria and artemisinin is being studied for a range of therapeutic effects related to cancer and other diseases[9-11]. Interestingly, SCO also contains artemisinin, and can be an alternative source for the therapeutic compound[12]. Although certain beneficial effects of *Artemisia* extracts are known[13-17], they have not been supported by rigorous basic or clinical research. One exception is the well documented effectiveness of *Artemisia dracunculus* L., to regulate insulin action [17,18,27,28,19-26]. However, the involvement of AT in the whole-body effects of *Artemisia* species has not been evaluated.

*Artemisia scoparia* (SCO): SCO has been investigated in various disease states, including a spontaneously hypertensive rat model of Alzheimer's disease, oxidative stress-related renal disorders, cancer, hypertension, viral infection, hepatotoxicity, and hemostatic disorders[29-37]. Anti-inflammatory properties of SCO have been observed in models such as acute lung injury, atopic dermatitis, and mast cell activation[38-43]. Quantitative ethnobotanical studies in various regions of Pakistan document the medicinal and common use of SCO, with a high-fidelity level for SCO and diabetes[44-46]. This type of research underscores the importance of traditional herbal preparations in remote regions, where they are often the only available form of medication.

Innovation:

SCO promotes adipocyte development in mouse and human adipocytes.

Three SCO bioactives promote adipogenesis.

SCO reduces lipolysis in vitro and in vivo.

SCO has anti-inflammatory effects on adipocytes in vitro.

SCO reduces some of the metabolically unhealthy effects of glucocorticoids on adipocytes.

SCO significantly increases longevity in *C. elegans*.

SCO enhances the development of both murine and human adipocytes in vitro and mitigates metabolic dysfunction in vivo in mouse models of diet-induced obesity. Our studies will validate metabolic mechanisms and pathways involved in the ability of SCO to modulate adipocyte function and promote metabolic health. We will employ innovative mouse models to study adipogenesis in vivo and to validate the role of the transcription factor, peroxisome proliferator-activated receptor, gamma (PPARγ), in mediating SCO's effects. We will use rigorous mechanistic studies to validate the pathways responsible for SCO's anti-inflammatory effects in adipocytes and evaluate the ability of individual bioactive compounds from SCO to mediate these effects. We will use state-of-the-art methodologies to validate genes that mediate the ability of SCO to increase longevity in worms. These studies, as well as experiments in glucocorticoidinduced insulin resistant mice, are of great translational relevance and will also reveal pathways and SCO compounds that mediate the anti-inflammatory effects of SCO.

Data:

We have shown that SCO promotes differentiation of 3T3-L1 adipocytes[4,5]. Activity-guided fractionation efforts have determined that non-overlapping fractions of SCO could recapitulate the effects of the parent extract on adipogenesis, indicating the presence of several active compounds[6]. Recently, we identified three distinct compounds in SCO that could independently promote lipid accumulation and adipogenic gene expression in 3T3-L1 cells (FIG. 5). One of these compounds, which can be referred to as "scoprenyl" (SP) is a new prenylated coumaric acid, while the other two bioactives, capillartemisin A and capillartemisin B, have been previously described in *Artemisae capillaris*[47].

Human subcutaneous preadipocytes from two lean donors were purchased from Zenbio, Inc. As shown in FIG. 6, SCO parent extract and scoprenyl promoted adipogenesis in human preadipocytes. This adipogenic capability occurred in both donors, but only one is shown (FIG. 6). The thiazolidinedione, rosiglitazone (ROSI) was used as positive control. We screened a nuclear receptor ligand-binding domain (LBD) library for activation by SCO in HEK293 cells, using vectors containing the LBDs of all 48 human nuclear receptors fused to the Gal4 DNA-binding domain, and a reporter construct encoding the Gal4 upstream activator sequence to drive luciferase expression. Of the 48 nuclear receptors, only PPARγ was significantly activated by SCO[4,5].

We also validated the ability of SCO to modulate transcriptional activity of PPARγ in NIH-3T3 fibroblasts using a consensus PPAR response element (PPRE) from the acyl CoA oxidase promoter element linked to a luciferase reporter. In these studies, we observed that ROSI activates PPARγ transcription activity in NIH-3T3 cells transfected with ectopic PPARγ. To our surprise, however, we did not observe an induction of PPARγ transcription activity with SCO (FIG. 7, panel A). Based on these results, without wishing to be bound by theory, SCO needs an "adipocyte background" to modulate PPARγ activity, so we transfected mature 3T3-L1 adipocytes with the PPRE luciferase reporter and once again observed that ROSI activated PPARγ transcription activity, but SCO did not (FIG. 7, panel B). Collectively, all of our data indicate that SCO can regulate PPARγ activity in a manner dependent on context, such as gene-specific promoter sequences, cell-type-specific coactivators or corepressors, or post-translational modifications of PPARγ.

PPARγ protein levels are significantly reduced in adipocytes in response to specific ligands such as thiazolidinediones[48]. Ligand-induced activation of PPARγ triggers its polyubiquitylation and proteasomal degradation, and is therefore associated with increased protein turnover[49]. To further examine the effects of SCO on PPARγ, we treated mature adipocytes with the protein synthesis inhibitor, cycloheximide. As shown in FIG. 14, SCO treatment accelerated PPARγ degradation, providing further support that SCO is associated with activation of PPARγ.

Lipolysis is the release of fatty acids and glycerol from adipocytes. Obesity and insulin resistance are associated with both AT inflammation and elevated basal lipolysis[50]. Also, enhancement of lipolysis by the inflammatory cytokine, tumor necrosis factor, alpha (TNFα), contributes to metabolic dysfunction[51-53]. Like TNFα, glucocorticoids (GCs) can cause insulin resistance in vivo and promote lipolysis in cultured adipocytes[54-57]. We have shown that SCO supplementation of a high-fat diet (HFD) reduces circulating levels of free fatty acids (C18:0, C18:1, C16:0, and C16:1) and glycerol[7]. SCO inhibits TNFα-induced lipolysis in 3T3-L1 adipocytes, but has no significant effect on isoproterenol-induced lipolysis, which is mediated by adrenergic signaling[7]. SCO can also attenuate GC (dexamethasone) induced lipolysis in adipocytes (FIG. 8), providing further evidence of a beneficial metabolic effect of SCO in the context of insulin resistance.

Both products of lipolysis, glycerol and non-esterified fatty acids (NEFA), were assayed. Cellular communication between immune cells and adipocytes plays an important role in insulin resistance, and in conditions of obesity and insulin resistance, there is an increase in macrophage-derived TNFα levels in AT. TNFα acts in a paracrine manner on preadipocytes to inhibit adipogenesis and on adipocytes to induce production of inflammatory mediators and promote insulin resistance. Hence, we examined the ability of SCO to modulate TNFα-induced inflammatory cytokine gene expression in fat cells. SCO pretreatment significantly inhibited TNFα-induced expression of lipocalin-2 (Lcn2), interleukin 6 (I16), and C-C motif chemokine ligand 2 (Ccl2), also known as monocyte chemoattractant protein 1 (Mcp1) in adipocytes (FIG. 9). These results are consistent with data showing that SCO supplementation of HFD reduced MCP-1 protein levels in retroperitoneal AT 4.

NF-κB signaling is induced by TNFα in adipocytes and contributes to metabolic dysfunction[53,58-60]. In addition, inflammatory cytokines induced by TNFα are known to be transcriptional targets of NF-κB (www.nf-kb.org). We have observed that a chronic pretreatment with SCO significantly attenuates TNFα-induced p65 nuclear translocation in mature 3T3-L1 adipocytes, indicating a role for NF-κB signaling in SCO's anti-inflammatory effects.

Aim 1: To Validate the Ability of SCO to Promote Adipogenesis In Vivo and to Determine if the Effects of SCO are Dependent on PPARγ Expression in Mature Adipocytes.

Rationale: Our data demonstrate that SCO promotes adipogenesis in murine and human adipocytes in vitro, and specifically activates the ligand binding domain (LBD) of PPARγ fused to the Gal4 DNA-binding domain (DBD). Since PPARγ agonists such as TZDs promote adipogenesis and improve metabolic health[62-65], without wishing to be bound by theory, the ability of SCO to increase adipogenesis during HFD feeding can confer at least part of its insulin sensitizing effects. Assessing SCO's effects on adipogenesis in vivo will be critical to understanding SCO's metabolic actions. The inability of SCO to induce PPARγ transcriptional activity in NIH-3T3 cells stably transfected with PPARγ, or in 3T3-L1 adipocytes, when a PPRE-luciferase reporter construct was used (FIG. 7), indicates that SCO acts as a partial or non-canonical activator of PPARγ similar to those described recently[66-70].

Clinical use of insulin-sensitizing full agonists of PPARγ, such as ROSI, has declined sharply in recent years, due to negative side effects including weight gain, fluid retention, bone loss, and heart problems[71]. However, so-called selective PPARγ modulators (SPPARMs) are the subject of intense study as therapeutics for obesity-related metabolic disease[72-75]. Therefore, SCO's partial PPARγ agonism could make it a therapeutic.

In our previous animal studies, we did not observe increased body weight or adiposity when mice were SCO treated from 2 to 12 weeks[4,5]. Moreover, mice consuming SCO-supplemented HFD for 12 weeks did not have decreased hematocrit levels (FIG. 15) associated with hemodilution, which would indicate fluid retention, while ROSI decreases hematocrit by as much as three percentage points after 14 days of treatment in leptin receptor-deficient (db/db) mice[76]. The experiments in this aim will allow us to validate if SCO can promote adipogenesis in vivo, and validate that the effects of SCO on metabolic health are dependent on PPARγ expression in mature adipocytes of adult male and female mice. Both sets of experiments will include ROSI treatment as a positive control. These experiments will provide information and allow for comparisons between SCO and ROSI.

Without wishing to be bound by theory, SCO promotes adipogenesis in vivo. Use the AdipoChaser mouse model to determine if SCO promotes the formation of new adipocytes in vivo. Adipocytes are long-lived cells, and technical limitations have long precluded in vivo assessment of adipocyte formation. However, the AdipoChaser mouse, an inducible adipocyte-tagging system established over five years ago[77], has provided important data on the development of AT and its modulation by various physiological challenges[78]. We will use this mouse model to validate that SCO modulates adipogenesis in subcutaneous and visceral AT depots in male and female mice under low- and high-fat feeding conditions. It is known that inhibiting AT expansion results in ectopic lipid accumulation and metabolic dysfunction[79-82]. Hence, without wishing to be bound by theory, SCO enhances metabolic health by promoting adipocyte expansion. To validate this, we will perform the experiment outlined in the FIG. 16.

To create the AdipoChaser mouse, we will cross three transgenic lines: the adiponectin promoter driven tetracycline-on (Teton) transcription factor rtTA (adiponectinP-rtTA)[83] line, a Tet-responsive Cre (TRE-cre) line that can be activated by rtTA in the presence of doxycycline (DOXY)[84], and another transgenic line carrying the Rosa26 promoter-driven loxP-stop-loxP-O-galactosidase (Rosa26-loxP-stop-loxP-lacZ)[77,85].

The triple transgenic AdipoChaser mice express the transcription factor rtTA in all of their mature adiponectin expressing adipocytes. DOXY administration activates Cre expression via the TRE promoter, and the Cre protein specifically excises the floxed transcriptional stop cassette and turns on LacZ expression, resulting in permanent LacZ expression in these adipocytes, even after removal of the DOXY. LacZ-expressing cells stain blue when histological AT sections are exposed to an appropriate β-galactosidase substrate.

Starting at 8 weeks of age (WOA), mice will be fed either low-fat diet (LFD) or HFD for 10 weeks, followed by 7 days of DOXY supplementation (600 mg/kg diet) and a 3-day DOXY washout period on their respective diets to label mature adipocytes. Based on data, this protocol labels 100% of the mature adipocytes and allows for complete washout of residual DOXY prior to additional treatment or intervention. This will be followed by LFD or HFD feeding with or without SCO or ROSI supplementation for 6 weeks. We have used this experimental design successfully to establish insulin resistance in HFD-fed mice and have observed positive effects of SCO.

Research Strategy

A total of 15 animals per treatment group will be used. At study's end, we will anesthetize and perfuse 6 mice from each group with 0.2% glutaraldehyde prior to collecting gonadal and inguinal white adipose tissue (gWAT and iWAT) for histology and 3-gal staining as described in 77. It will be critical to determine whether metabolic outcomes correlate with changes in adipocyte formation in this experiment. To that end, 6 animals per group will be subjected to insulin tolerance tests (ITT) one week prior to sacrifice. At the endpoint, these mice will be euthanized, and iWAT, gWAT, mesenteric WAT (mWAT), liver, and skeletal muscle will be excised and snap frozen. Markers of proliferation, inflammation, neurons, vasculature, and adipocyte function will be assessed in whole-tissue extracts. Finally, three animals per group will be used for ex vivo lipolysis assays, where basal, induced (adrenergic, TNFα), and suppressed (insulin) lipolysis will be assessed in the iWAT and gWAT explants, as measured by glycerol and NEFA release into incubation medium. Blood samples will be collected from all non-perfused mice (n=9/condition) at time of sacrifice, after a 4-hour fast, and assayed for glycerol and NEFA levels as indicators of in vivo lipolysis, and for circulating insulin, glucose, lipids, and adipokines. The HFD used for these experiments will be 45 kcal % fat (D12451 from Research Diets), and the LFD (D12450H) will have 10 kcal % fat with matching amount of sucrose.

Without wishing to be bound by theory, ROSI and SCO supplementation will both enhance adipogenesis in subcutaneous AT in both male and female mice, in both LFD and HFD conditions, and that ROSI will have a greater effect than SCO.

Without wishing to be bound by theory, SCO will improve glucose tolerance and reduce the hepatic lipid accumulation that occurs with high-fat feeding. Since female C57BL/6J mice are less metabolically compromised by HFD than male mice, we may not observe profound effects of SCO on metabolic outcomes (GTTs, fasting insulin levels, circulating lipids, adipogenesis) in females.

Without wishing to be bound by theory, SCO won't alter lipolysis in LFD-fed mice, but will lower circulating glycerol and NEFA levels in HFD mice. Ex vivo lipolysis will allow us to assess insulin's ability to suppress lipolysis in AT explants, which might be improved by SCO in HFD-fed mice.

Without wishing to be bound by theory, the ability of SCO to improve HFD-induced glucose intolerance is not dependent on PPARγ in mature adipocytes. Use an inducible adipocyte-specific PPARγ knockout mouse to determine if the metabolic effects of SCO in vivo are dependent on PPARγ expression in mature adipocytes. We have established that SCO exerts profound effects on adipocyte development and function in vitro, and on whole-body metabolism in vivo, and that it acts as a type of agonist for PPARγ. Although PPARγ is crucial in regulating the metabolic functions of AT, including lipolysis, inflammation, and adipokine secretion, studies have shown that the PPARγ agonist ROSI can improve glucose tolerance in mice that lack PPARγ only in mature adipocytes of adult mice89, indicating that PPARγ in mature adipocytes is not necessary for the metabolic benefits of ROSI. Our understanding of metabolic mechanisms of SCO will be enhanced if we can validate that its effects on metabolic health in vivo require the presence of PPARγ in mature adipocytes.

We will create triple transgenic inducible adipocyte-specific PPARγ knockout mice (Adn-PPARγ−/−) by crossing the adiponectinPrtTA 83 and TRE-cre lines[84] described herein for the AdipoChaser experiments with the PPARγflox/flox line from Jackson Laboratories (stock #: 004584) and treat with DOXY as described[89]. Cre expression will be selectively turned on in adipocytes following DOXY treatment, and the Cre protein will excise the floxed PPARγ locus to knock out PPARγ expression selectively in mature adipocytes in adult mice. We will use PPARγflox/flox mice as controls, and all mice will receive DOXY in the diet.

As shown in FIG. 17, beginning at 8 WOA, Adn-PPARγfl/fl mice and PPARγfl/fl control mice will be fed 45 kcal % fat HFD for 12 weeks to establish glucose intolerance and insulin resistance. After 4 days of DOXY/HFD feeding to establish the PPARγ knockout in mature adipocytes only, the mice will be switched to DOXY/HFD supplemented with SCO or ROSI for an additional 7 days. We have observed that 1 week of SCO treatment is sufficient to improve insulin sensitivity[4]. We will perform an oral glucose tolerance test (OGTT) on the mice after 11 weeks on HFD (19 WOA) to confirm that glucose intolerance has been achieved and ensure that no differences exist between control and Adn-PPARγfl/fl groups prior to inducing PPARγ knockout. A second OGTT will be performed after 4 days of DOXY treatment, and as an endpoint assessment, we will perform a final GTT on each mouse using intraperitoneal injection of 2 g/kg body weight [$^3$H]-labeled 2-deoxyglucose (2-[$^3$H]-DG), a non-metabolizable glucose analog, to examine tissue-specific glucose uptake in muscle, gWAT, iWAT, and liver. This method has been used to demonstrate shifts in glucose uptake between muscle and fat in muscle- and R-cell-specific insulin receptor knockout mice[90]. We will use this method to validate that SCO alters glucose accumulation in primary insulin sensitive tissues (fat, liver, and skeletal muscle). These studies will be performed in male and female mice.

Studies characterizing the inducible adipocyte PPARγ knockout model demonstrated, quite surprisingly, that ROSI could improve insulin sensitivity independently of PPARγ expression in mature adipocytes[89]. Without wishing to be bound by theory, this study will repeat this observation. Without wishing to be bound by theory, since SCO behaves as a partial PPARγ agonist, it can recapitulate some but not all of ROSI's actions. Should SCO improve glucose tolerance in the knockout, this would add to the similarities we have observed between ROSI and SCO. If SCO fails to improve glucose metabolism in the absence of adipocyte PPARγ, this can represent a difference between SCO and ROSI and demonstrate PPARγ independent effects of SCO. Without wishing to be bound by theory, PPARγ dependence of SCO's metabolic effects would indicate that SCO can have a distinct mode of action from TZDs.

Aim 2: Mechanisms Involved in SCO to Attenuate the Metabolic Dysfunction Induced by Glucocorticoids (GCs).

GCs are prescribed for a variety of serious and chronic medical conditions[91-93], but their use often results in a metabolic disease state[94]. Therefore, it is paramount to identify ways to attenuate the harmful effects of these drugs. GC signaling in AT plays a role in the development of insulin resistance and fatty liver disease associated with excess GCs[57,95,96]. Data has shown improvements in obesity-associated insulin resistance and a reduction in hepatic lipid accumulation following SCO treatment in HFD-fed mice[4,5,97]. However, until recently, we had not examined the effects of SCO on glucocorticoid-induced metabolic dysfunction. We therefore performed experiments to validate whether SCO could attenuate some of the negative effects of GCs on murine adipocytes, and found that SCO suppresses GC-induced lipolysis in 3T3-L1 adipocytes (FIG. 8). Elevated lipolysis can be associated with metabolic dysfunction in mammals, including humans[98-100], and GC-induced lipolysis is a primary driver of the insulin resistance associated with elevated GCs[101].

We validated the effects of dexamethasone (DEX), a synthetic glucocorticoid, on gene expression in 3T3-L1 adipocytes, with or without SCO pretreatment, and observed that SCO reduced the ability of DEX to induce serum/glucocorticoid regulated kinase 1 (Sgk1) and serine (or cysteine) peptidase inhibitor, clade A, member 3n (Serpina3n) mRNA expression, but not that of other known GC-regulated genes such as dual specificity phosphatase 1 (Dusp1) or lipin 1 (FIG. 18). Also, neither DEX nor SCO affected Pparg expression in this treatment paradigm, indicating some specificity in SCO's effects on DEX-induced gene regulation. Notably, both Sgk1 and Serpina3n can be signaling molecules in the progression of insulin resistance[102-111] Consistent with these observations, one month of SCO treatment in C57BL/6J mice results in a reduction of Serpina3n mRNA levels in the AT of diet-induced obese mice (FIG. 18, panel F).

Without wishing to be bound by theory, SCO attenuates effects of glucocorticoids on adipocytes in a cell-autonomous manner. Characterize SCO's effects on DEX-induced changes in SGK1 and SERPINA3N protein levels, glucocorticoid receptor (GR) translocation, and GR binding to Sgk1 and Serpina3n promoters. Our data have identified two glucocorticoid-induced genes, Sgk1 and Serpina3n, whose DEXmediated induction is attenuated by SCO in adipocytes. To identify mechanisms involved in this regulation, we will validate that alterations in Sgk1 and Serpina3n mRNA levels are accompanied by changes in protein levels. We will also validate that SCO reduces the nuclear translocation of the glucocorticoid receptor (GR) in adipocytes, and examine the binding of GR to the promoters of these two genes in the presence and absence of SCO, using Chromatin Immunoprecipitation (ChIP) analysis. A GRE (GC response element) has been characterized in the human Sgk1 promoter[112]. We will identify the GRE(s) in the mouse Sgk1 promoter and determine if there is a GRE in the Serpina3n promoter. These experiments will be conducted in mature primary murine adipocytes after treatment with SCO or vehicle control for 72 hours, an experimental paradigm in which SCO reduces DEX-induced lipolysis (FIG. 8) as well as the expression of some DEX-induced genes (FIG. 18).

Validate that regulation of Serpina3n or Sgk1 is required for SCO's effects on lipolysis and glucose uptake in glucocorticoid-treated adipocytes. DEX increases adipocyte lipolysis and regulates the mRNA and protein expression of several lipolytic enzymes and beta-adrenergic signaling proteins[55,113-116] and SCO reduces DEX-induced lipolysis in 3T3-L1 adipocytes (FIG. 8). Additionally, impaired glucose uptake in response to DEX is well documented in cultured human and rodent adipocyteslo[104,117-120]. However, the effects of SCO on glucose uptake in DEX-treated adipocytes have not been assessed. Given our data showing that SCO reduced the DEX-induced expression of Sgk1 and Serpina3n, and the roles of these genes in insulin resistance, we will prevent their downregulation using ectopic overexpression, and assess whether SCO can modulate lipolysis and/or glucose uptake without suppression of Sgk1 and/or Serpina3n expression.

Without wishing to be bound by theory, SCO will reduce the DEX-mediated induction of Sgk1 and Serpina3n protein expression, however these effects can or cannot be mediated by alterations in GR trafficking to the nucleus or in GR promoter binding. We have substantial experience performing ChIP[122], and have previously studied GR translocation in adipocytes[123]. Experiments will be conducted in murine adipocytes, and repeated in human adipocytes purchased from Zenbio, Inc. We have purchased and successfully used both human preadipocytes (FIG. 6) and adipocytes from this supplier. Studies in human adipocytes will increase the translational relevance of our observations. Overexpression of Serpina3n or Sgk1 can affect the action of SCO in adipocytes, but the mechanistic experiments will validate that either of these proteins plays a role in the SCO modulation of GC action in vitro. Without wishing to be bound by theory, the effects of GR and/or SCO on gene expression are not mediated via GREs, but rather through GR acting as a transcriptional co-activator/repressor, or that these effects are mediated by non-genomic actions of GR.

Without wishing to be bound by theory, SCO can attenuate glucocorticoid-induced insulin resistance in vivo. SCO reduces some of the metabolic dysfunction associated with HFD in mice[4,5], and a one-week treatment of corticosterone (CORT), the active endogenous GC in rodents, induces insulin resistance in mice[124]. Without wishing to be bound by theory, we will validate that SCO can mitigate CORT-induced insulin resistance in vivo. Since there are sex differences in obesity, diabetes, and GCs in various mouse models, such as C57BL/6 mice[125], both male and female C57BL/6J mice will be used. Mice will be ordered from the Jackson Laboratory at 5 WOA and will have 3 weeks to acclimate to their new surroundings, then body weight, body composition, and blood glucose will be used to determine randomization into groups. At 8 WOA, mice will be fed a LFD diet with or without 1% SCO supplementation for two weeks. Mice will then be treated with 100 mg/mL CORT, or 1% ethanol (vehicle), in their drinking water for an additional week while remaining on their respective diets. An ITT will be performed via intraperitoneal injection of insulin (1 U/kg of lean body mass) following 5 days of CORT treatment (FIG. 19).

Blood will be collected prior to diet switch, prior to CORT treatment, and prior to euthanasia, to assess various metabolic outcomes, including circulating glucose and insulin. Mice will be euthanized after one week of CORT treatment. At this time, liver and AT will be excised and either snap frozen or placed in formalin to examine GCregulated gene and protein expression or histology, respectively. Additionally, small samples of AT will be removed to assess ex vivo lipolysis.

Without wishing to be bound by theory, the GC treatment described above will induce insulin resistance as judged by an ITT 124, and that SCO supplementation can reduce this effect. SCO can improve GC-induced insulin resistance, this approach will help validate this effect. If SCO can ameliorate GC-induced metabolic dysfunction, this could be a very high-impact observation given the widespread use of GCs and the ongoing search for therapies to mitigate its unfavorable actions. In our cultured adipocyte experiments, not all DEXinduced genes were affected by the SCO supplementation (FIG. 18), and, without wishing to be bound by theory, SCO will reduce all the actions of GCs. We will identify mechanisms of SCO's effects on GC action (GR binding, GR translocation, requirements for Serpina3n or Sgk1 expression). They will allow us to validate the ability of SCO to antagonize specific actions of GCs in adipocytes and in vivo.

Aim 3—to Validate the Mechanisms Involved in the Ability of SCO and its Bioactives to Inhibit TNFα Action in Adipocytes.

TNFα acts via several signaling pathways including the nuclear factor of kappa light polypeptide gene enhancer in B-cells inhibitor, alpha (IκB)/NF-κB and MAP kinase pathways. NF-κB induces expression of many inflammatory cytokines through nuclear translocation of its p65 subunit, which then binds to its target gene promoters (reviewed in 53,58 & www.nf-kb.org). Our data show that SCO significantly inhibits the expression of the inflammatory genes Lcn2, I16, and Ccl2(Mcp1) in TNFα-treated 3T3-L1 adipocytes (FIG. 9). TNFα is known to induce LCN2 secretion from adipocytes 126 and we have observed that pretreating adipocytes for three days with SCO significantly diminishes this effect (FIG. 20).

These observations are of physiological importance, since circulating levels of LCN2 are elevated in obese and insulin resistant states[127-129]. We have also shown that SCO inhibits nuclear translocation of NF-κB p65 in TNFα-treated adipocytes (FIG. 10), indicating mechanism for SCO's inhibition of inflammatory gene expression. In this aim, we will conduct mechanistic studies of SCO's effects on inflammatory pathways and on the expression of inflammatory cytokines. We will also test three individual bioactive compounds from SCO to validate that they exhibit the same anti-inflammatory properties as the parent SCO extract.

Without wishing to be bound by theory, SCO attenuates TNFα-induced inflammatory cytokine expression through inhibition of NF-κB signaling in adipocytes.

We will validate that SCO can reduce TNFα-induced activation of an NF-κB response element. SCO substantially reduces the TNFα-induced expression of some inflammatory genes (FIG. 9) and nuclear translocation of the p65 subunit of NF-κB (FIG. 10). Because TNFα can activate several signaling pathways, and many factors can impact inflammatory gene expression, we will validate that SCO can inhibit direct activation of a NF-κB response element in a luciferase reporter assay. To accomplish this, we will transfect NIH-3T3 cells with a commercially available NF-κB luciferase reporter construct and assess induction by TNFα in the presence or absence of SCO.

We will validate that SCO can reduce p65 binding to promoters of specific genes induced by TNFα in adipocytes. NF-κB is required for TNFα-induced induction of Lcn2 in 3T3-L1 adipocytes 126 and 116 and Mcp1 are known to be induced by NF-κB in various cell types. To validate that SCO can inhibit TNFα-induced binding of p65 to these specific gene promoters in adipocytes, chromatin immunoprecipitation (ChIP) assays will be conducted in which we will assess binding of the p65 subunit of NF-κB to the promoters of Lcn2, Ccl2, and 116 in primary mouse adipocytes treated with TNFα.

We will validate that SCO affects TNFα-induced changes in phosphorylation of NF-κB p65 or degradation of IκB proteins in adipocytes. Induction of the NF-κB signaling pathway by TNFα involves the phosphorylation of IκB, which targets it for proteasomal degradation[13]. Nuclear translocation and transcriptional activity of the p65 subunit of NF-κB are also modulated by phosphorylation at several sites[131]. We will treat mouse primary adipocytes with TNFα and determine whether pretreatment with SCO can limit degradation of IκB or alter phosphorylation of p65 at Ser276 and Ser536, the principal sites involved in TNFα-induced gene activation[131,132].

Without wishing to be bound by theory, dicaffeoylquinic acids (DCQA) and/or prenylated coumaric acids (PCA) present in SCO can inhibit TNFα-induced inflammatory cytokine expression. We have purified three different prenylated coumaric acids (PCA) from SCO, each of which can enhance adipogenesis in 3T3-L1 preadipocytes (FIG. 5). The SCO parent extract is an activator of PPARγ in certain conditions[4,5], and there is evidence that PPARγ agonism can counter TNFα actions in adipocytes[133-136]. SCO's effects on PPARγ activity can therefore mediate its inhibitory effects on inflammatory cytokine expression. PCAs can mediate the adipogenic effects of propolis, and one such PCA present in propolis, Artepillin C, is a PPARγ agonist[137-139] Hence, we will examine the ability of three PCAs from SCO (capillartemisin A, capillartemisin B, and the new compound referred to as scoprenyl) to recapitulate SCO's effects on TNFα-treated adipocytes. In addition to the PCAs isolated from SCO fractions found to promote adipogenesis, we also identified two dicaffeoylquinic acids (DCQA) in SCO fractions that did not enhance adipocyte differentiation[6]. However, DCQAs have documented anti-inflammatory effects[140-144]. For example, in a mouse model of atopic dermatitis, SCO and some of its components could lessen clinical symptoms of skin lesions and reduce levels of various inflammatory mediators in both the lesions and the serum. DEQA (3,5-dicaffeoyl-epi-quinic acid) was a major component of a butanol-extracted SCO fraction in these studies, and can reduce caspase 1 activity[42]. A study in activated mast cells has shown anti-inflammatory effects of both SCO and DEQA, including inhibition of cytokine expression, p65 translocation, and caspase activity[43]. Therefore, we will validate that DCQAs from SCO have the same effects as SCO parent on TNFα-induced gene expression in adipocytes.

Since SCO inhibits TNFα-induced nuclear translocation of p65, without wishing to be bound by theory, SCO will modulate the transcriptional activity of p65, as measured by direct activation of the NF-κB response element. Also, SCO will reduce binding of p65 to the promoters of our genes of interest (I16, Ccl2, and Lcn2), whose expression levels are inhibited by SCO. However, the observed SCO effects on inflammatory cytokine expression may not require changes in p65 activity or DNA binding. Indeed, data from our laboratory show that transcription of Lcn2 induced by TNFα is suppressed by ERK inhibition, in the absence of any effects on binding of p65 to the Lcn2 promoter[59]. Also, the effects of SCO on DNA binding may be gene-specific, which would be an intriguing finding. Also, three MAP kinase pathways are known to be activated by TNFα in adipocytes (ERK 1/2, p38, and Jnk) 53; any one of them could be impacted by SCO in a way that interferes with NF-κB signaling and target gene expression. SCO can also alter the phosphorylation of specific sites in p65 and/or the degradation of IκB proteins known to be triggered by TNFα. Although SCO's effects on gene expression can occur without such changes, answering these questions will allow us to validate which signaling elements are modulated by SCO.

Vertebrate Animals:

1. Description of Procedures: We will isolate preadipocytes from inguinal adipose tissue of 5 to 6-week-old C57BL/6J, Adn-PPARgfl/fl, and PPARgfl/fl male and female mice; these cells will be differentiated to establish mouse primary adipocyte cultures as described in Aims 2 and 3. We will also breed AdipoQ-rtTA and TRE-Cre mice to either Rosa26-loxP-stop-loxP-lacZ or PPARgfl/fl mice to generate the AdipoChaser or doxycycline-inducible PPARg adipocyte knockout (Adn-PPARg−/−) in adult mice. All of the mice are on a C57BL/6J background. All mice will be genotyped between 2-3 weeks of age using a tail snip method. In Aim 1, male and female AdipoChaser mice, Adn-PPARgfl/fl, and control PPARgfl/fl mice will be fed doxycycline-supplemented LFD or HFD for 4-7 days. These mice will then be fed LFD or HFD plus or minus doxycycline and SCO or Rosi or appropriate control LFD or HFD for an additional 7 days-6 weeks. The HFD used for these experiments will be 45 kcal % fat, and the LFD will have 10 kcal % fat with matching amount of sucrose. Terminal assessment will be performed at 21 or 26 weeks of age. For adipocyte-specific inducible PPARg KO experiments, doxycycline-fed floxed littermates will be used as controls. In Aim 2, C57BL/6J will be fed LFD diet with or without SCO supplementation for 3 weeks with additional corticosterone or ethanol vehicle administration via their drinking water during the final week prior to euthanasia and blood and tissue collection at 11 weeks of age. Mice will undergo the following procedures: measurement of body weight and body composition (via NMR), OGTTs, IPGTT, and IP-ITT. Mice will also be subjected to 4 hours of fasting prior to GTT or ITT and euthanasia. During GTTs and IP-ITTs, blood will be collected via tail snip at baseline and 15, 30, 60, 90, and 120 min following glucose or insulin administration. For OGTTs, glucose will be delivered via oral gavage using a flexible, plastic gavage needle, and this procedure will be performed by a well-trained technician. IP-GTTs will be performed by injecting 2-[$^3$H]-DG for 120 min prior to euthanasia. Blood for adipokine, insulin, glucose, glycerol, and NEFA analyses may also be collected via submandibular vein. Terminally, mice will undergo glutaraldehyde perfusion (Aim 1, Adipochaser mice) or blood will be collected via cardiac puncture (Aims 1 and 2) under deep anesthesia by isoflurane gas inhalation. Mice will be euthanized by isoflurane overdose or carbon dioxide inhalation followed by cervical dislocation, and tissues will be removed for RNA, protein analyses, and histology. Male and female mice will be used for all animal studies.

REFERENCES CITED IN THIS EXAMPLE

1. Vidal-Puig A. Adipose tissue expandability, lipotoxicity and the metabolic syndrome. Endocrinol Nutr. 2013; 60(Supl. 1):39-43.
2. Kusminski C M, Bickel P E, Scherer P E. Targeting adipose tissue in the treatment of obesity-associated diabetes. Nat Rev Drug Discov. 2016; 15(9):639-660.
3. Rosen E D, Spiegelman B M. What we talk about when we talk about fat. Cell. 2014; 156(1-2):20-44.
4. Richard A J, Burris T P, Sanchez-Infantes D, Wang Y, Ribnicky D M, Stephens J M. *Artemisia* extracts activate PPARγ, promote adipogenesis, and enhance insulin sensitivity in adipose tissue of obese mice. Nutrition. 2014; 30(7-8 SUPPL.):S31-6.
5. Richard A J, Fuller S, Fedorcenco V, et al. *Artemisia scoparia* enhances adipocyte development and endocrine function in vitro and enhances insulin action in vivo. PLoS One. 2014; 9(6):e98897.
6. Boudreau A, Poulev A, Ribnicky D M, et al. Distinct fractions of an Artemisia scoparia extract contain compounds with novel adipogenic bioactivity. Front Nutr. 2019; 6:18.
7. Boudreau A, Richard A J, Burrell J A, et al. An ethanolic extract of Artemisia scoparia inhibits lipolysis in vivo and has antilipolytic effects on murine adipocytes in vitro. Am J Physiol Metab. 2018; 315(5): E1053-E1061.
8. Tu Y. Artemisinin—A Gift from Traditional Chinese Medicine to the World (Nobel Lecture). Angew Chemie—Int Ed. 2016; 55(35):10210-10226.
9. Wang K S, Li J, Wang Z, et al. Artemisinin inhibits inflammatory response via regulating NF-κB and MAPK signaling pathways. Immunopharmacol Immunotoxicol. 2017; 39(1):28-36.
10. Liu X, Cao J, Huang G, Zhao Q, Shen J. Biological Activities of Artemisinin Derivatives Beyond Malaria. Curr Top Med Chem. 2019; 19(3):205-222.
11. Lu B-W, Baum L, So K-F, Chiu K, Xie L-K. More than anti-malarial agents: therapeutic potential of artemisinins in neurodegeneration. Neural Regen Res. 2019; 14(9):1494.
12. Singh A, Sarin R. Artemisia scoparia—A new source of artemisinin. Bangladesh J Pharmacol. 2010; 5(1): 17-20.
13. WRIGHT M, WATSON M F. Tibetan Medicinal Plants. Edited by C. Kletter & M. Kriechbaum. Stuttgart: Medpharm Scientific Publishers. 2001. 383pp., 77 full-colour plates. ISBN 3 88763 067 X. €138.00 (hardback). Edinburgh J Bot. 2002.
14. Cha J-D, Jeong M-R, Jeong S-I, et al. Chemical Composition and Antimicrobial Activity of the Essential Oils of Artemisia scoparia and A. capillaris. Planta Med. 2005; 71(2):186-190.
15. Chandrasekharan I, Khan H A, Ghanim A. Flavonoids from Artemisia scoparia. Planta Med. 1981.
16. Hong J-H, Hwang E-Y, Kim H-J, Jeong Y-J, Lee I S. Artemisia capillaris Inhibits Lipid Accumulation in 3T3-L1 Adipocytes and Obesity in C57BL/6J Mice Fed a High Fat Diet. J Med Food. 2009; 12(4):736-745.
17. Ribnicky D M, Poulev A, Watford M, Cefalu W T, Raskin I. Antihyperglycemic activity of Tarralin™, an ethanolic extract of Artemisia dracunculus L. Phytomedicine. 2006; 13(8):550-557.

18. Aggarwal S, Shailendra G, Ribnicky D M, Burk D, Karki N, Qingxia Wang M S. An extract of Artemisia dracunculus L. stimulates insulin secretion from R cells, activates AMPK and suppresses inflammation. J Ethnopharmacol. 2015; 170:98-105.
19. Obanda D N, Ribnicky D M, Raskin I, Cefalu W T. Bioactives of Artemisia dracunculus L. enhance insulin sensitivity by modulation of ceramide metabolism in rat skeletal muscle cells. Nutrition. 2014; 30(7-8 SUPPL.)
20. Kheterpal I, Scherp P, Kelley L, et al. Bioactives from Artemisia dracunculus L. enhance insulin sensitivity via modulation of skeletal muscle protein phosphorylation. Nutrition. 2014; 30(7-8 SUPPL.)
21. Ribnicky D M, Roopchand D E, Poulev A, et al. Artemisia dracunculus L. polyphenols complexed to soy protein show enhanced bioavailability and hypoglycemic activity in C57BL/6 mice. Nutrition. 2014; 30(7-8 SUPPL.):S4.
22. Vandanmagsar B, Haynie K R, Wicks S E, et al. Artemisia dracunculus L. extract ameliorates insulin sensitivity by attenuating inflammatory signalling in human skeletal muscle culture. Diabetes, Obes Metab. 2014; 16(8):728-738.
23. Kirk-Ballard H, Wang Z Q, Acharya P, et al. An extract of Artemisia dracunculus L. inhibits ubiquitin-proteasome activity and preserves skeletal muscle mass in a murine model of diabetes. PLoS One. 2013; 8(2):1-12.
24. Scherp P, Putluri N, LeBlanc G J, et al. Proteomic analysis reveals cellular pathways regulating carbohydrate metabolism that are modulated in primary human skeletal muscle culture due to treatment with bioactives from Artemisia dracunculus L. J Proteomics. 2012; 75(11):3199-3210.
25. Obanda D N, Hemandez A, Ribnicky D, et al. Bioactives of Artemisia dracunculus L. mitigate the role of ceramides in attenuating insulin signaling in rat skeletal muscle cells. Diabetes. 2012; 61(3):597-605.
26. Weinoehrl S, Feistel B, Pischel I, Kopp B, Butterweck V. Comparative Evaluation of Two Different Artemisia dracunculus L. Cultivars for Blood Sugar Lowering Effects in Rats. Phyther Res. 2012; 26(4):625-629.
27. Kheterpal I, Coleman L, Ku G, Wang Z Q, Ribnicky D, Cefalu W T. Regulation of insulin action by an extract of Artemisia dracunculus L. in primary human skeletal muscle culture: A proteomics approach. Phyther Res. 2010; 24(9):1278-1284.
28. Wang Z Q, Ribnicky D, Zhang X H, Raskin I, Yu Y, Cefalu W T. Bioactives of Artemisia dracunculus L enhance cellular insulin signaling in primary human skeletal muscle culture. Metabolism. 2008; 57(SUPPL. 1).
29. Choi E, Park H, Lee J, Kim G. Anticancer, antiobesity, and anti-inflammatory activity of Artemisia species in vitro. J Tradit Chinese Med=Chung i tsa chih ying wen pan. 2013; 33(1):92-97.
30. Choi E, Kim G. Effect of Artemisia species on cellular proliferation and apoptosis in human breast cancer cells via estrogen receptor-related pathway. J Tradit Chinese Med=Chung i tsa chih ying wen pan. 2013; 33(5):658-663.
31. Geng C-A, Huang X-Y, Chen X-L, et al. Three new anti-HBV active constituents from the traditional Chinese herb of Yin-Chen (Artemisia scoparia). J Ethnopharmacol. 2015; 176:109-117.
32. Sajid M, Rashid Khan M R, Shah N A, et al. Evaluation of Artemisia scoparia for hemostasis promotion activity. Pak J Pharm Sci. 2017; 30(5):1709-1713.
33. Singh H P, Kaur S, Mittal S, Batish D R, Kohli R K. In vitro screening of essential oil from young and mature leaves of Artemisia scoparia compared to its major constituents for free radical scavenging activity. Food Chem Toxicol. 2010; 48(4):1040-1044.
34. Cho J-Y, Jeong S-J, Lee H La, et al. Sesquiterpene lactones and scopoletins from Artemisia scoparia Waldst. & Kit. and their angiotensin I-converting enzyme inhibitory activities. Food Sci Biotechnol. 2016; 25(6):1701-1708.
35. Cho J-Y, Park K-H, Hwang D, et al. Antihypertensive Effects of Artemisia scoparia Waldst in Spontaneously Hypertensive Rats and Identification of Angiotensin I Converting Enzyme Inhibitors. Molecules. 2015; 20(11):19789-19804.
36. Gilani A H, Janbaz K H. Hepatoprotective effects of Artemisia scoparia against carbon tetrachloride: an environmental contaminant. J Pak Med Assoc. 1994; 44(3):65-68.
37. Promyo K, Cho J Y, Park K H, Jaiswal L, Park S Y, Ham K S. Artemisia scoparia attenuates amyloid R accumulation and tau hyperphosphorylation in spontaneously hypertensive rats. Food Sci Biotechnol. 2017; 26(3):775-782.
38. Khan M A, Khan H, Tariq S A, Pervez S. In Vitro Attenuation of Thermal-Induced Protein Denaturation by Aerial Parts of Artemisia scoparia. J Evid Based Complementary Altem Med. 2015; 20(1):9-12.
39. Yahagi T, Yakura N, Matsuzaki K, Kitanaka S. Inhibitory effect of chemical constituents from Artemisia scoparia Waldst. et Kit. on triglyceride accumulation in 3T3-L1 cells and nitric oxide production in RAW 264.7 cells. J Nat Med. 2014; 68(2):414-420.
40. Habib M, Waheed I. Evaluation of anti-nociceptive, anti-inflammatory and antipyretic activities of Artemisia scoparia hydromethanolic extract. J Ethnopharmacol. 2013; 145(1):18-24.
41. Wang X, Huang H, Ma X, et al. Anti-inflammatory effects and mechanism of the total flavonoids from Artemisia scoparia Waldst. et kit. in vitro and in vivo. Biomed Pharmacother. 2018; 104:390-403.
42. Ryu K J, Yoou M S, Seo Y, Yoon K W, Kim H M, Jeong H J. Therapeutic effects of Artemisia scoparia Waldst. et Kitaib in a murine model of atopic dermatitis. Clin Exp Dermatol. 2018; 43(7):798-805.
43. Nam S-Y, Han N-R, Rah S-Y, Seo Y, Kim H-M, Jeong H-J. Anti-inflammatory effects of Artemisia scoparia and its active constituent, 3,5-dicaffeoyl-epi-quinic acid against activated mast cells. Immunopharmacol Immunotoxicol. 2018; 40(1):52-58.
44. Hussain W, Badshah L, Ullah M, Ali M, Ali A, Hussain F. Quantitative study of medicinal plants used by the communities residing in Koh-e-Safaid Range, northern Pakistani-Afghan borders. J Ethnobiol Ethnomed. 2018; 14(1):30.
45. Hussain W, Ullah M, Dastagir G, Badshah L. Quantitative ethnobotanical appraisal of medicinal plants used by inhabitants of lower Kurram, Kurram agency, Pakistan. Avicenna J phytomedicine. 2018; 8(4):313-329.
46. Ahmad K S, Hamid A, Nawaz F, et al. Ethnopharmacological studies of indigenous plants in Kel village, Neelum Valley, Azad Kashmir, Pakistan. J Ethnobiol Ethnomed. 2017; 13(1):68.

47. Kitagawa I, Fukuda Y, Yoshihara M, Yamahara J, Yoshikawa M. Capillartemisin A and B, two new choleretic principles from Artemisiae capillaris Herba. Chem Pharm Bull. 1983; 31(1):352-355.
48. Hauser S, Adelmant G, Sarraf P, Wright H M, Mueller E, Spiegelman B M. Degradation of the peroxisome proliferator-activated receptor γ is linked to ligand-dependent activation. J Biol Chem. 2000; 275(24): 18527-18533.
49. Floyd Z E, Stephens J M. Controlling a master switch of adipocyte development and insulin sensitivity: Covalent modifications of PPARγ. Biochim Biophys Acta—Mol Basis Dis. 2012; 1822(7):1090-1095.
50. Morigny P, Houssier M, Mouisel E, Langin D. Adipocyte lipolysis and insulin resistance. Biochimie. 2016; 125:259-266.
51. Langin D, Amer P. Importance of TNFα and neutral lipases in human adipose tissue lipolysis. Trends Endocrinol Metab. 2006; 17(8):314-320.
52. Fruhbeck G, Mendez-Gimenez L, Femindez-Formoso J-A, Femindez S, Rodriguez A. Regulation of adipocyte lipolysis. Nutr Res Rev. 2014; 27(01):63-93.
53. Cawthorn W P, Sethi J K. TNF-α and adipocyte biology. FEBS Lett. 2008; 582(1):117-131.
54. Divertie G D, Jensen M D, Miles J M. Stimulation of Lipolysis in Humans by Physiological Hypercortisolemia. Diabetes. 1991; 40(10):1228 LP-1232.
55. Harvey I, Stephenson E J, Redd J R, et al. Glucocorticoid-Induced Metabolic Disturbances Are Exacerbated in Obese Male Mice. Endocrinology. 2018; 159 (6):2275-2287.
56. Hochberg I, Harvey I, Tran Q T, et al. Gene expression changes in subcutaneous adipose tissue due to Cushing's disease. J Mol Endocrinol. 2015; 55(2):81-94.
57. Shen Y, Roh H C, Kumari M, Rosen E D. Adipocyte glucocorticoid receptor is important in lipolysis and insulin resistance due to exogenous steroids, but not insulin resistance caused by high fat feeding. Mol Metab. 2017; 6(10):1150-1160.
58. Baker R G, Hayden M S, Ghosh S. NF-κB, inflammation, and metabolic disease. Cell Metab. 2011; 13(1):11-22. 59. Zhao P, Stephens J M. STAT1, NF-κB and ERKs play a role in the induction of lipocalin-2 expression in adipocytes. Mol Metab. 2013; 2(3):161-170.
60. Arkan M C, Hevener A L, Greten F R, et al. IKK-P links inflammation to obesity-induced insulin resistance. Nat Med. 2005; 11(2):191-198.
61. Kenyon C J. The genetics of ageing. Nature. 2010; 464(7288):504-512.
62. Nolan J J, Ludvik B, Beerdsen P, Joyce M, Olefsky J. Improvement in glucose tolerance and insulin resistance in obese subjects treated with troglitazone. N Engl J Med. 1994; 331(18):1188-1193.
63. Olefsky J M. Treatment of insulin resistance with peroxisome proliferator-activated receptor γ agonists. J Clin Invest. 2000; 106(4):467-472.
64. Lehmann J M, Moore L B, Smith-Oliver T A, Wilkison W O, Willson T M, Kliewer S A. An antidiabetic thiazolidinedione is a high affinity ligand for peroxisome proliferator-activated receptor γ (PPARγ). J Biol Chem. 1995; 270(22):12953-12956.
65. Tontonoz P, Hu E, Graves R A, Budavari A I, Spiegelman B M. mPPAR gamma 2: tissue-specific regulator of an adipocyte enhancer. Genes Dev. 1994; 8(10):1224-1234.
66. Choi J H, Banks A S, Estall J L, et al. Anti-diabetic drugs inhibit obesity-linked phosphorylation of PPAR-gamma by Cdk5. Nature. 2010; 466(7305):451-456.
67. Choi J H, Banks A S, Kamenecka™, et al. Antidiabetic actions of a non-agonist PPARγ ligand blocking Cdk5-mediated phosphorylation. Nature. 2011; 477(7365): 477-481.
68. Park S, Kim J K, Oh C J, Choi S H, Jeon J H, Lee I K. Scoparone interferes with STAT3-induced proliferation of vascular smooth muscle cells. Exp Mol Med. 2015; 47.
69. Choi S-S, Kim E S, Koh M, et al. A novel non-agonist peroxisome proliferator-activated receptor γ (PPARγ) ligand UHC1 blocks PPARγ phosphorylation by cyclin-dependent kinase 5 (CDK5) and improves insulin sensitivity. J Biol Chem. 2014; 289(38):26618-26629.
70. Huan Y, Pan X, Peng J, et al. A novel specific peroxisome proliferator-activated receptor γ (PPARγ) modulator YR4-42 ameliorates hyperglycaemia and dyslipidaemia and hepatic steatosis in diet-induced obese mice. Diabetes, Obes Metab. 2019; 21(11):2553-2563.
71. Lipscombe L L, Gomes T, Levesque L E, Hux J E, Juurlink D N, Alter D A. Thiazolidinediones and Cardiovascular Outcomes in Older Patients With Diabetes. JAMA. 2007; 298(22):2634.
72. Feldman P, Lambert M, Henke B. PPAR Modulators and PPAR Pan Agonists for Metabolic Diseases: The Next Generation of Drugs Targeting Peroxisome Proliferator-Activated Receptors? Curr Top Med Chem. 2008.
73. Chigurupati S, Dhanaraj S A, Balakumar P. A step ahead of PPARγ full agonists to PPARγ partial agonists: Therapeutic perspectives in the management of diabetic insulin resistance. Eur J Pharmacol. 2015; 755: 50-57.
74. Dunn F L, Higgins L S, Fredrickson J, Depaoli A M. Selective modulation of PPARγ activity can lower plasma glucose without typical thiazolidinedione side-effects in patients with Type 2 diabetes. J Diabetes Complications. 2011.
75. Higgins L S, Depaoli A M. Selective peroxisome proliferator-activated receptor γ (PPARγ) modulation as a strategy for safer therapeutic PPARγ activation. In: American Journal of Clinical Nutrition; 2010.
76. Roy S, Khanna V, Mittra S, et al. Combination of dipeptidylpeptidase IV inhibitor and low dose thiazolidinedione: Preclinical efficacy and safety in db/db mice. Life Sci. 2007; 81(1):72-79.
77. Wang Q A, Tao C, Gupta R K, Scherer P E. Tracking adipogenesis during white adipose tissue development, expansion and regeneration. Nat Med. 2013; 19(10): 1338-1344.
78. Wang Q A, Scherer P E. The AdipoChaser mouse. Adipocyte. 2014; 3(2):146-150.
79. Gustafson B, Hedjazifar S, Gogg S, Hammarstedt A, Smith U. Insulin resistance and impaired adipogenesis. Trends Endocrinol Metab. 2015; 26(4):193-200.
80. Smith U, Kahn B B. Adipose tissue regulates insulin sensitivity: role of adipogenesis, de novo lipogenesis and novel lipids. J Intern Med. 2016; 280(5):465-475.

81. Danforth E. Failure of adipocyte differentiation causes type II diabetes mellitus? Nat Genet. 2000; 26(1):13-13.
82. Kim J-Y, van de Wall E, Laplante M, et al. Obesity-associated improvements in metabolic profile through expansion of adipose tissue. J Clin Invest. 2007; 117 (9):2621-2637.
83. Sun K, Asterholm I W, Kusminski C M, et al. Dichotomous effects of VEGF-A on adipose tissue dysfunction. Proc Natl Acad Sci. 2012; 109(15):5874-5879.
84. Perl A-K T, Wert S E, Nagy A, Lobe C G, Whitsett J A. Early restriction of peripheral and proximal cell lineages during formation of the lung. Proc Natl Acad Sci USA. 2002; 99(16):10482-10487.
85. Soriano P. Generalized lacZ expression with the ROSA26 Cre reporter strain. Nat Genet. 1999; 21(1): 70-71.
86. Strawford A, Antelo F, Christiansen M, Hellerstein M K. Adipose tissue triglyceride turnover, de novo lipogenesis, and cell proliferation in humans measured with 2 H 2 O. Am J Physiol Metab. 2004; 286(4):E577-E588.
87. Tchoukalova Y D, Fitch M, Rogers P M, et al. In vivo adipogenesis in rats measured by cell kinetics in adipocytes and plastic-adherent stroma-vascular cells in response to high-fat diet and thiazolidinedione. Diabetes. 2012; 61(1):137-144.
88. White U A, Fitch M D, Beyl R A, Hellerstein M K, Ravussin E. Differences in In Vivo Cellular Kinetics in Abdominal and Femoral Subcutaneous Adipose Tissue in Women. Diabetes. 2016; 65(6):1642-1647.
89. Wang Q A, Zhang F, Jiang L, et al. Peroxisome Proliferator-Activated Receptor γ and Its Role in Adipocyte Homeostasis and Thiazolidinedione-Mediated Insulin Sensitization. Mol Cell Biol. 2018; 38(10).
90. Mauvais-Jarvis F, Virkamaki A, Michael M D, et al. A model to explore the interaction between muscle insulin resistance and beta-cell dysfunction in the development of type 2 diabetes. Diabetes. 2000; 49(12):2126-2134.
91. Fardet L, Petersen I, Nazareth I. Prevalence of long-term oral glucocorticoid prescriptions in the U K over the past 20 years. Rheumatology (Oxford). 2011; 50(11):1982-1990.
92. Benard-Laribiere A, Pariente A, Pambrun E, Begaud B, Fardet L, Noize P. Prevalence and prescription patterns of oral glucocorticoids in adults: A retrospective cross-sectional and cohort analysis in France. BMJ Open. 2017; 7(7):1-7.
93. Overman R A, Yeh J Y, Deal C L. Prevalence of oral glucocorticoid usage in the United States: A general population perspective. Arthritis Care Res. 2013; 65(2): 294-298.
94. Vegiopoulos A, Herzig S. Glucocorticoids, metabolism and metabolic diseases. Mol Cell Endocrinol. 2007; 275(1-2):43-61.
95. Morgan S A, McCabe E L, Gathercole L L, et al. 110-HSD1 is the major regulator of the tissue-specific effects of circulating glucocorticoid excess. Proc Natl Acad Sci USA. 2014; 111(24).
96. Dalle H, Garcia M, Antoine B, et al. Adipocyte Glucocorticoid Receptor Deficiency Promotes Adipose Tissue Expandability and Improves the Metabolic Profile Under Corticosterone Exposure. Diabetes. 2019; 68(2):305 LP-317.
97. Wang Z Q, Zhang X H, Yu Y, et al. Artemisia scoparia extract attenuates non-alcoholic fatty liver disease in diet-induced obesity mice by enhancing hepatic insulin and AMPK signaling independently of FGF21 pathway. Metabolism. 2013; 62:1239-1249.
98. Gaggini M, Morelli M, Buzzigoli E, DeFronzo R A, Bugianesi E, Gastaldelli A. Non-alcoholic fatty liver disease (NAFLD) and its connection with insulin resistance, dyslipidemia, atherosclerosis and coronary heart disease. Nutrients. 2013; 5(5):1544-1560.
99. Bugianesi E, Gastaldelli A, Vanni E, et al. Insulin resistance in non-diabetic patients with non-alcoholic fatty liver disease: Sites and mechanisms. Diabetologia. 2005; 48(4):634-642.
100. Marchesini G, Brizi M, Bianchi G, et al. Nonalcoholic Fatty Liver Disease: A Feature of the Metabolic Syndrome. Diabetes. 2001; 50:1844-1850.
101. Perry R J, Cline G W, Shulman G I, et al. Mechanism for leptin's acute insulin-independent effect to reverse diabetic ketoacidosis. J Clin Invest. 2017; 127(2):657-669.
102. Wijayatunga N N, Pahlavani M, Kalupahana N S, et al. An integrative transcriptomic approach to identify depot differences in genes and microRNAs in adipose tissues from high fat fed mice. Oncotarget. 2018; 9(10):9246-9261.
103. Takahashi E, Unoki-Kubota H, Shimizu Y, et al. Proteomic analysis of serum biomarkers for prediabetes using the Long-Evans Agouti rat, a spontaneous animal model of type 2 diabetes mellitus. J Diabetes Investig. 2017; 8(5):661-671.
104. Kang S, Tsai L T, Zhou Y, et al. Identification of nuclear hormone receptor pathways causing insulin resistance by transcriptional and epigenomic analysis. Nat Cell Biol. 2015; 17(1):44-56.
105. Dalby M J, Aviello G, Ross A W, Walker A W, Barrett P, Morgan P J. Diet induced obesity is independent of metabolic endotoxemia and TLR4 signalling, but markedly increases hypothalamic expression of the acute phase protein, SerpinA3N. Sci Rep. 2018; 8(1).
106. Sergi D, Campbell F M, Grant C, et al. SerpinA3N is a novel hypothalamic gene upregulated by a highfat diet and leptin in mice. Genes Nutr. 2018; 13:28.
107. Gueugneau M, d'Hose D, Barbe C, et al. Increased Serpina3n release into circulation during glucocorticoid-mediated muscle atrophy. J Cachexia Sarcopenia Muscle. 2018; 9(5):929-946.
108. Li P, Pan F, Hao Y, Feng W, Song H, Zhu D. SGK1 is regulated by metabolic-related factors in 3T3-L1 adipocytes and overexpressed in the adipose tissue of subjects with obesity and diabetes. Diabetes Res Clin Pract. 2013; 102(1):35-42.
109. Li P, Hao Y, Pan F H, Zhang M, Ma J Q, Zhu D L. SGK1 inhibitor reverses hyperglycemia partly through decreasing glucose absorption. J Mol Endocrinol. 2016; 56(4):301-309.
110. Schernthaner-Reiter M, Kiefer F, Zeyda M, Stulnig T, Luger A, Vila G. Strong association of serum- and glucocorticoid-regulated kinase 1 with peripheral and adipose tissue inflammation in obesity. Int J Obes. 2015; 39:1143-1150.
111. Sierra-Ramos C, Velizquez-Garcia S, Vastola-Mascolo A, Hemnndez G, Faresse N, Alvarez de la Rosa D. SGK1 activation exacerbates diet-induced obesity, metabolic syndrome and hypertension. J Endocrinol. 2019.

112. Itani O A, Liu K Z, Cornish K L, Campbell J R, Thomas C P. Glucocorticoids stimulate human sgkl gene expression by activation of a GRE in its 5'-flanking region. Am J Physiol Endocrinol Metab. 2002; 283(5):E971-9.

113. Xu C, He J, Jiang H, et al. Direct effect of glucocorticoids on lipolysis in adipocytes. Mol Endocrinol. 2009; 23(8):1161-1170.

114. Lacasa D, Agli B, Giudicelli Y. Permissive action of glucocorticoids on catecholamine-induced lipolysis: Direct "in vitro" effects on the fat cell 0-adrenoreceptor-coupled-adenylate cyclase system. Biochem Biophys Res Commun. 1988; 153(2):489-497.

115. Campbell J E, Peckett A J, D'Souza A M, Hawke T J, Riddell M C. Adipogenic and lipolytic effects of chronic glucocorticoid exposure. Am J Physiol—Cell Physiol. 2011; 300(1):198-209.

116. Serr J, Suh Y, Oh S-A, et al. Acute Up-Regulation of Adipose Triglyceride Lipase and Release of Non-Esterified Fatty Acids by Dexamethasone in Chicken Adipose Tissue. Lipids. 2011; 46(9):813-820.

117. Lundgren M, Buren J, Ruge T, Myrnas T, Eriksson J W. Glucocorticoids Down-Regulate Glucose Uptake Capacity and Insulin-Signaling Proteins in Omental But Not Subcutaneous Human Adipocytes. J Clin Endocrinol Metab. 2004; 89(6):2989-2997.

118. Livingston J N, Lockwood D H. Effect of glucocorticoids on the glucose transport system of isolated fat cells. J Biol Chem. 1975; 250(21):8353-8360.

119. Gathercole L L, Bujalska I J, Stewart P M, Tomlinson J W. Glucocorticoid Modulation of Insulin Signaling in Human Subcutaneous Adipose Tissue. J Clin Endocrinol Metab. 2007; 92(11):4332-4339.

120. Sakoda H, Ogihara T, Anai M, et al. Dexamethasone-induced insulin resistance in 3T3-L1 adipocytes is due to inhibition of glucose transport rather than insulin signal transduction. Diabetes. 2000; 49(10):1700-1708.

121. Patel R, Williams-Dautovich J, Cummins C L. Minireview: New molecular mediators of glucocorticoid receptor activity in metabolic tissues. Mol Endocrinol. 2014; 28(7):999-1011.

122. Richard A J, Hang H, Stephens J M. Pyruvate dehydrogenase complex (PDC) subunits moonlight as interaction partners of phosphorylated STAT5 in adipocytes and adipose tissue. J Biol Chem. 2017; 292 (48):19733-19742.

123. Baugh J E, Floyd Z E, Stephens J M. The modulation of STAT5A/G R complexes during fat cell differentiation and in mature adipocytes. Obesity (Silver Spring). 2007; 15(3):583-590.

124. Burke S J, Batdorf H M, Huang T-Y, et al. One week of continuous corticosterone exposure impairs hepatic metabolic flexibility, promotes islet β-cell proliferation, and reduces physical activity in male C57BL/6 J mice. J Steroid Biochem Mol Biol. 2019; 195:105468.

125. Kaikaew K, Steenbergen J, van Dijk T H, Grefhorst A, Visser J A. Sex Difference in Corticosterone-Induced Insulin Resistance in Mice. Endocrinology. 2019; 160(10):2367-2387.

126. Zhao P, Elks C M, Stephens J M. The induction of lipocalin-2 protein expression in vivo and in vitro. J Biol Chem. 2014; 289(9):5960-5969.

127. Yan Q-W, Yang Q, Mody N, et al. The adipokine lipocalin 2 is regulated by obesity and promotes insulin resistance. Diabetes. 2007; 56(10):2533-2540.

128. Catalin V, Gómez-Ambrosi J, Rodriguez A, et al. Increased adipose tissue expression of lipocalin-2 in obesity is related to inflammation and matrix metalloproteinase-2 and metalloproteinase-9 activities in humans. J Mol Med (Berl). 2009; 87(8):803-813.

129. Wang Y, Lam KSL, Kraegen E W, et al. Lipocalin-2 is an inflammatory marker closely associated with obesity, insulin resistance, and hyperglycemia in humans. Clin Chem. 2007; 53(1):34-41.

130. Oeckinghaus A, Ghosh S. The NF-kappaB family of transcription factors and its regulation. Cold Spring Harb Perspect Biol. 2009; 1(4).

131. Viatour P, Merville M P, Bours V, Chariot A. Phosphorylation of NF-κB and IκB proteins: Implications in cancer and inflammation. Trends Biochem Sci. 2005; 30(1):43-52.

132. Christian F, Smith E, Carmody R. The Regulation of NF-κB Subunits by Phosphorylation. Cells. 2016; 5(1): 12.

133. Massaro M, Scoditti E, Pellegrino M, et al. Therapeutic potential of the dual peroxisome proliferator activated receptor (PPAR)α/γ agonist aleglitazar in attenuating TNF-α-mediated inflammation and insulin resistance in human adipocytes. Pharmacol Res. 2016; 107:125-136.

134. Miles P D G, Romeo O M, Higo K, Cohen A, Rafaat K, Olefsky J M. TNF-α-Induced Insulin Resistance In Vivo and Its Prevention by Troglitazone. Diabetes. 1997; 46(11):1678-1683.

135. Peraldi P, Xu M, Spiegelman B M. Thiazolidinediones block tumor necrosis factor-α-induced inhibition of insulin signaling. J Clin Invest. 1997; 100(7): 1863-1869.

136. Ruan H, Pownall H J, Lodish H F. Troglitazone antagonizes tumor necrosis factor-α-induced reprogramming of adipocyte gene expression by inhibiting the transcriptional regulatory functions of NF-κB. J Biol Chem. 2003; 278(30):28181-28192.

137. Nakashima K, Murakami T, Tanabe H, Inoue M. Identification of a naturally occurring retinoid X receptor agonist from Brazilian green propolis. Biochim Biophys Acta—Gen Subj. 2014; 1840(10):3034-3041.

138. Iio A, Ohguchi K, Inoue H, et al. Ethanolic extracts of Brazilian red propolis promote adipocyte differentiation through PPARγ activation. Phytomedicine. 2010; 17(12):974-979.

139. Choi S-S, Cha B-Y, lida K, et al. Artepillin C, as a PPARγ ligand, enhances adipocyte differentiation and glucose uptake in 3T3-L1 cells. Biochem Pharmacol. 2011; 81(7):925-933.

140. Zhao Y, Zhao J, Li X, et al. [Advances in caffeoylquinic acid research]. Zhongguo Zhong Yao Za Zhi. 2006; 31(11):869-874.

141. Wan P, Xie M, Chen G, et al. Anti-inflammatory effects of dicaffeoylquinic acids from Ilex kudingcha on lipopolysaccharide-treated RAW264.7 macrophages and potential mechanisms. Food Chem Toxicol. 2019; 126:332-342.

142. Kim Y, Kim J T, Park J, et al. 4,5-Di-O-Caffeoylquinic Acid from Ligularia fischeri Suppresses Inflammatory Responses Through TRPV1 Activation. Phytother Res. 2017; 31(10):1564-1570.

143. Abdel Motaal A, Ezzat S M, Tadros M G, El-Askary H I. In vivo anti-inflammatory activity of caffeoylquinic acid derivatives from Solidago virgaurea in rats. Pharm Biol. 2016; 54(12):2864-2870.

144. Puangpraphant S, Berhow M A, Vermillion K, Potts G, Gonzalez de Mejia E. Dicaffeoylquinic acids in Yerba mate (Ilex paraguariensis St. Hilaire) inhibit NF-κB nucleus translocation in macrophages and induce apoptosis by activating caspases-8 and -3 in human colon cancer cells. Mol Nutr Food Res. 2011; 55(10):1509-1522
145. Kamath R S, Fraser A G, Dong Y, et al. Systematic functional analysis of the Caenorhabditis elegans genome using RNAi. Nature. 2003.
146. Holzenberger M, Dupont J, Ducos B, et al. IGF-1 receptor regulates lifespan and resistance to oxidative stress in mice. Nature. 2003.
147. Houtkooper R H, Williams R W, Auwerx J. Metabolic Networks of Longevity. Cell. 2010.
148. Antebi A. Nuclear receptor signal transduction in C. elegans. WormBook. 2015.
149. Van Gilst M R, Hadjivassiliou H, Jolly A, Yamamoto K R. Nuclear hormone receptor NHR-49 controls fat consumption and fatty acid composition in C. elegans. PLoS Biol. 2005.
150. Qi W, Gutierrez G E, Gao X, et al. The ω-3 fatty acid α-linolenic acid extends Caenorhabditis elegans lifespan via NHR-49/PPARα and oxidation to oxylipins. Aging Cell. 2017.
151. McCormack S, Polyak E, Ostrovsky J, et al. Pharmacologic targeting of sirtuin and PPAR signaling improves longevity and mitochondrial physiology in respiratory chain complex I mutant Caenorhabditis elegans. Mitochondrion. 2015.
152. Sluder A E, Mathews S W, Hough D, Yin V P, Maina C V. The nuclear receptor superfamily has undergone extensive proliferation and diversification in nematodes. Genome Res. 1999.
153. Robinson-Rechavi M, Maina C V., Gissendanner C R, Laudet V, Sluder A. Explosive lineage-specific expansion of the orphan nuclear receptor HNF4 in nematodes. J Mol Evol. 2005.
154. Pathare P P, Lin A, Bomfeldt K E, Taubert S, van Gilst M R. Coordinate regulation of lipid metabolism by novel nuclear receptor partnerships. PLoS Genet. 2012.
155. Heestand B N, Shen Y, Liu W, et al. Dietary Restriction Induced Longevity Is Mediated by Nuclear Receptor NHR-62 in Caenorhabditis elegans. PLoS Genet. 2013.
156. Goudeau J, Bellemin S, Toselli-Mollereau E, Shamalnasab M, Chen Y, Aguilaniu H. Fatty acid desaturation links germ cell loss to longevity through NHR-80/HNF4 in C. elegans. PLoS Biol. 2011.
157. Noble T, Stieglitz J, Srinivasan S. An integrated serotonin and octopamine neuronal circuit directs the release of an endocrine signal to control C. Elegans body fat. Cell Metab. 2013.
158. Ashrafi K, Chang F Y, Watts J L, et al. Genome-wide RNAi analysis of Caenorhabditis elegans fat regulatory genes. Nature. 2003.
159. Wang M C, Min W, Freudiger C W, Ruvkun G, Xie X S. RNAi screening for fat regulatory genes with SRS microscopy. Nat Methods. 2011. doi 10.1038/nmeth.1556
160. Stiernagle T. Maintenance of C. elegans. WormBook. 2006.
161. Mitchell D H, Stiles J W, Santelli J, Rao Sanadi D. Synchronous growth and aging of Caenorhabditis elegans in the presence of fluorodeoxyuridine. Journals Gerontol. 1979.
162. Yang J S, Nam H J, Seo M, et al. OASIS: Online application for the survival analysis of lifespan assays performed in aging research. PLoS One. 2011.

Example 5

Prenylated Coumaric Acids from *Artemisia scoparia* Beneficially Modulate Adipogenesis Abstract Two new di-prenylated coumaric acid isomers (1a/b) and two known congeners, capillartemisin A (2) and B (3), were isolated from *Artemisia scoparia* as bioactive markers using bioactivity-guided HPLC fractionation. Their structures were determined by spectroscopic means, including 1D and 2D NMR, LC-MS, and their purity assessed by 1D $^1$H pure shift qNMR analysis. The bioactivity of 1a/b-3 was validated by enhanced accumulation of lipid, as measured using Oil Red O staining, and by increased expression of several adipocyte marker genes, including adiponectin, in 3T3-L1 adipocytes relative to untreated negative controls. Compared to the extract, 1a/b-3 showed significant but still weaker inhibition of TNFα-induced lipolysis in 3T3-L1 adipocytes. This indicates that additional bioactives can contribute to metabolically favorable effects on adipocytes observed with *Artemisia scoparia* extract.

Introduction

*Artemisia* is one of the largest and most diverse genera of the family Asteraceae and comprised of over 500 species, which contain a diverse array of phytochemicals that are used as traditional medicines and sources of pharmaceutical agents. *Artemisia scoparia* Waldst. & Kit is an annual herb distributed from Central Europe to Western Asia that has been studied for the biological activity of its essential oil as well as for other phytochemical preparations. We identified adipogenic activity in an EtOH extract of *A. scoparia* (SCO), as hundreds of screening results of plants for bioactivity related to metabolic syndrome.[1] Several bioactivities of SCO have been identified, including the promotion of adipogenesis in vitro, as measured by both lipid accumulation and the expression of adipogenic gene), as well as the enhancement of insulin sensitivity in high-fat diet-induced obese mice.[2,3] SCO also showed distinct inhibitory effects on lipolysis (the release of lipids) in both cultured murine adipocytes and in mice fed a high-fat diet supplemented with SCO.[4,5] In an effort to demonstrate how the constituents of SCO contribute to the observed adipogenic bioactivity, we conducted a series of the bioactivity-guided fractionation studies. This previously led to the putative identification of the principal bioactive constituents in SCO as prenylated coumaric acids, coumarin monoterpene ethers, 6-demethoxycapillarisin, and two polymethoxyflavones.[5]

A study by Yahagi et al. identified a collection of compounds isolated from an aqueous EtOH extract of *A. scoparia* that inhibited triglyceride accumulation in adipocytes.[6] Indeed, the inhibition of lipid accumulation and adipocyte differentiation was once considered an appropriate strategy for combating obesity-related metabolic dysfunction. However, it is well established that impairments in adipogenesis and adipose tissue expansion can promote the metabolic dysregulation associated with insulin resistance.[7-10] This is underscored by the potent insulin-sensitizing effects of the thiazolidinedione (TZD) drugs, which act by enhancing adipocyte differentiation.[11] The compounds identified as inhibitors of triglyceride accumulation were primarily chromane derivatives that were active at higher concentrations than those tested.[6] In our present studies, compounds 1-3 were purified from SCO using bioassay-guidance, structurally characterized by spectroscopic methods including NMR, and validated as bioactive markers for SCO by a panel of in vitro assays.

Results and Discussion

An extract of *A. scoparia*, SCO, was previously shown to have beneficial adipogenic properties in vitro and in vivo, which were maintained through the process of the bioactivity-guided fractionation and present in distinct fractions comprised of prenylated coumarins and related compounds.[5] Further separation of the fractions led to the isolation of six compounds that were subsequently structurally characterized and subject to bioassays. Three of those compounds retained some, i.e., a statistically significant portion, but not all the biological activity of their parent fractions. The structures of compounds 1-3 are shown in FIGS. 21 and 22. Compounds 1a/b are prenylated cinnamic acid isomers identified as new natural products, while 2 and 3 are isomers of the prenylated coumaric acids, capillartemisin A and B.

Bioactivity-guided fractionation is a method used to identify the active constituents of complex mixtures of compounds and relies on the use of appropriate in vitro assays where small amounts of separated materials can be tested. While it can lead to bioactive markers, the inability to assess "synergistic" bioactivity is its major and widely recognized limitation. Compared to the previously published process,[5] the separation and extraction process was optimized for this study in terms of compound yield and minimization of samples to be tested. EtOAc extraction of the dried *A. scoparia* plants replaced the broader polarity EtOH extraction and its subsequent fractionation by CPC. HPLC separation of the EtOAc extract produced three fractions that contained the bioactive compounds previously described. Individual HPLC methods utilizing a chiral column were then used to produce nearly pure compounds (see discussion herein about purity) from each of those fractions.[5] Compounds 1-3 were obtained from fractions III and V. While fraction IV was also separated further, no resulting component exhibited adipogenic activity and, thus, no structural studies were performed on these components.

Structure Elucidation of Di-prenylated Coumaric Acid Derivatives. The crude ethyl acetate partition of the aerial parts of *A. scoparia* was purified by HPLC column chromatography (CC), which led to two di-prenylated coumaric acids, 1a and 1b, isolated as a mixture, along with two known compounds, 2 and 3, which were characterized as capillartemisins A (2) and B (3) by 1D and 2D NMR spectroscopic data and comparison with reported spectroscopic data.[12-15]

Compound 1a was isolated as an amorphous solid and as a mixture with 1b. The HRESIMS (m/z 397.1616 $[M+Na]^+$, calcd for $C_{21}H_{26}O_6Na^+$, 397.1622) indicated a molecular formula of $C_{21}H_{26}O_6$ associated with an LC retention time of 5.8 min (FIG. 30). The $^1H$ NMR spectrum showed the characteristic resonances arising from a trans double bond [$\delta_H$ 7.453 (1H, d, J=15.8 Hz, H-7) and 6.280 (1H, d, J=15.8 Hz, H-8)], meta coupling in an aromatic ring [$\delta_H$ 7.174 (1H, d, J=2.3 Hz, H-6) and 7.164 (1H, d, J=2.3 Hz, H-2)], olefinic hydrogens in a di-prenylated moiety [$\delta_H$ 5.560 (1H, br t, J=7.7 Hz, H-2') and 5.400 (1H, br t, J=7.6 Hz, H-2")], and an acetyl group [$\delta_H$ 2.045 (3H, s, OAc-4')]. The DEPTQ-135 spectrum exhibited 21 well-dissolved signals assigned to two carbonyls [$^6$c 173.0 (C-9), 173.1 (COO-4')], twelve $sp^2$ carbons [$^6$c 128.1 (C-1), 128.6 (C-2), 129.4 (C-3), 155.9 (C-4), 129.2 (C-5), 129.1 (C-6), 144.9 (C-7), 118.5 (C-8), 129.5 (C-2'), 132.2 (C-3'), 126.8 (C-2") and 136.5 (C-3")], and two hydroxylated methylene carbons [$^6$c 64.2 (C-4'), 61.9 (C-4")]. All of this data indicated that 1a is a di-prenylated coumaric acid derivative. The 1D and 2D spectra confirmed key elements of the structure of 1a via key HMBC correlations (FIG. 21) as follows: from H-4' to [$\delta_C$ 129.5 (C-2), 132.2 (C-3'), and 21.7 (C-5')], H-4" to [$\delta_C$ 126.8 (C-2"), 136.5 (C-3"), and 22.1 (C-5")], H-1' to [$\delta_C$ 128.6 (C-2), 129.4 (C-3), 155.9 (C-4), 129.5 (C-2'), and 132.2 (C-3')], H-1" to [$\delta_C$ 155.9 (C-4), 129.2 (C-5), 129.1 (C-6), 126.8 (C-2"), and 136.5 (C-3")], H-7 to [$\delta_C$ 128.1 (C-1), 128.6 (C-2), 129.1 (C-6), 118.5 (C-8), and 173.1 (C-9)]. The HMBC correlation (FIG. 21) from H-4' to $\delta_C$ 173.1 (CO-4') confirmed the location of the acetyl group at C-4'. The $^1H$ NMR and $^{13}C$ NMR chemical shift of H-4', $\delta_C$ 64.2 (C-4), H4", and $\delta_C$ 61.9 (C-4") confirmed the Z arrangement of oxygenated the methylene group.[12-13] On the basis of this collective evidence (FIG. 24), 1a was determined to be 3-[4'-acetoxyprenyl]-5-[4"-hydroxyprenyl]-7(E)-p-coumaric acid and named cis-scopa-trans-coumancin.

The molecular formula of 1b ($C_{21}H_{26}O_6$), which was the second component in the mixture along with 1a, was also deduced from the HRESIMS (m/z 397.1627 $[M+Na]^+$), exhibiting the same molecular formula of $C_{21}H_{26}O_6$ ($[M+Na]^+$, calcd for $C_{21}H_{26}O_6Na^+$, 397.1622) as 1a, but exhibited at an LC retention time of 6.0 min. The $^1H$ and $^{13}C$ NMR data of 1b were almost identical to those of 1. The key difference of 1b arose from a cis double bond of coumaric acid with olefinic hydrogen resonating at $\delta_H$ 5.81 ppm and exhibiting a characteristic J coupling [d, J=12.6 Hz, H-7)/6c 122.6 (C-7) and $\delta_H$ 6.44 (d, J=12.6 Hz, H-8)/6c 136.2 (C-8)]. The di-prenylated group could be located via the HMBC correlation from H-1' to C-2 and C-3 ($\delta_C$ 130.5 and 128.3 ppm, esp.), and from H-1" to C-5 and C-6 ($\delta_C$ 128.5 and 130.5, resp.) The HMBC correlation (FIG. 21) from H-4' to COO-4' at $\delta_C$ 173.1 ppm confirmed the location of the acetyl group. Further analysis of 1D and 2D NMR data indicated that 1b otherwise shares the identical molecular scaffold as 1a. On the basis of all of the spectroscopic evidence, 1b (FIG. 24) was determined to be 3-[4'-acetoxyprenyl]-5-[4"-hydroxyprenyl]-7(Z)-p-coumaric acid and named cis-scopa-cis-coumancin.

Cis-trans Isomerism of Di-prenylated Coumaric Acid. Photochemical mechanisms are known to generate cis-trans isomerization of olefins. Other mechanisms are induced thermally, by acid or base catalysis, or by reaction with molecules that contain an odd number of electrons.[16,17] Among these isomerism factors, photoisomerization can occur spontaneously in the plant due to the exposure to sunlight. As the di-prenylated coumaric acids possess an α,β-unsaturation, absorption of longer wavelengths can promote trans-to-cis isomerization in these compounds.[18]

Without wishing to be bound by theory, the trans (E) isomer tends to be more stable than the cis (Z) isomer.[19,20] Notably, the di-prenylated coumaric acid has three α,β-unsaturated olefinic hydrogens, each can undergo cis-trans isomerization. Thus, besides the presence of the diastereomeric species 1a and 1b, additional cis-trans isomers exist in the plant, the mother fraction that contained 1a and 1b, and purified 1a/1b samples. To validate this, the sample containing the mixture of 1a/1b was evaluated using pure shift NMR spectroscopy confirmed the presence of the isomeric compounds which are shown as the singlet peaks at the characteristic chemical shift of di-prenylated proton region, aided by the extraction of additional ion traces from the total ion LC-MS chromatogram (FIG. 22-23 and FIG. 30). The common name of the isolated new compounds describes the demonstrated cis-trans-isomerism on the di-prenylated coumaric acids. Therefore, the nomenclature of isomers of this class of di-prenylated compounds follows the rational naming scheme, taking into account their cis trans isomerization properties.

Spectroscopic Detection of Isomeric Patterns. Representing a versatile structural tool, NMR is widely utilized to elucidate the structures of isolated ("pure") natural products. While the classical 1D $^1$H NMR spectrum contributes essential information (number of hydrogens, their chemical shift and spin-spin coupling constants), the spectra of pure compounds are often already (over) crowded, which explains why spectra of materials that contain other, near-identical structures as mixtures often challenge NMR data interpretation. One solution to the signal overlap challenge is the pure shift NMR spectrum,[21] which removes spin-spin coupling and, thereby, reduces the resonance of each hydrogen to a singlet. This improves the signal resolution and simplifies spectral analysis and interpretation.[22] In the given case of a mixture of closely related, diastereomeric congeners, the ability to distinguish molecular species is a valuable addition to the structural information obtained from coupling patterns to determine the cis-trans isomerization.

The pure shift $^1$H NMR spectrum of 1a and 1b was, thus, obtained to suppress the spin-spin coupling patterns in the crowded spectral regions between $\delta_H$ 1.70 and 5.70 ppm (FIG. 23). The results provide evidence for the presence of additional minor isomers involving di-prenylated coumaric acid moieties. The LC-MS analysis further verified these findings via the detection of additional low-abundance isomers. The use of a window function when extracting the ion chromatogram allowed the selective filtering of ions of a specific molecular weight in the LC-MS chromatogram (FIG. 30). The results showed that the theoretically plausible isomers of 1a, 1b, 2, and 3 can be observed in these samples and constitutes a case of Residual Complexity (go.uic.edu/residualcomplexity). These insights can be gained despite the limitation of their quantities due to differences in their LC retention time (as shown for 1a vs. 1b), confirmed by their identical molecular formula (FIG. 30).

Purity Analysis Using 100% PF-qNMR Method. The pure shift NMR data confirmed the presence of other isomeric di-prenylated coumaric acids, which gave rise to additional minor NMR signals resonating close-by those of 1a and 1b. The pure shift experiments also revealed that the presence of minor isomers were hidden under the "shoulders" of the main resonances of 1a and 1b. Applying the peak-fitting (PF) approach using peak deconvolution, PF-qNMR enabled the disentangling of the overlapped resonances for the purpose of their relative quantitation.[23] Subsequent application of the 100% qNMR method led to the measurement of the relative ratio of 1a and 1b to be calculated as 71.6% 5.70 and 28.4%±1.86, respectively (FIG. 25). The error of relative quantitation is due to the presence of residual amounts of the minor cis-trans isomers, which could be confirmed by peak deconvolution.

Compounds from *A. scoparia* promote adipogenesis. Bioactivity-guided fractionation studies were previously used to identify several fractions from SCO that can promote adipocyte differentiation, as assessed by enhanced accumulation of lipid and increased expression of adipogenic genes in differentiating 3T3-L1 adipocytes.[4,5] Six distinct sub-fractions were isolated from these fractions as "single" compounds in order to assign the bioactivity to individual compounds (FIG. 27). Oil Red O staining was used to examine neutral lipid accumulation in 3T3-L1 cells treated with the purified sub-fractions (FIG. 27 panels A) relative to the total extract SCO (50 μg/mL), rosiglitazone (2 μM) as the positive control, and DMSO as the negative control. The sub-fractions III-1 (2), III-2 (1a/b) and V-1 (3) showed enhanced lipid accumulation similar to SCO and rosiglitazone over most of the concentrations tested (2.5, 10, and 25 μM). The lowest dose for the sub-fractions was chosen to be similar to the concentration of the rosiglitazone positive control. Compound 2 was active in a dose-dependent manner, while 1a/b and 3 showed the best activity over the tested dose range.

Compounds 1a/b-3 also increased the expression of adipogenic genes for adiponectin (AdipoQ), fatty acid binding protein 4 (Fabp4), and peroxisome proliferation activated-receptor gamma (PPARγ) in 3T3-L1 adipocytes relative to the negative controls (FIG. 27 panels B-D). The rosiglitazone control had higher activity for Fabp4 than any *A. scoparia* compounds or SCO, as rosiglitazone is a potent PPARγ agonist drug used for treating insulin resistance. Sub-fraction V-2 showed enhanced adipogenic activity for each of these assays, but was consistently weak relative to 1a/b-3, and barely above the DMSO control. Sub-fractions IV-1 and IV-2 had no effect on any of the measured parameters for adipogenesis, while IV-2 inhibited lipid accumulation and adipogenic gene expression at the highest dose.

Compounds from *A. scoparia* inhibit TNFα-induced lipolysis. The sub-fractions were also tested in 3T3-L1 adipocytes relative to SCO for their ability to inhibit TNFα-induced lipolysis. SCO was previously shown to reduce lipolysis in vitro (TNFα-induced lipolysis in cultured adipocytes) and in vivo (mice fed a high-fat diet with SCO supplementation) bioassays.[4] In order to validate that the SCO compounds with pro-adipogenic activity in differentiating adipocytes also have anti-lipolytic effects in mature adipocytes, mature 3T3-L1 adipocytes were pretreated with each of the six sub-fractions and then with TNFα to induce lipolysis. Lipolysis was measured on the basis of glycerol release, which is enhanced by insulin resistance and TNFα treatment of cell cultures. SCO was able to reduce TNFα-induced lipolysis to basal levels as previously demonstrated, but only the highest concentration of 1a/b showed any statistically significant inhibitory activity (FIG. 28). Compounds 2 and 3 and the other sub-fractions that demonstrated adipogenic activity were not able to significantly mitigate TNFα-induced lipolysis at the concentrations tested. The lipolysis inhibitory activity of the pure compounds relative to the activity of the parent extract SCO (as well as the EtOAc extract, EA) indicates that other compound(s) can contribute to the anti-lipolytic activity of the parent extract results, For example, other compound(s) can be those that did not fractionate with the pure compounds. For example, such compounds can include those not only from the current isolates, but also from other compound(s) that did not fractionate with the adipogenic activity followed here. This outcome is common of bioassay-guided botanical studies and a strong indicator of botanical polypharmacology, as we have shown recently for hops (*Humulus lupulus*).[24,25] While the process of bioactivity-guided fractionation was not guided by anti-lipolytic activity, it was used to characterize the parent extract.

In conclusion, this study led to the characterization of bioactive marker compounds that are associated with the adipogenic bioactivity observed from an extract of *A. scoparia* (SCO). One of the compounds was identified as a new set prenylated cinnamic acid isomers, cis-scopa-trans-coumaricin and cis-scopa-cis-coumaricin (1a/b). The others were prenylated coumaric acid isomers previously indicated as capillartemisin A (2) and B (3). These compounds share the cinnamic acid core and di-prenyl substitution in both meta positions, which indicates this motif being the core of the pharmacophore. The adipogenic bioactivities used for the characterization of the extract could be replicated for the isolates.

Experimental Section

Plant Material. *Artemisia scoparia* Waldst. & Kit herb was grown in a greenhouse facility in New Brunswick, NJ (40° 28'41.9" N 74° 26'15.7" W) and harvested the whole aerial parts of the plant at the flowering stage for the production of extract. Some plants were left to produce seed to maintain the seed source for future cultivation. Voucher specimens are retained under the guidance of a taxonomist.

Extraction and Isolation. *A. scoparia* extract (SCO) was prepared from greenhouse-grown plants as described previously.[4] Briefly, the herb was freeze-dried and extracted in 80% EtOH (1:20 w/v). The preparation of distinct fractions from SCO was previously described in detail. Each of the fractions consisted of compounds that were not purified for structural characterization but maintained adipogenic activities were originally characterized from SCO. The fractions were created using multiple chromatographic techniques including solvent partitioning, CPC and HPLC.[5]

The chromatographic response of the active compounds obtained from the enriched fractions of SCO was used to enhance the purification process. Here, the *A. scoparia* plants were freeze-dried, ground into a powder and extracted directly with EtOAc (1:20 w/v), sonicated for one hour, and incubated at 22° C. for 24 h. Solids were removed by filtration, and the extract was dried by rotary evaporation. The yield of this crude extract was 4.6% from the dried plant.

The freeze-dried extract was dissolved in 90% EtOH (25 mg/mL) for initial HPLC separation. The sample was separated on a semi-preparatory HPLC system consisting of Waters™ Alliance e2695 Separations Module and 2998 Photodiode Array Detector with a Phenomenex Synergi 4μ 80 Å Hydro-RP column 250×21.2 mm. The mobile phases consisted of two components: Solvent A (0.1% ACS grade acetic acid in double-distilled de-ionized $H_2O$) and Solvent B ($CH_3CN$). The separation was completed using a linear gradient run of 40% B in A to 60% B over 20 min at a flow rate of 15 mL/min, followed by reconditioning of the column with 100% B for 5 min and return to initial conditions. Fractions III, IV and V were manually collected at 14-16 min, 16-17 min and 17-18 min, respectively. The yields of fractions III and V were 9.3% and 5.3%, respectively, from the total extract injected. Each fraction was dried by rotary evaporation.

Fraction III was separated and purified using the same HPLC system described above with a Phenomenex Lux® 5 μM Cellulose-2 chiral column 250×10 mm. The mobile phases consisted: Solvent A (0.1% ACS grade formic acid in double-distilled de-ionized $H_2O$), and Solvent B ($CH_3CN$). The separation was completed using a linear gradient run of 35% B in A to 65% B over 60 min at a flow rate of 5 mL/min, followed by reconditioning of the column with 100% B for 10 min and return to initial conditions. Fractions III-1 and III-2 were collected at 14-18 min and 21-25 min, respectively. Fractions III-1 and III-2 were analyzed by LC-MS for exact mass and identified using NMR.

Fraction IV was separated using the same HPLC system as fraction III. However, the separation was completed using a different linear gradient as 45% B in A to 60% B over 30 min, then to 100% B at 35 min at a flow rate of 5 mL/min, followed by reconditioning of the column with 100% B for 10 min and return to initial conditions. Fractions IV-1 and IV-2 were collected at 36-39 min and 39-41 min, respectively.

Fraction V was separated using the same HPLC system as fraction III with a linear gradient 40% B in A to 50% B over 20 min at a flow rate of 5 m/min, followed by reconditioning of the column with 100% B for 10 min and return to initial conditions. Fractions V-1 and V-2 were collected at 12-14 min and 29-30 min.

General NMR and MS Procedures. The samples were dissolved in 200 μL of methanol-d4, then transferred into a 3 mm NMR tube. 1D and 2D NMR spectra were acquired at 298 K using Bruker AVANCE I 900/225 NMR spectrometer. The spectrometer was equipped with a 5-mm Bruker TCI triple resonance, inverse-detection cryoprobe with a z-axis pulse field gradient. The pure shift spectroscopic data were acquired at 297.9 K using an AVANCE III NMR spectrometer equipped with an inverse-detection C/H Cryoprobe Bruker 600 MHz. Processing was accomplished using the Mnova software package (v.14.1.1, Mestrelab Research S.L., A Coruña, Spain). 1H spectra were processed with the following parameters: GM (LB−0.3 Hz, GB 0.5), zero filling to SI=256 k and with the application of automatic phasing, the pure shift spectra were processed with the following parameter: GM (LB−0.3 Hz, GB 0.5, zero fillings to SI=64k with a linear prediction of MIST method application of automatic phasing, using Mnova software. The integral values were obtained after using a fifth order polynomial fit baseline correction.

Mass spectrometry analyses were carried out using a Bruker Impact II, quadrupole time-of-flight (Bremen, Germany) coupled to a Shimadzu Nexera X2 UHPLC system (Kyoto, Japan). Data analyses were performed on the Compass Data Analysis software (Bruker Version 4.4). The machine is equipped with an electrospray source. And the analysis was made in positive mode a capillary voltage at 4.5 kV, nebulizer and drying gas ($N_2$) at 3.0 bar and 12.0 L/min, respectively, dry temperature of 225° C., and mass scan range set from m/z 200 to 800, along with the negative electrospray ionization mode using a capillary voltage at −2.5 kV, nebulizer and drying gas ($N_2$) at 4.0 bar and 12.0 L/min, respectively, dry temperature of 225° C., and mass scan range set from m/z 200 to 800. The separation was performed on a CORTECS C18 (100×3.0 mm, 2.7 μm) UHPLC column.

UPLC/MS Analysis of *A. scoparia* fractions: Compounds in samples were separated and analyzed during the process of fractionation by a UPLC/MS system (FIG. 30) including the Dionex® UltiMate 3000 RSLC ultra-high pressure liquid chromatography system, consisting of a workstation with ThermoFisher Scientific's Xcalibur v. 4.0 software package combined with Dionex®'s SII LC control software, solvent rack/degasser SRD-3400, pulseless chromatography pump HPG-3400RS, autosampler WPS-3000RS, column compartment TCC-3000RS, and photodiode array detector DAD-3000RS. After the photodiode array detector, the eluent flow was guided to a Q Exactive Plus Orbitrap high-resolution high-mass-accuracy mass spectrometer (MS). Mass detection was full MS scan with low collision energy induced dissociation (CID) from 100 to 1000 m z in either positive or negative ionization mode with electrospray ionization (ESI) interface. Sheath gas flow rate was 30 arbitrary units, the auxiliary gas flow rate was 7, and the sweep gas flow rate was 1. The spray voltage was 3500 volts (−3500 for negative ESI) with a capillary exr of 275° C. The mass resolution was 70,000 or higher. Substances were separated on a Phenomenex™ Kinetex C8 reverse phase column (100×2 mm, 2.6 μm particle size, and 100 Å pore size). The mobile phase consisted of two components: solvent A (0.5% ACS grade acetic acid in LCMS grade water, pH 3-3.5), and Solvent B (100% acetonitrile, LCMS grade). The mobile phase flow was 0.20 mL/min, and a gradient mode was used for all analyses. The initial conditions of the gradient were 95% A and 5% B; for 30.0 minutes the proportion reaches 5% A and 95% B which was kept for the next 8.0 minutes, and during the following 4 minutes the ratio was brought to initial conditions. An equilibration interval of 8.0 minutes was included between subsequent injections. The average pump pressure using these parameters was around 3900 psi for the initial conditions. Putative formulas of natural products were determined by performing isotope abundance analysis on the high-resolution mass spectral data with Xcalibur v. 4.0 software and reporting the best fitting empirical formula. Database searches were performed using www.reaxys.com (Elsevier RELX Intellectual Properties SA) and SciFinder (scifinder.cas.org, American Chemical Society).

Compound 1a and 1b:amorphous solid; UV (MeOH) λmax (log ε) action; $^{1}H$ NMR (900 MHz, methanol-d4) and $^{13}C$ NMR (225 MHz, methanol-d4) data, see FIG. 24; HRMS m/z 397.1616 for 1a and 397. 397.1627 for 1b $[M+Na]^+$ (calcd for $C_{21}H_{25}O_6Na^+$, 397.1622).

Cell Culture and Treatments. 3T3-L1 preadipocytes (murine) were cultured as previously described,[3] and induced to differentiate two days after reaching confluence. For experiments using mature adipocytes, cells were induced with a standard methylxanthine-dexamethasone-insulin (MDI) cocktail, which contains 0.5 mM isobutylmethylxanthine (IBMX), 1 μM dexamethasone (DEX), and 1.72 μM insulin in high-glucose Dulbecco's Modified Eagle Medium (DMEM) supplemented with 10% fetal bovine serum (FBS). IBMX, DEX, insulin, and DMEM were obtained from Sigma-Aldrich (St. Louis, Missouri), and FBS from Hyclone (GE Healthcare Life Sciences, Logan, UT). For differentiation experiments, cells were induced with half-strength MDI cocktail containing. In both cases, cells were fed with high-glucose DMEM+10% FBS with 0.43 μM insulin three days following MDI induction. Test compounds were dissolved in dimethylsulfoxide (DMSO) as 1000× stocks. For differentiation experiments, cells were treated with the compounds (or DMSO vehicle as a control) at the time of induction and at the first feeding there after (3 days post-MDI). For lipolysis experiments on mature adipocytes, cells were fed with high-glucose DMEM+10% FBS 6 days after MDI and treated with test compounds or DMSO vehicle for three days. On the third day cells were also treated overnight with 0.75 nM tumor necrosis factor alpha (TNFα) (Life Technologies, Carlsbad, CA) or its vehicle [0.1% bovine serum albumin (BSA) in phosphate buffered saline (PBS)]. The following morning, the culture medium was replaced with lipolysis incubation medium (low-glucose DMEM+2% BSA) and 0.75 nM TNFα(or vehicle). After 4 hours, conditioned medium and cell lysates were collected.

Lipid Accumulation Assay. Five days after MDI induction, cell monolayers were fixed in 10% neutral buffered formalin (ThermoFisher, Waltham, MA) and stained with the neutral lipid stain, Oil Red O (ORO). Plates were scanned to generate images of staining. The ORO was then eluted in isopropyl alcohol, and absorbance of eluates was measured at 520 nm for quantitation.

RNA Purification and Gene Expression. Four days after MDI induction, cells were harvested and RNA purified using the RNeasy Mini kit (Qiagen, Hilden, Germany). Reverse transcription was performed using the High-Capacity cDNA Reverse Transcription kit (Applied Biosystems, Foster City, CA), according to the manufacturer's protocol. Gene expression assays using primers from Integrated DNA Technologies (Skokie, IL). Primer sequences are shown. SYBR Premix (Takara Bio, Mountain View, CA) was used for quantitative polymerase chain reaction (qPCR), performed on the Applied Biosystems 7900HT system. Data analysis used SDS 2.3 software. Target gene data were normalized to the reference gene, non-POU-domain-containing, octamer binding protein (Nono). All primer sequences are shown in FIG. 26.

$^{1}H$ NMR spectrum of compounds 1a and 1b in $CD_3OD$ at 900 MHz; DEPTQ-135 spectrum of compounds 1a and 1b in $CD_3OD$ at 900 MHz; COSY spectrum of compounds 1a and 1b in $CD_3OD$ at 900 MHz; HSQC spectrum of compounds 1a and 1b in $CD_3OD$ at 900 MHz; HMBC spectrum of compounds 1a and 1b in $CD_3OD$ at 900 MHz, LC-MS chromatogram of compounds 1a and 1b; LC-MS chromatogram of capillartemisin A; LC-MS chromatogram of capillartemisin B; table of a rational nomenclature for the prospective naming scheme of di-prenylated coumaric acids; deconvolution of pure shift spectroscopic data of compounds 1a and 1b.

REFERENCES CITED IN THIS EXAMPLE (1) Dey, M.; Ripoll, C.; Pouleva, R.; Dom, R.; Aranovich, I.; Zaurov, D.; Kurmukov, A.; Eliseyeva, M.; Belolipov, I.; Akimaliev, A.; Sodombekov, I.; Akimaliev, D.; Lila, M. A.; Raskin, I. Phytother. Res. 2008, 22, 929-934.

(2) Richard, A. J.; Burris, T. P.; Sanchez-Infantes, D.; Wang, Y.; Ribnicky, D. M.; Stephens, J. M. Nutrition 2014, 30, S31-S36.

(3) Richard, A. J.; Fuller, S.; Fedorcenco, V.; Beyl, R.; Burns, T. P.; Mynatt, R.; Ribnicky, D. M.; Stephens, J. M. PLOS ONE 2014, 9, e98897.

(4) Boudreau, A.; Richard, A. J.; Burrell, J. A.; King, W. T.; Dunn, R.; Schwarz, J.-M.; Ribnicky, D. M.; Rood, J.; Salbaum, J. M.; Stephens, J. M. Am. J. Physiol.-Endocrinol. Metabol. 2018, 315, E1053-E1061.

(5) Boudreau, A.; Poulev, A.; Ribnicky, D. M.; Raskin, I.; Rathinasabapathy, T.; Richard, A. J.; Stephens, J. M. Frontiers Nutr. 2019, 6, 18.

(6) Yahagi, T.; Yakura, N.; Matsuzaki, K.; Kitanaka, S. J. Nat. Med. 2014, 68, 414-420.

(7) Gustafson, B.; Hedjazifar, S.; Gogg, S.; Hammarstedt, A.; Smith, U. Trends Endocrinol. Metabol. 2015, 26, 193-200.

(8) Smith, U.; Kahn, B. B. J. Intern. Med. 2016, 280, 465-475.

(9) Danforth, E. Nature Genetics 2000, 26, 13-13.

(10) Kim, J.-Y.; van de Wall, E.; Laplante, M.; Azzara, A.; Trujillo, M. E.; Hofmann, S. M.; Schraw, T.; Durand, J. L.; Li, H.; Li, G.; Jelicks, L. A.; Mehler, M. F.; Hui, D. Y.; Deshaies, Y.; Shulman, G. I.; Schwartz, G. J.; Scherer, P. E. J. Clin. Investig. 2007, 117, 2621-2637.

(11) Cignarelli, A.; Giorgino, F.; Vettor, R. Arch. Physiol. Biochem. 2013, 119, 139-150.

(12) Kitagawa, I.; Fukuda, Y.; Yoshihara, M.; Yamahara, J.; Yoshikawa, M. Chem. Pharm. Bull. 1983, 31, 352-355.

(13) Jakupovic, J.; Tan, R. X.; Bohlmann, J. Z. J.; Huneck, S. Phytochemistry 1991, 30, 1645-1648.

(14) Huneck, S.; Zdero, C.; Bohlmann, F. Phytochemistry 1986, 25, 883-889.

(15) Okuno, I.; Uchida, K.; Nakamura, M.; Sakurawi, K. Chem. Pharm. Bull. 1988, 36, 769-775.

(16) Simmler, C.; Lankin, D. C.; Nikolid, D.; van Breemen, R. B.; Pauli, G. F. Fitoterapia 2017, 121, 6-15.

(17) Sanchez, A. M.; Barra, M.; de Rossi, R. H. J. Org. Chem. 1999, 64, 1604-1609.

(18) Dugave, C.; Demange, L. Chem. Rev. 2003, 103, 2475-2532.

(19) Caccamese, S.; Azzolina, R.; Davino, M. Chromatographia 1979, 12, 545-547.

(20) Kort, R.; Vonk, H.; Xu, X.; Hoff, W. D.; Crielaard, W.; Hellingwerf, K. J. FEBS Lett. 1996, 382, 73-78.

(21) Zangger, K. Prog. Nucl. Magn. Reson. Spectrosc. 2015, 86-87, 1-20.

(22) Castañar, L. Magn. Reson. Chem. 2018, 56, 874-875.

(23) Phansalkar, R. S.; Simmler, C.; Bisson, J.; Chen, S.-N.; Lankin, D. C.; McAlpine, J. B.; Niemitz, M.; Pauli, G. F. J. Nat. Prod. 2017, 80, 634-647.

(24) Bolton, J. L.; Dunlap, T. L.; Hajirahimkhan, A.; Mbachu, O.; Chen, S.-N.; Chadwick, L.; Nikolic, D.; van Breemen, R. B.; Pauli, G. F.; Dietz, B. M. Chem. Res. Toxicol. 2019, 32, 222-233.

(25) Dietz, B. M.; Chen, S.-N.; Alvarenga, R. F. R.; Dong, H.; Nikolid, D.; Biendl, M.; van Breemen,
R. B.; Bolton, J. L.; Pauli, G. F. J. Nat. Prod. 2017, 80, 2284-2294.

Example 6

Mechansims of *Artemisia scoparia*'s Anti-Inflammatory Activity in Cultured Adipocytes, Macrophages, and Pancreatic β-Cells Abstract Objective: An ethanolic extract of *Artemisia scoparia* (SCO) improves adipose tissue function and reduces negative metabolic consequences of high-fat feeding. *A. scoparia* has a long history of medicinal use across Asia and has anti-inflammatory effects in various cell types and disease models. The objective of the current study was to validate SCO's effects on inflammation in cells relevant to metabolic health.

Methods: Inflammatory responses were assayed in cultured adipocytes, macrophages, and insulinoma cells, by quantitative PCR, immunoblotting, and NF-κB promoter reporter assays.

Results: In TNFα-treated adipocytes, SCO mitigated ERK and NF-κB signaling, as well as transcriptional responses, but had no effect on fatty acid-binding protein 4 (FABP4) secretion. SCO also reduced levels of deleted in breast cancer 1 (DBC1) protein in adipocytes, and inhibited inflammatory gene expression in stimulated macrophages. Finally, in pancreatic β-cells, SCO decreased NF-κB-responsive promoter activity induced by IL-1β treatment.

Conclusions: SCO's ability to promote adipocyte development and function can mediate its insulin-sensitizing actions in vivo. Our findings that SCO inhibits inflammatory responses through at least two distinct signaling pathways (ERK and NF-κB) in three cell types known to contribute to metabolic disease, reveal that SCO can act to improve metabolic health.

Study Questions

Adipose tissue inflammation plays a role in whole-body metabolic function in the context of obesity.

An ethanolic extract of *Artemisia scoparia* (SCO) improves measures of adipocyte and adipose tissue function, as well as whole-body insulin sensitivity in a mouse model of diet-induced obesity.

SCO inhibits inflammatory gene expression in cultured adipocyte and macrophages.

SCO inhibits ERK signaling in adipocytes, as well as NF-kB signaling in adipocytes and pancreatic β-cells.

SCO's effects on adipocyte function and development have been well studied. Our current results indicate that SCO may be acting on various cell types, through several mechanisms, to mitigate obesity-related metabolic dysfunction; this opens up new directions for the investigation of SCO's properties.

Our data validate SCO as a dietary supplement to promote metabolic resilience.

Introduction

The obesity epidemic and its associated metabolic disorders are among the major health challenges of our time (1). Adipose tissue plays a role in these metabolic disease states, and disruptions in adipocyte development and function negatively impact whole-body insulin sensitivity and systemic metabolic health (2). Adipocyte differentiation and adipose tissue expansion are often impaired in obese states, leading to insulin resistance and metabolic dysregulation (3, 4). In addition, obesity and insulin resistance are associated with enhanced basal lipolysis rates, which exacerbate metabolic disease (reviewed in (5)). Inflammatory processes in adipose tissue are also a feature of obesity and the metabolic syndrome, and there is crosstalk between inflammation, adipogenesis, endocrine function, and lipid metabolism in adipose tissue (5, 6). Because of its role in obesity and diabetes, adipose tissue is considered a target for therapeutic intervention (2).

Botanicals have a history of medicinal use across cultures the world over, and plants have been a source of pharmaceutical compounds. Metformin, the first-line drug in treating type 2 diabetes mellitus (T2DM), was derived from galegine, a bioactive first isolated from *Galega officinalis*, also known as goat's rue or French lilac (7). Screening efforts in our laboratory identified an extract of *Artemisia scoparia* (SCO) as a potent enhancer of adipocyte differentiation in vitro. Subsequent studies in a diet-induced obesity (DIO) mouse model have shown that SCO also has metabolically beneficial effects on adipose tissue in vivo (8, 9). In addition, SCO supplementation improves whole-body insulin sensitivity, and reduces circulating levels of fatty acids and triglycerides (8-10). More recently, we have demonstrated that SCO can act on adipocytes in vitro to reduce lipolysis induced by the inflammatory cytokine, TNFα(11).

*A. scoparia* has a history of medicinal use (12, 13), and it has been shown to have a range of effects in disease models related to Alzheimer's, renal oxidative stress, hepatotoxicity, hypertension, and others (14-17). Anti-inflammatory effects of *A. scoparia* have been described in a range of cell types and contexts (18-20). In adipose tissue, TNFα secreted from resident macrophages is a mediator of obesity-associated inflammation (6, 21, 22). Given the important role of adipose tissue inflammation in obesity-related metabolic dysfunction, we examined the ability of SCO to regulate TNFα action and inflammatory gene expression in adipocytes. We observed that SCO reduced TNFα's effects on inflammatory cytokine expression and NF-κB activation. SCO also reduced nuclear levels of deleted in breast cancer 1 (DBC1, also known as cell cycle and apoptosis regulator 2 or CCAR2), a protein associated with impaired metabolic function (23-26). Although SCO reduced lipolysis induced by TNFα, it had no effect on TNFα-induced secretion of FABP4, which has been shown to be enhanced by lipolytic stimuli and reduced by interventions that inhibit lipolysis. (27, 28). Finally, we observed anti-inflammatory effects of SCO in two other cell types critical in metabolic disease states: macrophages and pancreatic β-cells. Data presented herein validate SCO as a therapeutic in the treatment of metabolic disease.

Materials and Methods

Botanical extract source and preparation. *Artemisia scoparia* plants were grown and harvested, and ethanolic extracts were prepared as previously reported (8, 11). SCO extracts were dissolved in DMSO at 1000× final concentration (10 mg/ml and 50 mg/ml respectively for 10 or 50 μg/ml treatments).

Adipocyte cell culture and treatments. 3T3-L1 preadipocytes were grown and differentiated as previously described (8). Briefly, cells were grown in high-glucose DMEM supplemented with 10% bovine calf serum. Cells were induced to differentiate two days after reaching confluence, in DMEM plus 10% fetal bovine serum (FBS) containing 0.5 mM IBMX, 1 μM dexamethasone, and 1.7 μM insulin. Cells were fed 48-72 hours later with DMEM plus 10% FBS and 0.425 μM insulin, then every 48-72 hours with DMEM plus 10% FBS. DMEM, IBMX, dexamethasone, and insulin were obtained from Sigma-Aldrich (St. Louis, MO); calf serum and FBS were purchased from Hyclone (GE Life Sciences, Logan, UT). Treatments with SCO were initiated between 6 and 13 days after induction of differentiation. Murine TNFα was purchased from Life Technologies (Carlsbad, CA) and dissolved at 0.5 μM in PBS containing 0.1% bovine serum albumin BSA and added to cell culture media at the final concentrations indicated in figure legends.

Macrophage cell culture and treatments. RAW 264.7 macrophages were cultured in high-glucose DMEM supplemented with 10% FBS. Cells were pretreated for 2 hours with SCO, then lipopolysaccharide from *E. coli* 0111:B4 strain (LPS) (InvivoGen, San Diego, CA) was added for an additional 5.5-hour incubation before harvest.

Insulinoma cell culture and treatments. 832/13 rat insulinoma cells were cultured as described previously (29) and transfected with an adenoviral luciferase reporter construct under the control of 5 copies of a consensus NF-κB element (vector obtained from Vector Biolabs, Malvern, PA: catalog number 1740). 12 hours after transfection, cells were treated overnight with 5 or 10 μg/ml of *A. scoparia* (SCO) or *A. santolinaefolia*, then for 4 hours with 1 ng/ml IL-10. Luciferase reporter activity was assessed by luminometry and normalized to total protein content.

RNA isolation and gene expression analysis. Treated cells were harvested in RLT cell lysis buffer (Qiagen, Hilden, Germany). Lysates were stored at −80° C. prior to RNA extraction using the RNeasy Mini kit (Qiagen). The High-Capacity Reverse Transcription kit (Applied Biosystems, Foster City, CA) was used to reverse transcribe the RNA samples, and gene expression was assayed by qPCR with Takara SYBR premix (Takara Bio USA, Mountain View, CA) on the Applied Biosystems 7900HT system (cycling conditions: 2 min @ 50° C.; 10 min @ 95° C.; 40 cycles of 15 s @ 95° C. and 1 min @ 60° C.; dissociation stage: 15 s @ 95° C., 15 s @ 60° C., and 15 s @ 95° C. with end step ramp rate of 2%). Data were analyzed using SDS 2.3 or 2.4 software. Target gene data were normalized to the reference gene non-POU-domain-containing, octamer-binding protein (Nono). Primers were obtained from Integrated DNA Technologies (IDT, Skokie, IL), and sequences were as follows: Nono forward 5'-CATCATCAGCATCACCACCA-3' (SEQ ID NO: 1), reverse 5'-TCTTCAGGTCAATAGTCAAGCC-3' (SEQ ID NO: 2); Ccl2 (Mcp1) forward 5'-GCAGAGAGCCAGACGGGAGGA-3' (SEQ ID NO: 3), reverse 5'-TGGGGCGTTAACTGCATCTGG-3' (SEQ ID NO: 4); Il6 forward 5'-TCCTCTCTGCAAGAGACTTC-CATCC-3' (SEQ ID NO: 5), reverse 5'-AAGCCTCCGACTTGTGAAGTGGT-3' (SEQ ID NO: 6); Len2 forward 5'-TGCAAGTGGCCACCACGGAC-3' (SEQ ID NO: 7), reverse 5'-GCAT-TGGTCGGTGGGGACAGAGA-3' (SEQ ID NO: 8), Nos2 (iNos) forward 5'-CCCTCCTGATCTTGTGTTGGA-3' (SEQ ID NO: 2), reverse 5'-TCAACCCGAGCTCCTG-GAA-3' (SEQ ID NO: 10); Infa forward 5'-AGACCCT-CACACTCAGATCA-3' (SEQ ID NO: 11), reverse 5'-TCTTTGAGATCCATGCCGTTG-3' (SEQ ID NO: 12).

Protein samples and immunoblotting. For whole-cell extract preparation, adipocyte monolayers were harvested in radioimmunoprecipitation assay (RIPA) buffer (30) containing the following protease and phosphatase inhibitors: 1 mM phenylmethylsulfonyl fluoride, 1 μM pepstatin, 50 trypsin inhibitory milliunits of aprotinin, 10 μM leupeptin, 1 mM 10-phenanthroline, 0.2 mM sodium orthovanadate, and 100 μM sodium fluoride. Lysates were stored at −80° C., then thawed, passed through a 20 G needle three times and clarified by centrifugation at 13000 g. Supernatants were recovered, and protein concentrations were determined by bicinchoninic acid (BCA) assay (Sigma-Aldrich). Equal amounts of protein from each sample were loaded onto polyacrylamide gels, subjected to electrophoresis, and transferred to nitrocellulose. Standard immunoblotting techniques were applied to probe for target proteins. Primary antibodies were purchased from Cell Signaling Technologies (Danvers, MA) for ERK 1/2, CCAR2 (DBC1), and NF-κB p65; from R&D Systems (Bio-Techne, Minneapolis, MN) for lipocalin 2 (LCN2), Promega (Madison, WI) for phosphorylated ERK 1/2 (active MAPK), and Abcam (Cambridge, MA) for FABP4. Detection was performed with horseradish peroxidase-conjugated antibodies from Jackson Immunoresearch (West Grove, PA). Autoradiography films were scanned, and densitometry analysis performed using ImageStudio software from Li-Cor Biosciences (Lincoln, NE).

Subcellularfractionation. After treatment, adipocytes were harvested in nuclear homogenization buffer (NHB) (20 mM Tris pH 7.4, 10 mM NaCl, and 3 mM $MgCl_2$). IGEPAL CA-630 (Sigma-Aldrich) was added to the cell suspension at a final concentration of 0.15% prior to Dounce homogenization on ice. The nuclear fraction was pelleted by centrifugation at 517 g, washed in NHB, and resuspended in IP buffer. NHB and IP buffer were supplemented with protease and phosphatase inhibitors. Protein concentrations were determined by BCA assay.

FABP4 secretion and lipolysis assays. Cells pretreated for three days with SCO or DMSO vehicle, were treated overnight with or without 0.75 nM TNFα. The following morning, culture medium was replaced with lipolysis incubation medium (low-glucose DMEM+2% BSA). Cells treated with TNFα overnight were treated with the same concentration of TNFα for the lipolysis/FABP4 secretion analysis. The remaining cells were treated with either vehicle (controls), or 2 nM or 10 μM of isoproterenol. Conditioned media samples were collected after four hours and analyzed for FAPB4 content by immunoblotting. Lipolysis was also assessed by measuring glycerol concentrations in the samples, using free glycerol reagent from Sigma-Aldrich.

Results

SCO Inhibits TNFα-Induced Inflammatory Gene Expression in 3T3-L1 Adipocytes

Our previous studies have demonstrated that SCO could reduce protein levels of the inflammatory cytokine C-C motif chemokine ligand 2 (CCL2) (also known as monocyte chemoattractant protein 1, MCP-1) in the adipose tissue of high-fat diet-fed mice, and inflammatory gene expression in cultured adipocytes (9). We have sought to characterize the cell-autonomous anti-inflammatory effects of SCO in 3T3-L1 adipocytes treated with TNFα, a predominant mediator of adipose tissue inflammation that increases the expression of several inflammatory genes in adipocytes (21). As shown in FIG. 34, pretreatment of 3T3-L1 adipocytes with 50 μg/ml SCO significantly diminished TNFα-induced expression of Ccl2 and interleukin 6 (116), consistent with previously published studies (8), as well as lipocalin 2 (Lcn2) and nitric oxide synthase 2, inducible (Nos2 or iNos). We also examined the time course for induction of these genes and for the effects of SCO. As shown in FIG. 35, the temporal patterns of induction by TNFα and inhibition by SCO were different for all four genes assayed. While Ccl2 and Lcn2 both increased gradually over the 8-hour TNFα treatment, the effects of SCO were distinct. In the case of Ccl2, SCO significantly inhibited TNFα-induced gene expression at all time points. Yet, for Lcn2, SCO increased expression in basal conditions at all time points and at the early time points of TNFα treatment (1 and 2 hours). After 4 hours of TNFα treatment, SCO-treated cells had equivalent Lcn2 expression to the controls, and after 8 hours, expression was significantly lower in SCO-treated cells. Induction of I16 gene expression by TNFα was observed at all time points, but the response was biphasic. Specifically, expression strongly increased at 1 hour, subsided at 2 and 4 hours, then increased again at 8 hours. This same pattern of TNFα induction was observed in SCO-treated cells, but with lower 116 expression levels than without SCO at all time points. SCO attenuation of the TNFα effect on 116 was significant at 1, 4, and 8 hours, but not at 2 hours. Finally, Nos2 expression and nitric oxide production induced by TNFα have been implicated in the regulation of adipocyte lipolysis (31). TNFα induced Nos2 expression starting at the 2-hour time point, and SCO inhibited TNFα's effects, consistent with its previously described anti-lipolytic actions (11).

SCO inhibits TNFα-induced lipocalin 2 secretion in 3T3-L1 adipocytes

Lipocalin 2 (LCN2) is a pro-inflammatory mediator secreted by adipocytes (reviewed in (32)). We have previously shown that LCN2 expression and secretion are induced by TNFα in 3T3-L1 adipocytes (33). As shown in FIG. 36, the TNFα-induced expression and secretion of LCN2 from adipocytes was substantially reduced in the presence of SCO. These observations are consistent with the ability of SCO to impair TNFα induction of Lcn2 gene expression (FIGS. 34 and 35).

SCO reduces total and phosphorylated EFK levels

In adipocytes, TNFα signaling mediates transcriptional regulation of numerous target genes involved in adipocyte function (inflammation, insulin signaling, lipolysis, endocrine function, stress responses), through the activation of several signaling pathways (reviewed in (21)), including the MAP kinase, ERK. To further characterize the effects of SCO in the context of TNFα action in adipocytes, we examined ERK activation in the presence or absence of SCO. As shown in FIG. 37, TNFα regulates both the expression of ERK, and its activation, as judged by phosphorylation. TNFα induces ERK phosphorylation, and this activation is reduced in the presence of SCO. We also observed that total ERK1/2 levels were modulated by both TNFα(increased) and SCO (decreased). Comparison of the ratios of phosphorylated ERK 1/2 to total ERK 1/2 revealed that the effect of SCO on relative ERK activation was not significant.

SCO inhibits TNFα-induced nuclear translocation of NF-κB and reduces nuclear levels of Deleted in breast cancer 1 (DBC1) in 3T3-L1 adipocytes.

Another major signaling pathway engaged by TNFα in adipocytes is the IKK/NF-κB pathway. TNFα causes phosphorylation of the IKK complex, as well as phosphorylation and degradation of its target, inhibitor of nuclear factor-κB (IκB), resulting in the translocation of NF-κB to the nucleus. In order to determine whether SCO can modulate the TNFα activation of NF-κB in fat cells, we treated 3T3-L1 adipocytes with TNFα with or without a 3-day SCO pretreatment. The cytosolic and nuclear compartments were analyzed by immunoblotting. As shown in FIG. 38, TNFα treatment produced a very robust increase in nuclear levels of the NF-κB p65 subunit, and SCO pretreatment inhibited this response, indicating the ability of SCO to interfere with a major inflammatory signaling event.

The nuclear protein, Deleted in breast cancer 1 (DBC1), also known as cell cycle and apoptosis regulator 2 (CCAR2), has been implicated in several processes related to inflammation, adipocyte biology, and insulin resistance (23-25). Work in our laboratory has described a role for DBC1 in regulating TNFα-induced lipolysis in 3T3-L1 adipocytes (26). We examined DBC1 protein levels in cytosolic and nuclear fractions in TNFα-treated cells in the presence and absence of SCO (FIG. 38) and found that SCO-treated adipocytes had less nuclear DBC1 in both basal and TNFα-stimulated conditions. As previously reported, DBC1 is not detected in the cytosol of cultured adipocytes (26).

SCO does not reduce TNFα- or isoproterenol-induced FABP4 secretion

In addition to inducing expression of inflammatory mediators in adipocytes, TNFα also stimulates lipolysis, thereby increasing circulating fatty acid levels and promoting further metabolic dysregulation in obese and insulin-resistant states (5). We have shown that SCO inhibits TNFα-induced, but not adrenergic-stimulated lipolysis in adipocytes (11). Fatty acid-binding protein 4 (FABP4) is secreted from adipocytes and adipose tissue in response to lipolytic conditions, including exposure to forskolin, cyclic AMP, or isoproterenol (27, 28). To our knowledge, the effects of TNFα on FABP4 secretion have not been reported. Therefore, we induced lipolysis in adipocytes using TNFα or isoproterenol, with or without SCO pretreatment, and measured FABP4 levels in the conditioned medium to assess whether TNFα could induce secretion of FABP4 in 3T3-L1 adipocytes under prolipolytic conditions. Consistent with previous studies, both doses of isoproterenol tested stimulated FABP4 secretion (FIG. 39). We also made the observation that TNFα also promoted secretion of FABP4 in the presence and absence of SCO (FIG. 39). Additionally, we examined lipolysis, as measured by glycerol release, in these adipocytes. As shown in FIG. 39, SCO did not attenuate isoproterenol-induced lipolysis, but did attenuate TNFα-induced lipolysis. SCO had no effect on FABP4 secretion in any of the treatments (FIG. 39). Of note, SCO significantly reduced lipolysis, but not FABP4 secretion, in TNFα-treated adipocytes.

SCO Reduces LPS-induced expression of IIIb and Nos2 (iNos), but not Tnfa in macrophages Adipose tissue macrophages promote inflammation and contribute to adipocyte dysfunction in obese and insulin resistant states (6, 22). Hence, we validate that SCO can modulate inflammatory gene expression in RAW 264.7 cells treated with LPS. As shown in FIG. 40, LPS elicited a robust induction of Tnfa, IIIb, and Nos2. SCO pretreatment inhibited the LPS effect on IIIb and Nos2 in a dose-dependent manner, but had no effect on the induction of Tnfa gene expression by LPS, revealing a gene-specific anti-inflammatory effect of SCO in these cultured macrophages.

SCO reduces IL-1β-induced NF-κB activation in cultured pancreatic beta cells.

NF-κB signaling is involved in mediating the inflammatory transcriptional responses which contribute to pancreatic R-cell dysfunction in diabetes (34-38). To determine whether SCO could regulate NF-κB activation in β-cells, we transduced 823/13 rat insulinoma cells with a NF-κB luciferase reporter, then treated cells with SCO at 5 or 10 μg/ml, or vehicle overnight before stimulating cells with IL-1β for 4 hours. IL-1β treatment induced NF-κB promoter activation 28.6-fold over untreated controls. As shown in FIG. 41, we observed a dose-dependent reduction in NF-κB promoter activity in the presence of SCO. The higher dose of SCO resulted in a statistically significant decrease in IL-10-induced NF-κB promoter activity. This effect was not observed with an extract from *Artemisia santolinaefolia*, a different *Artemisia* species also known to have adipogenic effects in vitro, as well as some metabolically favorable effects in a mouse DIO model (9).

Discussion

The impacts of obesity, metabolic syndrome, and T2DM justify the search for therapeutic approaches, and adipose tissue is studied as a target for such interventions. Obesity is considered a pro-inflammatory state, and the importance of adipose tissue inflammation in the progression of insulin resistance is documented. In obesity, infiltration and activation of pro-inflammatory immune cells (such as macrophages) in adipose tissue contribute to impaired adipocyte differentiation and function, as well as to systemic insulin resistance, mediated at least in part by the paracrine actions of macrophage-derived TNFα on adipocytes (6, 21, 22). The study demonstrates that SCO can impede inflammatory processes through at least two different signaling pathways (MAP kinase and NF-κB), and in three cell types relevant to metabolic health (adipocytes, macrophages, and pancreatic β-cells).

In adipocytes, we discovered gene-specific temporal patterns of induction by TNFα and inhibition by SCO. For example, three of the four genes we examined showed a steady increase over an 8-hour TNFα treatment, while the fourth gene, Il6, showed a biphasic response (FIG. 35). Also, while SCO reduced expression of 16, Mcp1, and iNOS in all TNFα-treated conditions, SCO pretreatment increased Lcn2 expression in basal conditions and at the early time points of TNFα treatment, but was inhibitory with longer TNFα treatments. Given the low levels of Lcn2 expression in basal conditions and at early time points of TNFα induction, SCO's effects on these inflammatory genes under basal conditions can or cannot have physiological relevance. SCO's inhibition of Nos2 expression is modest after 2, 4, or 8 hours of TNFα treatment compared to the robust induction with TNFα and can or cannot be of any biological significance. These observations underscore the complexity of inflammatory signaling and indicate that SCO acts through distinct mechanisms on different genes.

Activation of the MAP kinase ERK by phosphorylation mediates some of TNFα's effects in adipocytes (21). Although phosphorylated:total ERK1/2 ratios were not significantly altered by SCO pretreatment, TNFα-treated cells had lower absolute levels of active phosphorylated ERK 1/2 when pretreated with SCO (FIG. 37), indicating suppression of MAPK signaling. This effect on ERK activation can contribute to the SCO-mediated reductions in inflammatory gene expression we observed, for example that of Lcn2, whose expression has been shown to be dependent on ERK 1/2 activation (39). The ability of SCO to decrease total levels of ERK 1/2 indicates that SCO pretreatment may alter its transcription, translation or stability. Avenues for further investigation of this observation can include studies of protein stability, unfolded protein response and endoplasmic reticulum stress, among others. Without wishing to be bound by theory, the effect of SCO on ERK expression is required for its anti-inflammatory actions.

The NF-κB pathway is also characterized and known to mediate TNFα's effects on inflammatory cytokine gene transcription through nuclear translocation of the p65 (RelA) subunit of NF-κB, and NF-κB signaling events are involved in inflammation-related metabolic disease (reviewed in (40)). A study in LPS-stimulated macrophages has shown that the total flavonoid fraction of *A. scoparia* can inhibit inflammatory signaling through MAP kinases and NF-κB (19). Our studies in adipocytes reveal that SCO caused substantial inhibition of both pathways in adipocytes, and provide further evidence that SCO impedes inflammatory signaling pathways in fat cells.

Without wishing to be bound by theory, DBC1 is a multi-functional protein at the interface between aging, cancer, and metabolism (41). Loss of DBC1 in adipocytes inhibits TNFα-induced lipolysis (26), and DBC1 knockout mice are protected from several metabolic effects of DIO (23). In addition, DBC1 knockdown in adipocytes promotes adipogenesis and reduces inflammatory cytokine expression (24, 25), while in B cells, DBC1 has been shown to interact with proteins of the IKK complex, which directly regulates NF-κB signaling (42). These studies link DBC1 inhibition with favorable metabolic effects. We have shown that SCO reduces DBC1 protein levels in adipocytes (FIG. 38), which can contribute to its anti-inflammatory, anti-lipolytic, and antidiabetic properties. Future studies can determine if loss of DBC1 plays an important role in the ability of SCO to promote metabolic health.

Elevated plasma levels of FABP4 are associated with obesity and insulin resistance in both mice and humans, and inhibition of plasma FABP4 activity improves glucose homeostasis in DIO mice (43). Acute activation of cAMP- or cGMP-dependent protein kinases (PKA and PKG) by increased intracellular cAMP or cGMP levels, respectively, stimulates lipolysis, and has been shown to promote FABP4 secretion from adipocytes. (28, 44). The mechanisms involved in the lipolytic effects of TNFα are distinct from those induced by fasting or adrenergic stimulation (5, 21). We report here that induction of lipolysis by TNFα is associated with increased FABP4 secretion (FIG. 39). While suppression of lipolysis with insulin or through pharmacological inhibition of PKA, PKG, or hormone-sensitive lipase has been shown to reduce FABP4 secretion in PKA- or PKG-stimulated conditions (27), we observed that SCO had no effect of TNFα-induced FABP4 secretion (FIG. 39) despite its ability to inhibit lipolysis, indicating that FABP4 secretion is not necessarily coupled to lipolysis. These data also argue against the involvement of FABP4 secretion in SCO's insulin-sensitizing effects.

In LPS-treated RAW 264.7 macrophages, SCO significantly inhibited Il6 and Nos2 expression, but had no effect on Tnfa expression (FIG. 40). Toll-like receptor 4 (TLR4) signaling, which mediates the effects of LPS in macrophages, engages at least two pathways which utilize distinct subsets of adaptor proteins. The so-called myeloid differentiation primary response 88 (MyD88)-dependent arm results in early-phase NF-κB activation and induction of inflammatory genes, including interleukins. The MyD88-independent arm involves activation of TIR domain-containing adaptor protein inducing interferon beta (TRIF) and interferon regulatory factor 3 (IRF3), and induction of genes such as the Type 1 interferons. Although TNFα is an NF-κB target gene, its regulation by TLR4 signaling is complex (45-47). It has been shown that activation of the NF-κB-independent TRIF/IRF3 pathway can induce early TNFα production and secretion, which in turn lead to a later-phase secondary autocrine activation of NF-κB signaling through TNFα receptor 1 (TNFR1) (48). In addition, transcriptional activation of NF-κB target genes is subject to complex regulation by many factors, including chromatin structure and epigenetic status of the target genes, as well as by various post-translational modifications of NF-κB subunits and variable subunit combinations of its dimers (46, 47, 49).

Interestingly, in a similar study in macrophages using a preparation of total flavonoids from *A. scoparia*, LPS-induced levels of 116 and Tnfa were both inhibited (19). Although the reason for this discrepancy cannot be ascertained, LPS treatment in this study was longer than ours (20 versus 5 hours). Under these more chronic conditions, regulation of Tnfa expression can be NF-κB dependent and thus susceptible to inhibition by SCO. Alternatively, differences in the composition of both extracts could explain these results. Analysis of our SCO extract by chromatography and mass spectrometry has revealed a complex mixture of compounds, many of which are not flavonoids (50). In addition, plants grown in different locations and conditions yield extracts with distinct chemical constituents and bioactivities. While SCO did not inhibit Tnfa gene expression in macrophages (FIG. 40) it did attenuate the response to TNFα treatment in adipocytes (FIGS. 34 and 35), which can contribute to improving adipose tissue metabolic function in the presence of inflammatory stimuli. Further studies can demonstrate the gene-specific effects of SCO in this context.

We have shown that SCO reduces NF-κB-responsive promoter activity in pancreatic β-cells. Recruitment of immune cells and activation of inflammatory pathways are contributors to the pancreatic-cell dysfunction that occurs with obesity and insulin resistance, and NF-κB is known to mediate these processes (36). The finding that SCO attenuates a measure of NF-κB activation in cultured-cells (FIG. 41) indicates that it can exert anti-inflammatory and metabolically favorable effects beyond adipose tissue.

Our laboratory has studied the effects of SCO on adipocyte differentiation and function, as well as in a DIO mouse model, for several years. We have now shown that SCO significantly impairs inflammatory signaling and transcriptional responses in three cell types that play roles in obesity, diabetes, and metabolic syndrome. In addition, we have described effects of SCO on adipocyte levels of DBC1, a protein that has garnered attention in recent years for its involvement in adipogenesis, inflammation, and metabolic dysfunction. We have also discovered that FABP4 secretion, known to be induced by various lipolytic agents, is stimulated by TNFα, although SCO did not modulate this response. Our findings reveal that SCO interferes with inflammatory signaling to attenuate responses that promote metabolic dysfunction, and demonstrate, for the first time, that SCO has favorable effects in pancreatic β-cells. These results support further investigation of SCO as a nutritional supplement to promote metabolic health in the context of obesity and insulin resistance.

REFERENCES CITED IN THIS EXAMPLE

1. Engin A. The definition and prevalence of obesity and metabolic syndrome. In: *Advances in Experimental Medicine and Biology. Vol* 960. Springer New York LLC, 2017, pp 1-17.
2. Kusminski C M, Bickel P E, Scherer P E. Targeting adipose tissue in the treatment of obesity-associated diabetes. *Nat Rev Drug Discov* 2016; 15:639-660.
3. Danforth E. Failure of adipocyte differentiation causes type II diabetes mellitus? *Nat Genet* 2000; 26:13-13.
4. Kim J-Y, van de Wall E, Laplante M, et al. Obesity-associated improvements in metabolic profile through expansion of adipose tissue. *J Clin Invest* 2007; 117: 2621-2637.
5. Morigny P, Houssier M, Mouisel E, Langin D. Adipocyte lipolysis and insulin resistance. *Biochimie* 2016; 125:259-266.
6. Engin A. The pathogenesis of obesity-associated adipose tissue inflammation. In: *Advances in experimental medicine and biology*. Vol 960, 2017, pp 221-245.
7. Thomas I, Gregg B. Metformin; a review of its history and future: from lilac to longevity. *Pediatr Diabetes* 2017; 18:10-16.
8. Richard A J, Fuller S, Fedorcenco V, et al. *Artemisia scoparia* Enhances Adipocyte Development and Endocrine Function In Vitro and Enhances Insulin Action In Vivo Dixit V D (ed.) *PLoS One* 2014; 9:e98897.
9. Richard A J, Burns T P, Sanchez-Infantes D, Wang Y, Ribnicky D M, Stephens J M. *Artemisia* extracts activate PPARγ, promote adipogenesis, and enhance insulin sensitivity in adipose tissue of obese mice. *Nutrition* 2014; 30:S31-536.
10. Wang Z Q, Zhang X H, Yu Y, et al. *Artemisia scoparia* extract attenuates non-alcoholic fatty liver disease in diet-induced obesity mice by enhancing hepatic insulin and AMPK signaling independently of FGF21 pathway. *Metabolism* 2013; 62:1239-1249.
11. Boudreau A, Richard A J, Burrell J A, et al. An ethanolic extract of *Artemisia scoparia* inhibits lipolysis in vivo and has antilipolytic effects on murine adipocytes in vitro. *Am J Physiol Metab* 2018; 315: E1053-E1061.
12. Hussain W, Ullah M, Dastagir G, Badshah L. Quantitative ethnobotanical appraisal of medicinal plants used by inhabitants of lower Kurram, Kurram agency, Pakistan. *Avicenna J phytomedicine* 2018; 8:313-329.
13. Hussain W, Badshah L, Ullah M, Ali M, Ali A, Hussain F. Quantitative study of medicinal plants used by the communities residing in Koh-e-Safaid Range, northern Pakistani-Afghan borders. *J Ethnobiol Ethnomed* 2018; 14:30.
14. Promyo K, Cho J Y, Park K H, Jaiswal L, Park S Y, Ham K S. *Artemisia scoparia* attenuates amyloid R accumulation and tau hyperphosphorylation in spontaneously hypertensive rats. *Food Sci Biotechnol* 2017; 26:775-782.
15. Sajid M, Rashid Khan M R, Shah N A, et al. Evaluation of *Artemisia scoparia* for hemostasis promotion activity. *Pak J Pharm Sci* 2017; 30:1709-1713.
16. Gilani A H, Janbaz K H. Hepatoprotective effects of *Artemisia scoparia* against carbon tetrachloride: an environmental contaminant. *J Pak Med Assoc* 1994; 44:65-8.

17. Cho J-Y, Park K-H, Hwang D, et al. Antihypertensive Effects of *Artemisia scoparia* Waldst in Spontaneously Hypertensive Rats and Identification of Angiotensin I Converting Enzyme Inhibitors. *Molecules* 2015; 20:19789-19804.

18. Habib M, Waheed I. Evaluation of anti-nociceptive, anti-inflammatory and antipyretic activities of *Artemisia scoparia* hydromethanolic extract. *J Ethnopharmacol* 2013; 145:18-24.

19. Wang X, Huang H, Ma X, et al. Anti-inflammatory effects and mechanism of the total flavonoids from *Artemisia scoparia* Waldst. et kit. in vitro and in vivo. *Biomed Pharmacother* 2018; 104:390-403.

20. Nam S-Y, Han N-R, Rah S-Y, Seo Y, Kim H-M, Jeong H-J. Anti-inflammatory effects of *Artemisia scoparia* and its active constituent, 3,5-dicaffeoyl-epi-quinic acid against activated mast cells. *Immunopharmacol Immunotoxicol* 2018; 40:52-58.

21. Cawthorn W P, Sethi J K. TNF-α and adipocyte biology. *FEBS Lett* 2008; 582:117-131.

22. Weisberg S P, McCann D, Desai M, Rosenbaum M, Leibel R L, Ferrante A W. Obesity is associated with macrophage accumulation in adipose tissue. *J Clin Invest* 2003; 112:1796-808.

23. Escande C, Nin V, Pirtskhalava T, et al. Deleted in breast cancer 1 limits adipose tissue fat accumulation and plays a key role in the development of metabolic syndrome phenotype. *Diabetes* 2015; 64:12-22.

24. Moreno-Navarrete J M, Moreno M, Vidal M, et al. Deleted in breast cancer 1 plays a functional role in adipocyte differentiation. *Am J Physiol Metab* 2015; 308:E554-E561.

25. Moreno-Navarrete J M, Moreno M, Vidal M, Ortega F, Ricart W, Femindez-Real J M. DBC1 is involved in adipocyte inflammation and is a possible marker of human adipose tissue senescence. *Obesity* 2015; 23:519-522.

26. Able A A, Richard A J, Stephens J. Loss of DBC1 (CCAR2) affects TNFα-induced lipolysis and Glut4 gene expression in murine adipocytes. *J Mol Endocrinol* 2018; 61:195-205.

27. Mita T, Furuhashi M, Hiramitsu S, et al. FABP4 is secreted from adipocytes by adenyl cyclase-PKA- and guanylyl cyclase-PKG-dependent lipolytic mechanisms. *Obesity* 2015; 23:359-367.

28. Ertunc M E, Sikkeland J, Fenaroli F, et al. Secretion of fatty acid binding protein aP2 from adipocytes through a nonclassical pathway in response to adipocyte lipase activity. *J Lipid Res* 2015; 56:423-434.

29. Hohmeier H E, Mulder H, Chen G, Henkel-Rieger R, Prentki M, Newgard C B. Isolation of INS-1-derived cell lines with robust ATP-sensitive K+ channel-dependent and -independent glucose-stimulated insulin secretion. *Diabetes* 2000; 49:424-430.

30. Kilroy G, Kirk-Ballard H, Carter L E, Floyd Z E. The Ubiquitin Ligase Siah2 Regulates PPARγ Activity in Adipocytes. *Endocrinology* 2012; 153:1206-1218.

31. Penfornis P, Marette A. Inducible nitric oxide synthase modulates lipolysis in adipocytes. *J Lipid Res* 2005; 46:135-42.

32. Li D, Yan Sun W, Fu B, Xu A, Wang Y. Lipocalin-2—The myth of its expression and function. *Basic Clin Pharmacol Toxicol* 2019:bcpt.13332.

33. Zhao P, Elks C M, Stephens J M. The induction of lipocalin-2 protein expression in vivo and in vitro. *J Biol Chem* 2014; 289:5960-5969.

34. Burke S J, Stadler K, Lu D, et al. IL-1β reciprocally regulates chemokine and insulin secretion in pancreatic 0-cells via NF-κB. *Am J Physiol Metab* 2015; 309: E715-E726.

35. Burke S J, Lu D, Sparer T E, et al. NF-κB and STAT1 control CXCL1 and CXCL2 gene transcription. *Am J Physiol Metab* 2014; 306:E131-E149.

36. Burke S, Collier J. Transcriptional Regulation of Chemokine Genes: A Link to Pancreatic Islet Inflammation? *Biomolecules* 2015; 5:1020-1034.

37. Burke S J, Updegraff B L, Bellich R M, et al. Regulation of iNOS gene transcription by IL-1β and IFN-γ requires a coactivator exchange mechanism. *Mol Endocrinol* 2013; 27:1724-1742.

38. Burke S J, Karlstad M D, Eder A E, et al. Pancreatic-Cell production of CXCR3 ligands precedes diabetes onset. *BioFactors* 2016; 42:703-715.

39. Zhao P, Stephens J M. STAT1, NF-κB and ERKs play a role in the induction of lipocalin-2 expression in adipocytes. *Mol Metab* 2013; 2:161-170.

40. Baker R G, Hayden M S, Ghosh S. NF-κB, inflammation, and metabolic disease. *Cell Metab* 2011; 13:11-22.

41. Chini E N, Chini C C S, Nin V, Escande C. Deleted in breast cancer-1 (DBC-1) in the interface between metabolism, aging and cancer. *Biosci Rep* 2013; 33:637-643.

42. Kong S, Dong H, Song J, et al. Deleted in Breast Cancer 1 Suppresses B Cell Activation through RelB and Is Regulated by IKKα Phosphorylation. *J Immunol* 2015; 195:3685-3693.

43. Xu A, Wang Y, Xu J Y, et al. Adipocyte fatty acid-binding protein is a plasma biomarker closely associated with obesity and metabolic syndrome. *Clin Chem* 2006; 52:405-413.

44. Cao H, Sekiya M, Ertunc M E, et al. Adipocyte lipid chaperone aP2 Is a secreted adipokine regulating hepatic glucose production. *Cell Metab* 2013; 17:768-778.

45. Doyle S L, O'Neill L A J. Toll-like receptors: From the discovery of NFκB to new insights into transcriptional regulations in innate immunity. *Biochem Pharmacol* 2006; 72:1102-1113.

46. Vaure C, Liu Y. A comparative review of toll-like receptor 4 expression and functionality in different animal species. *Front Immunol* 2014; 5:316.

47. Falvo J V., Tsytsykova A V., Goldfeld A E. Transcriptional control of the TNF Gene. *Curr Dir Autoimmun* 2010; 11:27-60.

48. Covert M W, Leung T H, Gaston J E, Baltimore D. Achieving stability of lipopolysaccharide-induced NF-κB activation. *Science* (80-) 2005; 309:1854-1857.

49. Ahmed A, Williams B, Hannigan G. Transcriptional Activation of Inflammatory Genes: Mechanistic Insight into Selectivity and Diversity. *Biomolecules* 2015; 5:3087-3111.

50. Boudreau A, Poulev A, Ribnicky D M, et al. Distinct fractions of an *Artemisia scoparia* extract contain compounds with novel adipogenic bioactivity. *Front Nutr* 2019; 6:18.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed:

1. A botanical composition consisting of an isolated and/or purified compound of

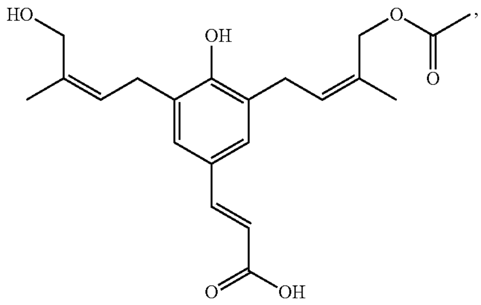

,

Scoprenyl (SP)

and a pharmaceutically acceptable carrier, excipient, or diluent.

2. The botanical composition of claim 1, wherein the botanical composition further consists of

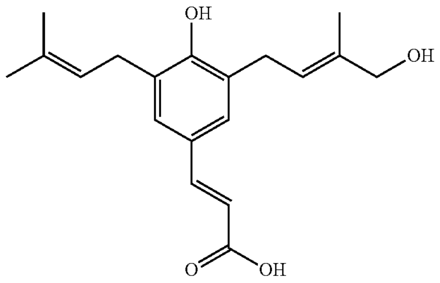

Capillartemisin A and/or

-continued

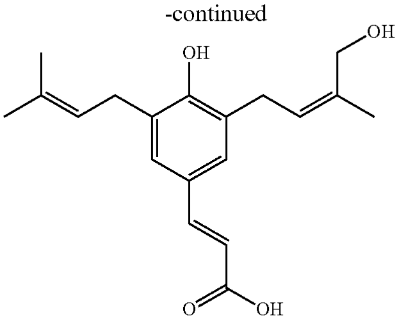

.

Capillartemisin B

Formula (IV)

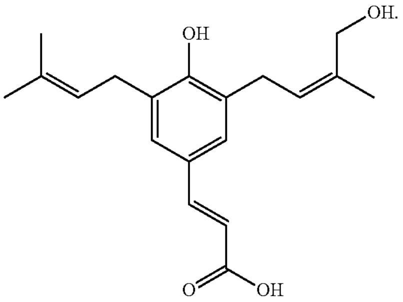

3. The botanical composition of claim 2, wherein the isolated and/or purified compound is an isomer of Scoprenyl (SP), Capillartemisin A, or Capillartemisin.

4. A method of treating or preventing obesity, diabetes, or metabolic syndrome, the method comprising administering to a subject in need thereof a therapeutically effective amount of the botanical composition of claim 1.

5. The method of claim 4, wherein the therapeutically effective amount comprises about 0.1 μg/kg to about 1000 mg/kg.

6. A method of treating or preventing a drug-induced metabolic disturbance, the method comprising administering to a subject in need thereof a therapeutically effective amount of the botanical composition of claim 1.

7. A method of extending the lifespan of a subject, the method comprising administering to a subject in need thereof a therapeutically effective amount of the botanical composition of claim 1.

* * * * *

SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 1
catcatcagc atcaccacca 20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 2
tcttcaggtc aatagtcaag cc 22

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 3
gcagagagcc agacgggagg a 21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 4
tggggcgtta actgcatctg g 21

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 5
tcctctctgc aagagacttc catcc 25

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 6
aagcctccga cttgtgaagt ggt 23

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 7
tgcaagtggc caccacggac 20

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 8
gcattggtcg gtggggacag aga 23

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 9
ccctcctgat cttgtgttgg a 21

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 10
tcaacccgag ctcctggaa 19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 11
agaccctcac actcagatca 20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 12
tctttgagat ccatgccgtt g 21

-continued

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 13
tgtctgtacg attgtcagtg g 21

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 14
ccctcctgtg ctgcagcctt tc 22

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 15
tcacaagaaa ttaccatggt tgaca 25

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 16
gcaggattaa gaggaacagg ag 22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 17
gtggcaaagc ccactcccac tt 22

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:
Synthetic polynucleotide

<400> SEQUENCE: 18
cgagtggtct tccatcacgg 20